(12) United States Patent
Hirano et al.

(10) Patent No.: US 8,771,916 B2
(45) Date of Patent: Jul. 8, 2014

(54) ACTINIC RAY-SENSITIVE OR RADIATION-SENSITIVE RESIN COMPOSITION AND PATTERN FORMING METHOD USING THE SAME

(75) Inventors: Shuji Hirano, Shizuoka (JP); Kaoru Iwato, Shizuoka (JP); Hiroshi Saegusa, Shizuoka (JP); Yusuke Iizuka, Shizuoka (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 13/139,074

(22) PCT Filed: Dec. 11, 2009

(86) PCT No.: PCT/JP2009/071189
§ 371 (c)(1), (2), (4) Date: Jun. 10, 2011

(87) PCT Pub. No.: WO2010/067905
PCT Pub. Date: Jun. 17, 2010

(65) Prior Publication Data
US 2011/0236828 A1    Sep. 29, 2011

Related U.S. Application Data

(60) Provisional application No. 61/122,166, filed on Dec. 12, 2008.

(30) Foreign Application Priority Data

| Dec. 12, 2008 | (JP) | 2008-317751 |
|---|---|---|
| Dec. 12, 2008 | (JP) | 2008-317752 |
| Dec. 12, 2008 | (JP) | 2008-317754 |
| Mar. 6, 2009 | (JP) | 2009-054291 |
| Apr. 3, 2009 | (JP) | 2009-091616 |
| May 20, 2009 | (JP) | 2009-122470 |
| May 29, 2009 | (JP) | 2009-131275 |
| Jul. 15, 2009 | (JP) | 2009-167004 |
| Oct. 30, 2009 | (JP) | 2009-251478 |

(51) Int. Cl.
*G03F 7/075* (2006.01)
*G03F 7/20* (2006.01)
*G03F 7/30* (2006.01)

(52) U.S. Cl.
USPC ........ 430/270.1; 430/311; 430/326; 430/907; 430/910; 430/921; 430/925

(58) Field of Classification Search
None
See application file for complete search history.

(56) References Cited

U.S. PATENT DOCUMENTS

| 2003/0194644 A1 | 10/2003 | Hatakeyama et al. |
|---|---|---|
| 2007/0059639 A1 | 3/2007 | Kanda et al. |
| 2007/0128555 A1 | 6/2007 | Harada et al. |
| 2007/0148595 A1 | 6/2007 | Kanda |
| 2007/0160929 A1 | 7/2007 | Hasegawa et al. |
| 2007/0178405 A1 | 8/2007 | Kanda et al. |
| 2008/0118860 A1 | 5/2008 | Harada et al. |
| 2008/0171287 A1* | 7/2008 | Kanda et al. ............... 430/270.1 |
| 2008/0305433 A1 | 12/2008 | Kanda et al. |
| 2009/0069521 A1 | 3/2009 | Nagai et al. |
| 2009/0098485 A1 | 4/2009 | Kanda |
| 2009/0197204 A1 | 8/2009 | Shiono et al. |
| 2010/0324329 A1 | 12/2010 | Nagai et al. |
| 2012/0077125 A1 | 3/2012 | Shiono et al. |

FOREIGN PATENT DOCUMENTS

| EP | 1975705 A2 | 10/2008 |
|---|---|---|
| JP | 2004-004697 A | 1/2004 |
| JP | 2005-326609 A | 11/2005 |
| JP | 2006-309245 A | 11/2006 |
| JP | 2007-153982 A | 6/2007 |
| JP | 2007-182488 A | 7/2007 |
| JP | 2007-199709 A | 8/2007 |
| JP | 2007-304537 A | 11/2007 |
| JP | 2007-304545 A | 11/2007 |
| JP | 2008-111103 A | 5/2008 |
| JP | 2008-231059 A | 10/2008 |
| JP | 2010-032994 A | 2/2010 |
| WO | 2006/121096 A1 | 11/2006 |

OTHER PUBLICATIONS

Written Opinion (PCT/ISA/237) issued in PCT/JP2009/071189 on Dec. 1, 2010.
International Search Report (PCT/ISA/210) issued in PCT/JP2009/071189 on Dec. 1, 2010.
Communication dated Oct. 29, 2013, issued by the Japanese Patent Office in corresponding Application No. 2009-281055.
Office Action dated Feb. 12, 2014 issued by the Japanese Patent Office in counterpart Japanese Patent Application No. 2009-281056.
Office Action issued in Taiwanese Patent Application No. 098142468 on Apr. 16, 2014.

* cited by examiner

*Primary Examiner* — Sin J. Lee
(74) *Attorney, Agent, or Firm* — Sughrue Mion, PLLC

(57) ABSTRACT

An actinic ray-sensitive or radiation-sensitive resin composition, includes: (A) a resin capable of increasing the solubility of the resin (A) in an alkali developer by the action of an acid; and (C) a resin having at least either a fluorine atom or a silicon atom and containing (c) a repeating unit having at least two or more polarity conversion groups.

21 Claims, No Drawings

ACTINIC RAY-SENSITIVE OR RADIATION-SENSITIVE RESIN COMPOSITION AND PATTERN FORMING METHOD USING THE SAME

TECHNICAL FIELD

The present invention relates to an actinic ray-sensitive or radiation-sensitive resin composition for use in the process of producing a semiconductor such as IC or in the lithography process at the production of a circuit board for liquid crystal, thermal head and the like or at other photo-fabrication, and a pattern forming method using the same. More specifically, the present invention relates to a positive resist composition suitable for exposure by an immersion projection exposure apparatus using a light source that emits a far ultraviolet ray at a wavelength of 300 nm or less, and a pattern forming method using the same.

BACKGROUND ART

Along with miniaturization of a semiconductor device, the trend is moving into a shorter wavelength of the exposure light source and a higher numerical aperture (higher NA) of the projection lens, and a so-called immersion method of filling a high refractive-index liquid (hereinafter sometimes referred to as an "immersion liquid") between the projection lens and the sample is known with an attempt to raise the resolution by more shortening the wavelength. The immersion method is effective for all pattern profiles and furthermore, can be combined with the super-resolution technology under study at present, such as phase-shift method and modified illumination method.

Since the advent of a resist for KrF excimer laser (248 nm), an image forming method called chemical amplification is used as an image forming method for a resist so as to compensate for sensitivity reduction caused by light absorption. For example, the image forming method by positive chemical amplification is an image forming method of decomposing an acid generator in the exposed area upon exposure to produce an acid, converting an alkali-insoluble group into an alkali-soluble group by using the generated acid as a reaction catalyst in the baking after exposure (PEB: Post Exposure Bake), and removing the exposed area by alkali development.

The resist for ArF excimer laser (193 nm) using this chemical amplification mechanism is predominating at present, but when the resist is immersion-exposed, this involves a pattern collapse problem of causing collapse of the formed line pattern to give rise to a defect at the production of a device, or the performance in terms of line edge roughness of the pattern side wall being roughened is not satisfied yet.

Also, it is pointed out that when the chemically amplified resist is applied to immersion exposure, the resist layer comes into contact with the immersion liquid at the exposure, as a result, the resist layer deteriorates or a component adversely affecting the immersion liquid bleeds out from the resist layer. To solve this problem, in JP-A-2006-309245 (the term "JP-A" as used herein means an "unexamined published Japanese patent application"), JP-A-2007-304537, JP-A-2007-182488 and JP-A-2007-153982, there is described an example of preventing the bleed-out by adding a resin containing a silicon atom or a fluorine atom Furthermore, in the immersion exposure process, when the exposure is performed using a scanning-type immersion exposure machine, unless the immersion liquid moves following the movement of lens, the exposure speed decreases and this may affect the productivity. In the case where the immersion liquid is water, the resist film is preferably hydrophobic because of good followability of water.

In JP-A-2008-111103, it is indicated that the resist pattern profile is improved by using a specific norbornane lactone derivative.

However, even when immersion exposure is performed using the above-described techniques, it is further demanded to more reduce a development defect called BLOB defect or generation of scum, particle or bubble defect and improve the pattern profile.

SUMMARY OF INVENTION

An object of the present invention is to provide an actinic ray-sensitive or radiation-sensitive resin composition enabling formation of a pattern improved in the line edge roughness and scum generation and reduced in the development defect and ensuring little elution of an acid into the immersion liquid, good followability for the immersion liquid, and various good performances in terms of particle suppression, pattern profile and bubble defect prevention, and a pattern forming method using the same.

As a result of intensive studies to attain the above-described object, the present inventors have accomplished the present invention described below.

The present invention has the following constitutions.

(1) An actinic ray-sensitive or radiation-sensitive resin composition, comprising:

(A) a resin capable of increasing a solubility of the resin (A) in an alkali developer by an action of an acid; and (C) a resin having at least either a fluorine atom or a silicon atom and containing (c) a repeating unit having at least two or more polarity conversion groups represented by —COO— in the structure represented by formula (KA-1) or (KB-1):

wherein $Z_{ka}$ represents an alkyl group, a cycloalkyl group, an ether group, a hydroxyl group, an amide group, an aryl group, a lactone ring group or an electron-withdrawing group, and when a plurality of $Z_{ka}$'s are present, the plurality of $Z_{ka}$'s are the same or different;

each $Z_{ka}$ may combine with every other $Z_{ka}$ to form a ring;

nka represents an integer of 0 to 10;

each of $X_{kb1}$ and $X_{kb2}$ independently represents an electron-withdrawing group;

each of nkb and nkb' independently represents 0 or 1; and each of $R_{kb1}$ to $R_{kb4}$ independently represents a hydrogen atom, an alkyl group, a cycloalkyl group, an aryl group or an electron-withdrawing group, at least two members of $R_{kb1}$, $R_{kb2}$ and $X_{kb1}$ may combine with each other to form a ring, and at least two members of $R_{kb3}$, $R_{kb4}$ and $X_{kb2}$ may combine with each other to form a ring.

(2) The actinic ray-sensitive or radiation-sensitive resin composition as described in (1) above, wherein the repeating unit (c) is (c') a repeating unit having the at least two or more polarity conversion groups and at least either a fluorine atom or a silicon atom on one side chain.

(3) The actinic ray-sensitive or radiation-sensitive resin composition as described in (1) above,
wherein the repeating unit (c) is (c*) a repeating unit having the at least two or more polarity conversion groups and having neither a fluorine atom nor a silicon atom, and
the resin (C) further contains a repeating unit having at least either a fluorine atom or a silicon atom.

(4) The actinic ray-sensitive or radiation-sensitive resin composition as described in (1) above,
wherein the repeating unit (c) is (c″) a repeating unit having the at least two or more polarity conversion groups on one side chain and at the same time, having at least either a fluorine atom or a silicon atom on a side chain different from said side chain in the same repeating unit.

(5) The actinic ray-sensitive or radiation-sensitive resin composition as described in any one of (1) to (4) above,
wherein the repeating unit (c) has a structure represented by the following formula (KY-1):

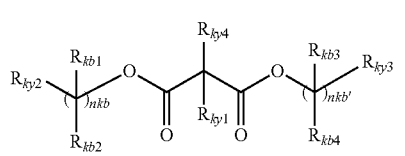

(KY-1)

wherein each of $R_{ky1}$ and $R_{ky4}$ independently represents a hydrogen atom, a halogen atom, an alkyl group, a cycloalkyl group, a carbonyl group, a carbonyloxy group, an oxycarbonyl group, an ether group, a hydroxyl group, a cyano group, an amide group or an aryl group, $R_{ky1}$ and $R_{ky4}$ may be bonded to the same atom to form a double bond;
each of $R_{ky2}$ and $R_{ky3}$ independently represents an electron-withdrawing group, or $R_{ky1}$ and $R_{ky2}$ are combined to form a lactone ring and at the same time, $R_{ky3}$ is an electron-withdrawing group;
at least two members of $R_{ky1}$, $R_{ky2}$ and $R_{ky4}$ may combine with each other to form a monocyclic or polycyclic structure; and
$R_{kb1}$ to $R_{kb4}$, nkb and nkb' have the same meanings as in formula (KB-1).

(6) The actinic ray-sensitive or radiation-sensitive resin composition as described in any one of (1) to (5) above,
wherein the repeating unit (c) has a structure represented by the following formula (KY-2):

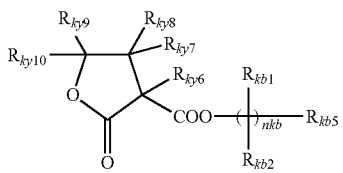

(KY-2)

wherein each of $R_{ky6}$ to $R_{ky10}$ independently represents a hydrogen atom, a halogen atom, an alkyl group, a cycloalkyl group, a carbonyl group, a carbonyloxy group, an oxycarbonyl group, an ether group, a hydroxyl group, a cyano group, an amide group or an aryl group;
two or more members of $R_{ky6}$ to $R_{ky10}$ may combine with each other to form a monocyclic or polycyclic structure;
$R_{ky5}$ represents an electron-withdrawing group; and
$R_{kb1}$, $R_{kb2}$ and nkb have the same meanings as in formula (KB-1).

(7) The actinic ray-sensitive or radiation-sensitive resin composition as described in any one of (1) to (6) above,
wherein the resin (C) has at least one group represented by any one of formulae (F2) to (F4) and formulae (CS-1) to (CS-3):

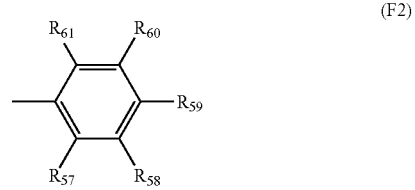

(F2)

(F3)

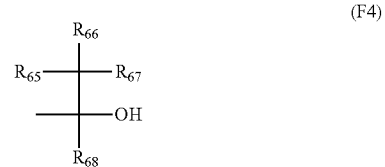

(F4)

wherein each of $R_{57}$ to $R_{68}$ independently represents a hydrogen atom, a fluorine atom, a linear or branched alkyl group or an aryl group, provided that at least one of $R_{57}$ to $R_{61}$, at least one of $R_{62}$ to $R_{64}$ and at least one of $R_{65}$ to $R_{68}$ each independently represent a fluorine atom or an alkyl group with at least one hydrogen atom being replaced by a fluorine atom, and $R_{62}$ and $R_{63}$ may combine with each other to form a ring:

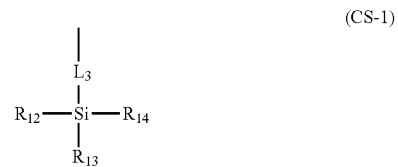

(CS-1)

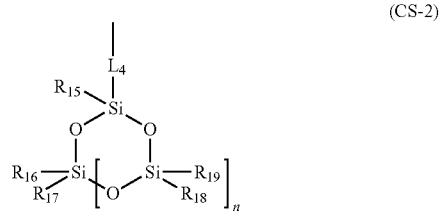

(CS-2)

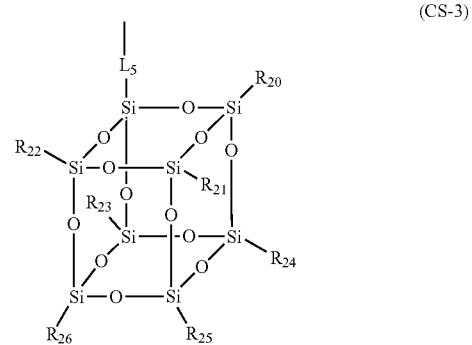

(CS-3)

wherein each of $R_{12}$ to $R_{26}$ independently represents a linear or branched alkyl group or a cycloalkyl group;

each of $L_3$ to $L_5$ represents a single bond or a divalent linking group; and n represents an integer of 1 to 5.

(8) The actinic ray-sensitive or radiation-sensitive resin composition as described in (7) above, wherein the resin (C) contains at least one acrylate or methacrylate repeating unit having the group represented by any one of formulae (F2) to (F4) and formulae (CS-1) to (CS-3).

(9) The actinic ray-sensitive or radiation-sensitive resin composition as described in any one of (1) to (8) above, wherein a content of the resin (C) is from 0.01 to 10 mass % based on the entire solid content in the actinic ray-sensitive or radiation-sensitive resin composition.

(10) The actinic ray-sensitive or radiation-sensitive resin composition as described in any one of (1) to (9) above, which further comprises:

(B) a compound capable of generating an acid upon irradiation with an actinic ray or radiation.

(11) The actinic ray-sensitive or radiation-sensitive resin composition as described in any one of (1) to (10) above, wherein the resin (A) contains a lactone structure-containing repeating unit.

(12) The actinic ray-sensitive or radiation-sensitive resin composition as described in any one of (1) to (11) above, wherein the resin (A) has a monocyclic or polycyclic acid-decomposable group.

(13) A resist film, which is formed from the actinic ray-sensitive or radiation-sensitive resin composition as described in any one of (1) to (12) above.

(14) A pattern forming method, comprising:

immersion-exposing and developing the resist film as described in (13) above.

DESCRIPTION OF EMBODIMENTS

The present invention is described in detail below.

Incidentally, in the present invention, when a group (atomic group) is denoted without specifying whether substituted or unsubstituted, the group includes both a group having no substituent and a group having a substituent. For example, "an alkyl group" includes not only an alkyl group having no substituent (unsubstituted alkyl group) but also an alkyl group having a substituent (substituted alkyl group).

In the present invention, the term "actinic ray" or "radiation" indicates, for example, a bright line spectrum of a mercury lamp, a far ultraviolet ray typified by an excimer laser, an extreme-ultraviolet ray, an X-ray or an electron beam. Also, in the present invention, the "light" means an actinic ray or radiation.

Furthermore, in the present invention, unless otherwise indicated, the "exposure" includes not only exposure with a mercury lamp, a far ultraviolet ray typified by an excimer laser, an X-ray, EUV light or the like but also lithography with a particle beam such as electron beam and ion beam.

The actinic ray-sensitive or radiation-sensitive resin composition of the present invention contains (A) a resin capable of increasing the solubility in an alkali developer by the action of an acid and (C) a resin having at least either a fluorine atom or a silicon atom and containing a repeating unit having at least two or more polarity conversion groups and preferably further contains (B) a compound capable of generating an acid upon irradiation with an actinic ray or radiation.

[1] Resin Capable of Increasing the Solubility in an Alkali Developer by the Action of an Acid (A)

The resin of the component (A) is a resin capable of increasing the solubility in an alkali developer by the action of an acid, and this is a resin having a group capable of decomposing by the action of an acid to produce an alkali-soluble group (hereinafter sometimes referred to as an "acid-decomposable group"), on either one or both of the main chain and the side chain of the resin.

Examples of the alkali-soluble group include a phenolic hydroxyl group, a carboxyl group, a fluorinated alcohol group, a sulfonic acid group, a sulfonamide group, a sulfonylimide group, an (alkylsulfonyl)(alkylcarbonyl)methylene group, an (alkylsulfonyl)(alkylcarbonyl)imide group, a bis(alkylcarbonyl)methylene group, a bis(alkylcarbonyl)imide group, a bis(alkylsulfonyl)methylene group, a bis(alkylsulfonyl)imide group, a tris(alkylcarbonyl)methylene group and a tris(alkylsulfonyl)methylene group.

Preferred examples of the alkali-soluble group include a carboxyl group, a fluorinated alcohol group (preferably hexafluoroisopropanol) and a sulfonic acid group.

The group preferred as the acid-decomposable group is a group where a hydrogen atom of the alkali-soluble group above is replaced by a group capable of leaving by the action of an acid.

Examples of the group capable of leaving by the action of an acid include —C($R_{36}$)($R_{37}$)($R_{38}$) and —C($R_{01}$)($R_{02}$)(O$R_{39}$).

In the formulae, each of $R_{36}$ to $R_{39}$ independently represents an alkyl group, a cycloalkyl group, an aryl group, an aralkyl group or an alkenyl group, and $R_{36}$ and $R_{37}$ may combine with each other to form a ring.

Each of $R_{01}$ and $R_{02}$ independently represents a hydrogen atom, an alkyl group, a cycloalkyl group, an aryl group, an aralkyl group or an alkenyl group.

The acid-decomposable group is preferably a cumyl ester group, an enol ester group, an acetal ester group, a tertiary alkyl ester group or the like, more preferably a tertiary alkyl ester group.

The resin of the component (A) preferably has a monocyclic or polycyclic acid-decomposable group. As for the monocyclic or polycyclic acid-decomposable group, a structure where any of $R_{36}$ to $R_{39}$ is a cycloalkyl group or $R_{36}$ and $R_{37}$ are combined to form a ring is preferred.

The resin of the component (A) preferably contains a repeating unit having an acid-decomposable group. The repeating unit having an acid-decomposable group is preferably a repeating unit represented by the following formula (AI):

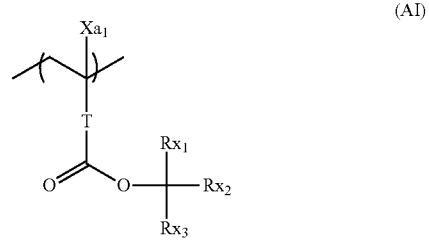

In formula (AI), $Xa_1$ represents a hydrogen atom, a methyl group which may have a substituent, or a group represented by $—CH_2—R_9$. $R_9$ represents a hydroxyl group or a monovalent organic group, and examples of the monovalent organic group include an alkyl group having a carbon number of 5 or less and an acyl group having a carbon number of 5 or less. The monovalent organic group is preferably an alkyl group having a carbon number of 3 or less, more preferably a methyl group. $Xa_1$ is preferably a hydrogen atom, a methyl group, a trifluoromethyl group or a hydroxymethyl group.

T represents a single bond or a divalent linking group.

Each of $Rx_1$ to $Rx_3$ independently represents an alkyl group (linear or branched) or a cycloalkyl group (monocyclic or polycyclic).

Two members out of $Rx_1$ to $Rx_3$ may combine to form a cycloalkyl group (monocyclic or polycyclic).

Examples of the divalent linking group of T include an alkylene group, a —COO-Rt-group and a —O-Rt- group, wherein Rt represents an alkylene group or a cycloalkylene group.

T is preferably a single bond or a —COO-Rt- group. Rt is preferably an alkylene group having a carbon number of 1 to 5, more preferably a $—CH_2—$ group or a $—(CH_2)_3—$ group.

The alkyl group of $Rx_1$ to $Rx_3$ is preferably an alkyl group having a carbon number of 1 to 4, such as methyl group, ethyl group, n-propyl group, isopropyl group, n-butyl group, isobutyl group and tert-butyl group.

The cycloalkyl group of $Rx_1$ to $Rx_3$ is preferably a monocyclic cycloalkyl group such as cyclopentyl group and cyclohexyl group, or a polycyclic cycloalkyl group such as norbornyl group, tetracyclodecanyl group, tetracyclododecanyl group and adamantyl group.

The cycloalkyl group formed by combining two members out of $Rx_1$ to $Rx_3$ is preferably a monocyclic cycloalkyl group such as cyclopentyl group and cyclohexyl group, or a polycyclic cycloalkyl group such as norbornyl group, tetracyclodecanyl group, tetracyclododecanyl group and adamantyl group. A monocyclic cycloalkyl group having a carbon number of 5 to 6 is more preferred.

An embodiment where $Rx_1$ is a methyl group or an ethyl group and $Rx_2$ and $Rx_3$ are combined to form the above-described cycloalkyl group is preferred.

Each of the groups above may have a substituent, and examples of the substituent include an alkyl group (having a carbon number of 1 to 4), a halogen atom, a hydroxyl group, an alkoxy group (having a carbon number of 1 to 4), a carboxyl group and an alkoxycarbonyl group (having a carbon number of 2 to 6). The carbon number is preferably 8 or less.

The content in total of the acid-decomposable group-containing repeating units is preferably from 20 to 70 mol %, more preferably from 30 to 50 mol %, based on all repeating units in the resin.

Specific preferred examples of the repeating unit having an acid-decomposable group are set forth below, but the present invention is not limited thereto.

In specific examples, each of Rx and $Xa_1$ represents a hydrogen atom, $CH_3$, $CF_3$ or $CH_2OH$, and each of Rxa and Rxb represents an alkyl group having a carbon number of 1 to 4. Z represents, when a plurality of Z's are present, each independently represents, a polar group or a polar group-containing substituent. Specifically, Z includes the same as those of $R_{10}$ of formula (2-1) described later. p represents 0 or a positive integer.

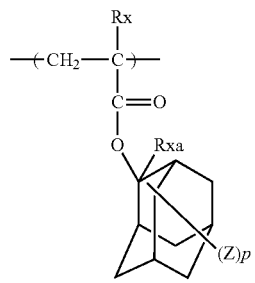

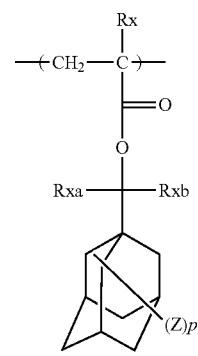

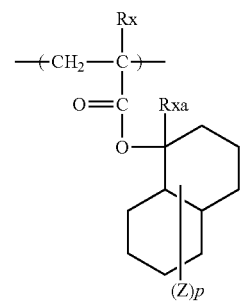

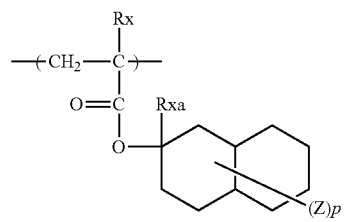

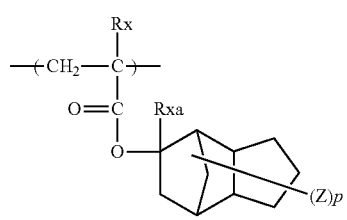

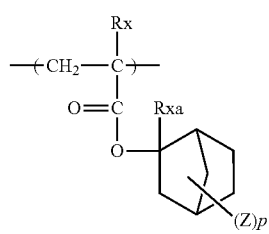

7
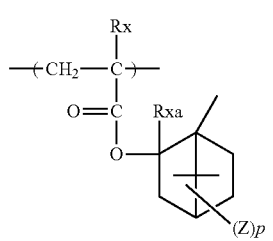
8
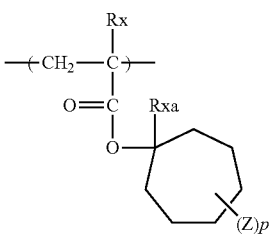
9
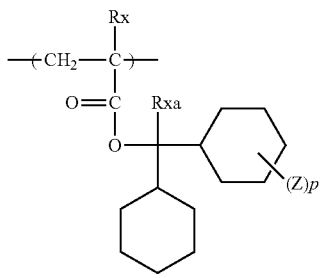
10
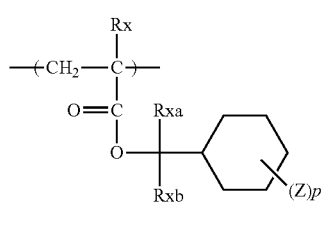
11
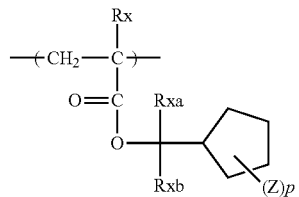
12
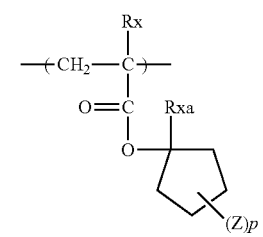
13
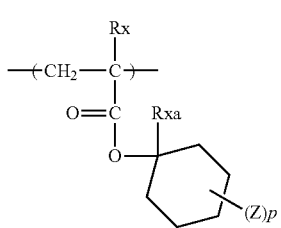
14
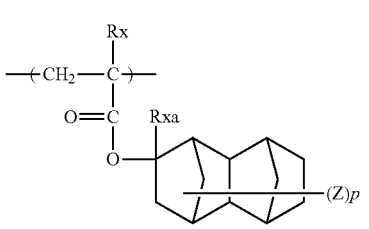
15
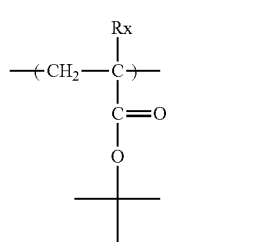
16
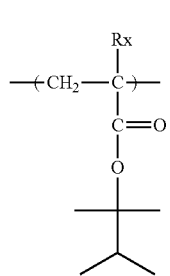
17
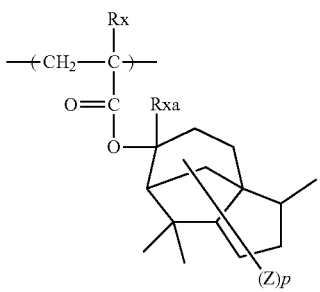
18
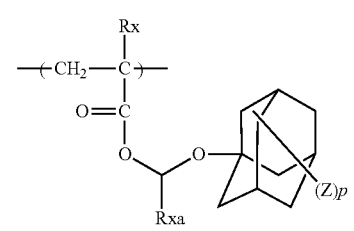
19
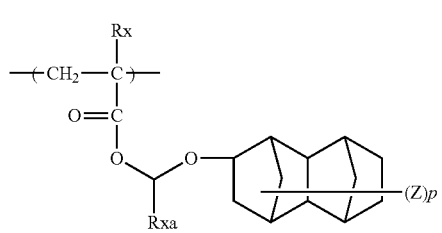

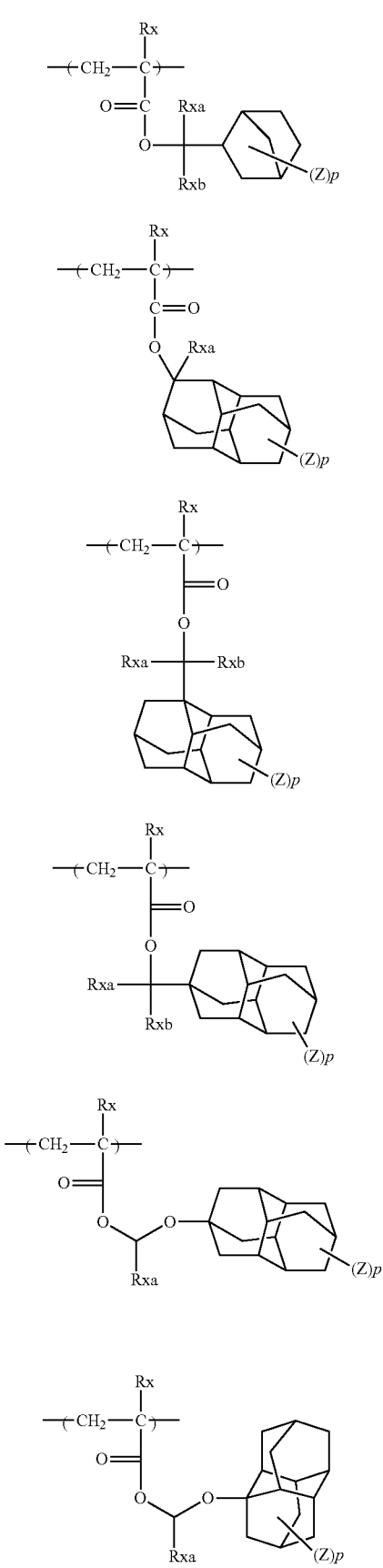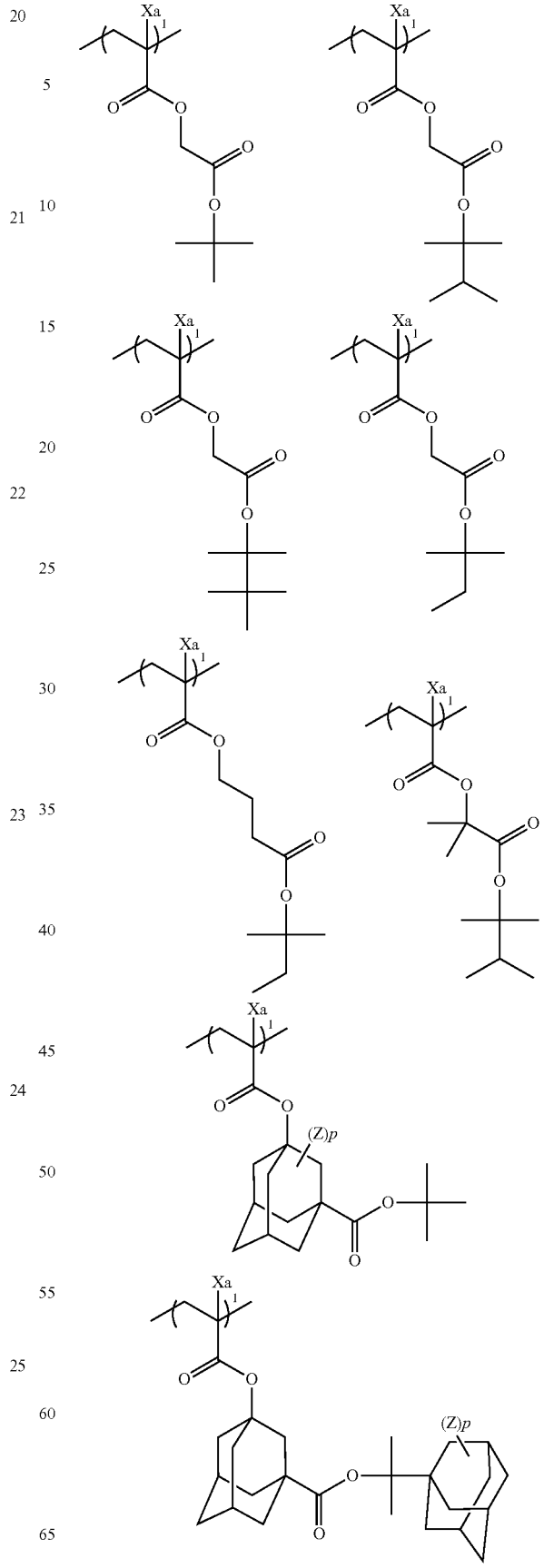

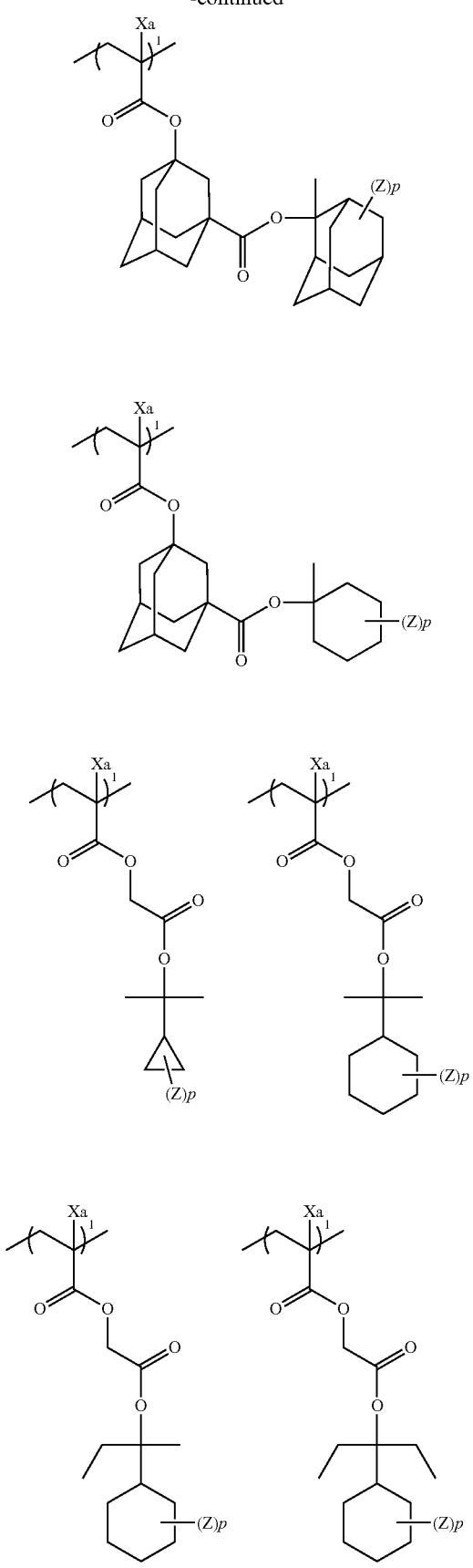

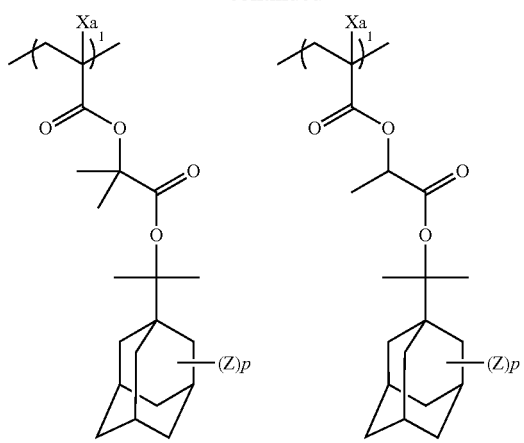
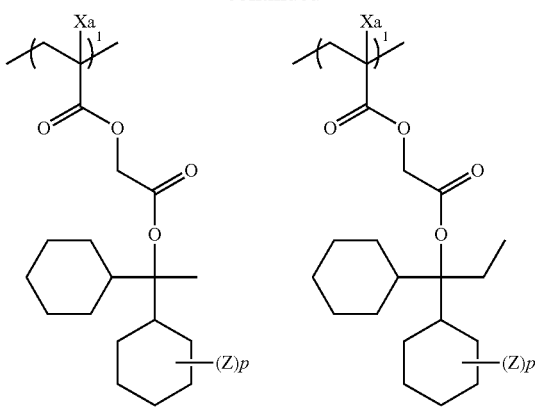
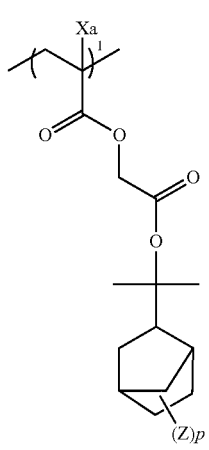
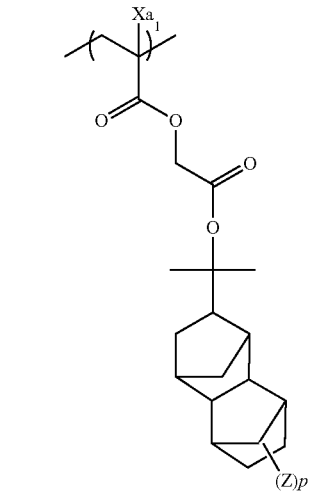
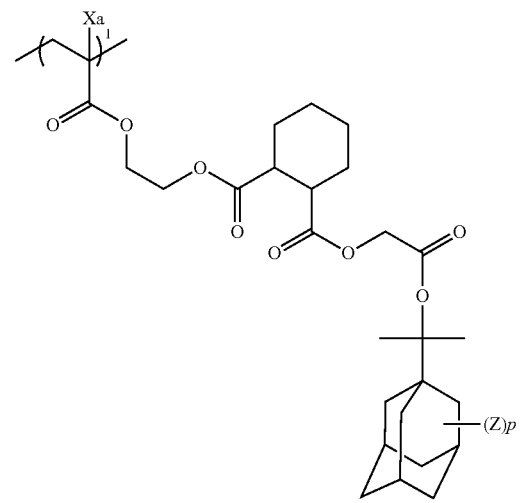
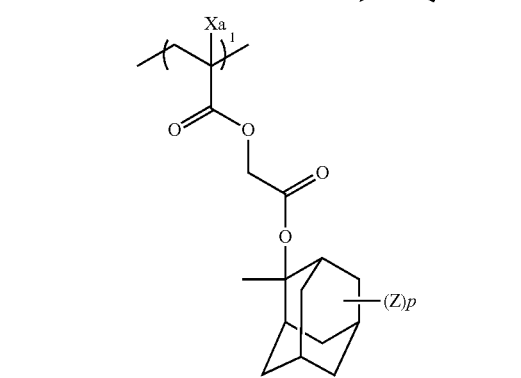
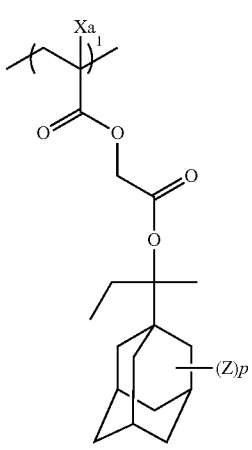
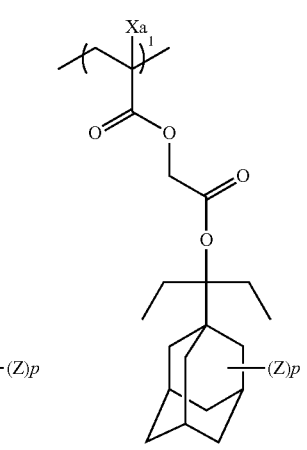
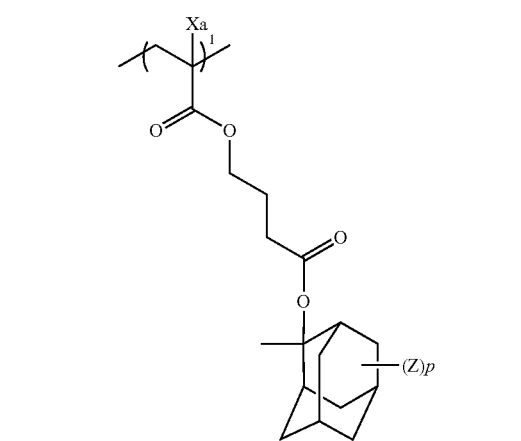

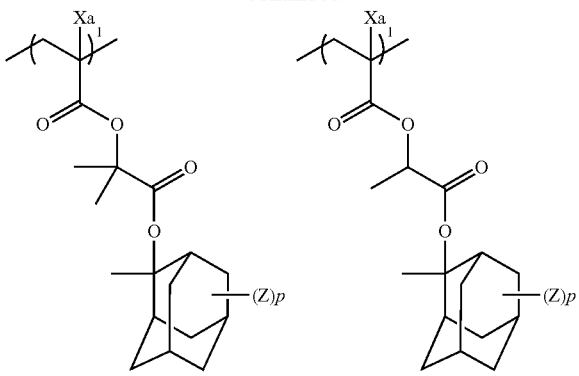
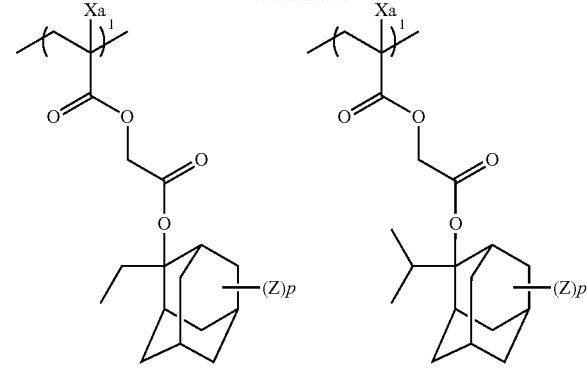
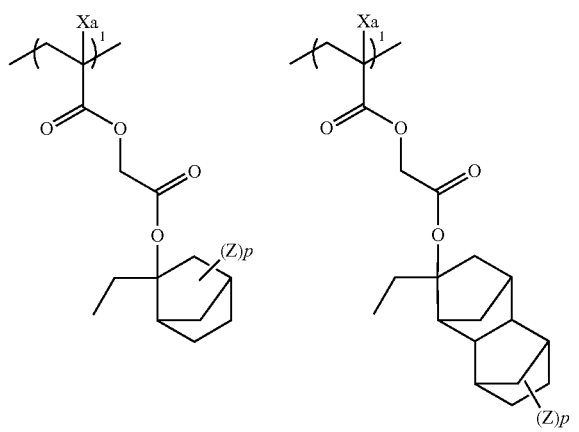
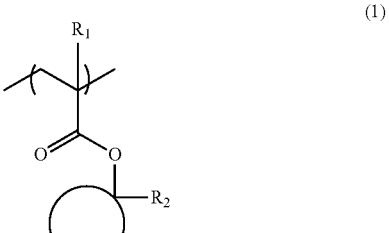

The resin (A) is more preferably a resin having, as the repeating unit represented by formula (AI), at least either one of a repeating unit represented by formula (1) and a repeating unit represented by formula (2).

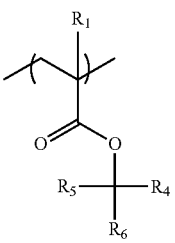

(1)

(2)

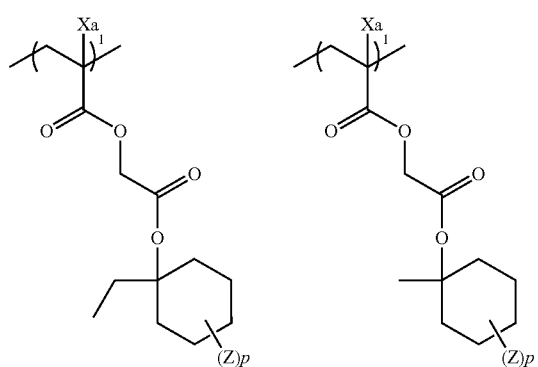

In formulae (1) and (2), each of $R_1$ and $R_3$ independently represents a hydrogen atom, a methyl group which may have a substituent, or a group represented by —$CH_2$—$R_9$. $R_9$ represents a hydroxyl group or a monovalent organic group.

Each of $R_2$, $R_4$, $R_5$ and $R_6$ independently represents an alkyl group or a cycloalkyl group.

R represents an atomic group necessary for forming an alicyclic structure together with the carbon atom.

$R_1$ is preferably a hydrogen atom, a methyl group, a trifluoromethyl group or a hydroxymethyl group.

The alkyl group in $R_2$ may be linear or branched and may have a substituent.

The cycloalkyl group in $R_2$ may be monocyclic or polycyclic and may have a substituent.

$R_2$ is preferably an alkyl group, more preferably an alkyl group having a carbon number of 1 to 10, still more preferably an alkyl group having a carbon number of 1 to 5, and examples thereof include a methyl group and an ethyl group.

R represents an atomic group necessary for forming an alicyclic structure together with the carbon atom.

The alicyclic structure formed by R is preferably a monocyclic alicyclic structure, and the carbon number thereof is preferably from 3 to 7, more preferably 5 or 6.

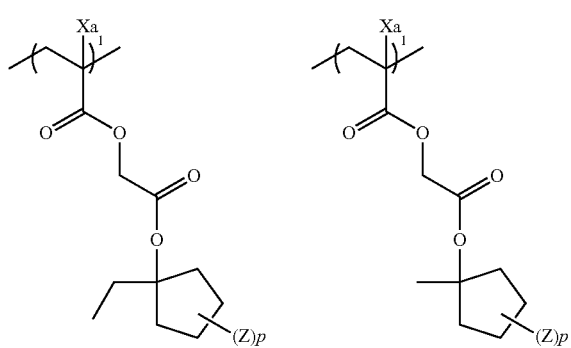

R$_3$ is preferably a hydrogen atom or a methyl group, more preferably a methyl group.

The alkyl group in R$_4$, R$_5$ and R$_6$ may be linear or branched and may have a substituent. The alkyl group is preferably an alkyl group having a carbon number of 1 to 4, such as methyl group, ethyl group, n-propyl group, isopropyl group, n-butyl group, isobutyl group and tert-butyl group.

The cycloalkyl group in R$_4$, R$_5$ and R$_6$ may be monocyclic or polycyclic and may have a substituent. The cycloalkyl group is preferably a monocyclic cycloalkyl group such as cyclopentyl group and cyclohexyl group, or a polycyclic cycloalkyl group such as norbornyl group, tetracyclodecanyl group, tetracyclododecanyl group and adamantyl group.

Specific examples and preferred examples of the organic group or R$_9$ are the same as those described for R$_9$ of formula (AI).

Examples of the repeating unit represented by formula (1) include a repeating unit represented by the following formula (I-1). In the formula, R$_1$ and R$_2$ have the same meanings as those in formula (1).

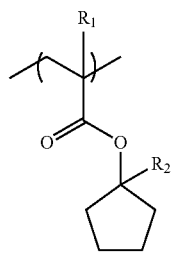

(1-1)

The repeating unit represented by formula (2) is preferably a repeating unit represented by the following formula (2-1):

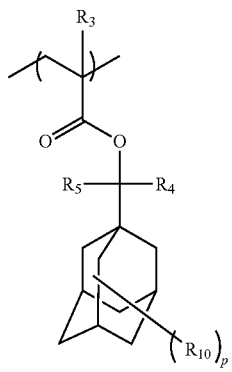

(2-1)

In formula (2-1), R$_3$ to R$_5$ have the same meanings as those in formula (2).

R$_{10}$ represents a polar group or a polar group-containing substituent. In the case where a plurality of R$_{10}$'s are present, each R$_{10}$ may be the same as or different from every other R$_{10}$. The polar group is, for example, a hydroxyl group, a cyano group, an amino group, an alkylamide group or a sulfonamide group. The polar group-containing substituent is preferably a linear or branched alkyl group or cycloalkyl group having such a polar group, more preferably an alkyl group having a hydroxyl group, still more preferably a branched alkyl group having a hydroxyl group, and the branched alkyl group is preferably an isopropyl group.

p represents an integer of 0 to 15. p is preferably an integer of 0 to 2, more preferably 0 or 1.

The resin (A) may contain a plurality of acid-decomposable group-containing repeating units.

As described above, the resin (A) is preferably a resin containing, as the repeating unit represented by formula (AI), at least either one of a repeating unit represented by formula (1) and a repeating unit represented by formula (2). In another embodiment, the resin (A) is preferably a resin containing, as the repeating unit represented by formula (AI), at least two kinds of repeating units represented by formula (1) or both a repeating unit represented by formula (1) and a repeating unit represented by formula (2).

Also, the resist composition of the present invention may contain a plurality of kinds of resins (A), and the acid-decomposable group-containing repeating units contained in the plurality of resins (A) may be different from each other. For example, a resin (A) containing a repeating unit represented by formula (1) and a resin (A) containing a repeating unit represented by formula (2) may be used in combination.

Preferred examples of the combination when the resin (A) contains a plurality of acid-decomposable group-containing repeating units and when a plurality of resins (A) contain different acid-decomposable group-containing repeating units, are set forth below. In the formulae below, each R independently represents a hydrogen atom or a methyl group.

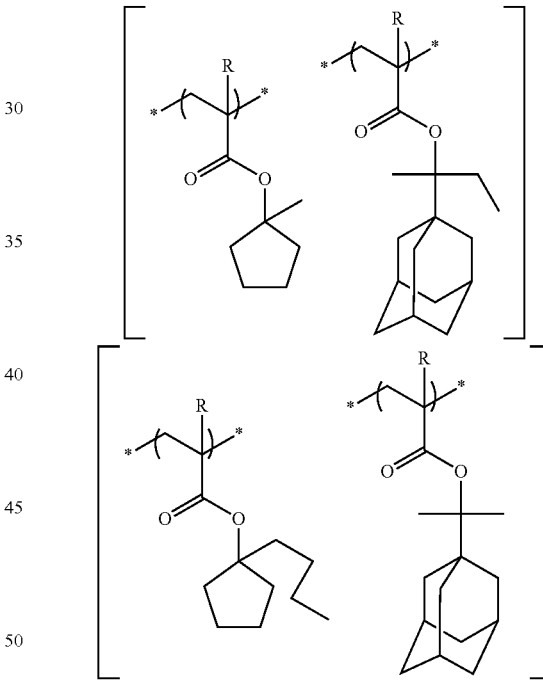

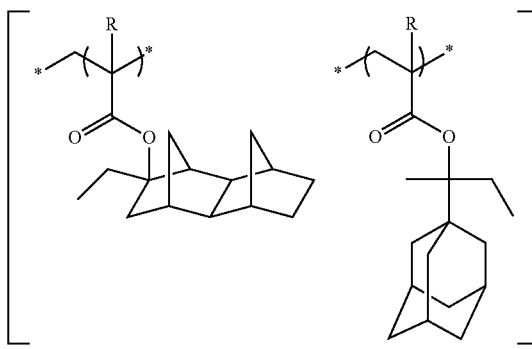

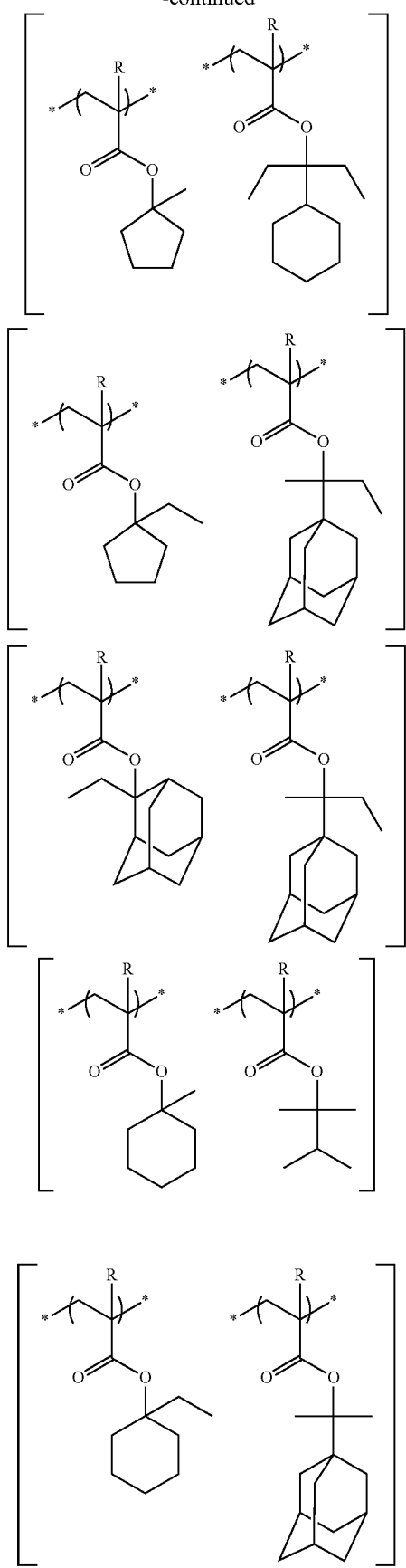
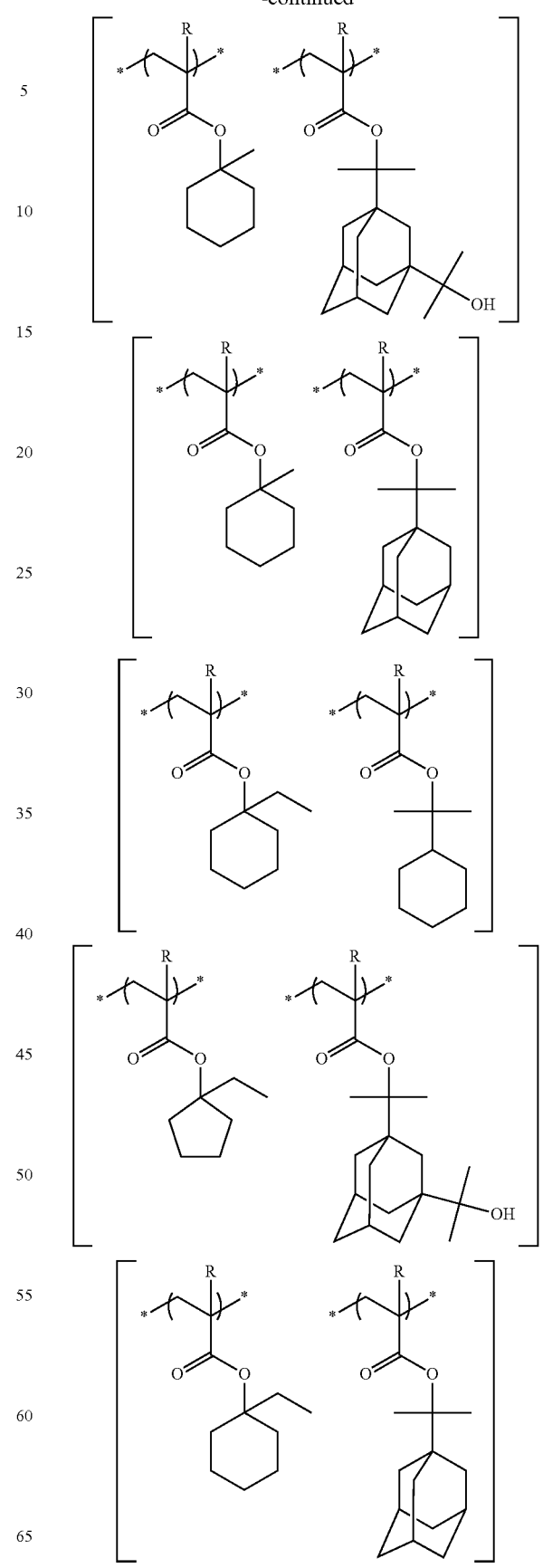

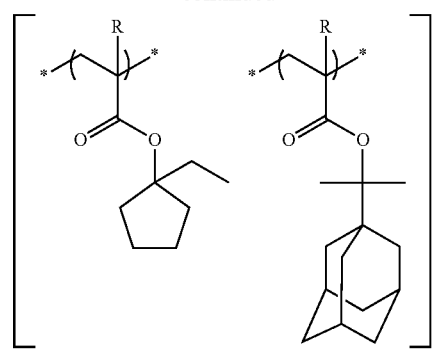
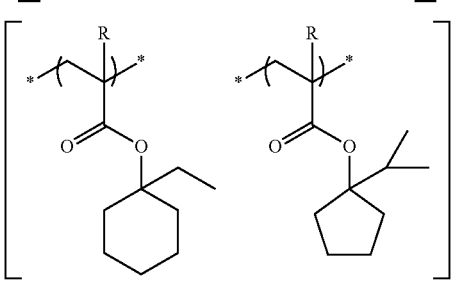
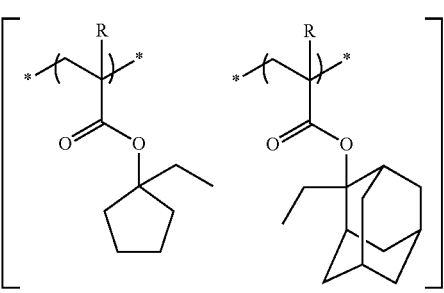
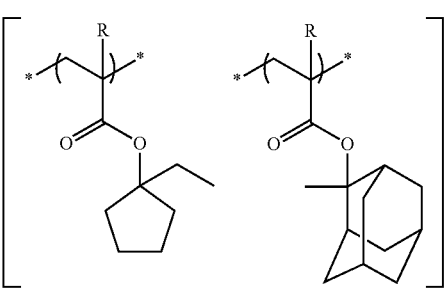
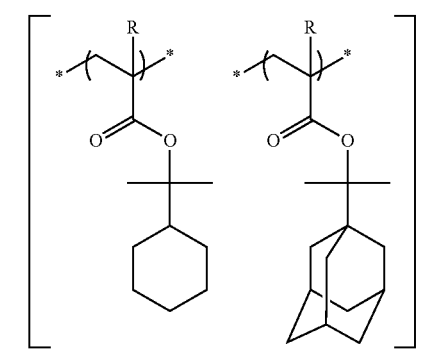
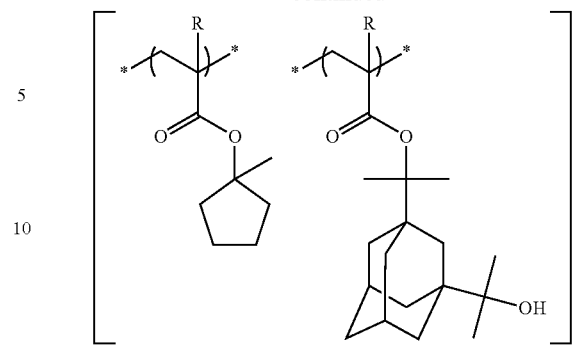
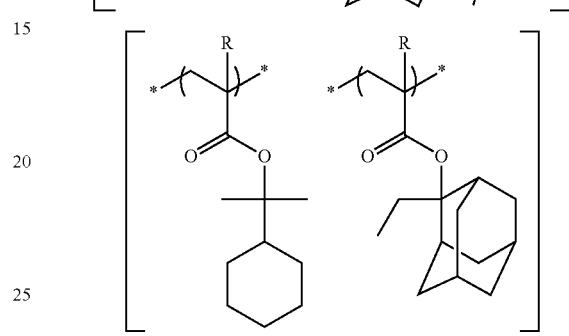
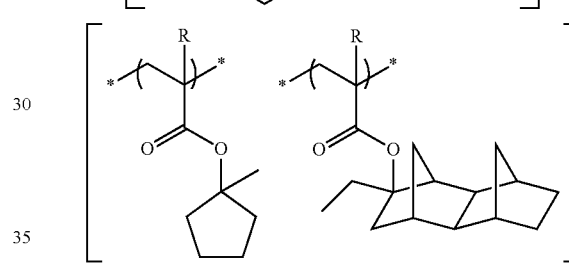
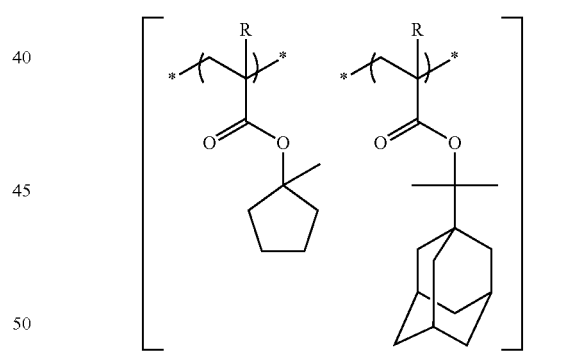
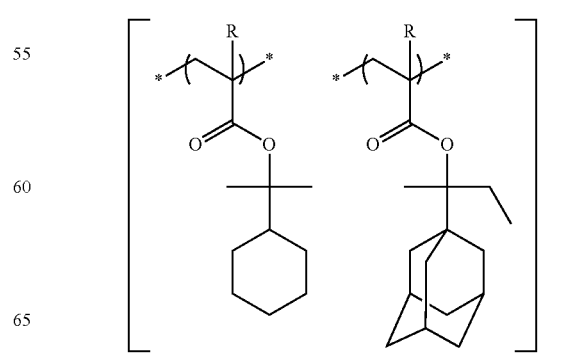

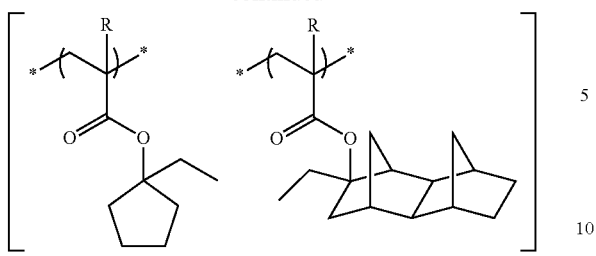

The resin of the component (A) preferably further contains a repeating unit having at least one kind of a group selected from a lactone group, a hydroxyl group, a cyano group and an alkali-soluble group.

The lactone group-containing repeating unit that can be contained in the resin of the component (A) is described below.

As for the lactone group, any group may be used as long as it has a lactone structure, but the lactone structure is preferably a 5- to 7-membered ring lactone structure, and a structure where another ring structure is condensed to a 5- to 7-membered ring lactone structure in the form of forming a bicyclo or Spiro structure is preferred. The resin more preferably contains a repeating unit having a lactone structure represented by any one of the following formulae (LC1-1) to (LC1-17). The lactone structure may be bonded directly to the main chain. Among these lactone structures, preferred are (LC1-1), (LC1-4), (LC1-5), (LC1-6), (LC1-13), (LC1-14) and (LC1-17). By selecting an optimal lactone group, the pattern profile, iso/dense bias, line edge roughness and development defect are improved.

LC1-1

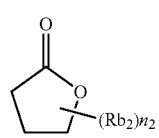

LC1-2

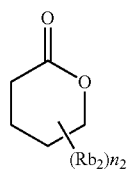

LC1-3

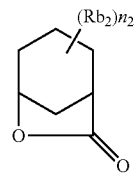

LC1-4

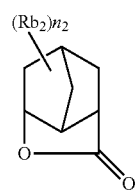

LC1-5

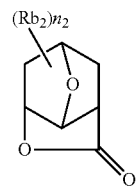

LC1-6

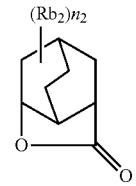

LC1-7

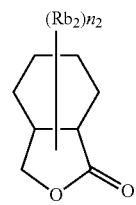

LC1-8

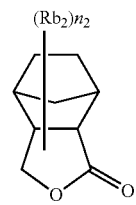

LC1-9

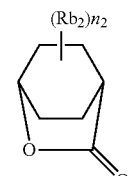

LC1-10

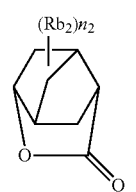

LC1-11

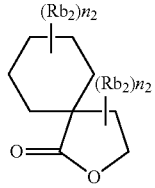

LC1-12

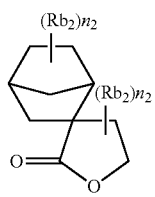

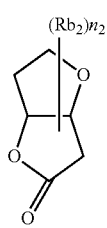

LC1-13

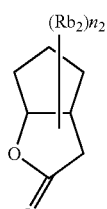

LC1-14

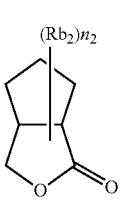

LC1-15

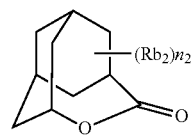

LC1-16

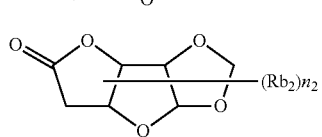

LC1-17

The lactone structure moiety may or may not have a substituent ($Rb_2$). Preferred examples of the substituent ($Rb_2$) include an alkyl group having a carbon number of 1 to 8, a cycloalkyl group having a carbon number of 4 to 7, an alkoxy group having a carbon number of 1 to 8, an alkoxycarbonyl group having a carbon number of 2 to 8, a carboxyl group, a halogen atom, a hydroxyl group, a cyano group and an acid-decomposable group. Among these, an alkyl group having a carbon number of 1 to 4, a cyano group and an acid-decomposable group are more preferred. $n_2$ represents an integer of 0 to 4. When $n_2$ is an integer of 2 or more, each substituent ($Rb_2$) may be the same as or different from every other substituents ($Rb_2$) and also, each substituent ($Rb_2$) may combine with every other substituents ($Rb_2$) to form a ring.

The repeating unit having a lactone structure represented by any one of formulae (LC1-1) to (LC1-17) includes a repeating unit represented by the following formula (AII):

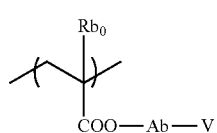

(AII)

In formula (AII), $Rb_0$ represents a hydrogen atom, a halogen atom or an alkyl group having a carbon number of 1 to 4 which may have a substituent. Preferred examples of the substituent which the alkyl group of $Rb_0$ may have include a hydroxyl group and a halogen atom. The halogen atom of $Rb_0$ includes a fluorine atom, a chlorine atom, a bromine atom and an iodine atom. As $Rb_0$, a hydrogen atom, a methyl group, a hydroxymethyl group or a trifluoromethyl group is preferred, a hydrogen atom or a methyl group is more preferred.

Ab represents a single bond, an alkylene group, a divalent linking group having a monocyclic or polycyclic alicyclic hydrocarbon structure, an ether group, an ester group, a carbonyl group, or a divalent linking group comprising a combination thereof, and is preferably a single bond or a divalent linking group represented by -$Ab_1$-$CO_2$—.

$Ab_1$ represents a linear or branched alkylene group or a monocyclic or polycyclic cycloalkylene group and is preferably a methylene group, an ethylene group, a cyclohexylene group, an adamantylene group or a norbornylene group.

V represents a group having a structure represented by any one of formulae (LC1-1) to (LC1-17).

The repeating unit having a lactone group usually has an optical isomer, but any optical isomer may be used. One optical isomer may be used alone or a mixture of a plurality of optical isomers may be used. In the case of mainly using one optical isomer, the optical purity (ee) thereof is preferably 90% or more, more preferably 95% or more.

The repeating unit having a lactone group is preferably a lactone structure-containing repeating unit represented by the following formula (3):

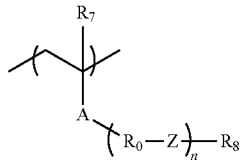

(3)

In formula (3), A represents an ester bond (—COO—) or an amide bond (—CONH—).

$R_0$ represents, when a plurality of $R_0$'s are present, each independently represents, an alkylene group, a cycloalkylene group or a combination thereof.

Z represents, when a plurality of Z's are present, each independently represents, an ether bond, an ester bond, an amide bond, a urethane bond or a urea bond.

$R_8$ represents a monovalent organic group having a lactone structure.

n is a repetition number of the structure represented by —$R_0$—Z— in the repeating unit of formula (3) and represents an integer of 1 to 5.

$R_7$ represents a hydrogen atom, a halogen atom or an alkyl group which may have a substituent.

Each of the alkylene group and cycloalkylene group of $R_0$ may have a substituent.

Z is preferably an ether bond or an ester bond, more preferably an ester bond.

The alkyl group of $R_7$ is preferably an alkyl group having a carbon number of 1 to 4, more preferably a methyl group or an ethyl group, still more preferably a methyl group. The alkyl group in $R_7$ may be substituted, and examples of the substituent include a halogen atom such as fluorine atom, chlorine atom and bromine atom, a mercapto group, a hydroxy group, an alkoxy group such as methoxy group, ethoxy group, isopropoxy group, tert-butoxy group and benzyloxy group, and an acyloxy group such as acetyloxy group and propionyloxy group. $R_7$ is preferably a hydrogen atom, a methyl group, a trifluoromethyl group or a hydroxymethyl group.

The chain alkylene group in $R_o$ is preferably a chain alkylene group having a carbon number of 1 to 10, more preferably a chain alkylene group having a carbon number of 1 to 5, and examples thereof include a methylene group, an ethylene group and a propylene group. The cycloalkylene is preferably a cycloalkylene having a carbon number of 4 to 20, and examples thereof include cyclohexylene, cyclopentylene, norbornylene and adamantylene. For bringing out the effects of the present invention, a chain alkylene group is more preferred, and a methylene group is still more preferred.

The lactone structure-containing substituent represented by $R_8$ is not limited as long as it has a lactone structure. Specific examples thereof include lactone structures represented by formulae (LC1-1) to (LC1-17) and of these, a structure represented by (LC1-4) is preferred. Structures where $n_2$ in (LC1-1) to (LC1-17) is an integer of 2 or less are more preferred.

$R_8$ is preferably a monovalent organic group having an unsubstituted lactone structure or a monovalent organic group containing a lactone structure having a methyl group, a cyano group or an alkoxy carbonyl group as the substituent, more preferably a monovalent organic group containing a lactone structure having a cyano group as the substituent (cyanolactone).

The lactone structure-containing repeating unit is preferably a repeating unit represented by the following formula (3-1):

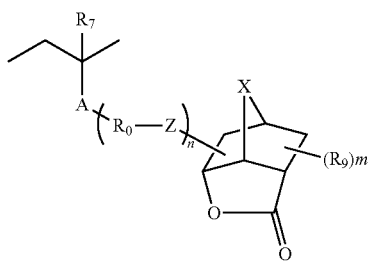

(3-1)

In formula (3-1), $R_7$, A, $R_0$, Z and n have the same meanings as in formula (3).

$R_9$ represents, when a plurality of $R_9$'s are present, each independently represents, an alkyl group, a cycloalkyl group, an alkoxycarbonyl group, a cyano group, a hydroxyl group or an alkoxy group, and when a plurality of $R_9$'s are present, two members thereof may combine to form a ring.

X represents an alkylene group, an oxygen atom or a sulfur atom.

m is the number of substituents and represents an integer of 0 to 5. m is preferably 0 or 1.

The alkyl group of $R_9$ is preferably an alkyl group having a carbon number of 1 to 4, more preferably a methyl group or an ethyl group, and most preferably a methyl group. The cycloalkyl group includes a cyclopropyl group, a cyclobutyl group, a cyclopentyl group and a cyclohexyl group. Examples of the alkoxycarbonyl group include a methoxycarbonyl group, an ethoxycarbonyl group, an n-butoxycarbonyl group and a tert-butoxycarbonyl group. Examples of the alkoxy group include a methoxy group, an ethoxy group, a propoxy group and a butoxy group. These groups may have a substituent, and the substituent includes a hydroxy group, an alkoxy group such as methoxy group and ethoxy group, a cyano group, and a halogen atom such as fluorine atom. $R_9$ is preferably a methyl group, an alkoxycarbonyl group or a cyano group, more preferably a cyano group.

Examples of the alkylene group of X include a methylene group and an ethylene group. X is preferably an oxygen atom or a methylene group, more preferably a methylene group.

When m is an integer of 1 or more, at least one $R_9$ is preferably substituted at the α-position or β-position, more preferably at the α-position, of the carbonyl group of lactone.

Particularly preferred examples of the repeating unit having a lactone group are set forth below.

In these specific examples, Rx represents H, $CH_3$, $CH_2OH$ or $CF_3$.

R represents a hydrogen atom, an alkyl group which may have a substituent, or a halogen atom and is preferably a hydrogen atom, a methyl group or an alkyl group having a substituent, that is, a trifluoromethyl group, a hydroxymethyl group or an acetyloxymethyl group.

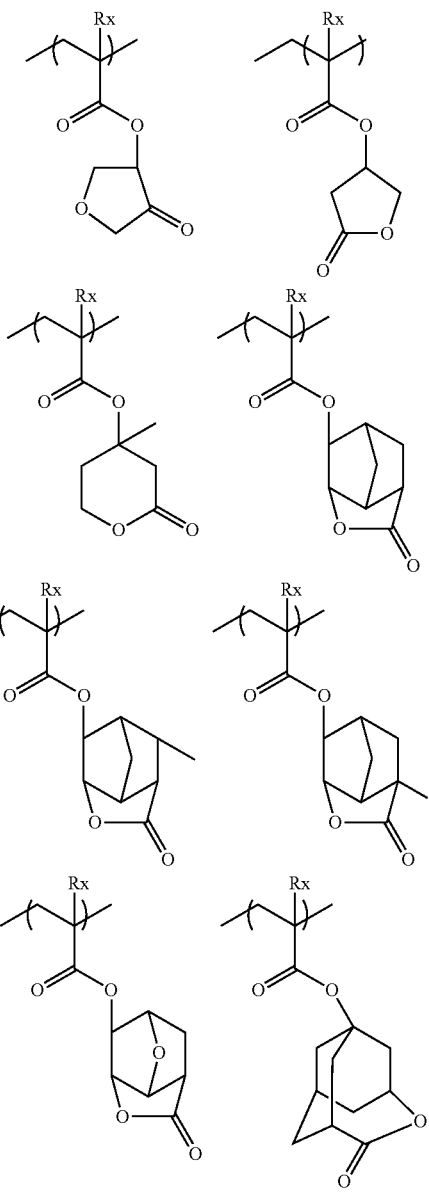

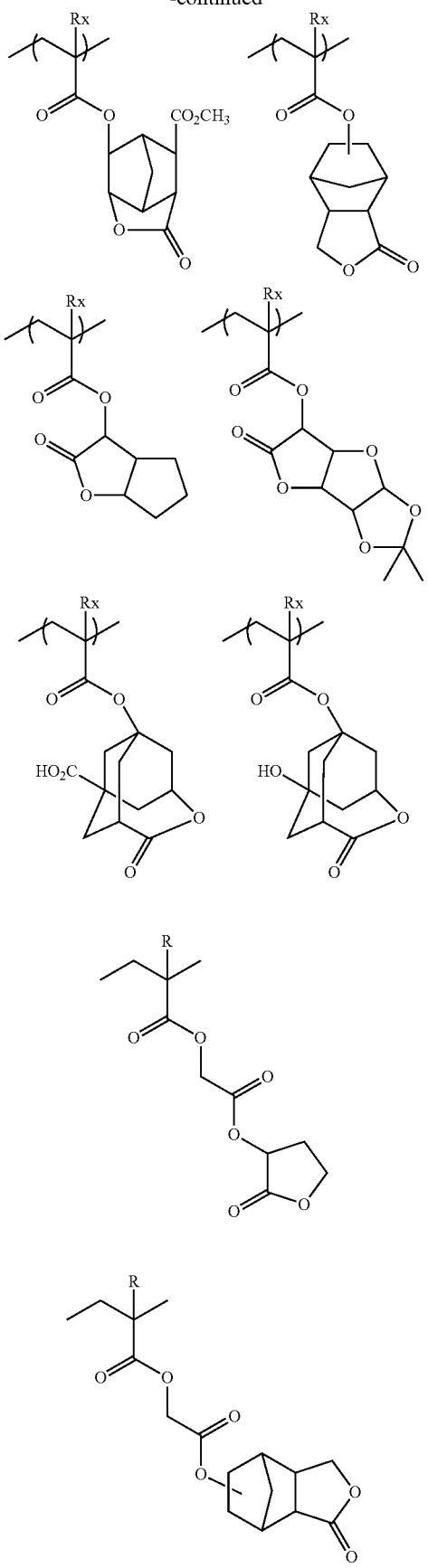
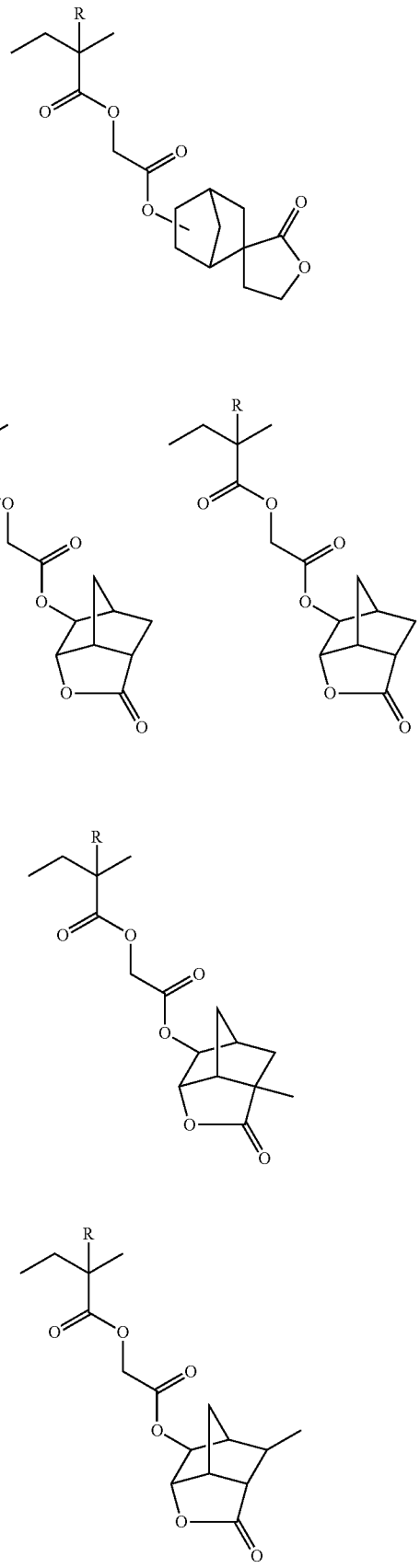

33
-continued
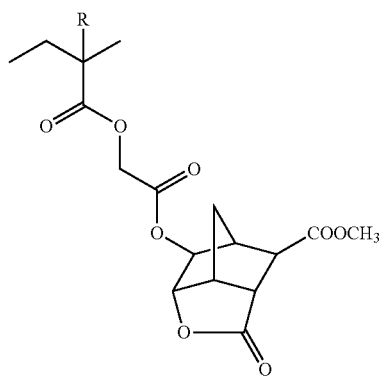
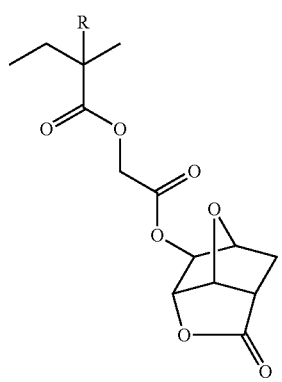
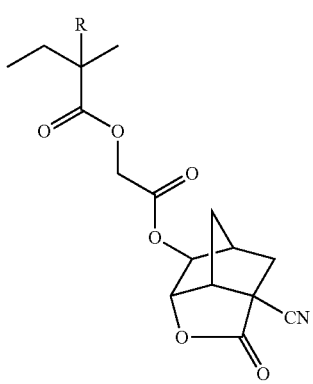
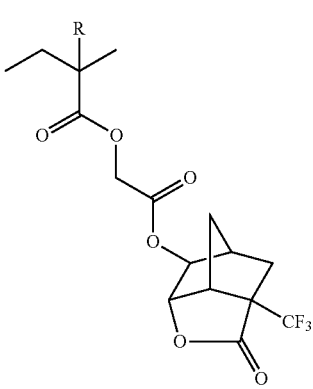
34
-continued
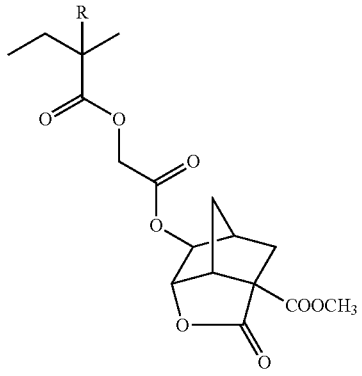
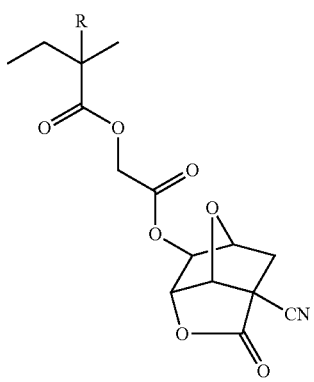
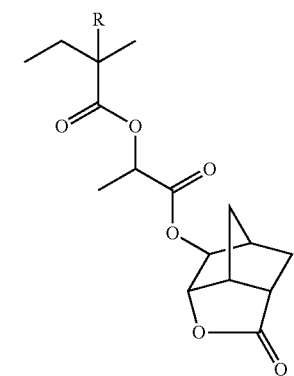
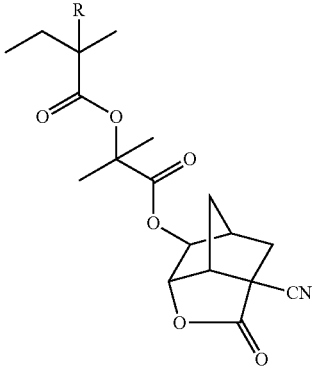

-continued

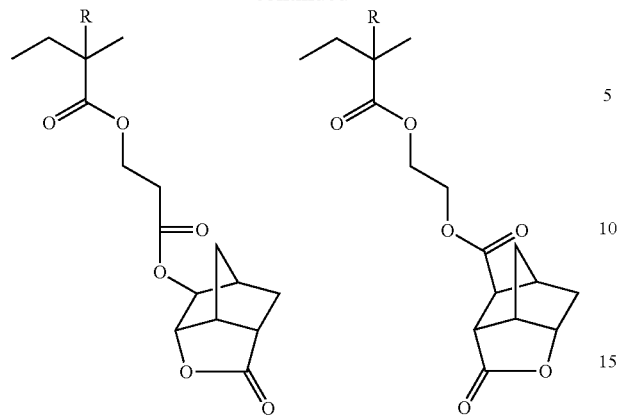
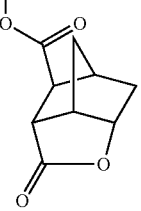
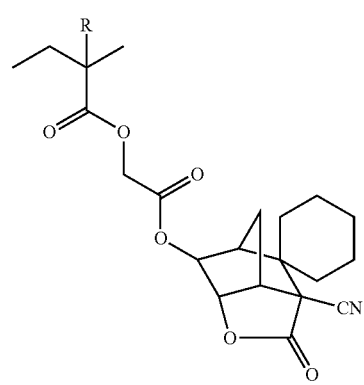
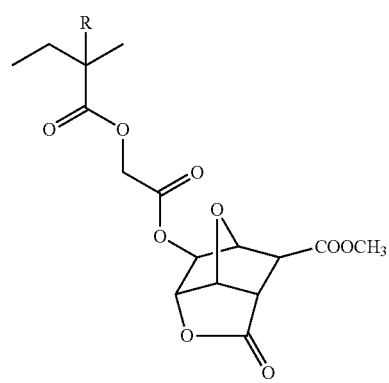
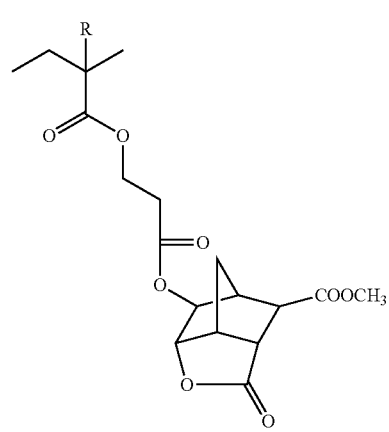

-continued

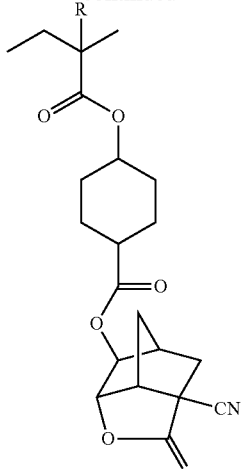
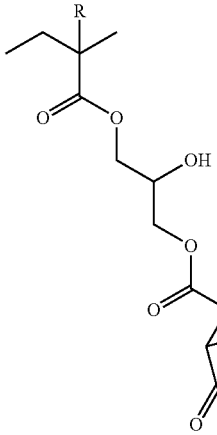
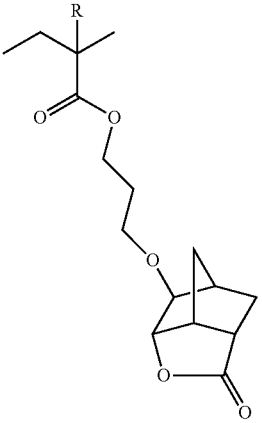
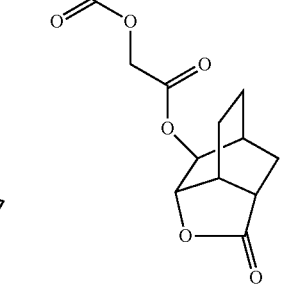

The content of the repeating unit having a lactone group is preferably from 15 to 60 mol %, more preferably from 20 to 50 mol %, still more preferably from 30 to 50 mol %, based on all repeating units in the resin.

The resin (A) may contain one kind of a lactone group-containing repeating unit or a plurality of kinds of lactone group-containing repeating units.

Two or more kinds of lactone repeating units selected from formula (3) may also be used in combination for raising the effects of the present invention. When used in combination, two or more kinds of repeating units selected from lactone repeating units where n is 1 out of formula (3) are preferably used in combination. It is also preferred that a lactone repeating unit where Ab in formula (AII) is a single bond and a lactone repeating unit where n is 1 out of formula (3) are used in combination.

The resin of the component (A) preferably contains a repeating unit having a hydroxyl group or a cyano group, separately from a repeating unit represented by formula (AI) and a lactone group-containing repeating unit (when these repeating units contain a hydroxyl group or a cyano group). Thanks to this repeating unit, the adherence to substrate and the affinity for developer are enhanced. The repeating unit having a hydroxyl group or a cyano group is preferably a repeating unit having an alicyclic hydrocarbon structure substituted by a hydroxyl group or a cyano group and preferably contains no acid-decomposable group. The alicyclic hydrocarbon structure in the alicyclic hydrocarbon structure substituted by a hydroxyl group or a cyano group is preferably an adamantyl group, a diamantyl group or a norbornane group. Preferred examples of the alicyclic hydrocarbon structure substituted by a hydroxyl group or a cyano group include a monohydroxyadamantyl group, a dihydroxyadamantyl group, a monohydroxydiamantyl group, a dihydroxydiamantyl group and a cyano group-substituted norbornyl group.

The alicyclic hydrocarbon structure substituted by a hydroxyl group or a cyano group is preferably a partial structure represented by the following formulae (VIIa) to (VIId):

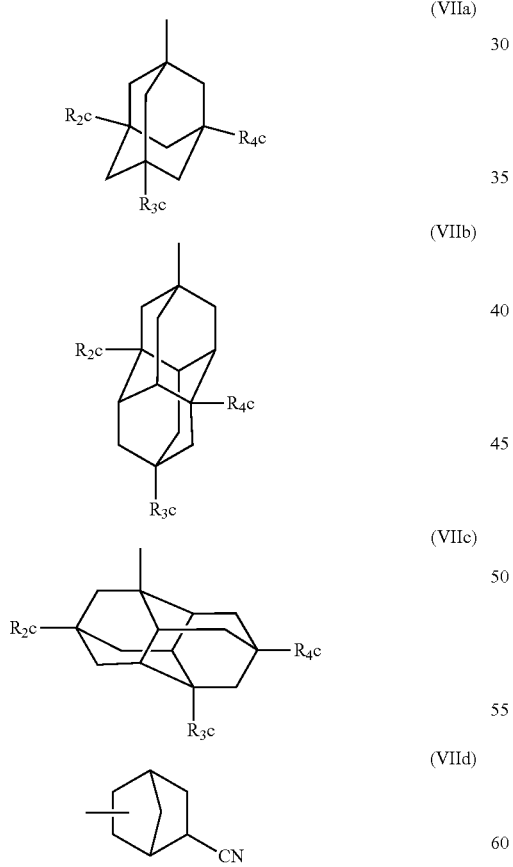

In formulae (VIIa) to (VIII), each of $R_2c$ to $R_4c$ independently represents a hydrogen atom, a hydroxyl group or a cyano group, provided that at least one of $R_2c$ to $R_4c$ represents a hydroxyl group or a cyano group. A structure where one or two members out of $R_2c$ to $R_4c$ are a hydroxyl group with the remaining being a hydrogen atom is preferred. In formula (VIIa), it is more preferred that two members out of $R_2c$ to $R_4c$ are a hydroxyl group and the remaining is a hydrogen atom.

The repeating unit having a partial structure represented by formulae (VIIa) to (VIId) includes repeating units represented by the following formulae (AIIa) to (AIId):

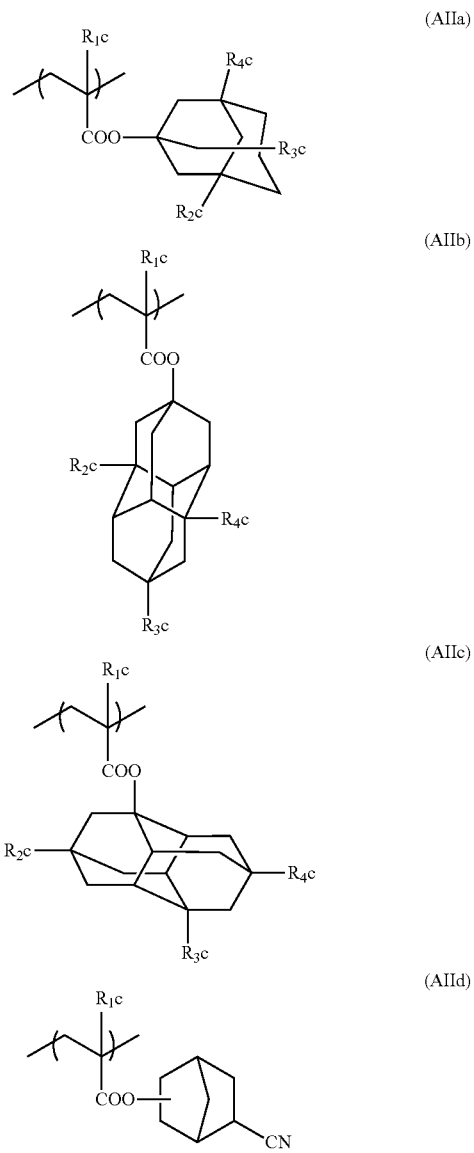

In formulae (AIIa) to (AIId), $R_1c$ represents a hydrogen atom, a methyl group, a trifluoromethyl group or a hydroxymethyl group.

$R_2c$ to $R_4c$ have the same meanings as $R_2c$ to $R_4c$ in formulae (VIIa) to (VIIc).

The content of the repeating unit having a hydroxyl group or a cyano group is preferably from 5 to 40 mol %, more preferably from 5 to 30 mol %, still more preferably from 10 to 25 mol %, based on all repeating units in the resin (A).

Specific examples of the repeating unit having a hydroxyl group or a cyano group are set forth below, but the present invention is not limited thereto.

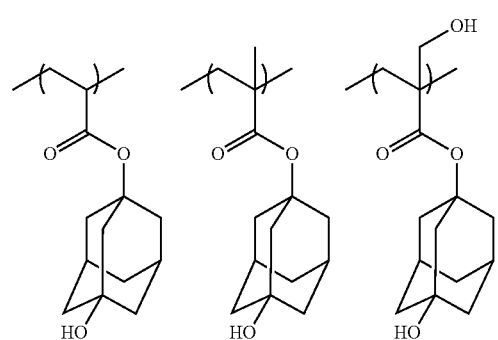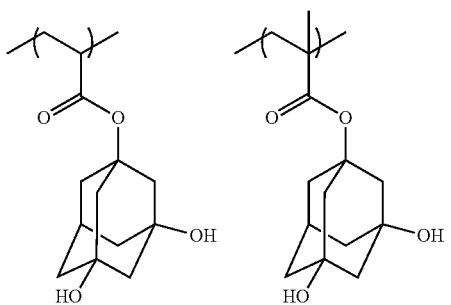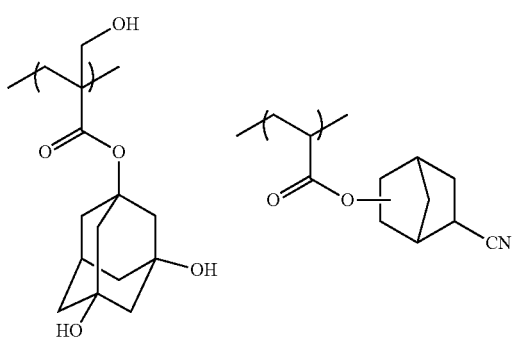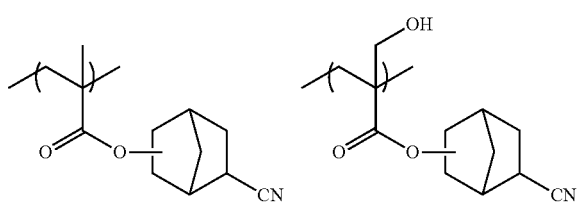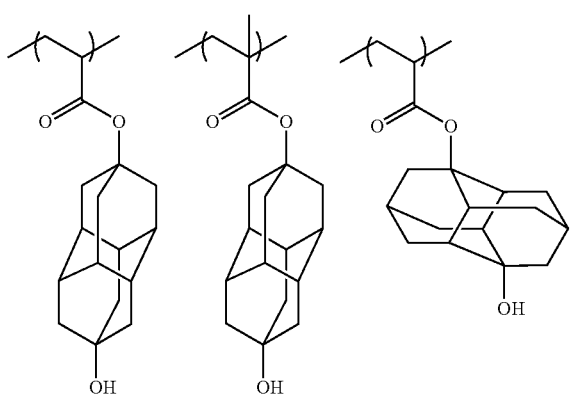

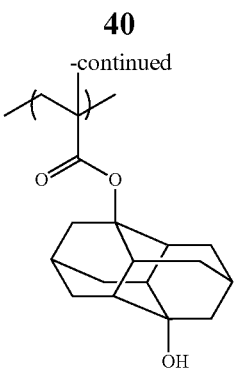

The resin of the component (A) preferably contains a repeating unit having an alkali-soluble group. The alkali-soluble group includes a carboxyl group, a sulfonamide group, a sulfonylimide group, a bisulfonylimide group, and an aliphatic alcohol with the α-position being substituted by an electron-withdrawing group, such as hexafluoroisopropanol group. It is more preferred to contain a repeating unit having a carboxyl group. By virtue of containing the repeating unit having an alkali-soluble group, the resolution increases in the usage of forming contact holes. As for the repeating unit having an alkali-soluble group, all of a repeating unit where an alkali-soluble group is directly bonded to the resin main chain, such as repeating unit by an acrylic acid or a methacrylic acid, a repeating unit where an alkali-soluble group is bonded to the resin main chain through a linking group, and a repeating unit where an alkali-soluble group is introduced into the polymer chain terminal by using an alkali-soluble group-containing polymerization initiator or chain transfer agent at the polymerization, are preferred. The linking group may have a monocyclic or polycyclic cyclohydrocarbon structure. In particular, a repeating unit by an acrylic acid or a methacrylic acid is preferred.

The content of the repeating unit having an alkali-soluble group is preferably from 0 to 20 mol %, more preferably from 3 to 15 mol %, still more preferably from 5 to 10 mol %, based on all repeating units in the resin (A).

Specific examples of the repeating unit having an alkali-soluble group are set forth below, but the present invention is not limited thereto. Rx represents a hydrogen atom, $CH_3$, $CF_3$ or $CH_2OH$.

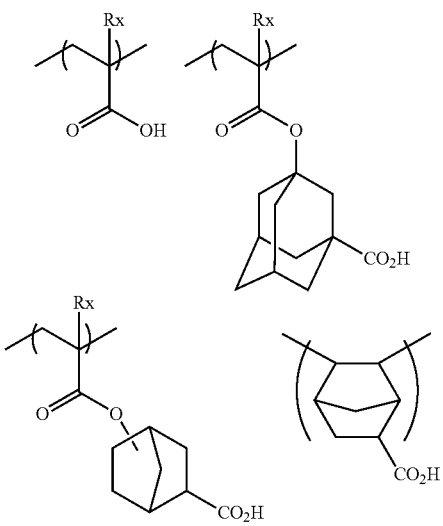

-continued

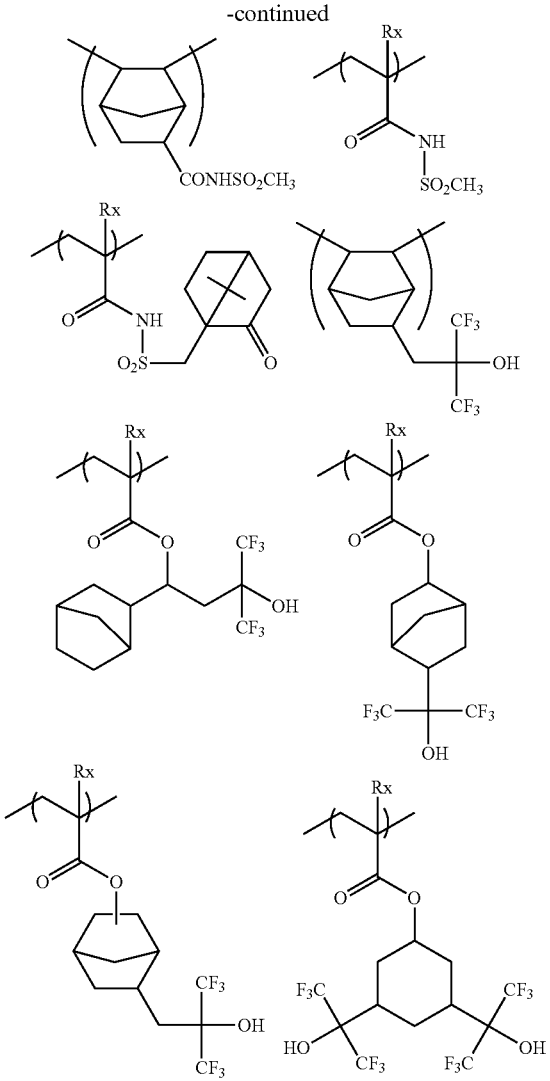

The repeating unit having at least one kind of a group selected from a lactone group, a hydroxyl group, a cyano group and an alkali-soluble group is preferably a repeating unit having at least two members selected from a lactone group, a hydroxyl group, a cyano group and an alkali-soluble group, more preferably a repeating unit having a cyano group and a lactone group. In particular, a repeating unit having a structure where a cyano group is substituted on the lactone structure of (LC1-4) is preferred.

The resin of the component (A) preferably further contains a repeating unit represented by formula (I) having neither a hydroxyl group nor a cyano group.

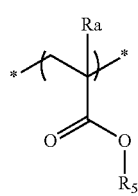

(I)

In formula (I), $R_5$ represents a hydrocarbon group having at least one cyclic structure and having neither a hydroxyl group nor a cyano group.

Ra represents a hydrogen atom, an alkyl group or a —$CH_2$—O—$Ra_2$ group, wherein $Ra_2$ represents an alkyl group or an acyl group. Examples of Ra include H, $CH_3$ and $CF_3$.

The cyclic structure possessed by $R_5$ includes a monocyclic hydrocarbon group and a polycyclic hydrocarbon group. Examples of the monocyclic hydrocarbon group include a cycloalkyl group having a carbon number of 3 to 12, such as cyclopentyl group, cyclohexyl group, cycloheptyl group and cyclooctyl group, and a cycloalkenyl group having a carbon number of 3 to 12, such as cyclohexenyl group. The monocyclic hydrocarbon group is preferably a monocyclic hydrocarbon group having a carbon number of 3 to 7, more preferably a cyclopentyl group or a cyclohexyl group.

The polycyclic hydrocarbon group includes a ring gathered hydrocarbon group and a crosslinked cyclic hydrocarbon group. Examples of the ring gathered hydrocarbon group include a bicyclohexyl group and a perhydronaphthalenyl group. Examples of the crosslinked hydrocarbon ring include a bicyclic hydrocarbon ring such as pinane ring, bornane ring, norpinane ring, norbornane ring and bicyclooctane ring (e.g., bicyclo[2.2.2]octane ring, bicyclo[3.2.1]octane ring), a tricyclic hydrocarbon ring such as homobledane ring, adamantane ring, tricyclo[5.2.1.0$^{2,6}$]decane ring and tricyclo[4.3.1.1$^{2,5}$] undecane ring, and a tetracyclic hydrocarbon ring such as tetracyclo[4.4.0.1$^{2,5}$.1$^{7,10}$]dodecane ring and perhydro-1,4-methano-5,8-methanonaphthalene ring. The crosslinked cyclic hydrocarbon ring also includes a condensed cyclic hydrocarbon ring, for example, a condensed ring formed by condensing a plurality of 5- to 8-membered cycloalkane rings, such as perhydronaphthalene (decalin) ring, perhydroanthracene ring, perhydrophenathrene ring, perhydroacenaphthene ring, perhydrofluorene ring, perhydroindene ring and perhydrophenalene ring.

Preferred examples of the crosslinked cyclic hydrocarbon ring include a norbornyl group, an adamantyl group, a bicyclooctanyl group and a tricyclo[5,2,1,0$^{2,6}$]decanyl group, with a norbornyl group and an adamantyl group being more preferred.

Such an alicyclic hydrocarbon group may have a substituent, and preferred examples of the substituent include a halogen atom, an alkyl group, a hydroxyl group protected by a protective group, and an amino group protected by a protective group. The halogen atom is preferably bromine atom, chlorine atom or fluorine atom, and the alkyl group is preferably a methyl group, an ethyl group, a butyl group or a tert-butyl group. This alkyl group may further have a substituent, and the substituent which the alkyl group may further have includes a halogen atom, an alkyl group, a hydroxyl group protected by a protective group, and an amino group protected by a protective group.

Examples of the protective group include an alkyl group, a cycloalkyl group, an aralkyl group, a substituted methyl group, a substituted ethyl group, an alkoxycarbonyl group and an aralkyloxycarbonyl group. The alkyl group is preferably an alkyl group having a carbon number of 1 to 4, the substituted methyl group is preferably a methoxymethyl group, a methoxythiomethyl group, a benzyloxymethyl group, a tert-butoxymethyl group or a 2-methoxyethoxymethyl group, the substituted ethyl group is preferably a 1-ethoxyethyl group or a 1-methyl-1-methoxyethyl group, the acyl group is preferably an aliphatic acyl group having a carbon number of 1 to 6, such as formyl group, acetyl group, propionyl group, butyryl group, isobutyryl group, valeryl group and pivaloyl group, and the alkoxycarbonyl group is preferably an alkoxycarbonyl group having a carbon number of 2 to 4.

The content of the repeating unit represented by formula (I) having neither a hydroxyl group nor a cyano group is preferably from 0 to 40 mol %, more preferably from 0 to 20 mol %, based on all repeating units in the resin (A).

Specific examples of the repeating unit represented by formula (I) are set forth below, but the present invention is not limited thereto. In the formulae, Ra represents H, $CH_3$ or $CF_3$.

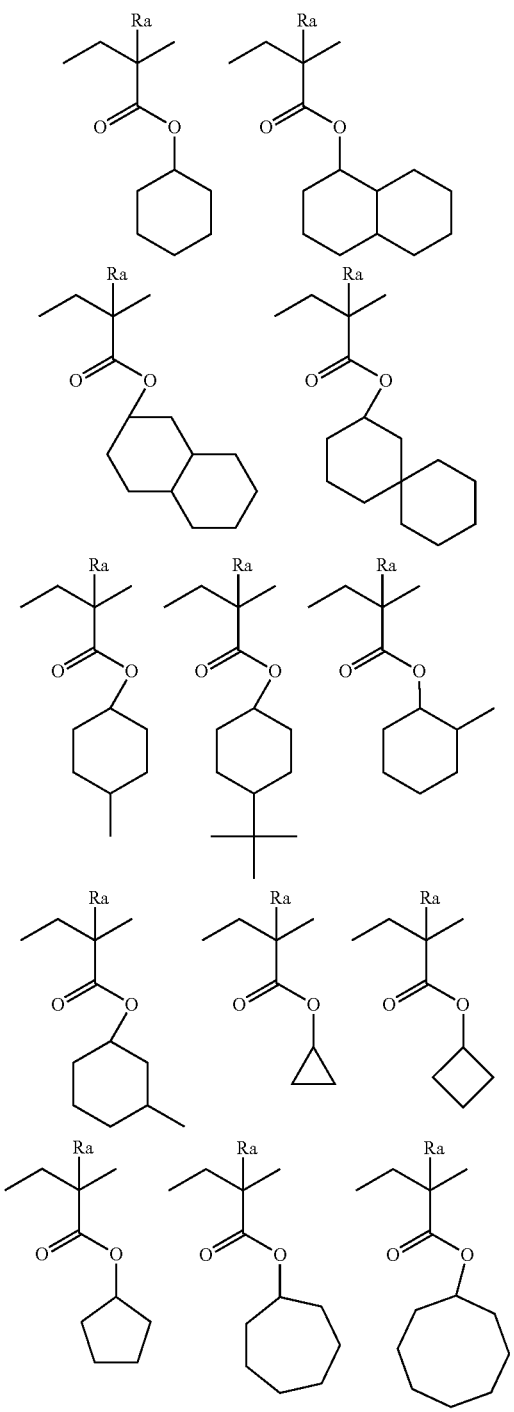

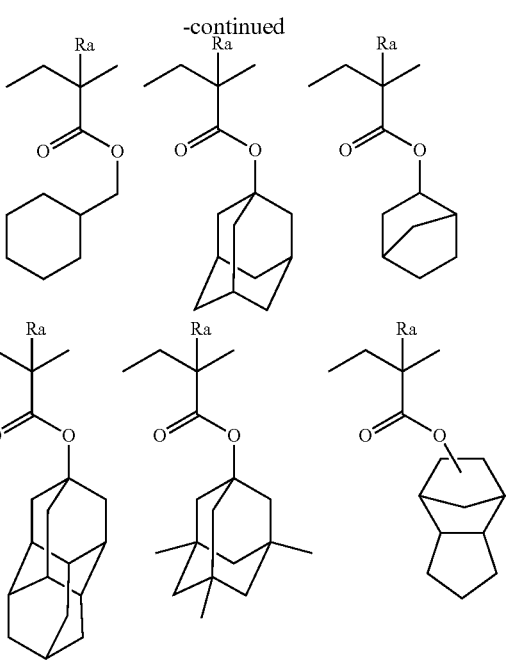

The resin of the component (A) may contain, in addition to the above-described repeating structural units, various repeating structural units for the purpose of controlling the dry etching resistance, suitability for standard developer, adherence to substrate, resist profile and properties generally required of the resist, such as resolution, heat resistance and sensitivity.

Examples of such a repeating structural unit include, but are not limited to, repeating structural units corresponding to the monomers described below.

Thanks to such a repeating structural unit, the performance required of the resin of the component (A), particularly (1) solubility in the coating solvent,
(2) film-forming property (glass transition point),
(3) alkali developability,
(4) film loss (selection of hydrophilic, hydrophobic or alkali-soluble group),
(5) adherence of unexposed area to substrate,
(6) dry etching resistance, and the like, can be subtly controlled.

Examples of the monomer include a compound having one addition-polymerizable unsaturated bond selected from acrylic acid esters, methacrylic acid esters, acrylamides, methacrylamides, allyl compounds, vinyl ethers and vinyl esters.

Other than these, an addition-polymerizable unsaturated compound copolymerizable with the monomers corresponding to the above-described various repeating structural units may be copolymerized.

In the resin of the component (A), the molar ratio of respective repeating structural units contained is appropriately determined to control the dry etching resistance of resist, suitability for standard developer, adherence to substrate, resist profile and performances generally required of the resist, such as resolution, heat resistance and sensitivity.

In the case where the actinic ray-sensitive or radiation-sensitive resin composition of the present invention is used for ArF exposure, the resin of the component (A) preferably has no aromatic group (specifically, in the resin, the ratio of an aromatic group-containing repeating is preferably 5 mol % or less, more preferably 3 mol % or less, and ideally 0 mol %, that is, no aromatic group is contained) in view of transparency to ArF light, and the resin (A) preferably has a monocyclic or polycyclic alicyclic hydrocarbon structure.

Also, the resin of the component (A) of the present invention is preferably a resin different from the resin (C) and in view of compatibility with the resin (C), preferably contains no fluorine atom and no silicon atom.

The resin of the component (A) is preferably a resin where all repeating units are composed of a (meth)acrylate-based repeating unit. In this case, all repeating units may be a methacrylate-based repeating unit, all repeating units may be an acrylate-based repeating unit, or all repeating unit may be composed of a methacrylate-based repeating unit and an acrylate-based repeating unit, but the content of the acrylate-based repeating unit is preferably 50 mol % or less based on all repeating units. The resin is more preferably a copolymerized polymer containing from 20 to 50 mol % of an acid decomposable group-containing (meth)acrylate-based repeating unit represented by formula (AI), from 20 to 50 mol % of a lactone group-containing (meth)acrylate-based repeating unit, from 5 to 30 mol % of a (meth)acrylate-based repeating unit having an alicyclic hydrocarbon structure substituted by a hydroxyl group or a cyano group, and from 0 to 20 mol % of other (meth)acrylate-based repeating units.

In the case where the actinic ray-sensitive or radiation-sensitive resin composition of the present invention is irradiated with KrF excimer laser light, electron beam, X-ray or high-energy beam at a wavelength of 50 nm or less (e.g., EUV), the resin of the component (A) preferably further contains, in addition to the repeating unit represented by formula (AI), a hydroxystyrene-based repeating unit, more preferably a hydroxystyrene-based repeating unit, a hydroxystyrene-based repeating unit protected by an acid-decomposable group, and an acid-decomposable repeating unit such as tertiary alkyl(meth)acrylate.

Preferred examples of the repeating unit having an acid-decomposable group include a repeating unit composed of a tert-butoxycarbonyloxystyrene, a 1-alkoxyethoxystyrene or a tertiary alkyl(meth)acrylate. A repeating unit composed of a 2-alkyl-2-adamantyl(meth)acrylate or a dialkyl(1-adamantyl)methyl(meth)acrylate is more preferred.

The resin of the component (A) can be synthesized by an ordinary method (for example, radical polymerization). Examples of the synthesis method in general include a batch polymerization method of dissolving monomer species and an initiator in a solvent and heating the solution, thereby effecting the polymerization, and a dropping polymerization method of adding dropwise a solution containing monomer species and an initiator to a heated solvent over 1 to 10 hours. A dropping polymerization method is preferred. Examples of the reaction solvent include ethers such as diisopropyl ether, tetrahydrofuran, 1,4-dioxane, ketones such as methyl ethyl ketone and methyl isobutyl ketone, an ester solvent such as ethyl acetate, an amide solvent such as dimethylformamide and dimethylacetamide, and the later-described solvent capable of dissolving the composition of the present invention, such as propylene glycol monomethyl ether acetate (PG-MEA, also known as 1-methoxy-2-acetoxypropane), propylene glycol monomethyl ether (PGME, also known as 1-methoxy-2-propanol) and cyclohexanone. The polymerization is more preferably performed using the same solvent as the solvent used in the actinic ray-sensitive or radiation-sensitive resin composition of the present invention. By the use of this solvent, production of particles during storage can be suppressed.

The polymerization reaction is preferably performed in an inert gas atmosphere such as nitrogen or argon. As for the polymerization initiator, the polymerization is started using a commercially available radical initiator (e.g., azo-based initiator, peroxide). The radical initiator is preferably an azo-based initiator, and an azo-based initiator having an ester group, a cyano group or a carboxyl group is preferred. Preferred examples of the initiator include azobisisobutyronitrile, azobisdimethylvaleronitrile and dimethyl 2,2'-azobis(2-methylpropionate). The initiator is added additionally or in parts, if desired. After the completion of reaction, the reaction product is charged into a solvent, and the desired polymer is recovered by a method such as powder or solid recovery. The reaction concentration is from 5 to 50 mass %, preferably from 10 to 30 mass %, and the reaction temperature is usually from 10 to 150° C., preferably from 30 to 120° C., more preferably from 60 to 100° C. (In this specification, mass ratio is equal to weight ratio.)

The weight average molecular weight of the resin of the component (A) is preferably from 1,000 to 200,000, more preferably from 2,000 to 20,000, still more preferably from 3,000 to 15,000, yet still more preferably from 5,000 to 13,000, in terms of polystyrene by the GPC method. When the weight average molecular weight is from 1,000 to 200,000, deterioration of the heat resistance, dry etching resistance and developability can be prevented and the film-forming property can be prevented from deterioration due to increase in the viscosity.

The polydispersity (molecular weight distribution) is usually from 1 to 3, preferably from 1 to 2.6, more preferably from 1 to 2, still more preferably from 1.4 to 1.7. As the molecular weight distribution is smaller, the resolution and resist profile are more excellent, the side wall of the resist pattern is smoother, and the roughness is more improved.

In the actinic ray-sensitive or radiation-sensitive resin composition of the present invention, the amount of the resin of the component (A) blended in the entire composition is preferably from 50 to 99 mass %, more preferably from 70 to 98 mass %, still more preferably from 70 to 95 mass %, based on the entire solid content.

In the present invention, as regards the resin of the component (A), one kind may be used or a plurality of kinds may be used in combination (polymer blend).

[2] Compound Capable of Generating an Acid Upon Irradiation with an Actinic Ray or Radiation (B)

The actinic ray-sensitive or radiation-sensitive resin composition of the present invention preferably contains a compound capable of generating an acid upon irradiation with an actinic ray or radiation (hereinafter sometimes referred to as an "acid generator").

The acid generator which can be used may be appropriately selected from a photo-initiator for cationic photopolymerization, a photo-initiator for radical photopolymerization, a photo-decoloring agent for dyes, a photo-discoloring agent, a compound known to generate an acid upon irradiation with an actinic ray or radiation and used for microresist or the like, and a mixture thereof.

Examples of such a compound include a diazonium salt, a phosphonium salt, a sulfonium salt, an iodonium salt, imidosulfonate, oxime sulfonate, diazodisulfone, disulfone and o-nitrobenzyl sulfonate.

Also, a compound where such a group or compound capable of generating an acid upon irradiation with an actinic ray or radiation is introduced into the main or side chain of the polymer, for example, compounds described in U.S. Pat. No. 3,849,137, German Patent 3,914,407, JP-A-63-26653, JP-A-

55-164824, JP-A-62-69263, JP-A-63-146038, JP-A-63-163452, JP-A-62-153853 and JP-A-63-146029, may be used.

Furthermore, compounds capable of generating an acid by the effect of light described, for example, in U.S. Pat. No. 3,779,778 and European Patent 126,712 may also be used.

Out of the acid generators, compounds represented by the following formulae (ZI), (ZII) and (ZIII) are preferred.

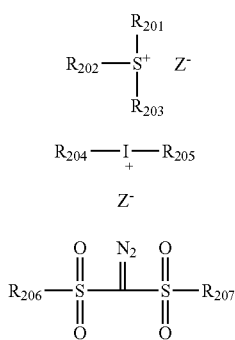

In formula (ZI), each of $R_{201}$, $R_{202}$ and $R_{203}$ independently represents an organic group.

The number of carbons in the organic group as $R_{201}$, $R_{202}$ and $R_{203}$ is generally from 1 to 30, preferably from 1 to 20.

Two members out of $R_{201}$ to $R_{203}$ may combine to form a ring structure, and the ring may contain an oxygen atom, a sulfur atom, an ester bond, an amide bond or a carbonyl group. Examples of the group formed by combining two members out of $R_{201}$ to $R_{203}$ include an alkylene group (e.g., butylene, pentylene).

$Z^-$ represents a non-nucleophilic anion.

Examples of the non-nucleophilic anion as $Z^-$ include sulfonate anion, carboxylate anion, sulfonylimide anion, bis(alkylsulfonyl)imide anion and tris(alkylsulfonyl)methyl anion.

The non-nucleophilic anion is an anion having an extremely low ability of causing a nucleophilic reaction and this anion can suppress the decomposition with aging due to intramolecular nucleophilic reaction. Thanks to this anion, the aging stability of the resist is enhanced.

Examples of the sulfonate anion include an aliphatic sulfonate anion, an aromatic sulfonate anion and a camphorsulfonate anion.

Examples of the carboxylate anion include an aliphatic carboxylate anion, an aromatic carboxylate anion and an aralkylcarboxylate anion.

The aliphatic moiety in the aliphatic sulfonate anion may be an alkyl group or a cycloalkyl group but is preferably an alkyl group having a carbon number of 1 to 30 or a cycloalkyl group having a carbon number of 3 to 30, and examples thereof include a methyl group, an ethyl group, a propyl group, an isopropyl group, an n-butyl group, an isobutyl group, a sec-butyl group, a pentyl group, a neopentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an eicosyl group, a cyclopropyl group, a cyclopentyl group, a cyclohexyl group, an adamantyl group, a norbornyl group and a bornyl group.

The aromatic group in the aromatic sulfonate anion is preferably an aryl group having a carbon number of 6 to 14, and examples thereof include a phenyl group, a tolyl group and a naphthyl group.

Each of the alkyl group, cycloalkyl group and aryl group in the aliphatic sulfonate anion and aromatic sulfonate anion may have a substituent. Examples of the substituent of the alkyl group, cycloalkyl group and aryl group in the aliphatic sulfonate anion and aromatic sulfonate anion include a nitro group, a halogen atom (e.g., fluorine, chlorine, bromine, iodine), a carboxyl group, a hydroxyl group, an amino group, a cyano group, an alkoxy group (preferably having a carbon number of 1 to 15), a cycloalkyl group (preferably having a carbon number of 3 to 15), an aryl group (preferably having a carbon number of 6 to 14), an alkoxycarbonyl group (preferably having a carbon number of 2 to 7), an acyl group (preferably having a carbon number of 2 to 12), an alkoxycarbonyloxy group (preferably having a carbon number of 2 to 7), an alkylthio group (preferably having a carbon number of 1 to 15), an alkylsulfonyl group (preferably having a carbon number of 1 to 15), an alkyliminosulfonyl group (preferably having a carbon number of 1 to 15), an aryloxysulfonyl group (preferably having a carbon number of 6 to 20), an alkylaryloxysulfonyl group (preferably having a carbon number of 7 to 20), a cycloalkylaryloxysulfonyl group (preferably having a carbon number of 10 to 20), an alkyloxyalkyloxy group (preferably having a carbon number of 5 to 20), and a cycloalkylalkyloxyalkyloxy group (preferably having a carbon number of 8 to 20). As for the aryl group or ring structure in each group, examples of the substituent further include an alkyl group (preferably having a carbon number of 1 to 15).

Examples of the aliphatic moiety in the aliphatic carboxylate anion include the same alkyl group and cycloalkyl group as those in the aliphatic sulfonate anion.

Examples of the aromatic group in the aromatic carboxylate anion include the same aryl group as those in the aromatic sulfonate anion.

The aralkyl group in the aralkylcarboxylate anion is preferably an aralkyl group having a carbon number of 6 to 12, and examples thereof include a benzyl group, a phenethyl group, a naphthylmethyl group, a naphthylethyl group and a naphthylbutyl group.

Each of the alkyl group, cycloalkyl group, aryl group and aralkyl group in the aliphatic carboxylate anion, aromatic carboxylate anion and aralkylcarboxylate anion may have a substituent. Examples of the substituent of the alkyl group, cycloalkyl group, aryl group and aralkyl group in the aliphatic carboxylate anion, aromatic carboxylate anion and aralkylcarboxylate anion include the same halogen atom, alkyl group, cycloalkyl group, alkoxy group and alkylthio group as those in the aromatic sulfonate anion.

Examples of the sulfonylimide anion include saccharin anion.

The alkyl group in the bis(alkylsulfonyl)imide anion and tris(alkylsulfonyl)methyl anion is preferably an alkyl group having a carbon number of 1 to 5, and examples thereof include a methyl group, an ethyl group, a propyl group, an isopropyl group, an n-butyl group, an isobutyl group, a sec-butyl group, a pentyl group and a neopentyl group. Examples of the substituent of such an alkyl group include a halogen atom, a halogen atom-substituted alkyl group, an alkoxy group, an alkylthio group, an alkyloxysulfonyl group, an aryloxysulfonyl group, and a cycloalkylaryloxysulfonyl group, with a fluorine atom-substituted alkyl group being preferred.

Other examples of the non-nucleophilic anion include fluorinated phosphorus, fluorinated boron and fluorinated antimony.

The non-nucleophilic anion of $Z^-$ is preferably an aliphatic sulfonate anion substituted by a fluorine atom at the α-position of the sulfonic acid, an aromatic sulfonate anion substituted by a fluorine atom or a fluorine atom-containing group, a bis(alkylsulfonyl)imide anion with the alkyl group being substituted by a fluorine atom, or a tris(alkylsulfonyl)methide anion with the alkyl group being substituted by a fluorine atom. The non-nucleophilic anion is more preferably a perfluoroaliphatic sulfonate anion having a carbon number of 4 to 8 or a benzenesulfonate anion having a fluorine atom, still more preferably nonafluorobutanesulfonate anion, perfluorooctanesulfonate anion, pentafluorobenzenesulfonate anion or 3,5-bis(trifluoromethyl)benzenesulfonate anion.

Examples of the organic group as $R_{201}$, $R_{202}$ and $R_{203}$ include the corresponding groups in the compounds (ZI-1) to (ZI-4) described later.

The compound may be a compound having a plurality of structures represented by formula (ZI), for example, a compound having a structure where at least one of $R_{201}$ to $R_{203}$ in the compound represented by formula (ZI) is bonded to at least one of $R_{201}$ to $R_{203}$ in another compound represented by formula (ZI).

In formulae (ZII) and (ZIII), each of $R_{204}$ to $R_{207}$ independently represents an aryl group, an alkyl group or a cycloalkyl group.

The aryl group of $R_{204}$ to $R_{207}$ is preferably a phenyl group or a naphthyl group, more preferably a phenyl group. The aryl group of $R_{204}$ to $R_{207}$ may be an aryl group having a heterocyclic structure containing an oxygen atom, a nitrogen atom, a sulfur atom or the like. Examples of the aryl group having a heterocyclic structure include a pyrrole residue (a group formed by removing one hydrogen atom from a pyrrole), a furan residue (a group formed by removing one hydrogen atom from a furan), a thiophene residue (a group formed by removing one hydrogen atom from a thiophene), an indole residue (a group formed by removing one hydrogen atom from an indole), a benzofuran residue (a group formed by removing one hydrogen atom from a benzofuran) and a benzothiophene residue (a group formed by removing one hydrogen atom from a benzothiophene).

The alkyl group and cycloalkyl group in $R_{204}$ to $R_{207}$ are preferably a linear or branched alkyl group having a carbon number of 1 to 10 (e.g., methyl, ethyl, propyl, butyl, pentyl) and a cycloalkyl group having a carbon number of 3 to 10 (e.g., cyclopentyl, cyclohexyl, norbornyl).

Each of the aryl group, alkyl group and cycloalkyl group of $R_{204}$ to $R_{207}$ may have a substituent. Examples of the substituent which the aryl group, alkyl group and cycloalkyl group of $R_{204}$ to $R_{207}$ may have include an alkyl group (for example, having a carbon number of 1 to 15), a cycloalkyl group (for example, having a carbon number of 3 to 15), an aryl group (for example, having a carbon number of 6 to 15), an alkoxy group (for example, having a carbon number of 1 to 15), a halogen atom, a hydroxyl group and a phenylthio group.

$Z^-$ represents a non-nucleophilic anion, and examples thereof are the same as those of the non-nucleophilic anion of $Z^-$ in formula (ZI).

As for the component (ZI), the compounds (ZI-1) to (ZI-4) described below are more preferred.

The compound (ZI-1) is an arylsulfonium compound where at least one of $R_{201}$ to $R_{203}$ in formula (ZI) is an aryl group, that is, a compound having arylsulfonium as the cation.

In the arylsulfonium compound, all of $R_{201}$ to $R_{203}$ may be an aryl group or a part of $R_{201}$ to $R_{203}$ may be an aryl group with the remaining being an alkyl group or a cycloalkyl group.

Examples of the arylsulfonium compound include a triarylsulfonium compound, a diarylalkylsulfonium compound, an aryldialkylsulfonium compound, a diarylcycloalkylsulfonium compound and an aryldicycloalkylsulfonium compound.

The aryl group in the arylsulfonium compound is preferably a phenyl group or a naphthyl group, more preferably a phenyl group. The aryl group may be an aryl group having a heterocyclic structure containing an oxygen atom, a nitrogen atom, a sulfur atom or the like. Examples of the aryl group having a heterocyclic structure include a pyrrole residue (a group formed by removing one hydrogen atom from a pyrrole), a furan residue (a group formed by removing one hydrogen atom from a furan), a thiophene residue (a group formed by removing one hydrogen atom from a thiophene), an indole residue (a group formed by removing one hydrogen atom from an indole), a benzofuran residue (a group formed by removing one hydrogen atom from a benzofuran) and a benzothiophene residue (a group formed by removing one hydrogen atom from a benzothiophene). In the case where the arylsulfonium compound has two or more aryl groups, these two or more aryl groups may be the same or different.

The alkyl or cycloalkyl group which is present, if desired, in the arylsulfonium compound is preferably a linear or branched alkyl group having a carbon number of 1 to 15 or a cycloalkyl group having a carbon number of 3 to 15, and examples thereof include a methyl group, an ethyl group, a propyl group, an n-butyl group, a sec-butyl group, a tert-butyl group, a cyclopropyl group, a cyclobutyl group and a cyclohexyl group.

Each of the aryl group, alkyl group and cycloalkyl group of $R_{201}$ to $R_{203}$ may have, as the substituent, an alkyl group (for example, having a carbon number of 1 to 15), a cycloalkyl group (for example, having a carbon number of 3 to 15), an aryl group (for example, having a carbon number of 6 to 14), an alkoxy group (for example, having a carbon number of 1 to 15), a halogen atom, a hydroxyl group or a phenylthio group. The substituent is preferably a linear or branched alkyl group having a carbon number of 1 to 12, a cycloalkyl group having a carbon number of 3 to 12, or a linear, branched or cyclic alkoxy group having a carbon number of 1 to 12, more preferably an alkyl group having a carbon number of 1 to 4, or an alkoxy group having a carbon number of 1 to 4. The substituent may be substituted to any one of three members $R_{201}$ to $R_{203}$ or may be substituted to all of these three members. In the case where $R_{201}$ to $R_{203}$ are an aryl group, the substituent is preferably substituted at the p-position of the aryl group.

The compound (ZI-2) is described below.

The compound (ZI-2) is a compound where each of $R_{201}$ to $R_{203}$ in formula (ZI) independently represents an aromatic ring-free organic group. The aromatic ring as used herein includes an aromatic ring containing a heteroatom.

The aromatic ring-free organic group as $R_{201}$ to $R_{203}$ has a carbon number of generally from 1 to 30, preferably from 1 to 20.

Each of $R_{201}$ to $R_{203}$ independently represents preferably an alkyl group, a cycloalkyl group, an allyl group or a vinyl group, more preferably a linear or branched 2-oxoalkyl group, a 2-oxocycloalkyl group or an alkoxycarbonylmethyl group, still more preferably a linear or branched 2-oxoalkyl group.

The alkyl group and cycloalkyl group of $R_{201}$ to $R_{203}$ are preferably a linear or branched alkyl group having a carbon number of 1 to 10 (e.g., methyl, ethyl, propyl, butyl, pentyl) and a cycloalkyl group having a carbon number of 3 to 10 (e.g., cyclopentyl, cyclohexyl, norbornyl). The alkyl group is more preferably a 2-oxoalkyl group or an alkoxycarbonylmethyl group. The cycloalkyl group is more preferably a 2-oxocycloalkyl group.

The 2-oxoalkyl group may be either linear or branched and is preferably a group having >C=O at the 2-position of the above-described alkyl group.

The 2-oxocycloalkyl group is preferably a group having >C=O at the 2-position of the above-described cycloalkyl group.

The alkoxy group in the alkoxycarbonylmethyl group is preferably an alkoxy group having a carbon number of 1 to 5 (e.g., methoxy, ethoxy, propoxy, butoxy, pentoxy).

Each of $R_{201}$ to $R_{203}$ may be further substituted by a halogen atom, an alkoxy group (for example, having a carbon number of 1 to 5), a hydroxyl group, a cyano group or a nitro group.

The compound (ZI-3) is a compound represented by the following formula (ZI-3), and this is a compound having a phenacylsulfonium salt structure.

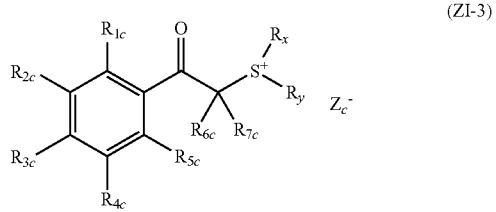

(ZI-3)

In formula (ZI-3), each of $R_{1c}$ to $R_{5c}$ independently represents a hydrogen atom, an alkyl group, a cycloalkyl group, an aryl group, an alkoxy group, an aryloxy group, an alkoxycarbonyl group, an alkylcarbonyloxy group, a cycloalkylcarbonyloxy group, a hydroxyl group, a nitro group or a halogen atom.

Each of $R_{6c}$ and $R_{7c}$ independently represents a hydrogen atom, an alkyl group or a cycloalkyl group.

Each of $R_x$ and $R_y$ independently represents an alkyl group, a cycloalkyl group, an allyl group or a vinyl group.

Any two or more members out of $R_{1c}$ to $R_{5c}$, a pair of $R_{6c}$ and $R_{7c}$, and a pair of $R_x$ and $R_y$ may combine together to form a ring structure, respectively. This ring structure may contain an oxygen atom, a sulfur atom, an ester bond or an amide bond.

The ring structure above includes an aromatic or non-aromatic hydrocarbon ring, an aromatic or non-aromatic heterocyclic ring, and a polycyclic condensed ring formed by combining two or more of these rings. The ring structure is a 3- to 10-membered ring, preferably a 4- to 8-membered ring, more preferably a 5- or 6-membered ring.

Examples of the group formed by combining any two or more members out of $R_{1c}$ to $R_{5c}$, a pair of $R_{6c}$ and $R_{7c}$, and a pair of $R_x$ and $R_y$ include a butylene group and a pentylene group.

$Z_c^-$ represents a non-nucleophilic anion, and examples thereof are the same as those of the non-nucleophilic anion of Z" in formula (ZI).

The alkyl group as $R_{1c}$ to $R_{7c}$ may be either linear or branched and is, for example, an alkyl group having a carbon number of 1 to 20, preferably a linear or branched alkyl group having a carbon number of 1 to 12 (e.g., methyl, ethyl, linear or branched propyl, linear or branched butyl, linear or branched pentyl). The cycloalkyl group is, for example, a cycloalkyl group having a carbon number of 3 to 8 (e.g., cyclopentyl, cyclohexyl).

The aryl group as $R_{1c}$ to $R_{5c}$ is preferably an aryl group having a carbon number of 5 to 15, and examples thereof include a phenyl group and a naphthyl group.

The alkoxy group as $R_{1c}$ to $R_{5c}$ may be linear, branched or cyclic and is, for example, an alkoxy group having a carbon number of 1 to 10, preferably a linear or branched alkoxy group having a carbon number of 1 to 5 (e.g., methoxy, ethoxy, linear or branched propoxy, linear or branched butoxy, linear or branched pentoxy) or a cyclic alkoxy group having a carbon number of 3 to 8 (e.g., cyclopentyloxy, cyclohexyloxy).

Specific examples of the alkoxy group in the alkoxycarbonyl group as $R_{1c}$ to $R_{5c}$ are the same as specific examples of the alkoxy group as $R_{1c}$ to $R_{5c}$ above.

Specific examples of the alkyl group in the alkylcarbonyloxy group as $R_{1c}$ to $R_{5c}$ are the same as specific examples of the alkyl group as $R_{1c}$ to $R_{5c}$ above.

Specific examples of the cycloalkyl group in the cycloalkylcarbonyloxy group as $R_{1c}$ to $R_{5c}$ are the same as specific examples of the cycloalkyl group as $R_{1c}$ to $R_{5c}$ above.

Specific examples of the aryl group in the aryloxy group as $R_{1c}$ to $R_{5c}$ are the same as specific examples of the aryl group as $R_{10}$ to $R_{5c}$ above.

A compound where any one of $R_{1c}$ to $R_{5c}$ is a linear or branched alkyl group, a cycloalkyl group or a linear, branched or cyclic alkoxy group is preferred, and a compound where the sum of carbon numbers of $R_{1c}$ to $R_{5c}$ is from 2 to 15 is more preferred. Thanks to such a compound, the solvent solubility is more enhanced and production of particles during storage can be suppressed.

The ring structure which may be formed by combining any two or more members of $R_{1c}$ to $R_{5c}$ is preferably a 5- or 6-membered ring, more preferably a 6-membered ring (e.g., phenyl ring).

Examples of the alkyl group and cycloalkyl group as $R_x$ and $R_y$ are the same as those of the alkyl group and cycloalkyl group in $R_{1c}$ to $R_{7c}$. Among these, a 2-oxoalkyl group, a 2-oxocycloalkyl group and an alkoxycarbonylmethyl group are preferred.

Examples of the 2-oxoalkyl group and 2-oxocycloalkyl group include a group having >C=O at the 2-position of the alkyl group or cycloalkyl group as $R_{1c}$ to $R_{7c}$.

Examples of the alkoxy group in the alkoxycarbonylmethyl group are the same as those of the alkoxy group in $R_{1c}$ to $R_{5c}$.

Each of $R_x$ and $R_y$ is preferably an alkyl or cycloalkyl group having a carbon number of 4 or more, more preferably 6 or more, still more preferably 8 or more.

The allyl group is not particularly limited but is preferably an unsubstituted allyl group or an allyl group substituted by a monocyclic or polycyclic cycloalkyl group (preferably a cycloalkyl group having a carbon number of 3 to 10).

The vinyl group is not particularly limited but is preferably an unsubstituted vinyl group or a vinyl group substituted by a monocyclic or polycyclic cycloalkyl group (preferably a cycloalkyl group having a carbon number of 3 to 10).

The compound (ZI-4) is a compound represented by the following formula (ZI-4):

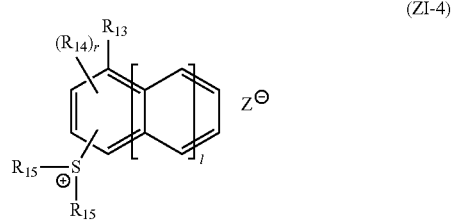

(ZI-4)

In formula (ZI-4), $R_{13}$ represents a hydrogen atom, a fluorine atom, a hydroxyl group, an alkyl group, a cycloalkyl group, an alkoxy group or an alkoxycarbonyl group.

$R_{14}$ represents, when a plurality of $R_{14}$'s are present, each independently represents a hydroxyl group, an alkyl group, a cycloalkyl group, an alkoxy group, an alkylsulfonyl group or a cycloalkylsulfonyl group.

Each $R_{15}$ independently represents an alkyl group, a cycloalkyl group or a naphthyl group. Two $R_{15}$'s may combine to form a ring.

l represents an integer of 0 to 2.

r represents an integer of 0 to 10.

Z− represents a non-nucleophilic anion, and examples thereof are the same as those of the non-nucleophilic anion of Z− in formula (ZI).

In formula (ZI-4), the alkyl group as $R_{13}$, $R_{14}$ and $R_{15}$ is a linear or branched alkyl group preferably having a carbon number of 1 to 10, and examples thereof include a methyl group, an ethyl group, an n-propyl group, an i-propyl group, an n-butyl group, a 2-methylpropyl group, a 1-methylpropyl group, a tert-butyl group, an n-pentyl group, a neopentyl group, an n-hexyl group, an n-heptyl group, an n-octyl group, a 2-ethylhexyl group, an n-nonyl group and an n-decyl group. Among these alkyl groups, a methyl group, an ethyl group, an n-butyl group and a tert-butyl group are preferred.

Examples of the cycloalkyl group of $R_{13}$, $R_{14}$ and $R_{15}$ include cyclopropyl, cyclobutyl, cyclopentyl, cyclohexyl, cycloheptyl, cyclooctyl, cyclododecanyl, cyclopentenyl, cyclohexenyl, cyclooctadienyl, norbornyl, tricyclodecanyl, tetracyclodecanyl and adamantyl. Above all, cyclopropyl, cyclopentyl, cyclohexyl, cycloheptyl and cyclooctyl are preferred.

The alkoxy group of $R_{13}$ and $R_{14}$ is a linear or branched alkoxy group preferably having a carbon number of 1 to 10, and examples thereof include a methoxy group, an ethoxy group, an n-propoxy group, an i-propoxy group, an n-butoxy group, a 2-methylpropoxy group, a 1-methylpropoxy group, a tert-butoxy group, an n-pentyloxy group, a neopentyloxy group, an n-hexyloxy group, an n-heptyloxy group, an n-octyloxy group, a 2-ethylhexyloxy group, an n-nonyloxy group and an n-decyloxy group. Among these alkoxy groups, a methoxy group, an ethoxy group, an n-propoxy group and an n-butoxy group are preferred.

The alkoxycarbonyl group of $R_{13}$ is a linear or branched alkoxycarbonyl group preferably having a carbon number of 2 to 11, and examples thereof include a methoxycarbonyl group, an ethoxycarbonyl group, an n-propoxycarbonyl group, an i-propoxycarbonyl group, an n-butoxycarbonyl group, a 2-methylpropoxycarbonyl group, a 1-methylpropoxycarbonyl group, a tert-butoxycarbonyl group, an n-pentyloxycarbonyl group, a neopentyloxycarbonyl group, an n-hexyloxycarbonyl group, an n-heptyloxycarbonyl group, an n-octyloxycarbonyl group, a 2-ethylhexyloxycarbonyl group, an n-nonyloxycarbonyl group and an n-decyloxycarbonyl group. Among these alkoxycarbonyl groups, a methoxycarbonyl group, an ethoxycarbonyl group and an n-butoxycarbonyl group are preferred.

The alkylsulfonyl group and cycloalkylsulfonyl group of $R_{14}$ are linear, branched or cyclic and preferably have a carbon number of 1 to 10, and examples thereof include a methanesulfonyl group, an ethanesulfonyl group, an n-propanesulfonyl group, an n-butanesulfonyl group, a tert-butanesulfonyl group, an n-pentanesulfonyl group, a neopentanesulfonyl group, an n-hexanesulfonyl group, an n-heptanesulfonyl group, an n-octanesulfonyl group, a 2-ethylhexanesulfonyl group, an n-nonanesulfonyl group, an n-decanesulfonyl group, a cyclopentanesulfonyl group and a cyclohexanesulfonyl group. Among these alkylsulfonyl groups, a methanesulfonyl group, an ethanesulfonyl group, an n-propanesulfonyl group, an n-butanesulfonyl group, a cyclopentanesulfonyl group and a cyclohexanesulfonyl group are preferred.

l is preferably 0 or 1, more preferably 1, and r is preferably a number of 0 to 2.

Examples of the substituent which each of the groups of $R_{13}$, $R_{14}$ and $R_{15}$ may have include a halogen atom (e.g., fluorine), a hydroxyl group, a carboxyl group, a cyano group, a nitro group, an alkoxy group, an alkoxyalkyl group, an alkoxycarbonyl group and an alkoxycarbonyloxy group.

Examples of the alkoxy group include a linear, branched or cyclic alkoxy group having a carbon number of 1 to 20, such as methoxy group, ethoxy group, n-propoxy group, i-propoxy group, n-butoxy group, 2-methylpropoxy group, 1-methylpropoxy group, tert-butoxy group, cyclopentyloxy group and cyclohexyloxy group.

Examples of the alkoxyalkyl group include a linear, branched or cyclic alkoxyalkyl group having a carbon number of 2 to 21, such as methoxymethyl group, ethoxymethyl group, 1-methoxyethyl group, 2-methoxyethyl group, 1-ethoxyethyl group and 2-ethoxyethyl group.

Examples of the alkoxycarbonyl group include a linear, branched or cyclic alkoxycarbonyl group having a carbon number of 2 to 21, such as methoxycarbonyl group, ethoxycarbonyl group, n-propoxycarbonyl group, i-propoxycarbonyl group, n-butoxycarbonyl group, 2-methylpropoxycarbonyl group, 1-methylpropoxycarbonyl group, tert-butoxycarbonyl group, cyclopentyloxycarbonyl group and cyclohexyloxycarbonyl group.

Examples of the alkoxycarbonyloxy group include a linear, branched or cyclic alkoxycarbonyloxy group having a carbon number of 2 to 21, such as methoxycarbonyloxy group, ethoxycarbonyloxy group, n-propoxycarbonyloxy group, i-propoxycarbonyloxy group, n-butoxycarbonyloxy group, tert-butoxycarbonyloxy group, cyclopentyloxycarbonyl group and cyclohexyloxycarbonyl group.

As for the ring structure which may be formed by combining two $R_{15}$'s, a group capable of forming a 5- or 6-membered ring together with the sulfur atom in formula (ZI-4) is preferred, and a group capable of forming a 5-membered ring (that is, a tetrahydrothiophene ring) is more preferred. Examples of the substituent on the ring structure include a hydroxyl group, a carboxyl group, a cyano group, a nitro group, an alkoxy group, an alkoxyalkyl group, an alkoxycarbonyl group and an alkoxycarbonyloxy group. A plurality of substituents may be present on the ring structure, and these substituents may combine to form a ring (an aromatic or non-aromatic hydrocarbon ring, an aromatic or non-aromatic heterocyclic ring, or a polycyclic condensed ring formed by combining two or more of these rings).

$R_{15}$ is preferably, for example, a methyl group, an ethyl group, a naphthyl group, or a divalent group of combining two $R_{15}$'s to form a tetrahydrothiophene ring structure together with the sulfur atom.

As described above, the alkyl group, cycloalkyl group, alkoxy group and alkoxycarbonyl group of $R_{13}$ and the alkyl group, cycloalkyl group, alkoxy group, alkylsulfonyl group and cycloalkylsulfonyl group of $R_{14}$ each may be substituted, and the substituent is preferably a hydroxyl group, an alkoxy group, an alkoxycarbonyl group or a halogen atom (particularly a fluorine atom).

Specific preferred examples of the cation in the compound represented by formula (ZI-4) are set forth below.

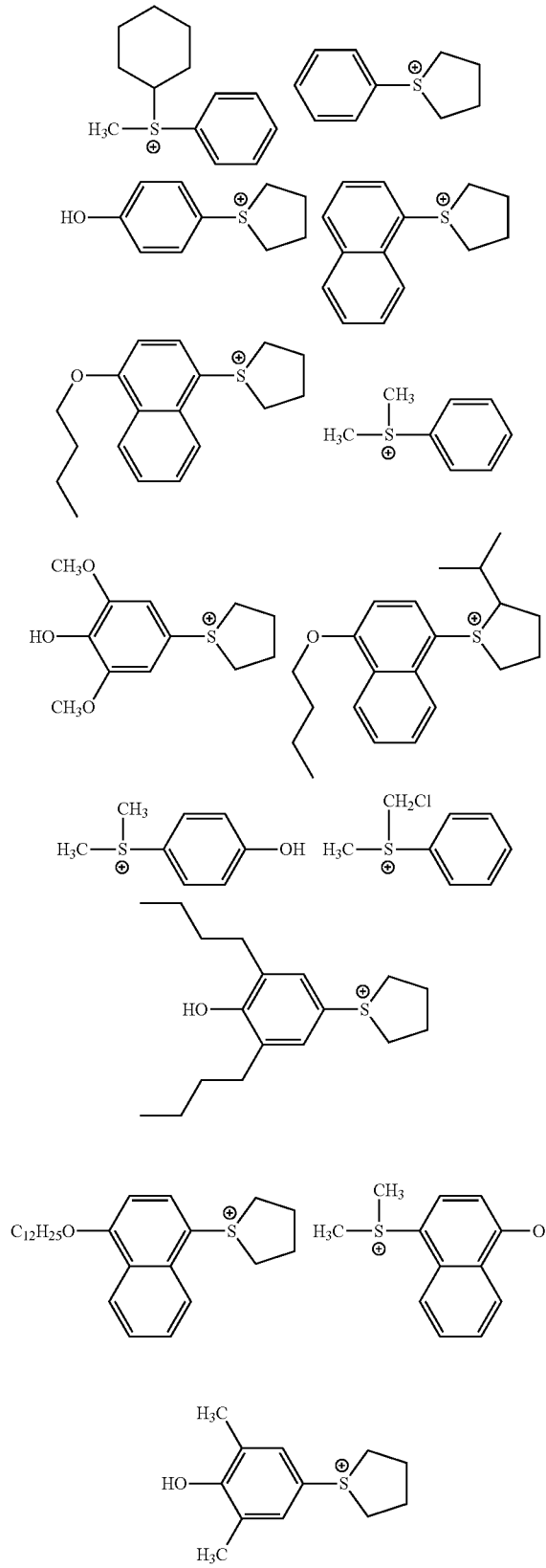

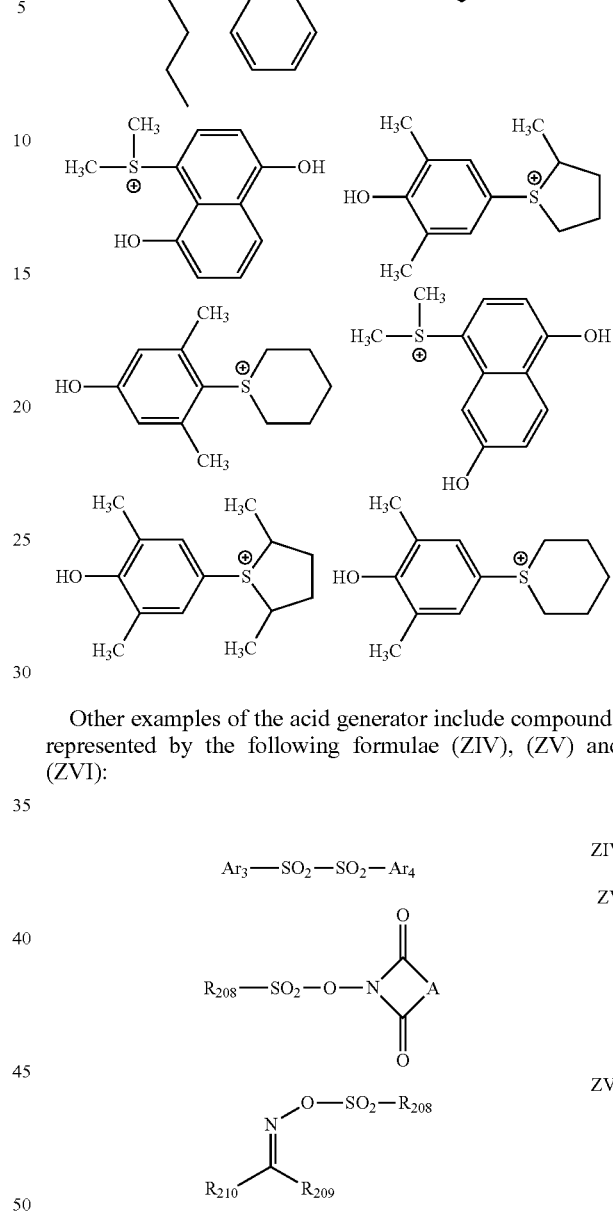

Other examples of the acid generator include compounds represented by the following formulae (ZIV), (ZV) and (ZVI):

$$Ar_3-SO_2-SO_2-Ar_4 \quad \text{ZIV}$$

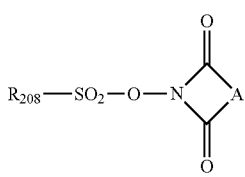

ZV

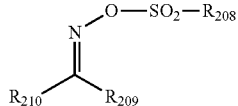

ZVI

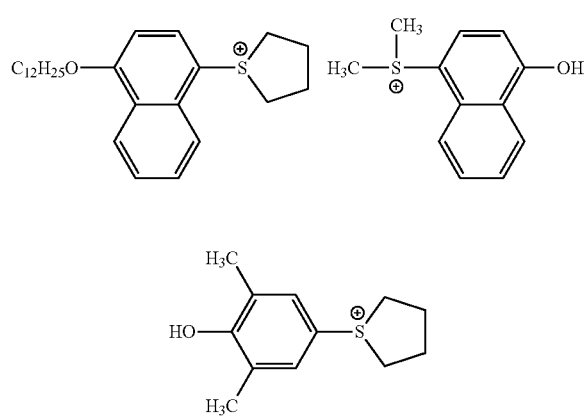

In formulae (ZIV) to (ZVI), each of $Ar_3$ and $Ar_4$ independently represents an aryl group.

Each of $R_{208}$, $R_{209}$ and $R_{210}$ independently represents an alkyl group, a cycloalkyl group or an aryl group.

A represents an alkylene group, an alkenylene group or an arylene group.

Specific examples of the aryl group of $Ar_3$, $Ar_4$, $R_{208}$, $R_{209}$ and $R_{210}$ are the same as specific examples of the aryl group as $R_{201}$, $R_{202}$ and $R_{203}$ in formula (ZI-1).

Specific examples of the alkyl group and cycloalkyl group of $R_{208}$, $R_{209}$ and $R_{210}$ are the same as specific examples of the alkyl group and cycloalkyl group as $R_{201}$, $R_{202}$ and $R_{203}$ in formula (ZI-2).

The alkylene group of A includes an alkylene group having a carbon number of 1 to 12 (e.g., methylene, ethylene, propylene, isopropylene, butylene, isobutylene), the alkenylene of A includes an alkenylene group having a carbon number of 2 to 12 (e.g., ethynylene, propenylene, butenylene), and the arylene group of A includes an arylene group having a carbon number of 6 to 10 (e.g., phenylene, tolylene, naphtylene).

Among the acid generators, more preferred are the compounds represented by formulae (ZI) to (ZIII).

Specific preferred examples of the cation produced from an acid generator include cations indicated by the following formulae.

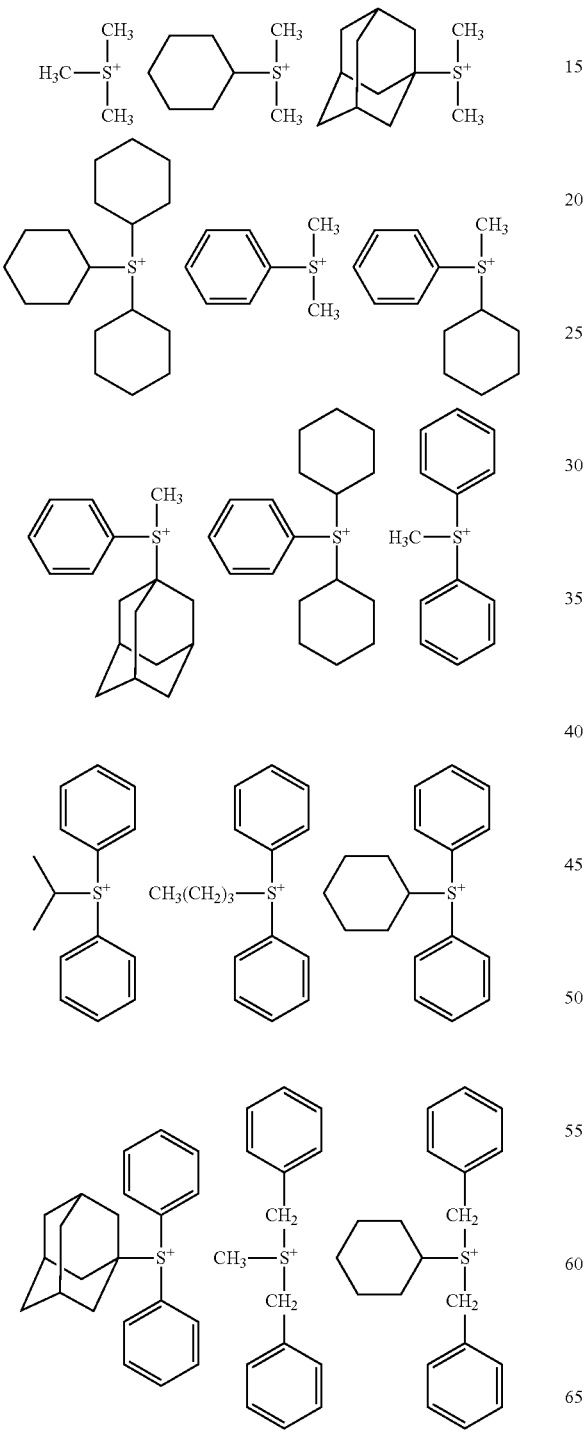

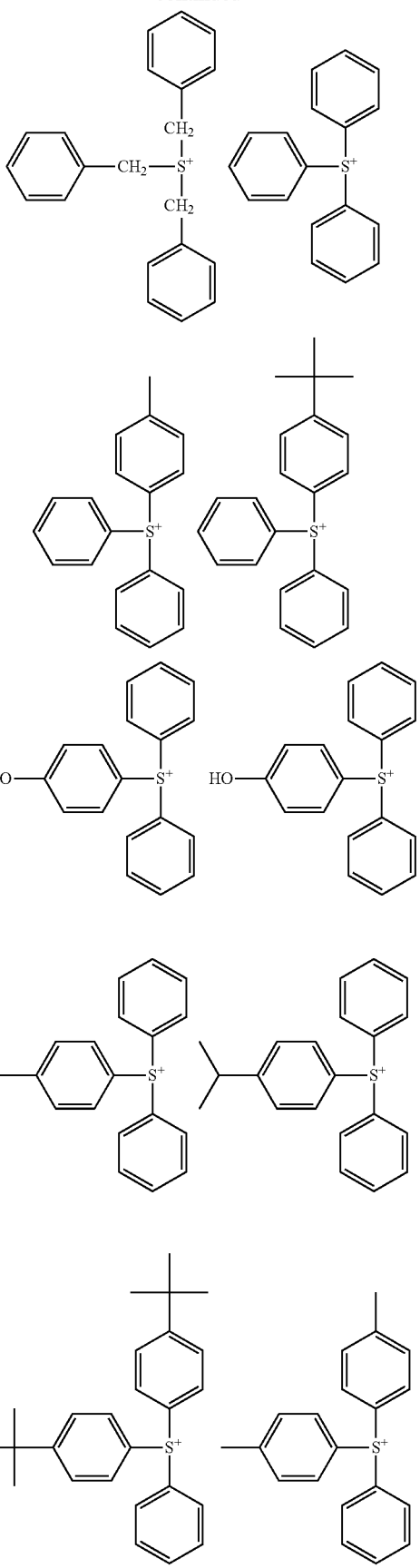

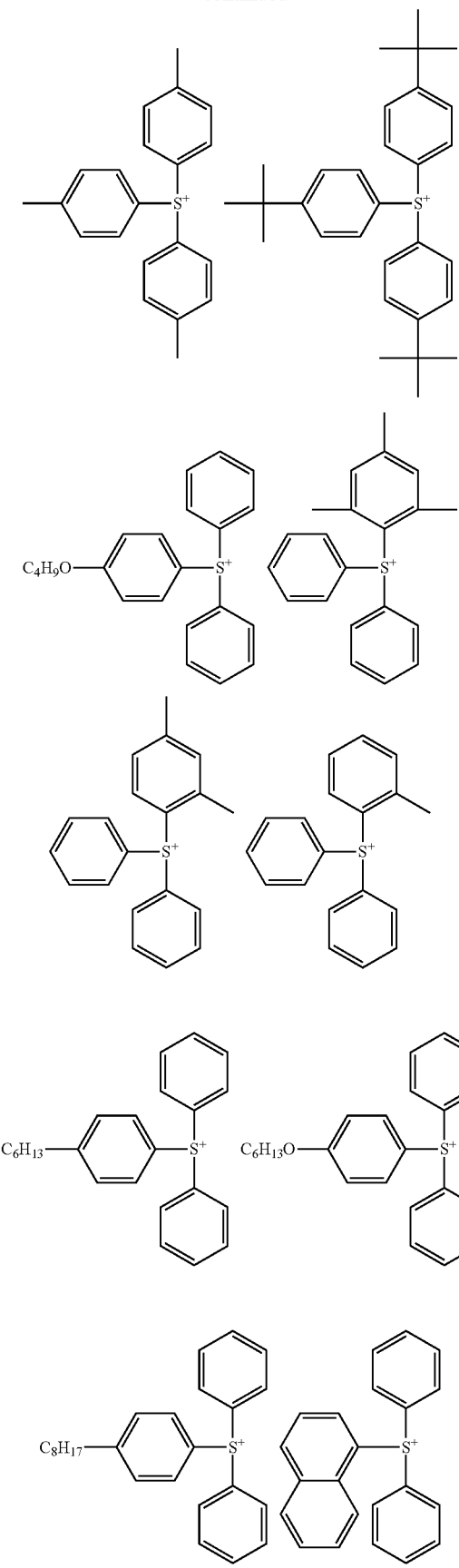
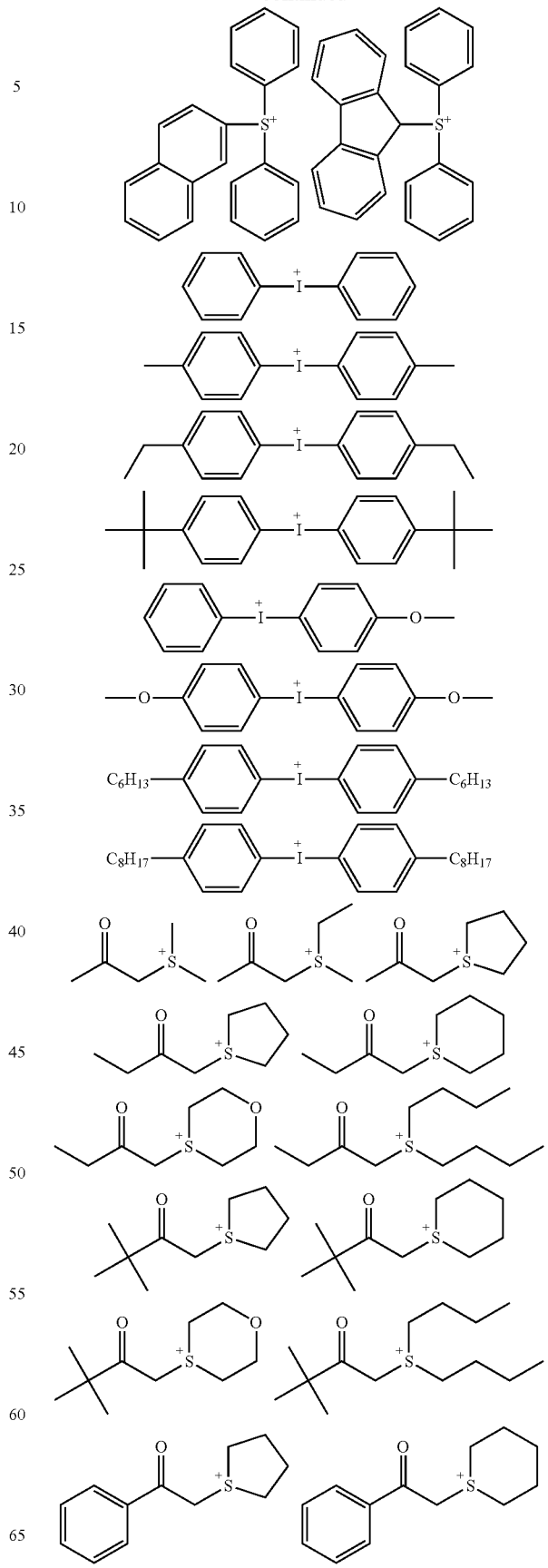

-continued
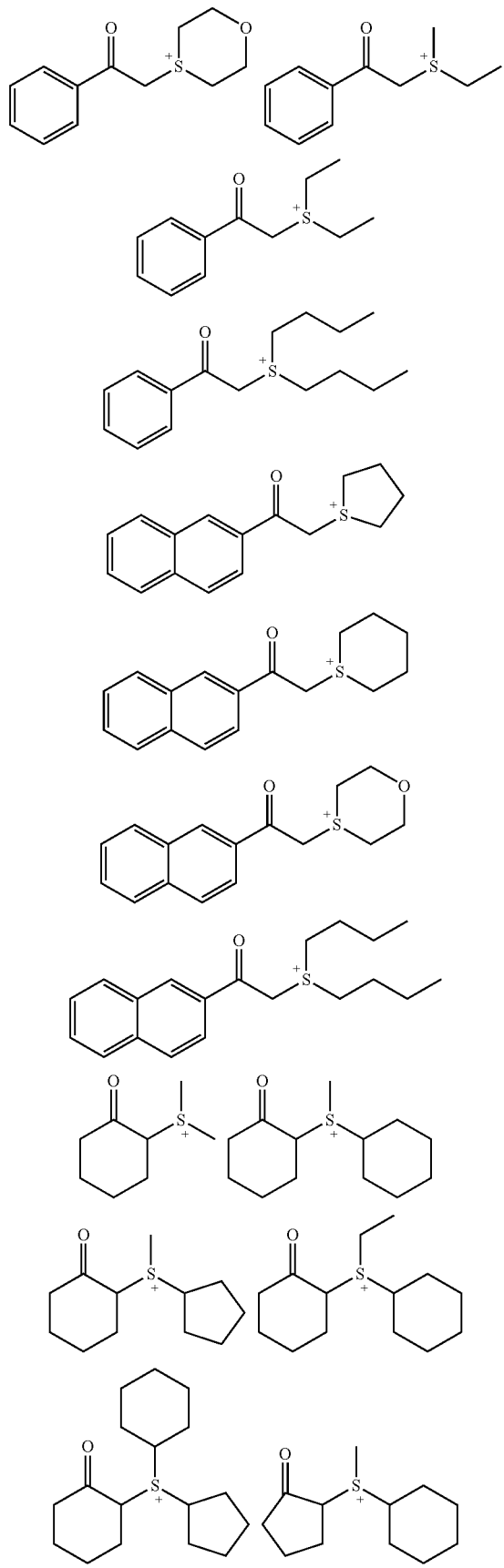
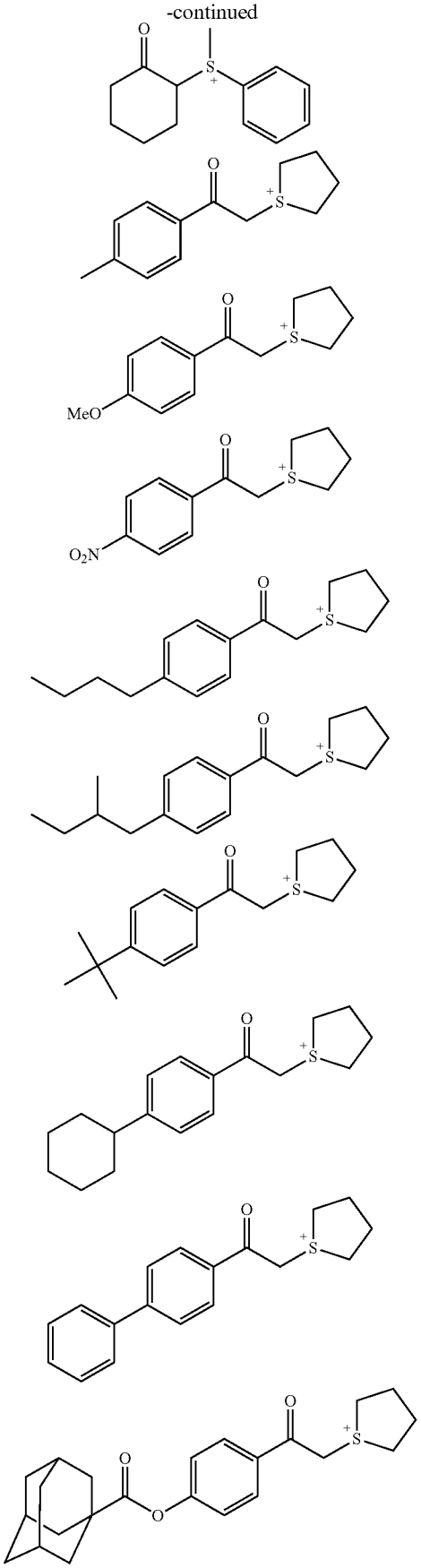

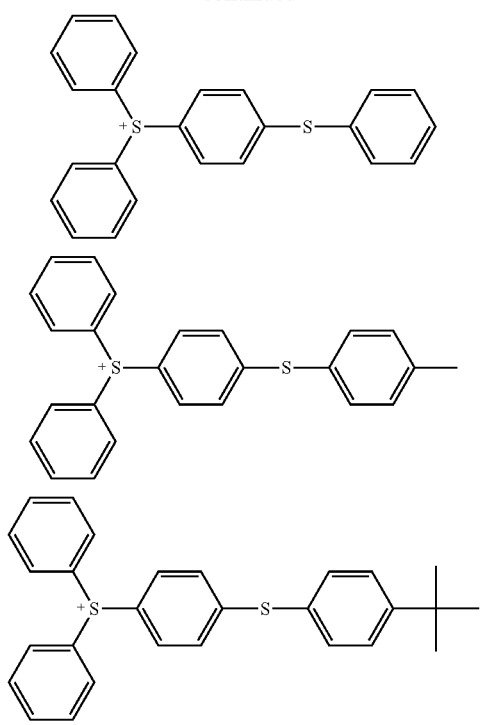
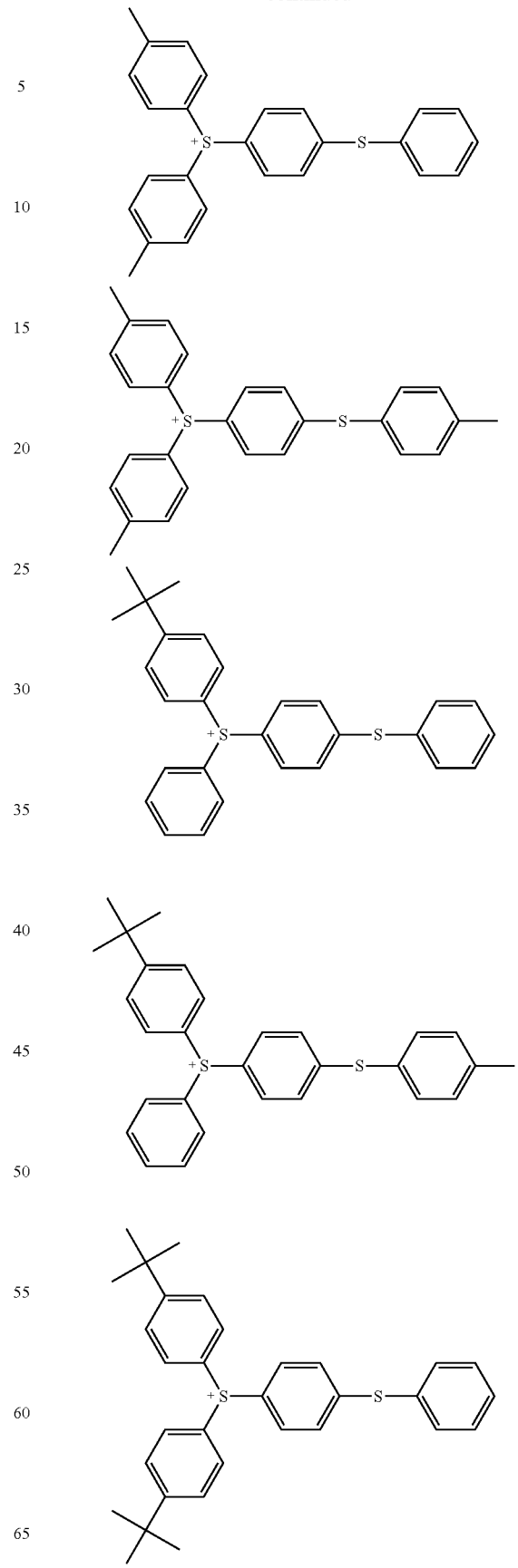

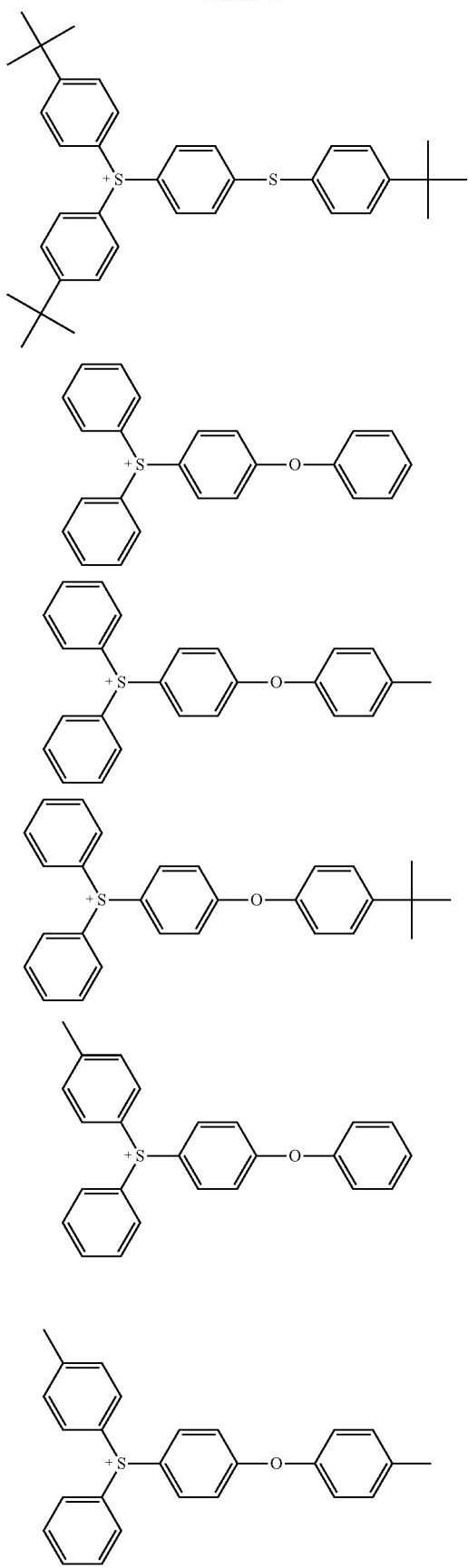
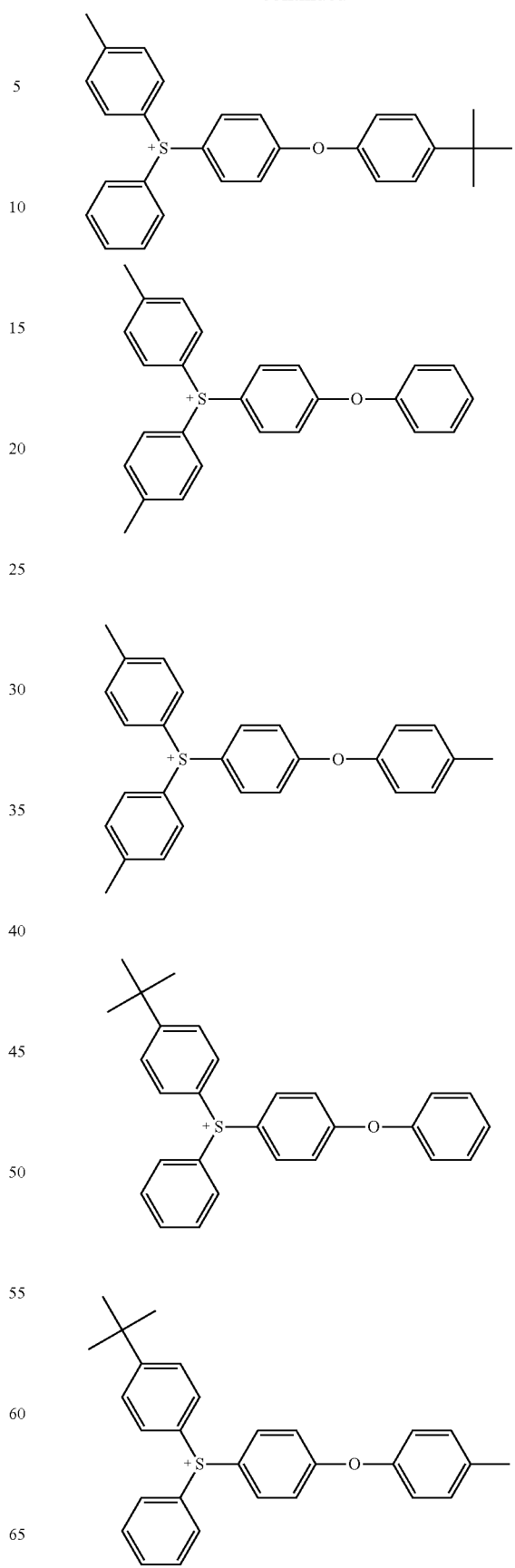

-continued

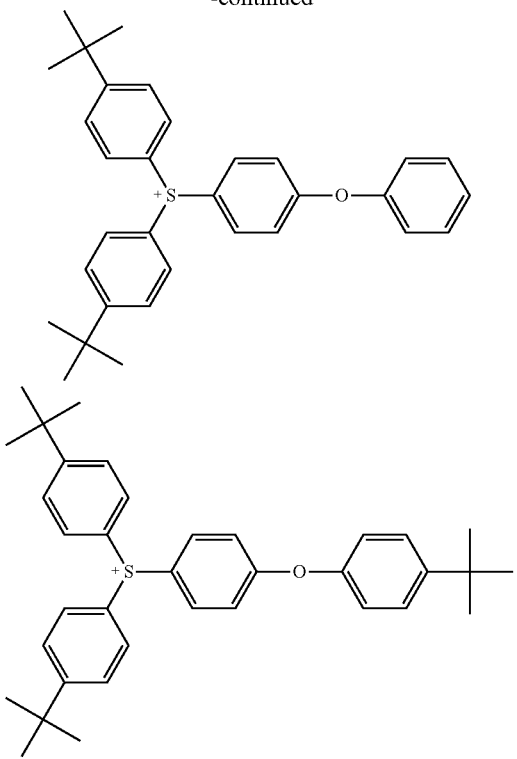

The acid generator is preferably a compound capable of generating an acid having one sulfonic acid group or imide group, more preferably a compound capable of generating a monovalent perfluoroalkanesulfonic acid, a compound capable of generating a monovalent aromatic sulfonic acid substituted by a fluorine atom or a fluorine atom-containing group, or a compound capable of generating a monovalent imide acid substituted by a fluorine atom or a fluorine atom-containing group, still more preferably a sulfonium salt of fluoro-substituted alkanesulfonic acid, fluorine-substituted benzenesulfonic acid, fluorine-substituted imide acid or fluorine-substituted methide acid. In particular, the acid generator which can be used is preferably a compound capable of generating a fluoro-substituted alkanesulfonic acid, a fluoro-substituted benzenesulfonic acid or a fluoro-substituted imide acid, where pKa of the acid generated is −1 or less, and in this case, the sensitivity can be enhanced.

The compound capable of generating the above-described acid is preferably a compound capable of generating an acid represented by the following formula (1):

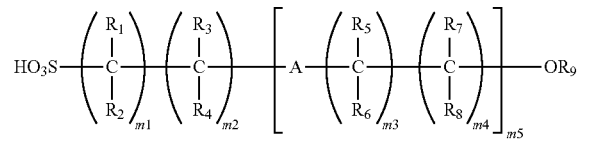

(1)

In formula (1), each of $R_1$ to $R_8$ independently represents a hydrogen atom, an alkyl group, a cycloalkyl group, a halogen atom or a hydroxyl group. $R_9$ represents a hydrogen atom, an alkyl group, a cycloalkyl group, an alkenyl group, —CORx or —SO$_2$Rs. A represents a heteroatom-containing divalent linking group or a single bond. Rx represents an alkyl group, a cycloalkyl group, an aryl group or a heteroaryl group. Rs represents an alkyl group, a cycloalkyl group or an aryl group. Each of m1 to m4 independently represents an integer of 0 to 12, provided that m3+m4≥1. m5 represents an integer of 1 to 3. When any of m1 to m5 is an integer of 2 or more, a plurality of members for each of $R_1$ to $R_8$ and A may be the same or different.

Here, the alkyl group, cycloalkyl group and alkenyl group may have a fluorine atom as the substituent. Also, Rs may further have one or more substituents, and examples of the substituent include an alkyl group (preferably a linear or branched alkyl group having a carbon number of 1 to 4) and an alkoxy group (preferably a linear or branched alkoxy group having a carbon number of 1 to 4).

The heteroatom-containing divalent linking group of A includes an oxygen atom, —CO—, —CONR—, —SO$_2$NR—, —CONRCO—, —SO$_2$NRCO—, —SO$_2$NRSO$_2$— and —OCONR—, wherein R represents a hydrogen atom, an alkyl group or a cycloalkyl group.

Each of $R_1$ to $R_8$ is independently, preferably a hydrogen atom, a perfluoroalkyl group or a fluorine atom, more preferably a perfluoroalkyl group or a fluorine atom. A is preferably a single bond or an oxygen atom. $R_9$ is preferably an acyl group represented by —CORx. Rx is preferably a cycloalkyl group or an aryl group. In formula (1), the carbon atom adjacent to SO$_3$H is preferably substituted by a fluorine atom or a trifluoromethyl group.

The compound capable of generating an acid having a structure represented by formula (1) is preferably a structure represented by the following formula (1-A):

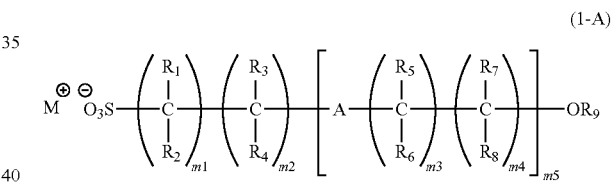

(1-A)

In formula (1-A), $R_1$ to $R_9$, A and m1 to m5 have the same meanings as $R_1$ to $R_9$, A and m1 to m5 in formula (1), respectively, and M$^+$ represents an organic counter cation.

The organic counter ion represented by M$^+$ is preferably an iodonium or sulfonium ion, more preferably sulfonium ion.

Examples of the organic counter ion represented by M$^+$ include cations in formulae (ZI) and (ZII) and a cation represented by formula (IIId) described later.

The onium cation M$^+$ is more preferably a cation in the compound represented by formula (ZI-4).

The acid represented by formula (1) is more preferably a structure represented by the following formulae (1-B) to (1-D):

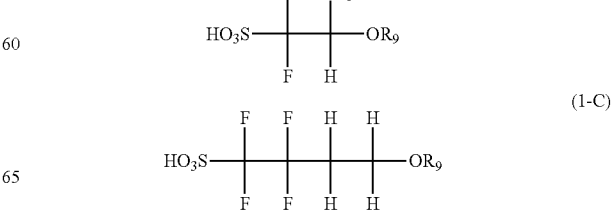

(1-B)

(1-C)

-continued

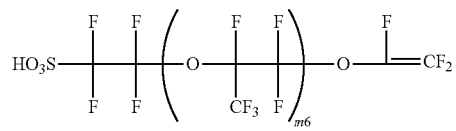
(1-D)

In formulae (1-B) to (1-D), $R_9$ has the same meaning as $R_9$ in formula (1), and m6 represents an integer of 0 to 2.

The compound capable of generating an acid represented by formula (1) is more preferably a structure represented by the following formulae (1-E) to (1-G):

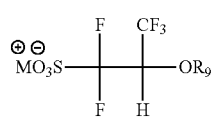
(1-E)

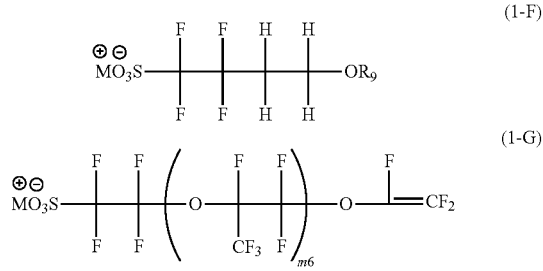

In formulae (1-E) to (1-G), m6 has the same meaning as m6 in formula (1-D) above, and $R_9$ and $M^+$ have the same meanings as $R_9$ and $M^+$ in formula (1-A) above.

Specific examples of the acid generator capable of generating an acid represented by formula (1) are set forth below, but the present invention is not limited thereto. In specific examples, $M^+$ represents the above-described organic counter cation.

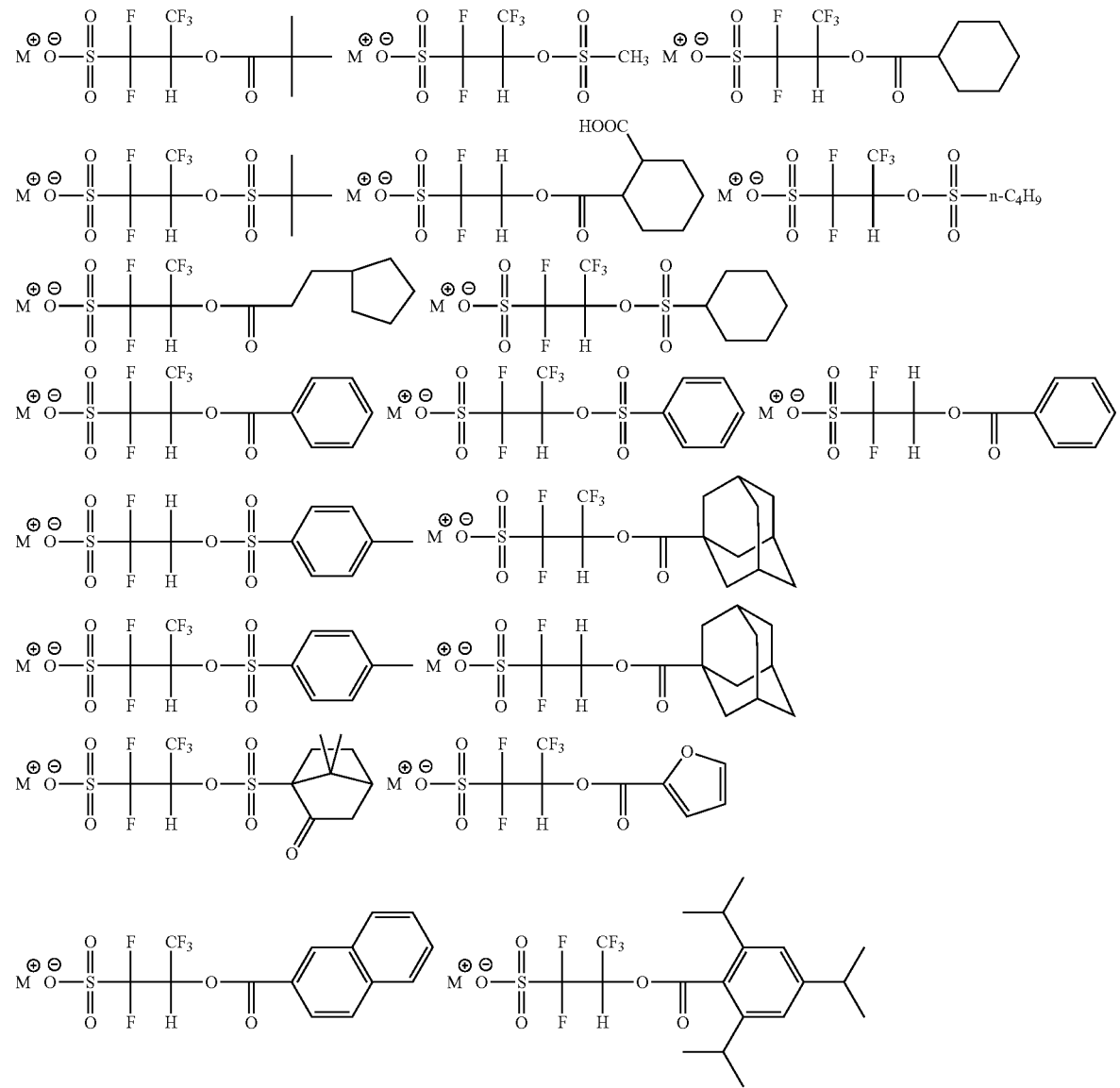

-continued
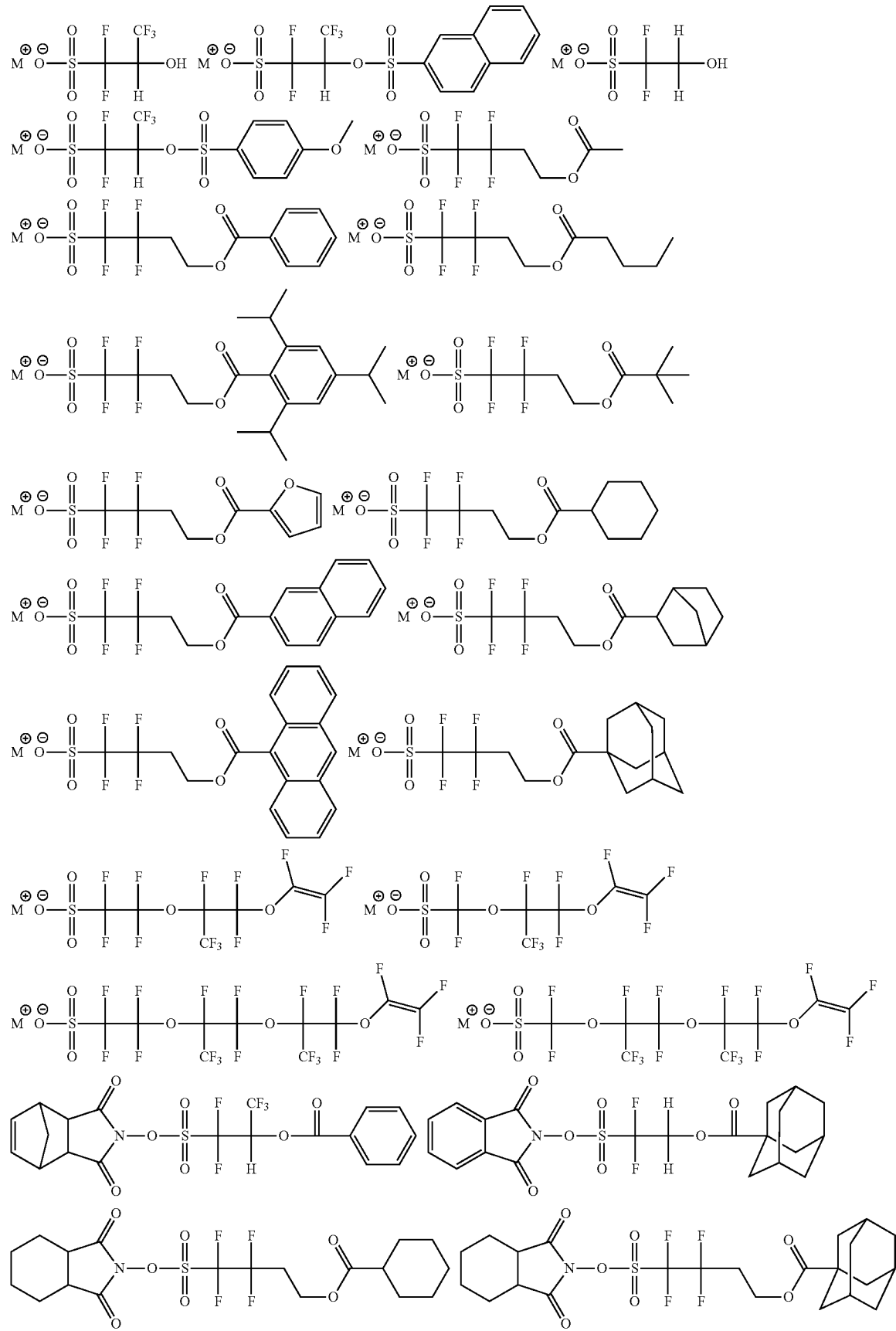

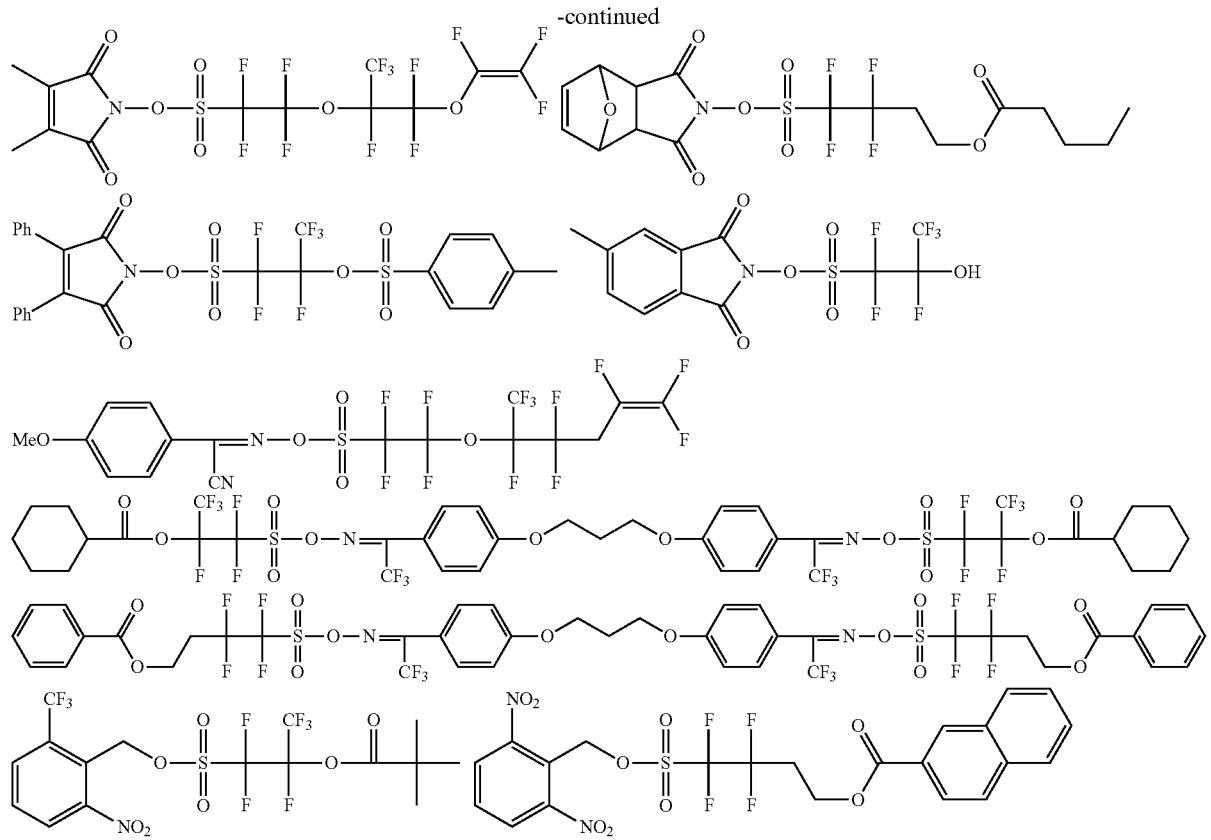

A compound represented by the following formula (I) is also preferred as the acid generator.

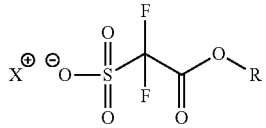

In formula (I), X⁺ represents an organic counter ion, and R represents a hydrogen atom or an organic group.

R represents a hydrogen atom or an organic group and is preferably an organic group having a carbon number of 1 to 40, more preferably an organic group having a carbon number of 3 to 20, and most preferably an organic group represented by the following formula (II).

The organic group of R is sufficient if it has one or more carbon atoms. The organic group is preferably an organic group where the atom bonded to the oxygen atom in the ester bond shown in formula (1) is a carbon atom, and examples thereof include an alkyl group, a cycloalkyl group, an aryl group, an aralkyl group and a group having a lactone structure. The organic group may contain a heteroatom such as oxygen atom and sulfur atom in the chain. Also, one of these groups may have another as a substituent, or the organic group may have a substituent such as hydroxyl group, acyl group, acyloxy group, oxo group (=O) or halogen atom.

—(CH$_2$)$_n$—Rc-(Y)$_m$ (II)

In formula (II), Rc represents a monocyclic or polycyclic organic group (preferably having a carbon number of 3 to 30) which may contain a cyclic ether, cyclic thioether, cyclic ketone, cyclic carbonate, lactone or lactam structure.

Y represents a hydroxyl group, a halogen atom, a cyano group, a carboxyl group, a hydrocarbon group (preferably having a carbon number of 1 to 10), a hydroxyalkyl group (preferably having a carbon number of 1 to 10), an alkoxy group (preferably having a carbon number of 1 to 10), an acyl group (preferably having a carbon number of 2 to 10), an alkoxycarbonyl group (preferably having a carbon number of 2 to 10), an acyloxy group (preferably having a carbon number of 2 to 10), an alkoxyalkyl group (preferably having a carbon number of 2 to 10), or an alkyl halide group (preferably having a carbon number of 1 to 8).

m represents an integer of 0 to 6, and when a plurality of Y's are present, each Y may be the same as or different from every other Y.

n represents an integer of 0 to 10.

The total number of carbon atoms constituting the organic group represented by formula (II) is preferably 40 or less.

It is preferred that n is an integer of 0 to 3 and RC is a monocyclic or polycyclic organic group having a carbon number of 7 to 16.

The molecular weight of the compound represented by formula (I) is generally from 300 to 1,000, preferably from 400 to 800, more preferably from 500 to 700.

Examples of the organic counter ion of X⁺ include sulfonium cation and iodonium cation.

The preferred embodiment of the compound represented by formula (I) includes compounds represented by formulae (Z$_{SC1}$) and V$_{IC1}$).

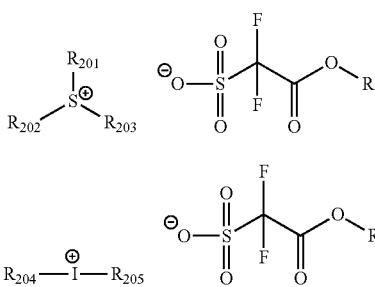

In formula ($Z_{SC1}$), the definition and preferred range of R are the same as those defined in formula (I).

Each of $R_{201}$, $R_{202}$ and $R_{203}$ independently represents an organic group.

Specific examples, preferred embodiments and the like of the organic group of $R_{201}$, $R_{202}$ and $R_{203}$ are the same as those for $R_{201}$, $R_{202}$ and $R_{203}$ in formula (ZI).

In formula ($Z_{IC1}$), the definition and preferred range of R are the same as those defined in formula (I).

Each of $R_{204}$ and $R_{205}$ independently represents an aryl group, an alkyl group or a cycloalkyl group.

Specific examples and preferred embodiments of the aryl group, alkyl group and cycloalkyl group of $R_{204}$ and $R_{205}$ are the same as those described above for the aryl group, alkyl group and cycloalkyl group of $R_{204}$ and $R_{205}$ in formulae (ZII) and (ZIII).

The compound may be a compound having a plurality of structures represented by formula ($Z_{SC1}$). For example, the compound may be a compound having a structure where at least one of $R_{201}$ to $R_{203}$ in the compound represented by formula ($Z_{SC1}$) is bonded to at least one of $R_{201}$ to $R_{203}$ in another compound represented by formula ($Z_{SC1}$).

The compound represented by formula (I) can be synthesized by a known method, for example, in accordance with the method described in JP-A-2007-161707.

As for the acid generator, a compound capable of generating an acid represented by formula (I-A) or (I-B) upon irradiation with an actinic ray or radiation is also preferred.

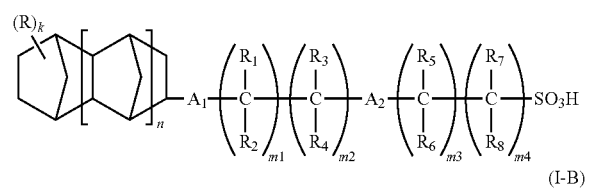

(I-A)

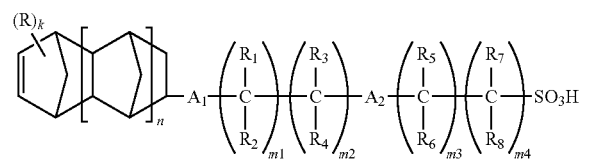

(I-B)

In formulae (I-A) and (I-B), each of $R_1$ to $R_8$ independently represents a hydrogen atom, an alkyl group, a cycloalkyl group, a halogen atom or a hydroxyl group, provided that at least one of $R_1$ to $R_8$ is a fluorine atom or a fluorine atom-containing group.

Each of $A_1$ and $A_2$ independently represents a divalent linking group or a single bond.

R represents a substituent. When a plurality of R's are present, two or more R's may combine to form a ring.

k represents an integer of 0 to 5, n represents an integer of 0 to 5, and each of m1 to m4 independently represents an integer of 0 to 12, provided that at least one of m1 to m4 is an integer of 1 or more.

Examples of the divalent linking group of $A_1$ and $A_2$ include —O—, —S—, a carbonyl group, an ester group, a sulfinyl group, a sulfonyl group, a methylene group, a 1,1-ethylene group, a 1,2-ethylene group, a propylene group, a 1-methylpropylene group, a 1-ethylpropylene group, a trimethylene group, a difluoromethylene group, a tetrafluoro-1,2-ethylene group, a 1,2-phenylene group, a 1,3-phenylene group, a 1,4-phenylene group, and a group formed by combining two or more of these groups. Among these divalent groups, a carbonyl group, an ester group, a methylene group, a difluoromethylene group and a tetrafluoro-1,2-ethylene group are preferred.

Examples of the substituent of R include an oxo group (=O), a hydroxyl group, a carboxyl group, a formyl group, an alkyl group (linear or branched, preferably having a carbon number of 1 to 10), a vinylidene group (linear or branched, preferably having a carbon number of 1 to 10), a monovalent cyclic organic group (preferably having a carbon number of 3 to 12), an aryl group (preferably having a carbon number of 6 to 20), an alkoxy group (linear or branched, preferably having a carbon number of 1 to 10), an aryloxy group (preferably having a carbon number of 6 to 20), an alkylcarbonyl group (linear or branched, preferably having a carbon number of 2 to 10), an arylcarbonyl group (preferably having a carbon number of 7 to 20), an alkoxycarbonyl group (linear or branched, preferably having a carbon number of 2 to 10) and an aryloxycarbonyl group (preferably having a carbon number of 7 to 20).

The substituent of R is preferably an oxo group (=O), an alkyl group, an alkoxy group, an alkylcarbonyl group (linear or branched, preferably having a carbon number of 2 to 10) or an alkoxycarbonyl group.

Examples of the alkyl group include a methyl group, an ethyl group, an n-propyl group, an i-propyl group, an n-butyl group, a tert-butyl group, an n-pentyl group, an n-hexyl group, an n-heptyl group, an n-octyl group, an n-nonyl group and an n-decyl group.

Examples of the vinylidene group include a carbenzyl group, a 1,1-ethylidenyl group, a propylidenyl group, a 1-methylpropylidenyl group and a 1-ethylpropylidenyl group.

Examples of the monovalent cyclic organic group include a cyclopentyl group, a cyclohexyl group, an adamantyl group, a norbornyl group and campholoyl group.

Examples of the aryl group include a phenyl group, an o-tolyl group, an m-tolyl group, a p-tolyl group, a p-hydroxyphenyl group, a 1-naphthyl group, a 1-anthracenyl group and a benzyl group.

Examples of the alkoxy group include a methoxy group, an ethoxy group, an n-propoxy group, an i-propoxy group, an n-butoxy group and a tert-butoxy group.

Examples of the aryloxy group include a phenoxy group, a p-hydroxyphenoxy group, an o-tolyloxy group, an m-tolyloxy group and a p-tolyloxy group.

Examples of the alkylcarbonyl group include a methylcarbonyl group, an ethylcarbonyl group, an n-propylcarbonyl group, an i-propylcarbonyl group, an n-butylcarbonyl group and a tert-butylcarbonyl group.

Examples of the arylcarbonyl group include a phenylcarbonyl group and a benzylcarbonyl group.

Examples of the alkoxycarbonyl group include a methoxycarbonyl group, an ethoxycarbonyl group, an n-propoxycarbonyl group, an i-propoxycarbonyl group, an n-butoxycarbonyl group and a tert-butoxycarbonyl group.

Examples of the aryloxycarbonyl group include a phenoxycarbonyl group and a benzyloxycarbonyl group. These substituents may further have an arbitrary substituent, for example, one or more of the above-mentioned substituents.

R may be bonded any of the carbon atoms constituting the norbornene ring or norbornane ring, and when a plurality of R's are present, each may be the same as or different from every other R. Also, when a plurality of R's are present, two or more R's may combine to form a ring. That is, at least two or more R's may combine with each other to form a ring together with the carbon atom to which these R's are bonded.

k is preferably 0, and n is preferably 0 or 1.

Out of the structure represented by formula (I-A) and the structure represented by formula (I-B), the structure represented by formula (I-A) is preferred in view of absorption strength at a wavelength of 193 nm or the like.

Preferred examples of the acid represented by formulae (I-A) and (I-B) include structures shown by the following formulae.

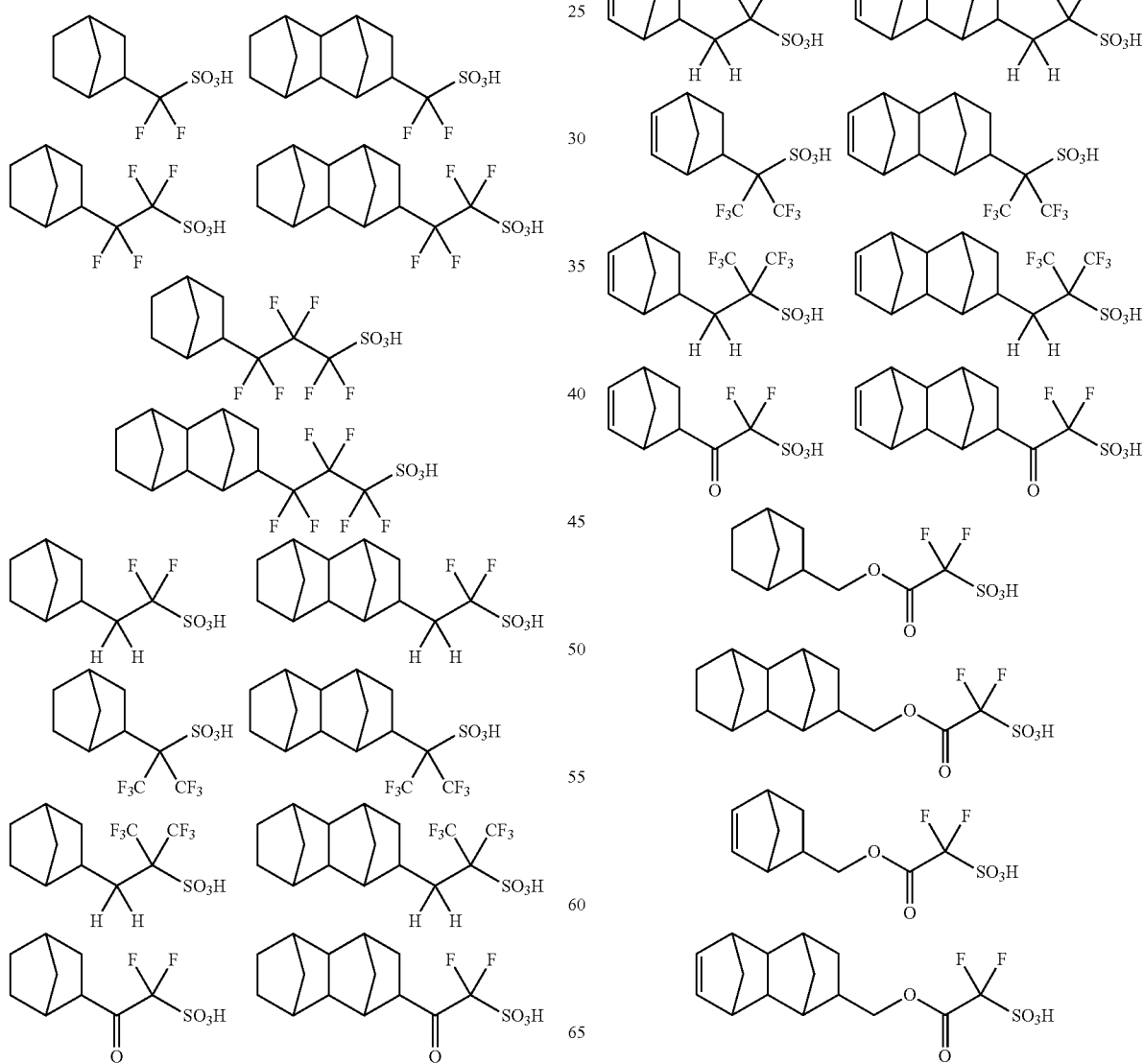

-continued

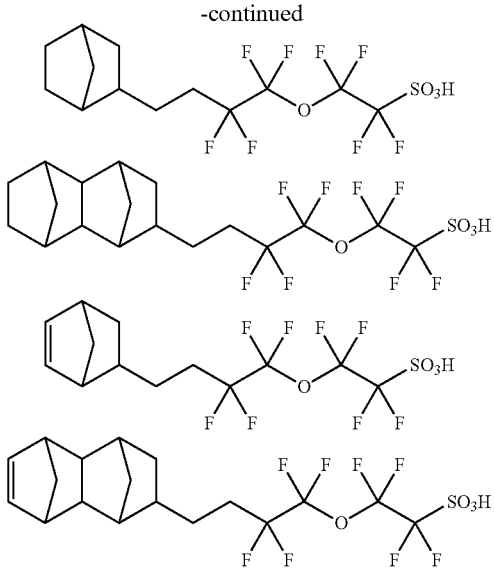

The compound capable of generating an acid represented by formula (I-A) or (I-B) is more preferably a structure represented by the following formula (II-A) or (II-B).

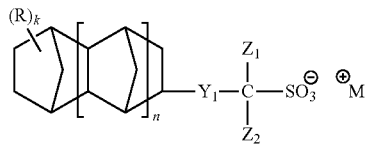

(II-A)

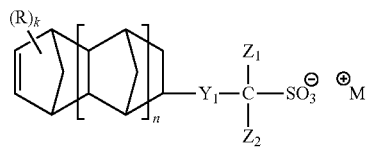

(II-B)

In formulae (II-A) and (II-B), each of $Z_1$ and $Z_2$ independently represents a fluorine atom, a perfluoroalkyl group or a perfluorocycloalkyl group.

$Y_1$ represents a single bond or a divalent linking group.

R represents a substituent. When a plurality of R's are present, two or more R's may combine to form a ring.

$M^+$ represents a monovalent onium cation.

k represents an integer of 0 to 5, and n represents an integer of 0 to 5.

The perfluoroalkyl group of $Z_1$ and $Z_2$ may be linear or branched and is preferably a perfluoroalkyl group having a carbon number of 1 to 10.

The perfluorocycloalkyl group of $Z_1$ and $Z_2$ may be monocyclic or polycyclic and is preferably, for example, a perfluorocyclohexyl group or a perfluorocyclopentyl group.

Examples of the divalent group of $Y_1$ are the same as those for $A_1$ and $A_2$ in formulae (I-A) and (I-B). R, k and n are the same as those in formulae (I-A) and (I-B).

The monovalent onium cation represented by $M^+$ is preferably an iodonium or sulfonium ion, more preferably a sulfonium ion. Specific examples thereof include cations in formulae (ZI) and (ZII), with the cation in formula (ZI) being preferred.

A cation represented by the following formula (IIId) is also preferred.

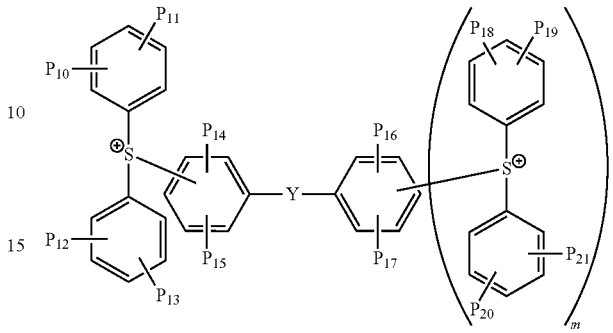

(IIId)

In formula (IIId), each of $P_{10}$ to $P_{21}$ independently represents a hydrogen atom, a hydroxyl group, an alkyl group (preferably having a carbon number of 1 to 12), a cycloalkyl group (preferably having a carbon number of 3 to 12), an alkoxy group (preferably having a carbon number of 1 to 12) or a halogen atom (fluorine, chlorine, bromine, iodine).

Y represents a sulfur atom or an oxygen atom.

m represents 0 or 1.

Examples of the alkyl group, cycloalkyl group and alkoxy group of $P_{10}$ to $P_{21}$ are the same as those for $R_{1c}$ to $R_{5c}$ in formula (ZI-3).

Each of these groups may further have a substituent, and the substituent which each group may further have includes an organic group (preferably an organic group having a carbon number of 1 to 40, more preferably an organic group having a carbon number of 3 to 20. Examples of the organic group include an alkyl group, a cycloalkyl group, an aryl group, an aralkyl group and a lactone structure-containing group, and the organic group may contain a heteroatom such as oxygen atom and sulfur atom in the chain.

One preferred embodiment of the sulfonium ion as $M^+$ in formulae (II-A) and (II-B) is a sulfonium ion represented by the following formula (IIIe):

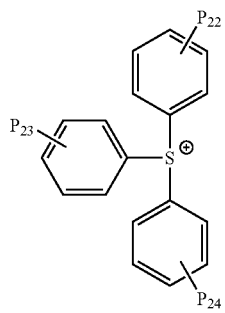

(IIIe)

In the formula, each of $P_{22}$ to $P_{24}$ independently represents a hydrogen atom or an alkyl group (preferably having a carbon number of 1 to 12).

Examples of the alkyl group of $P_{22}$ to $P_{24}$ are the same as those for $R_{1c}$ to $R_{5c}$ in formula (ZI-3).

Each of these groups may further have a substituent, and examples of the substituent which each group may further have are the same as specific examples of the substituent which each of the groups in formula (IIId) may further have.

Out of the acid generators, particularly preferred examples are set forth below.
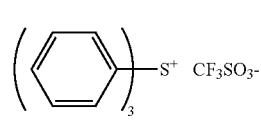 (z1)
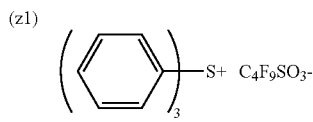 (z2)
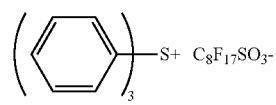 (z3)
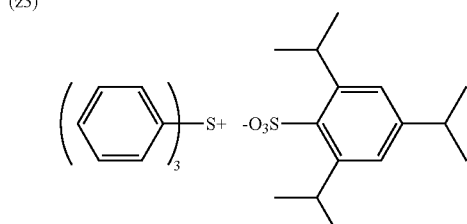 (z4)
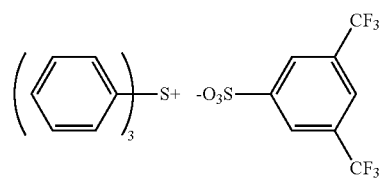 (z5)
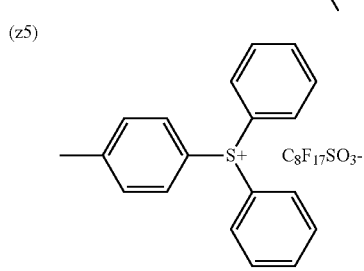 (z6)
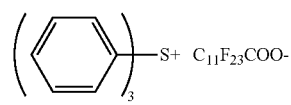 (z7)
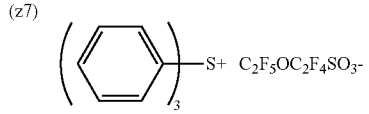 (z8)
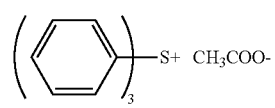 (z9)
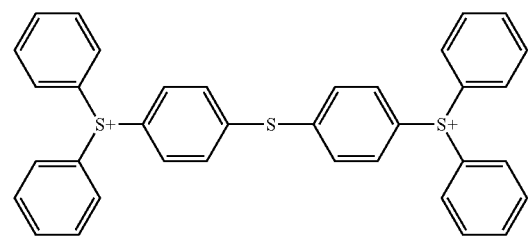 (z10)
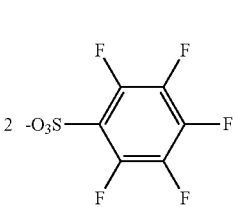 (z11)
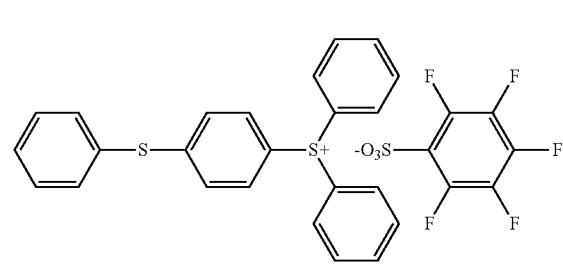 (z12)
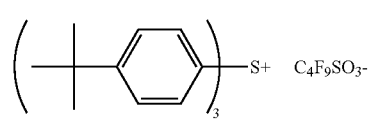 (Z13)
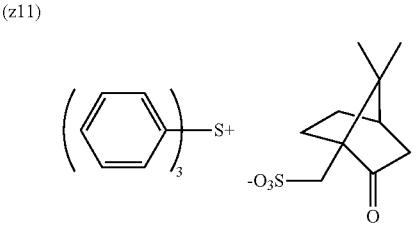 (Z14)

-continued
(z15) 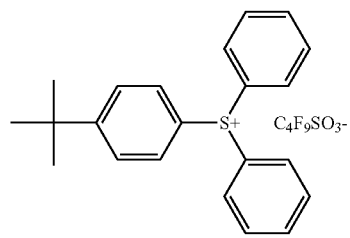
(z16) 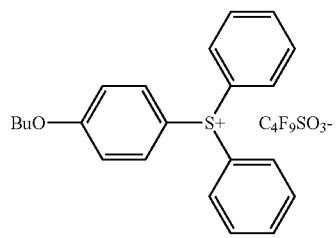
(z17) 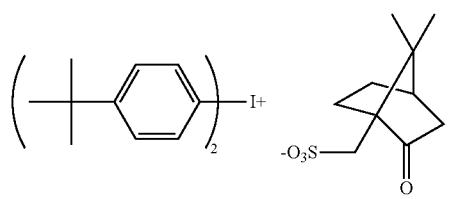
(z18) 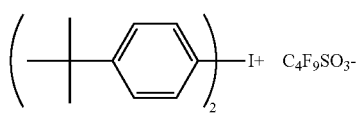
(z19) 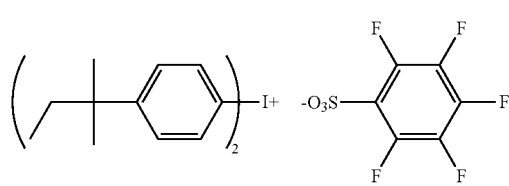
(z20) 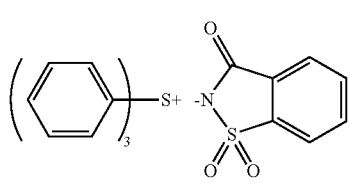
(z21) 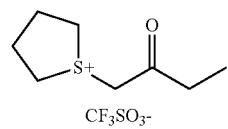
(z22) 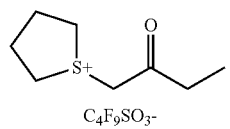
(z23) 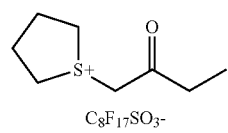
(z24) 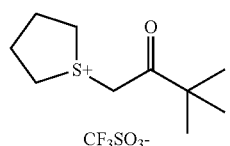
(z25) 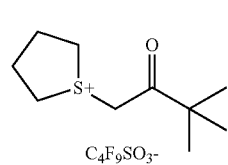
(z26) 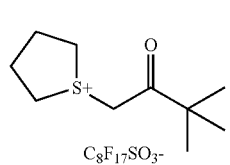
(z27) 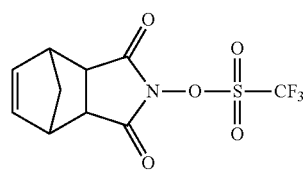
(z28) 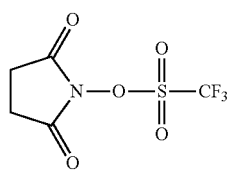
(z29) 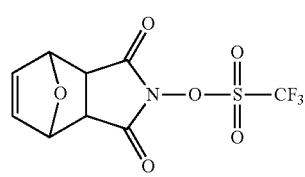
(z30) 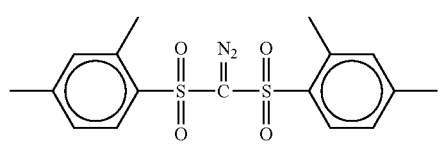
(z31) 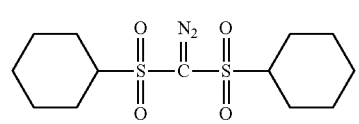
(z32) 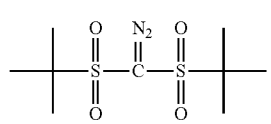

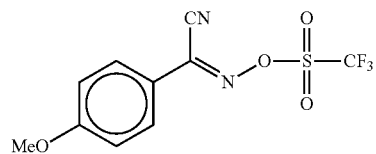 (z33)
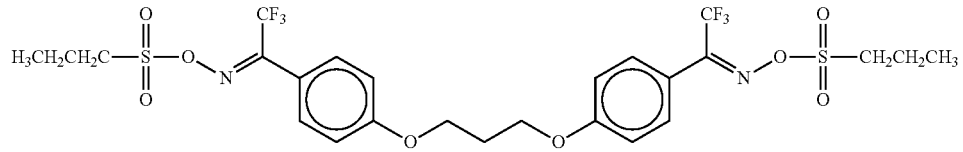 (z34)
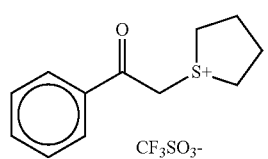 (z35)
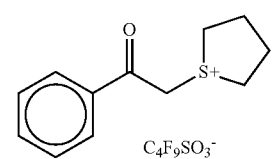 (z36)
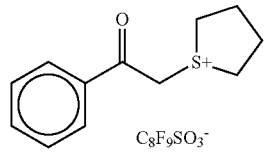 (z37)
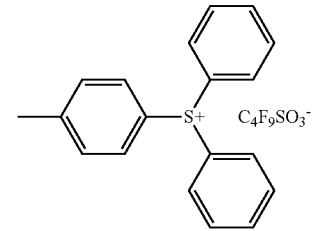 (z38)
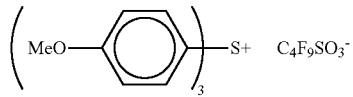 (z39)
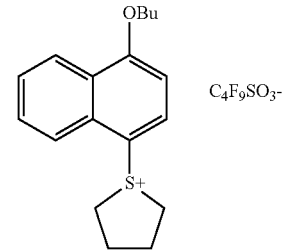 (z40)
 (z41)
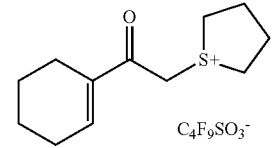 (z42)
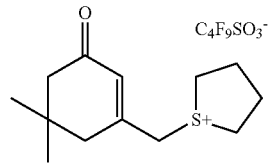 (z43)
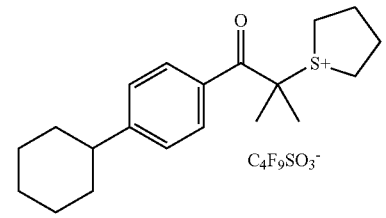 (z44)
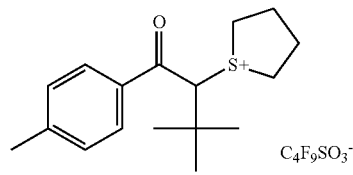 (z45)
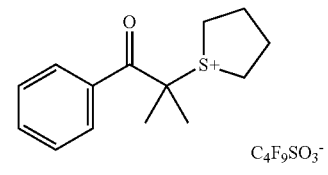 (z46)

-continued
(z47) 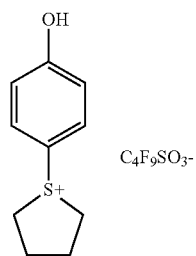
(z48) 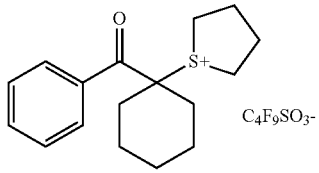
(z49) 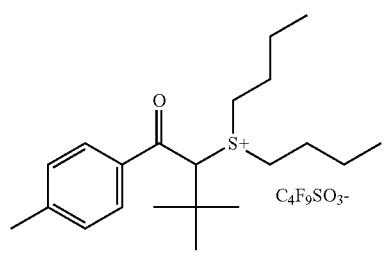
(z50) 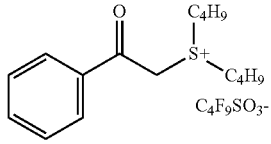
(z51) 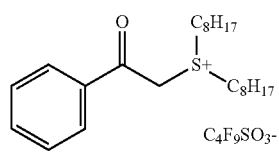
(z52) 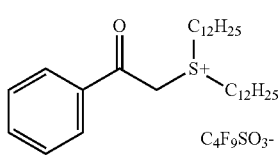
(z53) 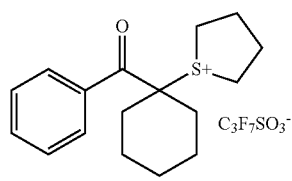
(z54) 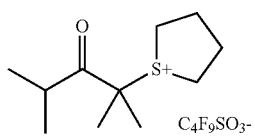
(z55) 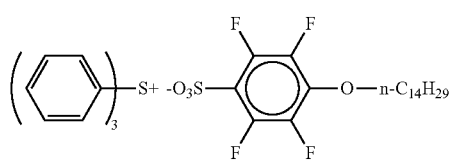
(z56) 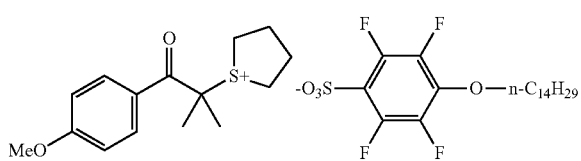
(Z57) 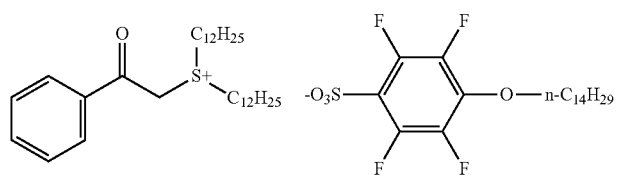
(z58) 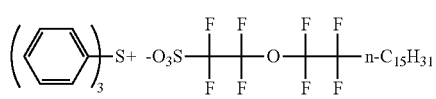
(z59) 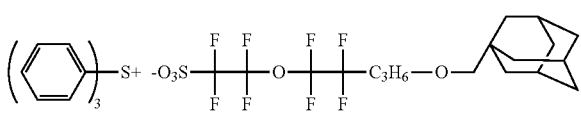
(z60) 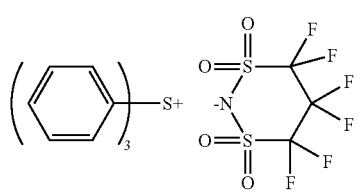
(z61) 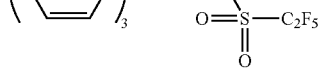

-continued
(z62) 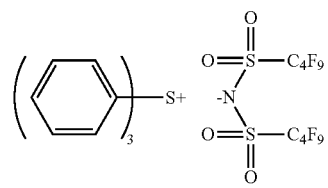
(z63) 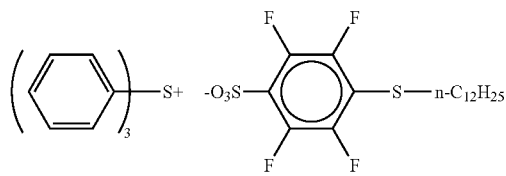
(z64) 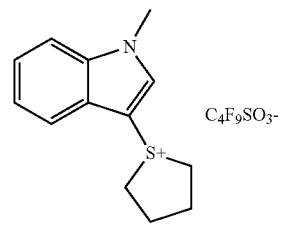
(z65) 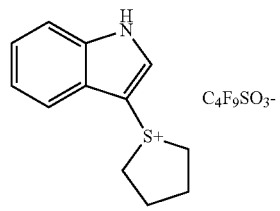
(z66) 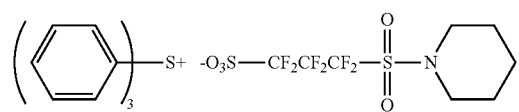
(z67) 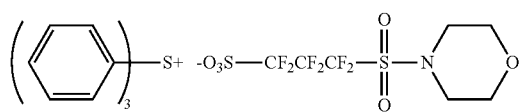
(z68) 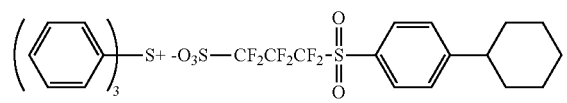
(z69) 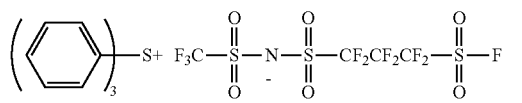
(z70) 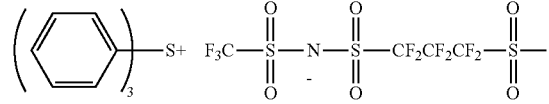
(z71) 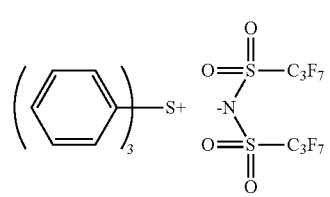
(z72) 
(z73) 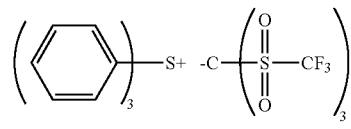
(z74) 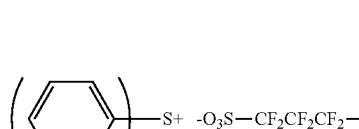
(z75)
(z76)
(z77)
(z78) 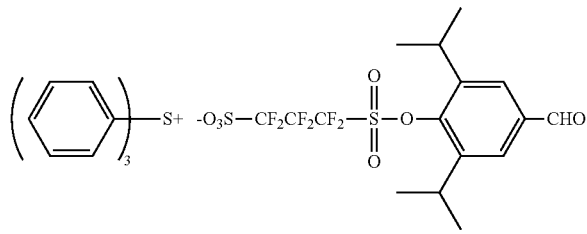

-continued
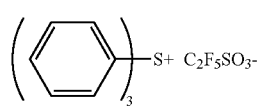 (z79)
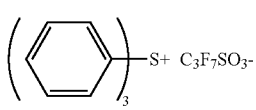 (z80)
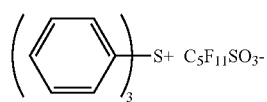 (z81)
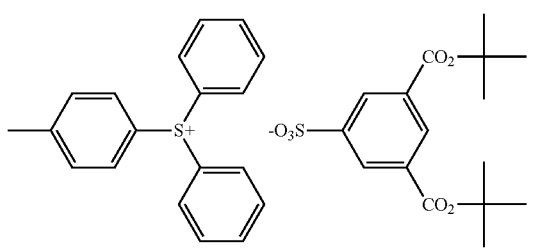 (z82)
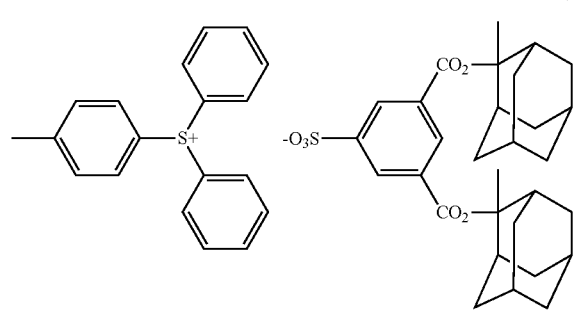 (z83)
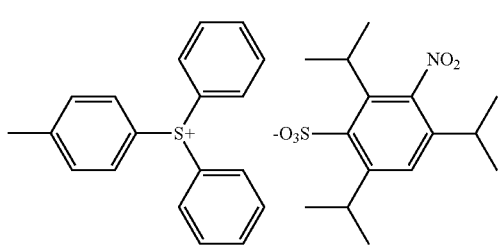 (z84)
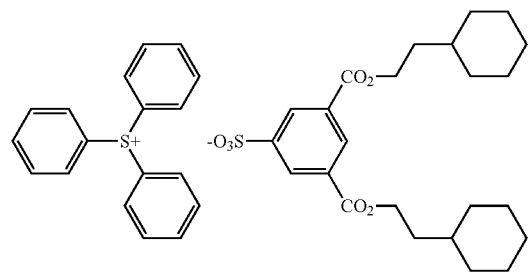 (z85)
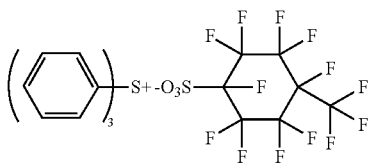 (z86)
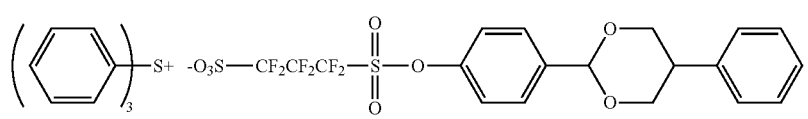 (z87)
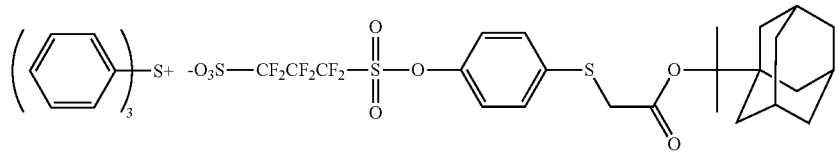 (z88)
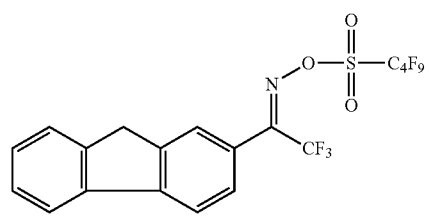 (z89)
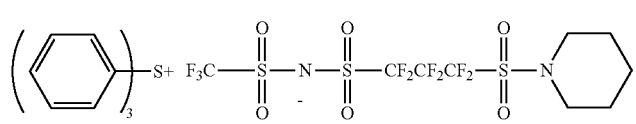 (z90)

(z91)
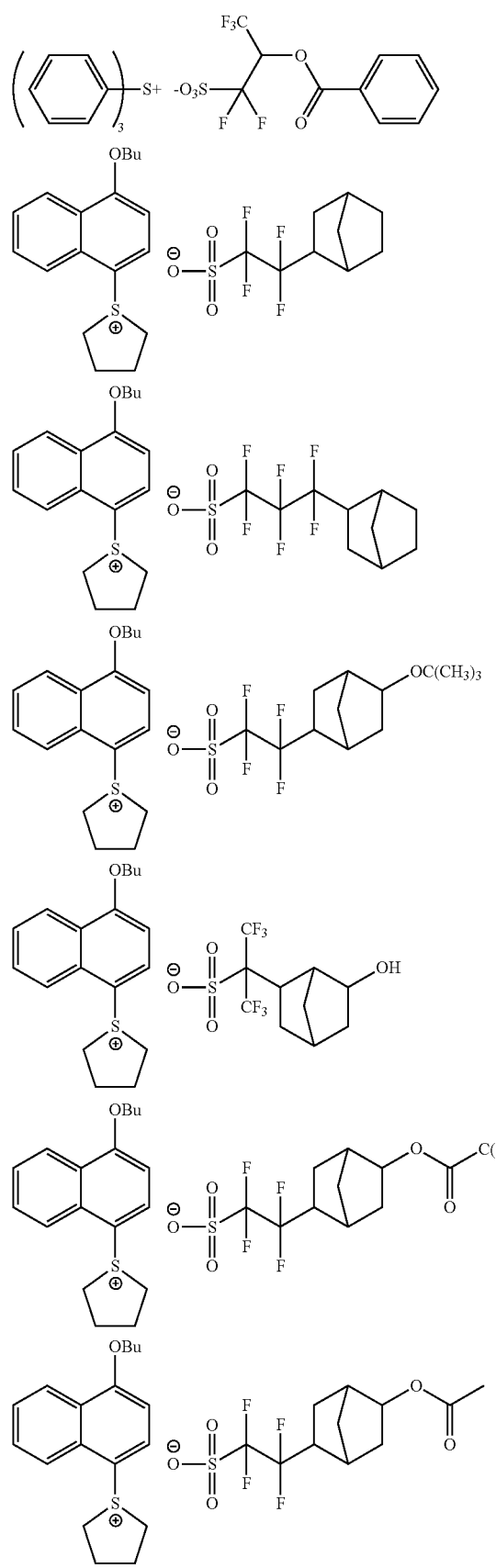
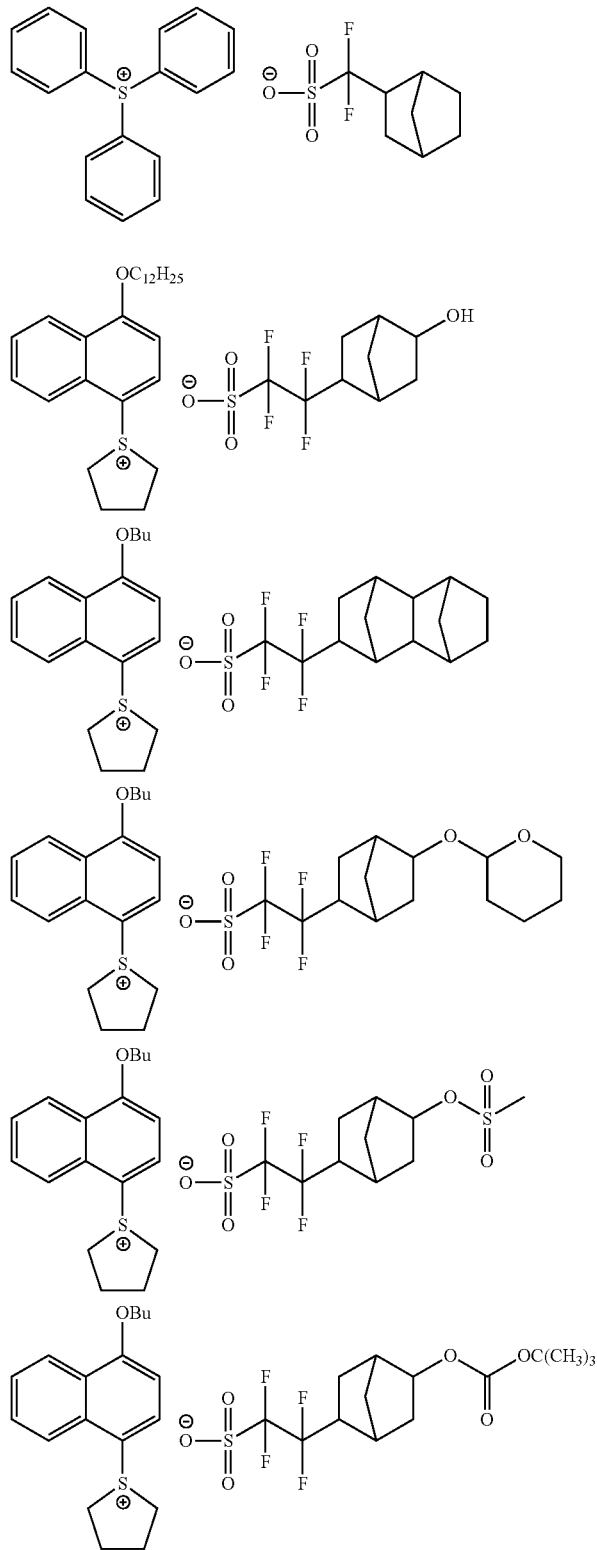

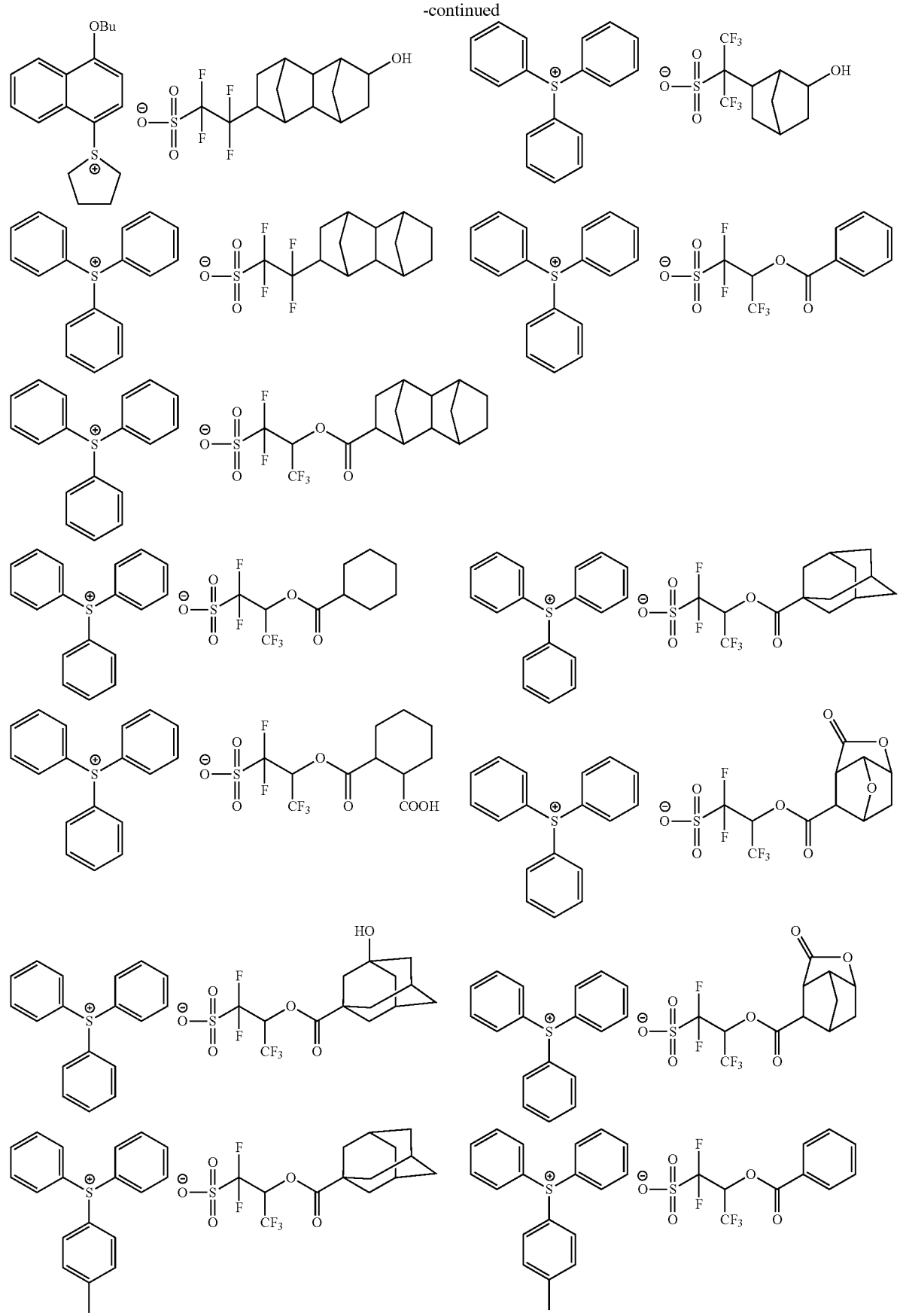

-continued
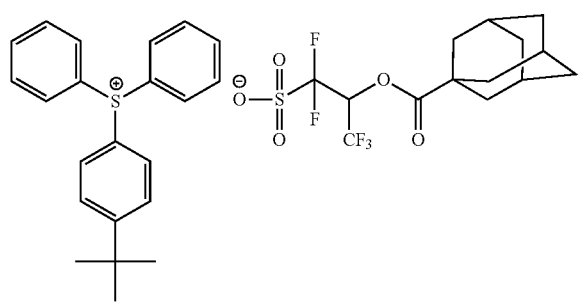
(Y-1)
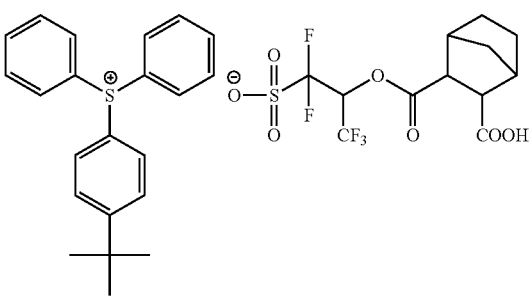
(Y-2)
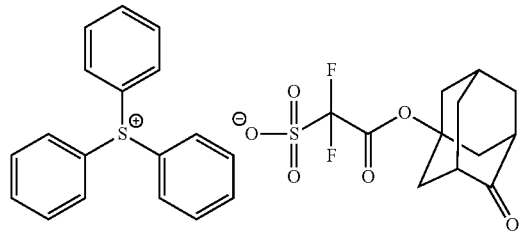
(Y-3)
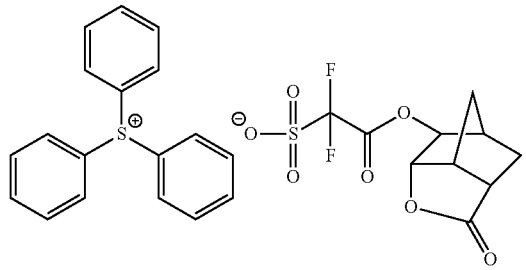
(Y-4)
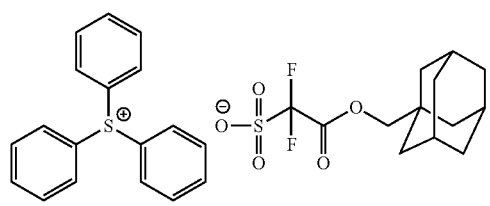
(Y-5)
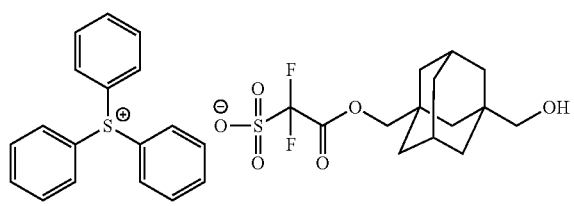
(Y-6)
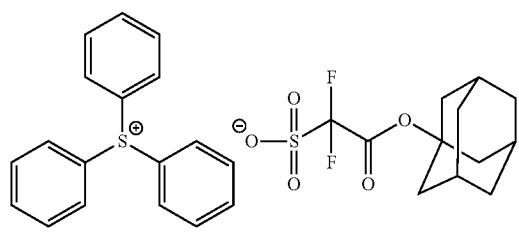
(Y-7)
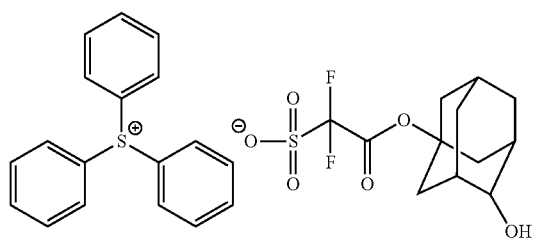
(Y-8)
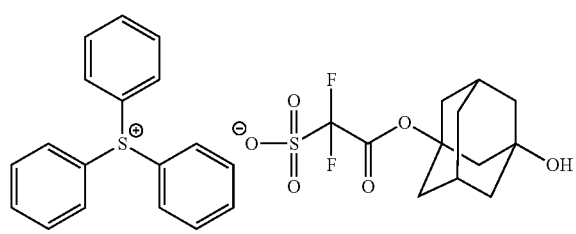
(Y-9)
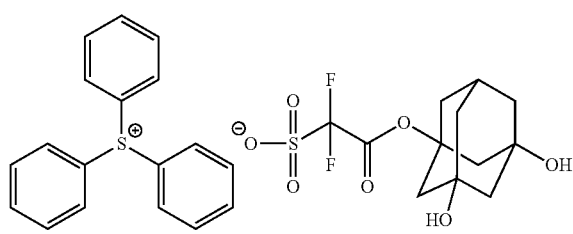
(Y-10)
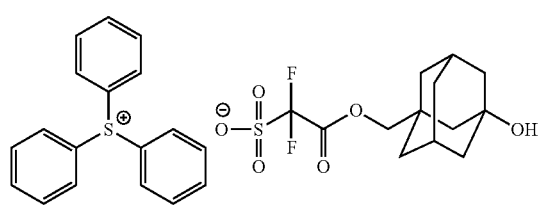

-continued
(Y-11)
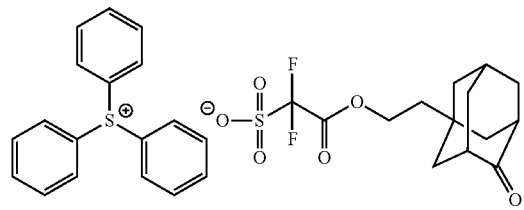
(Y-12)
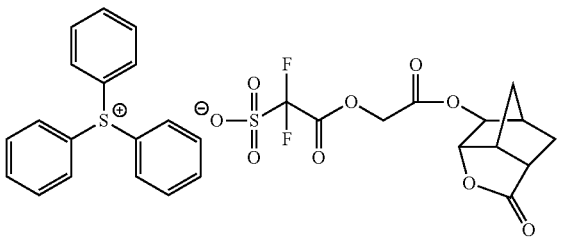
(Y-13)
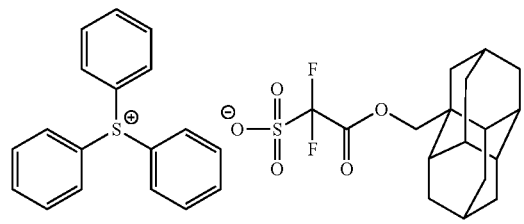
(Y-14)
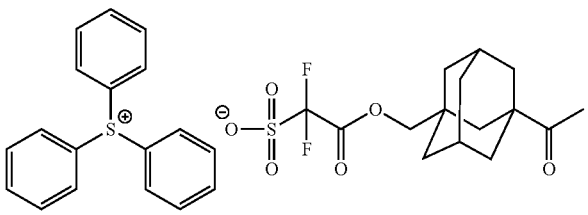
(Y-15)
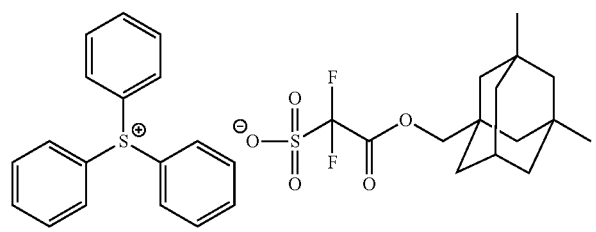
(Y-16)
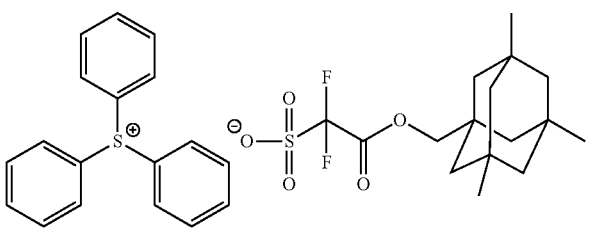
(Y-17)
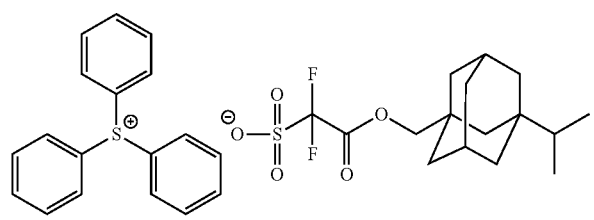
(Y-19)
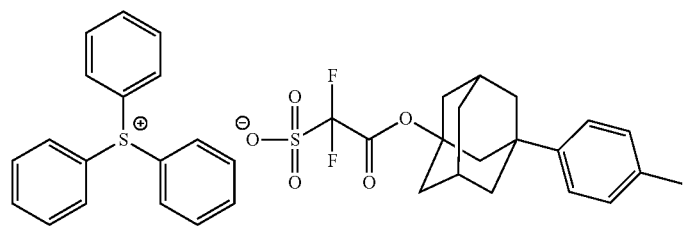
(Y-20)
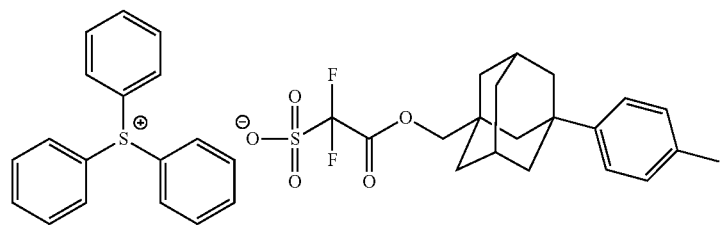

-continued
(Y-21)
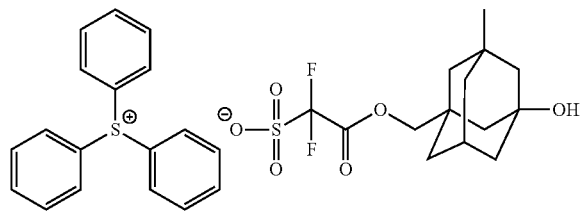
(Y-22)
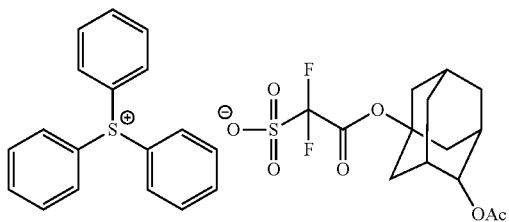
(Y-23)
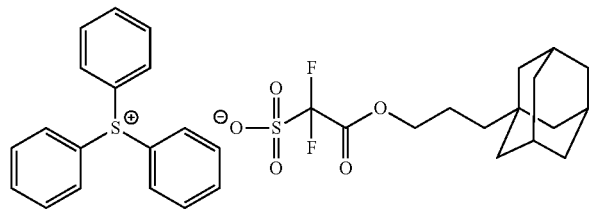
(Y-24)
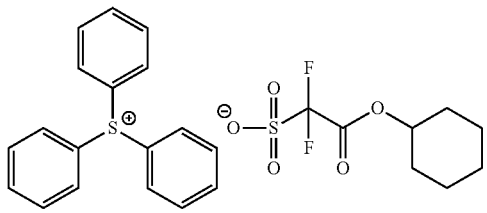
(Y-25)
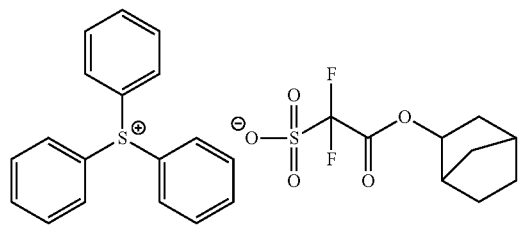
(Y-26)
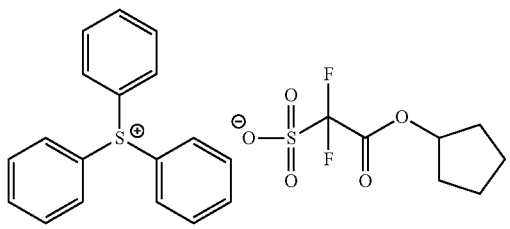
(Y-27)
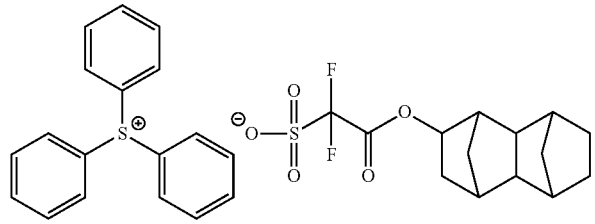
(Y-28)
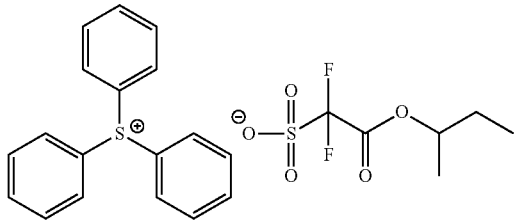
(Y-29)
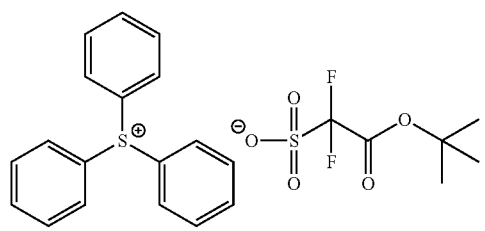
(Y-30)
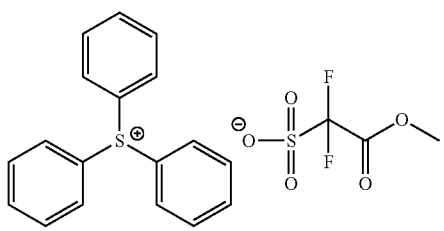
(Y-31)
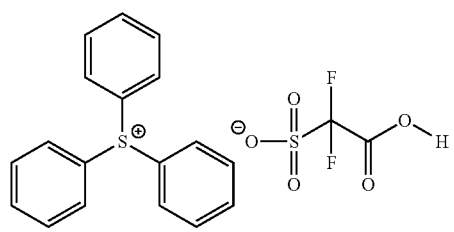
(Y-32)
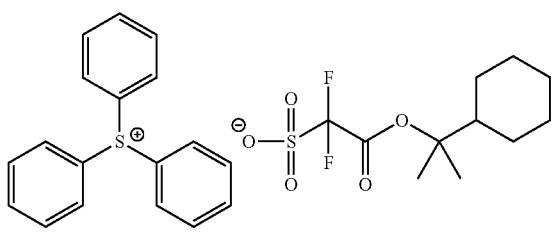

-continued
(Y-33)
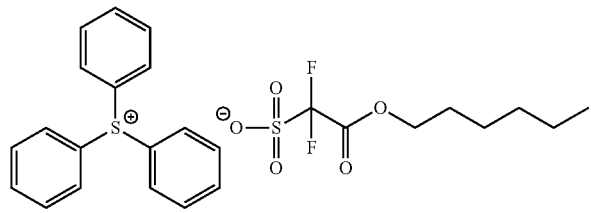
(Y-34)
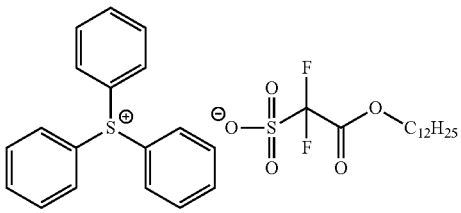
(Y-35)
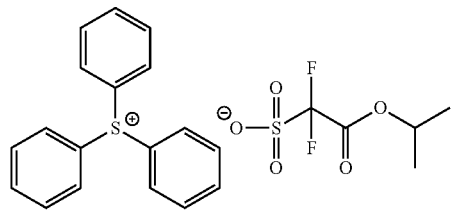
(Y-36)
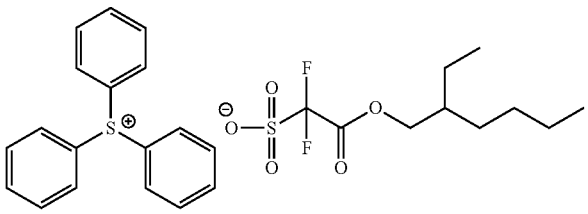
(Y-37)
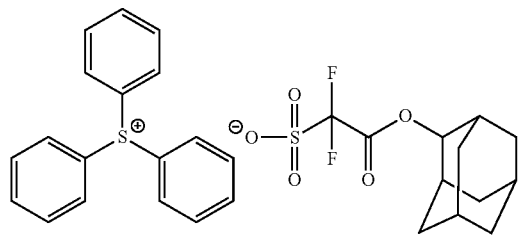
(Y-38)
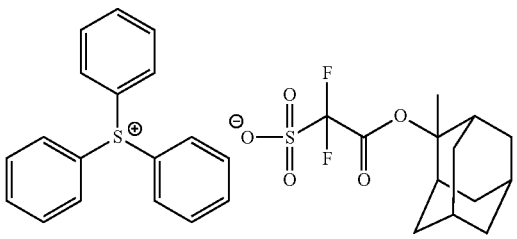
(Y-39)
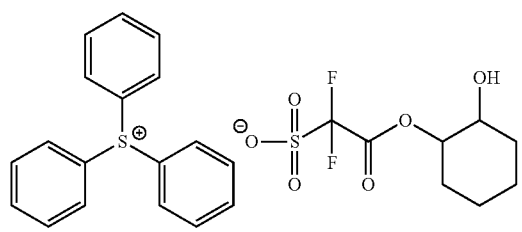
(Y-40)
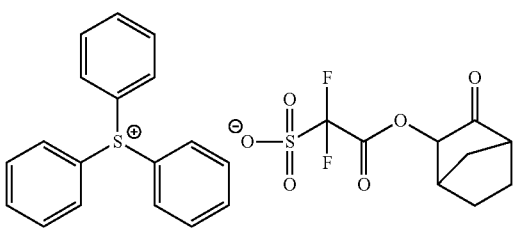
(Y-41)
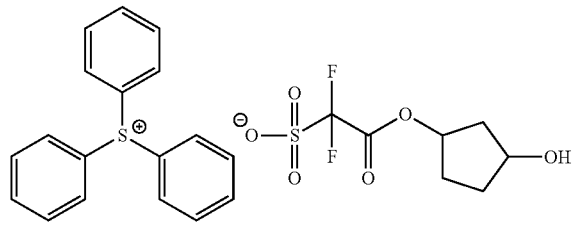
(Y-42)
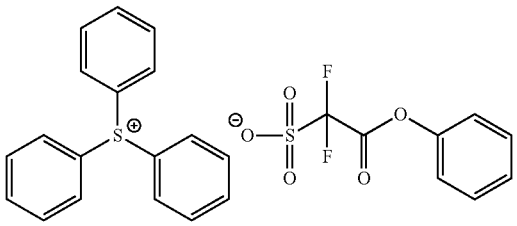
(Y-43)
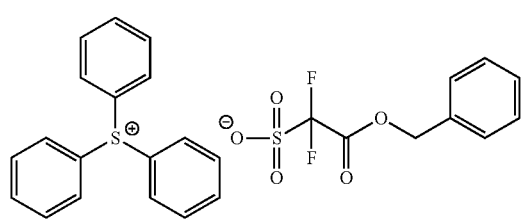
(Y-44)
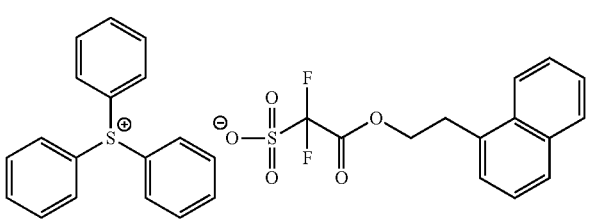

-continued
(Y-45)
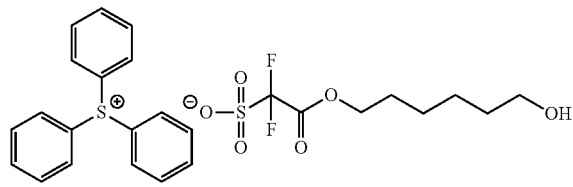
(Y-46)
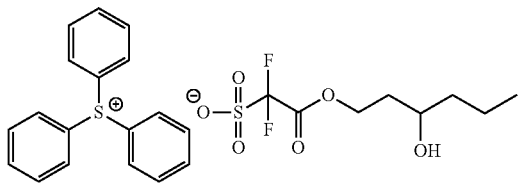
(Y-47)
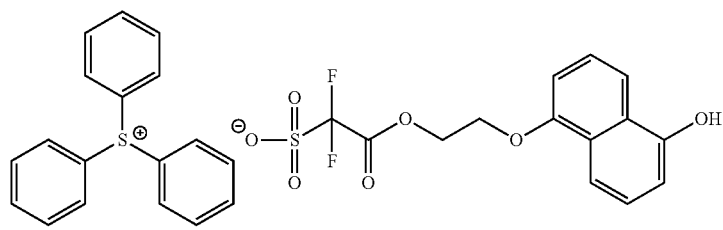
(Y-48)
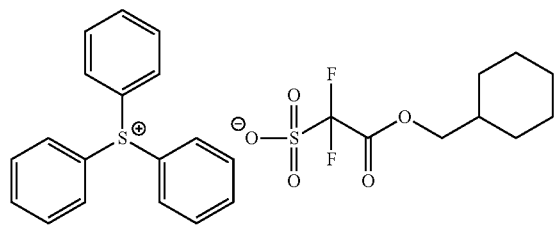
(Y-49)
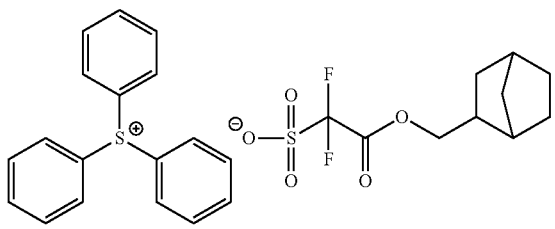
(Y-50)
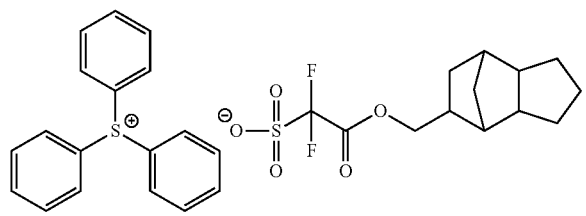
(Y-51)
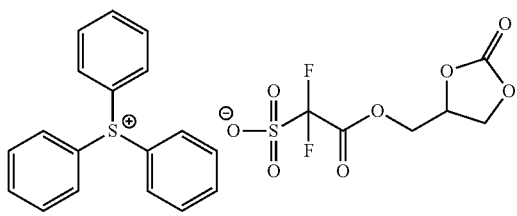
(Y-52)
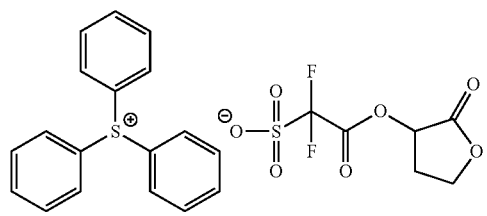
(Y-53)
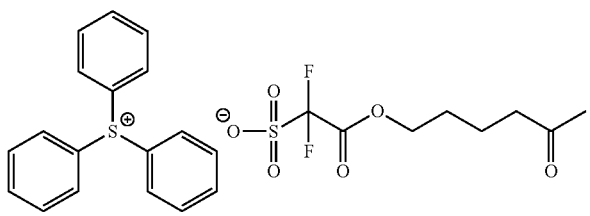
(Y-54)
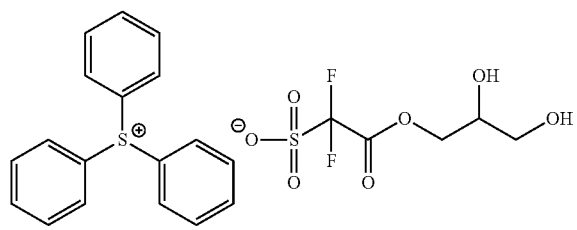
(Y-55)
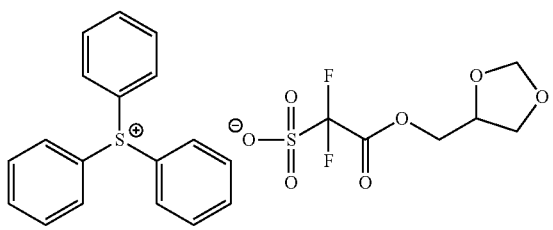

(Y-56)
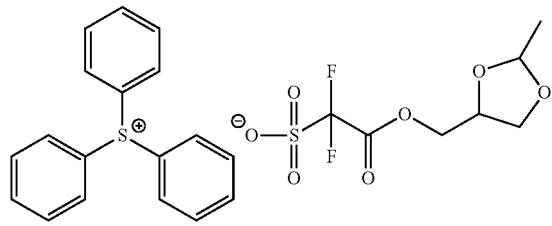
(Y-57)
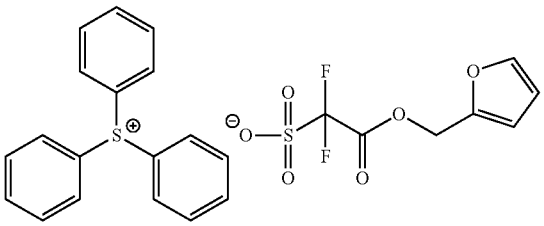
(Y-58)
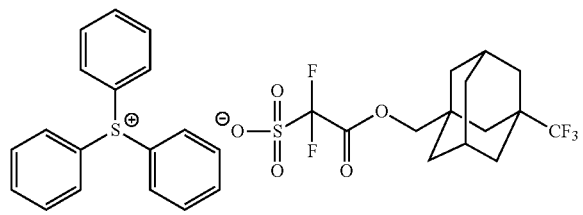
(Y-59)
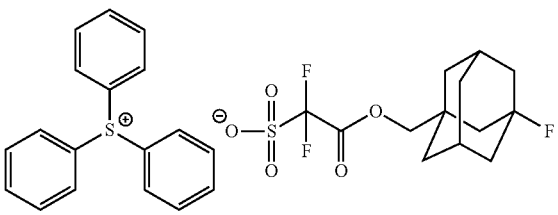
(Y-60)
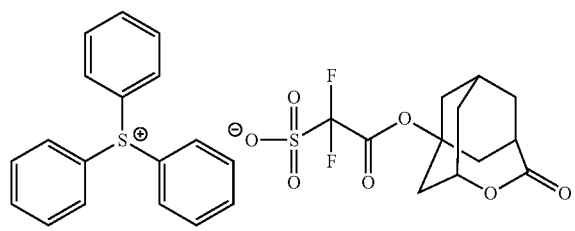
(Y-61)
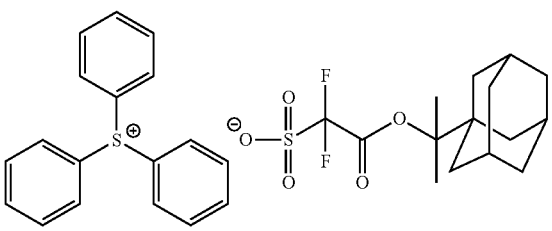
(Y-62)
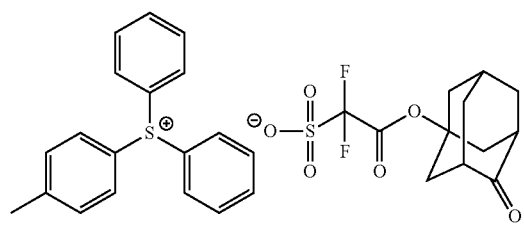
(Y-63)
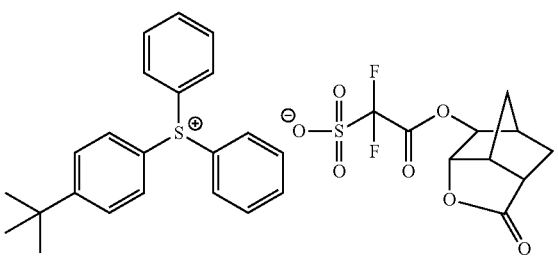
(Y-64)
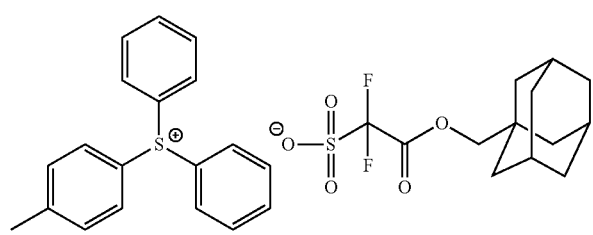
(Y-65)
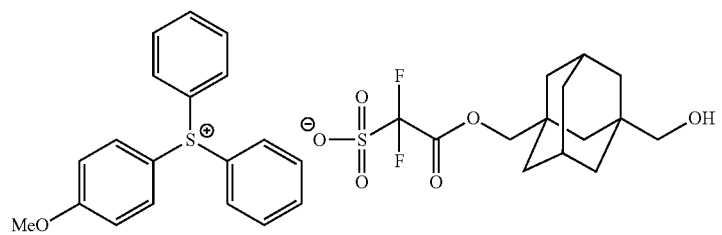

(Y-66)
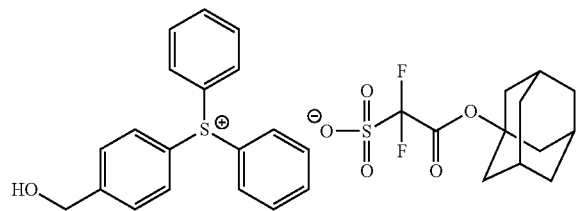
(Y-67)
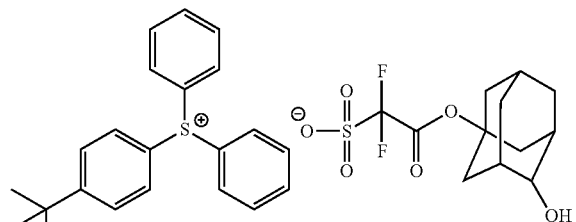
(Y-68)
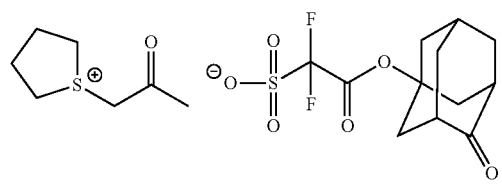
(Y-69)
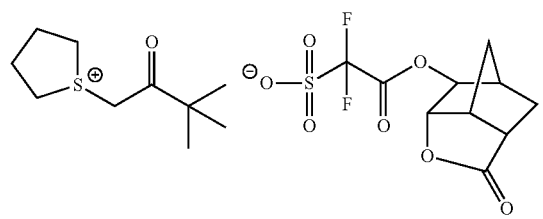
(Y-70)
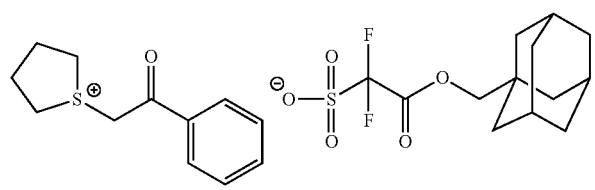
(Y-71)
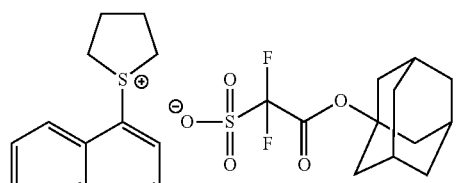
(Y-72)
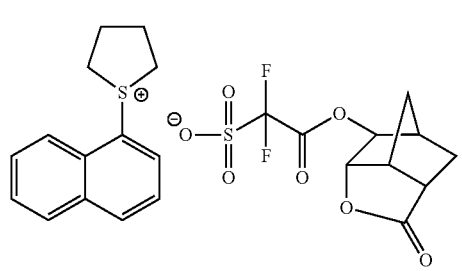
(Y-73)
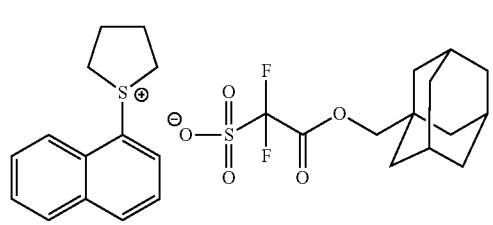
(Y-74)
(Y-75)
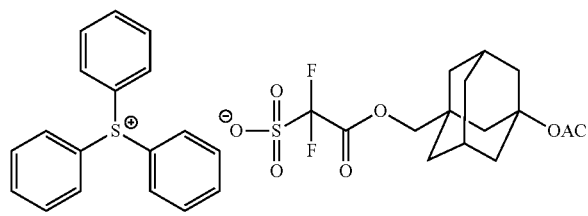
Examples of the compound capable of generating a sulfonic acid represented by formula (I-A) or (I-B) include, but are not limited to, the following compounds.
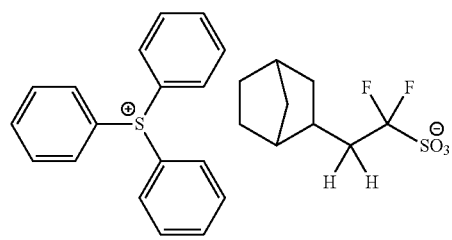
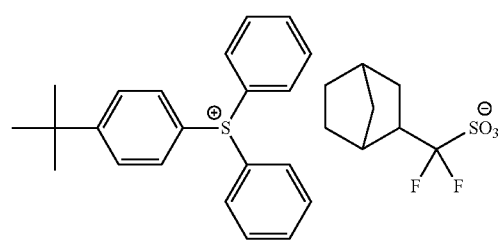

111
-continued
112
-continued
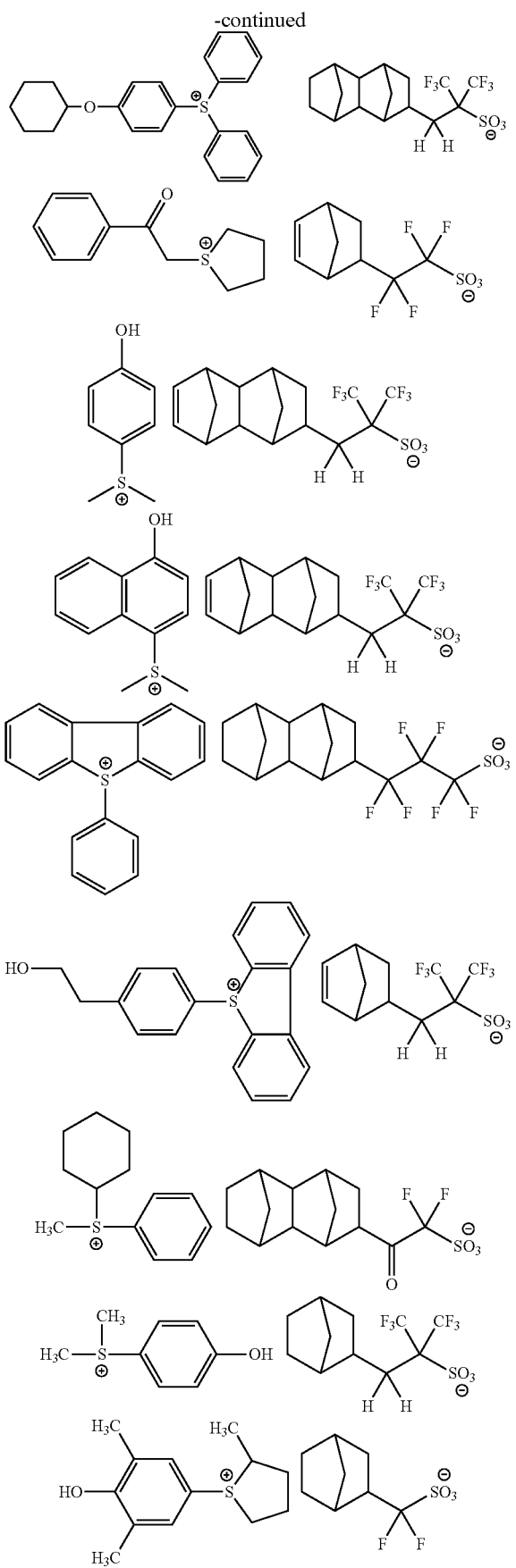
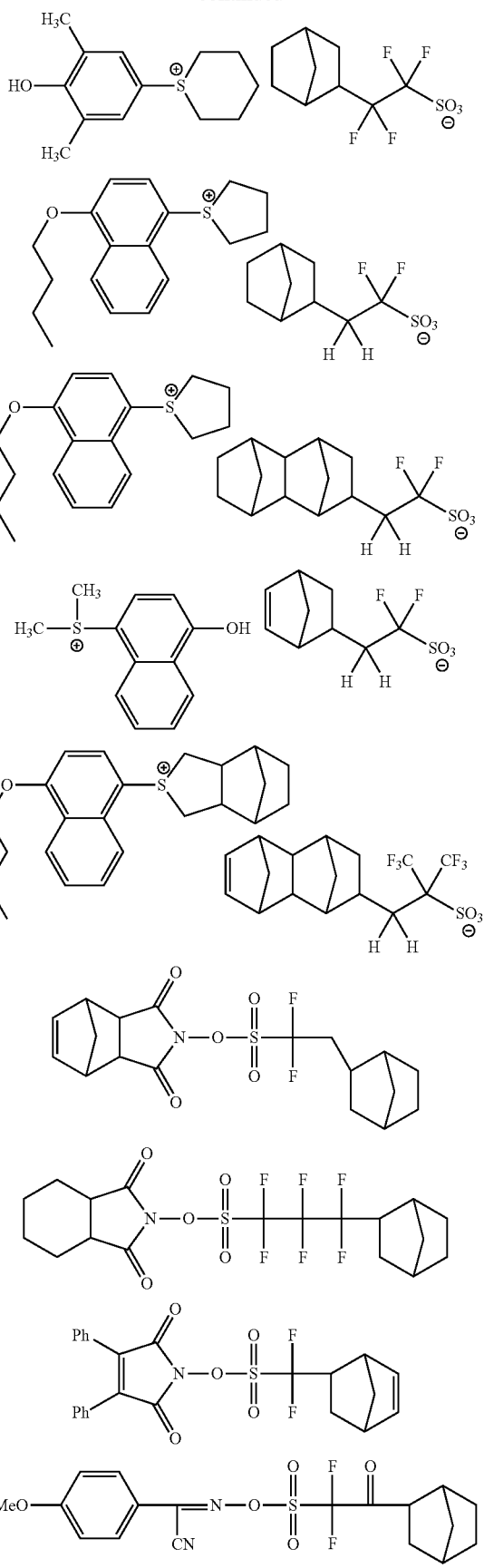

-continued

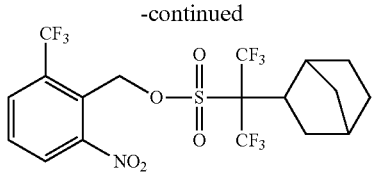

As for the acid generator, one kind may be used alone, or two or more kinds may be used in combination.

The content of the acid generator in the actinic ray-sensitive or radiation-sensitive resin composition is preferably from 0.1 to 30 mass %, more preferably from 0.1 to 20 mass %, still more preferably from 0.5 to 15 mass %, yet still more preferably from 1 to 13 mass %, based on the entire solid content of the actinic ray-sensitive or radiation-sensitive resin composition.

[3] Resin Having at Least Either a Fluorine Atom or a Silicon Atom and Containing a Repeating Unit Having at Least Two or More Polarity Conversion Groups (C)

The actinic ray-sensitive or radiation-sensitive resin composition of the present invention contains (C) a resin having at least either a fluorine atom or a silicon atom and containing (c) a repeating unit having at least two or more polarity conversion groups. The resin (C) has hydrophobicity, and addition of the resin (C) is preferred particularly in view of reducing the development defect.

The fluorine atom may be either a fluorine atom as an electron-withdrawing group in the polarity conversion group described later or a fluorine atom different from a fluorine atom as the electron-withdrawing group.

The repeating unit (c) is preferably (c') a repeating unit having at least two or more polarity conversion groups and at least either a fluorine atom or a silicon atom on one side chain, that is, a repeating unit having a structure where at least either a fluorine atom or a silicon atom is present on a side chain having a plurality of polarity conversion groups.

It is also preferred that the repeating unit (c) is (c*) a repeating unit having at least two or more polarity conversion groups and having neither a fluorine atom nor a silicon atom and the resin (C) further contains a repeating unit having at least either a fluorine atom or a silicon atom.

Alternatively, it is preferred that the repeating unit (c) is (c") a repeating unit having at least two or more polarity conversion groups on one side chain and at the same time, having at least either a fluorine atom or a silicon atom on a side chain different from the side chain above in the same repeating unit. In this case, the side chain having polarity conversion groups and the side chain having at least either a fluorine atom or a silicon atom are preferably in a positional relationship of facing at the α-position through a carbon atom on the main chain, that is, in the positional relationship of the following formula (4). In the formula, B1 represents a partial structure having polarity conversion groups, and B2 represents a partial structure having at least either a fluorine atom or a silicon atom.

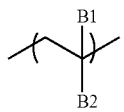

(4)

Out of these embodiments of the resin (C), it is more preferred to have a repeating unit (c').

Here, the polarity conversion group is a group capable of decomposing by the action of an alkali developer to increase the solubility in an alkali developer and is a partial structure represented by —COO— in the structure of formula (KA-1) or (KB-1).

As for the lactone structure represented by formula (KA-1), any group may be used as long as it has a lactone ring, but the group is preferably a group having a 5- to 7-membered ring lactone structure, and a group where another ring structure is condensed to a 5- to 7-membered ring lactone structure in the form of forming a bicyclo or Spiro structure is preferred.

Incidentally, an ester group directly bonded to the resin main chain in the repeating unit (for example, —COO— in acrylate) is poor in the function as a polarity conversion group and is not included in the polarity conversion group of the present invention.

The repeating unit (c) may not have two entire structures represented by (KA-1) or (KB-1) separately, but even when the structures are partially overlapped, for example, in a form of sandwiching one electron-withdrawing group by two ester structures or taking the embodiment of formula (KY-1) described later, this is construed as containing two polarity conversion groups.

Also, in the repeating unit (c*) and the repeating unit (c"), the polarity conversion group is more preferably a partial structure represented by —COO— in the structure of formula (KA-1).

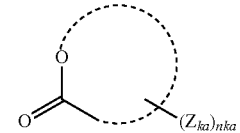

(KA-1)

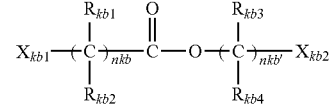

(KB-1)

In formulae (KA-1) and (KB-1), $Z_{ka}$ represents an alkyl group, a cycloalkyl group, an ether group, a hydroxyl group, an amide group, an aryl group, a lactone ring group or an electron-withdrawing group, and when a plurality of $Z_{ka}$'s are present, the plurality of $Z_{ka}$'s are the same or different.

Each $Z_{ka}$ may combine with every other $Z_{ka}$ to form a ring. Examples of the ring formed by combining $Z_{ka}$'s with each other include a cycloalkyl ring and a hetero ring (e.g., cyclic ether ring, lactone ring).

nka represents an integer of 0 to 10 and is preferably an integer of 0 to 8, more preferably an integer of 0 to 5, still more preferably an integer of 1 to 4, and most preferably an integer of 1 to 3.

Each of $X_{kb1}$ and $X_{kb2}$ independently represents an electron-withdrawing group.

Each of nkb and nkb' independently represents 0 or 1. Here, when nkb and kkb' are 0, this indicates that each of $X_{kb1}$ and $X_{kb2}$ is bonded directly to the ester group (—COO—).

Each of $R_{kb1}$ to $R_{kb4}$ independently represents a hydrogen atom, an alkyl group, a cycloalkyl group, an aryl group or an electron-withdrawing group, at least two members of $R_{kb1}$, $R_{kb2}$ and $X_{kb1}$ may combine with each other to form a ring, and at least two members of $R_{kb3}$, $R_{kb4}$ and $X_{kb2}$ may combine with each other to form a ring.

The ring which may be formed by combining at least two members of $R_{kb3}$, $R_{kb4}$ and $X_{kb2}$ with each other is preferably a cycloalkyl group or a heterocyclic group, and the heterocyclic group is preferably a lactone ring group. Examples of the lactone ring include structures represented by formulae (KA-1-1) to (KA-1-17) described later.

Incidentally, the structure represented by formula (KA-1) or (KB-1) is, when not having a bond, a monovalent or greater valent partial structure resulting from removing at least one arbitrary hydrogen atom in the structure, as in the case of a structure represented by formula (KA-1) and a structure represented by formula (KB-1) where $X_{kb1}$ and $X_{kb2}$ are monovalent.

The electron-withdrawing group in $Z_{ka}$, $X_{kb1}$, $X_{kb2}$ and $R_{kb1}$ to $R_{kb4}$ includes a halogen atom, a cyano group, an oxy group, a carbonyl group, a carbonyloxy group, an oxycarbonyl group, a nitrile group, a nitro group, a sulfonyl group, a sulfinyl group, a halo(cyclo)alkyl group or haloaryl group represented by —C($R_{f1}$)($R_{f2}$)—$R_{f3}$, and a combination thereof.

The term "halo(cyclo)alkyl group" indicates an alkyl or cycloalkyl group with at least a part being halogenated. In the case where the electron-withdrawing group is a divalent or greater valent group, the remaining bond forms a bond with an arbitrary atom or substituent and may combine with the main chain of the resin (C) through a further substituent.

In the formula above, $R_{f1}$ represents a halogen atom, a perhaloalkyl group, a perhalocycloalkyl group or a perhaloaryl group and is preferably a fluorine atom, a perfluoroalkyl group or a perfluorocycloalkyl group, more preferably a fluorine atom or a trifluoromethyl group.

Each of $R_{f2}$ and $R_{f3}$ independently represents a hydrogen atom, a halogen atom or an organic group, and $R_{f2}$ and $R_{f3}$ may combine to form a ring. Examples of the organic group include an alkyl group, a cycloalkyl group and an alkoxy group.

At least two members of $R_{f1}$ to $R_{f3}$ may combine to form a ring, and examples of the ring formed include a (halo)cycloalkyl ring and a (halo)aryl ring.

The (halo)alkyl group in $R_{f1}$ to $R_{f3}$ is, for example, an alkyl group in $Z_{ka}$ or a structure formed by halogenating it.

The (per)halocycloalkyl group or (per)haloaryl group in $R_{f1}$ to $R_{f3}$ or in the ring formed by combining $R_{f2}$ and $R_{f3}$ is, for example, a structure formed by halogenating the cycloalkyl group in $Z_{ka}$, preferably a fluorocycloalkyl group represented by —$C_{(n)}F_{(2n-2)}H$ or a perfluoroaryl group represented by —$C_{(n)}F_{(n-1)}$. Here, the carbon number n is not particularly limited but is preferably from 5 to 13, more preferably 6.

$R_{f2}$ preferably represents the same group as $R_{f1}$ or combines with $R_{f3}$ to form a ring.

The electron-withdrawing group is preferably a halogen atom or a halo(cyclo)alkyl group or haloaryl group represented by —C($R_{f1}$)($R_{f2}$)—$R_{f3}$ above, more preferably —C(CF$_3$)$_2$H or —C(CF$_3$)$_2$CH$_3$.

In the electron-withdrawing group above, a part of fluorine atoms may be replaced by another electron-withdrawing group.

$Z_{ka}$ is preferably an alkyl group, a cycloalkyl group, an ether group, a hydroxyl group or an electron-withdrawing group, more preferably an alkyl group, a cycloalkyl group or an electron-withdrawing group. The ether group is preferably an ether group substituted, for example, by an alkyl group or a cycloalkyl group, that is, an alkyl ether group or the like is preferred. The electron-withdrawing group has the same meaning as above.

The halogen atom as $Z_{ka}$ includes a fluorine atom, a chlorine atom, a bromine atom and an iodine atom and is preferably a fluorine atom.

The alkyl group as $Z_{ka}$ may have a substituent and may be either linear or branched. The linear alkyl group is preferably an alkyl group having a carbon number of 1 to 30, more preferably from 1 to 20, and examples thereof include a methyl group, an ethyl group, an n-propyl group, an n-butyl group, an n-pentyl group, an n-hexyl group, an n-heptyl group, an n-octyl group, an n-nonyl group and an n-decanyl group. The branched alkyl group is preferably an alkyl group having a carbon number of 3 to 30, more preferably from 3 to 20, and examples thereof include an i-propyl group, an i-butyl group, a sec-butyl group, a tert-butyl group, an i-pentyl group, a tert-pentyl group, an i-hexyl group, a tert-hexyl group, an i-heptyl group, a tert-heptyl group, an i-octyl group, a tert-octyl group, an i-nonyl group and a tert-decenoyl group. An alkyl group having a carbon number of 1 to 4, such as methyl group, ethyl group, n-propyl group, i-propyl group, n-butyl group, i-butyl group and tert-butyl group, is preferred.

The cycloalkyl group of $Z_{ka}$ may be monocyclic or polycyclic. In the latter case, the cycloalkyl group may be crosslinked. That is, in this case, the cycloalkyl group may have a bridged structure. Incidentally, a part of carbon atoms in the cycloalkyl group may be replaced by a heteroatom such as oxygen atom.

The monocyclic cycloalkyl group is preferably a cycloalkyl group having a carbon number of 3 to 8, and examples thereof include a cyclopropyl group, a cyclobutyl group, a cyclopentyl group, a cyclohexyl group and a cyclooctyl group.

Examples of the polycyclic cycloalkyl group include a group having a bicyclo, tricyclo or tetracyclo structure and having a carbon number of 5 or more. A polycyclic cycloalkyl group having a carbon number of 6 to 20 is preferred, and examples thereof include an adamantyl group, a norbornyl group, an isobornyl group, a camphanyl group, a dicyclopentyl group, an α-pinel group, a tricyclodecanyl group, a tetracyclododecyl group and an androstanyl group.

Examples of such a cycloalkyl group include those shown by the following formulae.

(1)

(2)

(3)

(4)

(5)

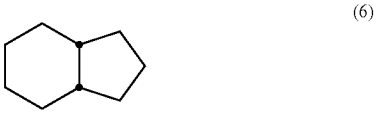

(6)

(7)
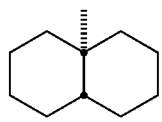
(8)
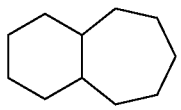
(9)
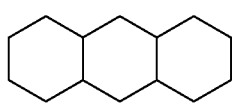
(10)
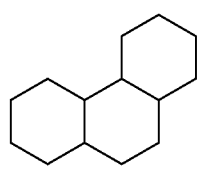
(11)
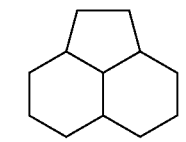
(12)
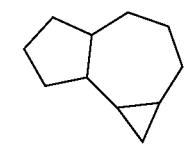
(13)
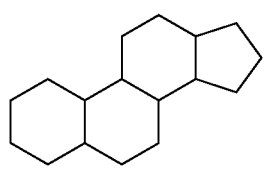
(14)
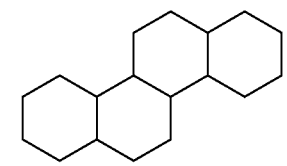
(15)
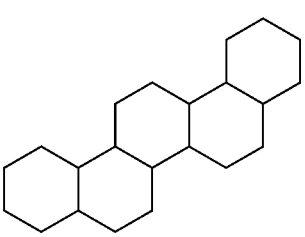
(16)
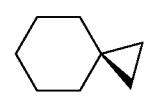
(17)
(18)
(19)
(20)
(21)
(22)
(23)
(24)
(25)
(26)
(27)
(28)
(29)

(30) 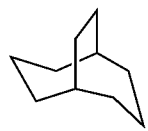

(31) 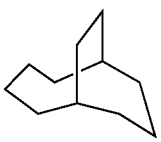

(32) 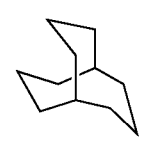

(33) 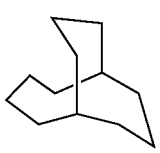

(34) 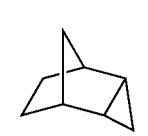

(35) 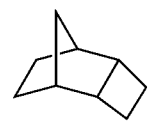

(36) 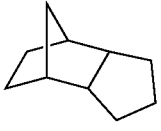

(37) 

(38) 

(39) 

(40) 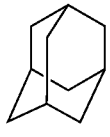

(41) 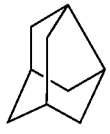

(42) 

(43) 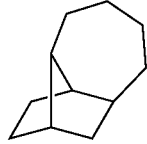

(44) 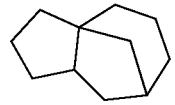

(45) 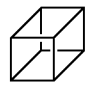

(46) 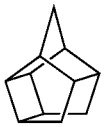

(47) 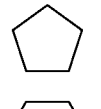

(48) 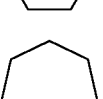

(49) 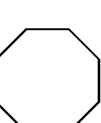

(50) 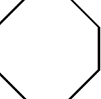

The preferred alicyclic moiety includes an adamantyl group, a noradamantyl group, a decalin group, a tricyclodecanyl group, a tetracyclododecanyl group, a norbornyl group, a cedrol group, a cyclohexyl group, a cycloheptyl group, a cyclooctyl group, a cyclodecanyl group and a cyclododecanyl group. An adamantyl group, a decalin group, a norbornyl group, a cedrol group, a cyclohexyl group, a cycloheptyl group, a cyclooctyl group, a cyclodecanyl group, a cyclododecanyl group and a tricyclodecanyl group are more preferred.

The substituent of the alicyclic structure includes an alkyl group, a halogen atom, a hydroxyl group, an alkoxy group, a carboxyl group and an alkoxycarbonyl group. The alkyl group is preferably a lower alkyl group such as methyl group, ethyl group, propyl group, isopropyl group and butyl group, more preferably a methyl group, an ethyl group, a propyl group or an isopropyl group. The alkoxy group is preferably an alkoxy group having a carbon number of 1 to 4, such as methoxy group, ethoxy group, propoxy group and butoxy group. Examples of the substituent which the alkyl group and alkoxy group may have include a hydroxyl group, a halogen atom and an alkoxy group (preferably having a carbon number of 1 to 4).

Examples of the aryl group of $Z_{ka}$ include a phenyl group and a naphthyl group.

Examples of the substituent which the alkyl group, cycloalkyl group and aryl group of $Z_{ka}$ may further have include a hydroxyl group, a halogen atom, a nitro group, a cyano group, the above-described alkyl group, an alkoxy group such as methoxy group, ethoxy group, hydroxyethoxy group, propoxy group, hydroxypropoxy group, n-butoxy group, isobutoxy group, sec-butoxy group and tert-butoxy group, an alkoxycarbonyl group such as methoxycarbonyl group and ethoxycarbonyl group, an aralkyl group such as benzyl group, phenethyl group and cumyl group, an aralkyloxy group, an acyl group such as formyl group, acetyl group, butyryl group, benzoyl group, cinnamyl group and valeryl group, an acyloxy group such as butyryloxy group, an alkenyl group, an alkenyloxy group such as vinyloxy group, propenyloxy group, allyloxy group and butenyloxy group, the above-described aryl group, an aryloxy group such as phenoxy group, and an aryloxycarbonyl group such as benzoyloxy group.

The polarity conversion group decomposes by the action of an alkali developer to effect polarity conversion, whereby the receding contact angle with water of the resin composition film after alkali development can be decreased.

The receding contact angle with water of the resin composition film after alkali development is preferably 50° or less, more preferably 40° or less, still more preferably 35° or less, and most preferably 30° or less, at the temperature during exposure, usually at room temperature 23±3° C., and a humidity of 45±5%.

The receding contact angle is a contact angle measured when a contact line recedes on the liquid droplet-substrate interface, and this is generally known to be useful in simulating the mobility of a liquid droplet in the dynamic state. In a simple manner, the receding contact angle can be defined as a contact angle at the time of the liquid droplet interface receding when a liquid droplet ejected from a needle tip is landed on a substrate and then the liquid droplet is again suctioned into the needle. In general, the receding contact angle can be measured by a contact angle measuring method called expansion/contraction method.

The hydrolysis rate of the resin (C) for an alkali developer is preferably 0.001 nm/sec or more, more preferably 0.01 nm/sec or more, still more preferably 0.1 nm/sec or more, and most preferably 1 nm/sec or more.

The hydrolysis rate of the resin (C) for an alkali developer is a rate at which the thickness of the film formed of the resin (C) alone decreases when developed with TMAH (an aqueous tetramethylammonium hydroxide solution) (2.38 mass %) at 23° C.

As for the lactone ring structure in formula (KA-1), a group having a lactone structure represented by any one of the following formulae (KA-1-1) to (KA-1-17) is more preferred. The lactone structure-containing group may be bonded directly to the main chain. Preferred lactone structures are (KA-1-1), (KA-1-4), (KA-1-5), (KA-1-6), (KA-1-13), (KA-1-14) and (KA-1-17).

Specific examples of the lactone structure-containing skeleton are set forth below, but the present invention is not limited thereto.

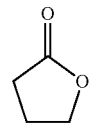

KA-1-1

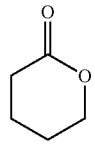

KA-1-2

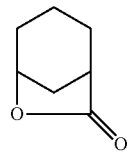

KA-1-3

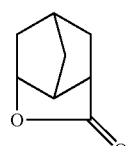

KA-1-4

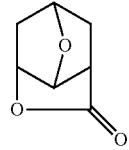

KA-1-5

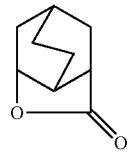

KA-1-6

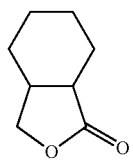

KA-1-7

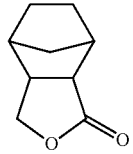

KA-1-8

KA-1-9

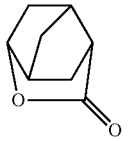

KA-1-10

KA-1-11

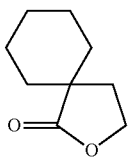

KA-1-12

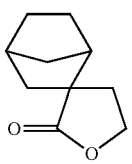

KA-1-13

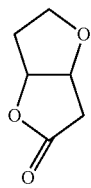

KA-1-14

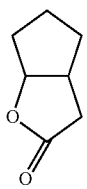

KA-1-15

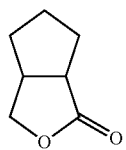

KA-1-16

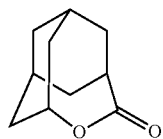

KA-1-17

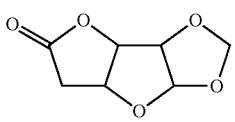

The lactone structure moiety may or may not have a substituent. Preferred examples of the substituent include an alkyl group having a carbon number of 1 to 8, a cycloalkyl group having a carbon number of 4 to 7, an alkoxy group having a carbon number of 1 to 8, an alkoxycarbonyl group having a carbon number of 2 to 8, a carboxyl group, a halogen atom, a hydroxyl group, a cyano group and an acid-decomposable group. Among these, an alkyl group having a carbon number of 1 to 4, a cycloalkyl group having a carbon number of 5 to 6, a cyano group, an alkoxycarbonyl group having a carbon number of 2 to 4, a carboxyl group, a halogen atom, a hydroxyl group and an acid-decomposable group are more preferred. When a plurality of substituents are present, these may be the same or different and also, one substituent may combine with another substituent to form a ring.

Some lactone structures have an optical isomer, but any optical isomer may be used. One optical isomer may be used alone or a mixture of a plurality of optical isomers may be used. In the case of mainly using one optical isomer, the optical purity (ee) thereof is preferably 90% or more, more preferably 95% or more, and most preferably 98% or more.

The structure represented by (KB-1) has a high polarity converting ability, because an electron-withdrawing group is present at the position near the ester structure.

$X_{kb2}$ is preferably a halogen atom or a halo(cyclo)alkyl group or haloaryl group represented by —C($R_{f1}$)($R_{f2}$)—$R_{f3}$ above.

As for at least two polarity conversion groups in the repeating unit (c), a partial structure having two polarity conversion groups represented by the following formula (KY-1) is more preferred. The structure represented by formula (KY-1) is a group having a monovalent or greater valent group resulting from removing at least one arbitrary hydrogen atom in the structure.

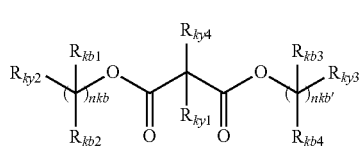

(KY-1)

In formula (KY-1), each of $R_{ky1}$ and $R_{ky4}$ independently represents a hydrogen atom, a halogen atom, an alkyl group, a cycloalkyl group, a carbonyl group, a carbonyloxy group, an oxycarbonyl group, an ether group, a hydroxyl group, a cyano group, an amide group or an aryl group. Alternatively, $R_{ky1}$ and $R_{ky4}$ may be bonded to the same atom to form a double bond. For example, $R_{ky1}$ and $R_{ky4}$ may be bonded to the same oxygen atom to form a part (=O) of a carbonyl group.

Each of $R_{ky2}$ and $R_{ky3}$ independently represents an electron-withdrawing group, or $R_{ky1}$ and $R_{ky2}$ are combined to form a lactone ring and at the same time, $R_{ky3}$ is an electron-withdrawing group. The lactone ring formed is preferably a structure of (KA-1-1) to (KA-1-17). Examples of the electron-withdrawing group is the same as those for $X_{kb1}$ in formula (KB-1), and a halogen atom and a halo(cyclo)alkyl group or haloaryl group represented by —C($R_{f1}$)($R_{f2}$)—$R_{f3}$ above are preferred.

At least two members of $R_{ky1}$, $R_{ky2}$ and $R_{ky4}$ may combine with each other to form a monocyclic or polycyclic structure.

$R_{kb1}$ to $R_{kb4}$, nkb and nkb' have the same meanings as in formula (KB-1).

$R_{ky1}$ and $R_{ky4}$ specifically include the same groups as those for $Z_{ka}$ in formula (KA-1).

The lactone ring formed by combining $R_{ky1}$ and $R_{ky2}$ is preferably a structure of (KA-1-1) to (KA-1-17). The electron-withdrawing group includes the same groups as those for $X_{kb1}$ in formula (KB-1).

The structure represented by formula (KY-1) is preferably a structure represented by the following formula (KY-2). Here, the structure represented by formula (KY-2) is a group having a monovalent or greater valent group resulting from removing at least one hydrogen atom in the structure.

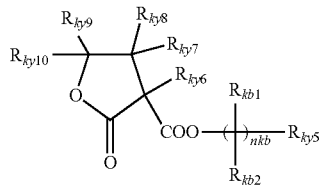

(KY-2)

In formula (KY-2), each of $R_{ky6}$ to $R_{ky10}$ independently represents a hydrogen atom, a halogen atom, an alkyl group, a cycloalkyl group, a carbonyl group, a carbonyloxy group, an oxycarbonyl group, an ether group, a hydroxyl group, a cyano group, an amide group or an aryl group.

Two or more members of $R_{ky6}$ to $R_{ky10}$ may combine with each other to form a monocyclic or polycyclic structure.

$R_{ky5}$ represents an electron-withdrawing group. The electron-withdrawing group includes the same groups as those for $X_{kb1}$ in formula (KB-1), and a halogen atom and a halo(cyclo)alkyl group or haloaryl group represented by —C($R_{f1}$)($R_{f2}$)—$R_{f3}$ above are preferred.

$R_{kb1}$, $R_{kb2}$ and nkb have the same meanings as in formula (KB-1).

$R_{ky5}$ to $R_{ky10}$ specifically include the same groups as those for $Z_{ka}$ in formula (KA-1).

The structure represented by formula (KY-2) is preferably a partial structure represented by the following formula (KY-3).

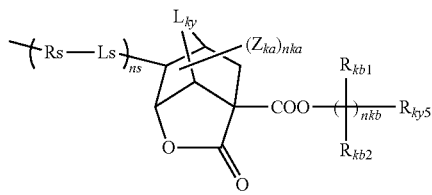

(KY-3)

In formula (KY-3), $Z_{ka}$ and nka have the same meanings as in formula (KA-1). $R_{ky5}$ has the same meaning as in formula (KY-2).

$R_{kb1}$, $R_{kb2}$ and nkb have the same meanings as in formula (KB-1).

$L_{ky}$ represents an alkylene group, an oxygen atom or a sulfur atom. Examples of the alkylene group of $L_{ky}$ include a methylene group and an ethylene group. $L_{ky}$ is preferably an oxygen atom or a methylene group, more preferably a methylene group.

$R_s$ represents a chain or cyclic alkylene group, and when a plurality of $R_s$'s are present, these may be the same or different.

$L_s$ represents a single bond, an ether bond, an ester bond, an amide bond, a urethane bond or a urea bond, and when a plurality of $L_s$'s are present, these may be the same or different.

ns is a repetition number of the linking group represented by —($R_s$-$L_s$)- and represents an integer of 0 to 5.

The repeating unit (c) preferably has a structure represented by formula (KO):

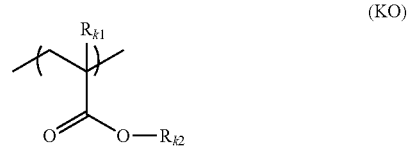

(KO)

In the formula, $R_{k1}$ represents a hydrogen atom, a halogen atom, a hydroxyl group, an alkyl group, a cycloalkyl group, an aryl group or a group having a polarity conversion group.

$R_{k2}$ represents an alkyl group, a cycloalkyl group, an aryl group or a group having a polarity conversion group, provided that $R_{k1}$ and $R_{k2}$ as a whole have two or more polarity conversion groups.

Incidentally, as described above, the ester group directly bonded to the main chain of the repeating unit represented by formula (K0) is not included in the polarity conversion group as used in the present invention.

The repeating unit (c) is not limited as long as it is a repeating unit obtained by polymerization such as addition polymerization, condensation polymerization and addition condensation, but a repeating unit obtained by addition polymerization of a carbon-carbon double bond is preferred. Examples thereof include an acrylate-based repeating unit (including a system having a substituent at the α- or β-position), a styrene-based repeating unit (including a system having a substituent at the α- or β-position), a vinyl ether-based repeating unit, a norbornene-based repeating unit, and a maleic acid derivative (e.g., maleic anhydride or a derivative thereof, maleimide) repeating unit. An acrylate-based repeating unit, a styrene-based repeating unit, a vinyl ether-based repeating unit and a norbornene-based repeating unit are preferred, an acrylate-based repeating unit, a vinyl ether-based repeating unit and a norbornene-based repeating unit are more preferred, and an acrylate-based repeating unit is most preferred.

The resin (C) contained in the actinic ray-sensitive or radiation-sensitive resin composition of the present invention contains a repeating unit having at least either a fluorine atom or a silicon atom.

Thanks to this repeating unit, the resin (C) is unevenly distributed to the surface layer of the actinic ray-sensitive or radiation-sensitive resin film and when the immersion medium is water, the actinic ray-sensitive or radiation-sensitive resin film formed can be enhanced in the receding contact angle for water on the resist film surface as well as in the followability of the immersion liquid.

The receding contact angle of the actinic ray-sensitive or radiation-sensitive resin film is preferably from 60 to 90°, more preferably 65° or more, still more preferably 70° or more, at the temperature during exposure, usually at room temperature 23±3° C., and a humidity of 45±5%.

The resin (C) in the actinic ray-sensitive or radiation-sensitive resin composition may be used by appropriately adjusting its content to give an actinic ray-sensitive or radiation-sensitive resin film having a receding contact angle in the range above, but the content is preferably from 0.01 to 10 mass %, more preferably from 0.1 to 5 mass %, based on the entire solid content of the actinic ray-sensitive or radiation-sensitive resin composition. The resin (C) is, as described above, unevenly distributed to the interface but unlike a surfactant, need not have necessarily a hydrophilic group in the molecule and may not contribute to uniform mixing of polar/nonpolar substances.

In the immersion exposure step, the immersion liquid needs to move on a wafer following the movement of an exposure head that is scanning the wafer at a high speed and forming an exposure pattern. Therefore, the contact angle of the immersion liquid with the resist film in a dynamic state is important, and the resist is required to have a performance of allowing a liquid droplet to follow the high-speed scanning of an exposure head with no remaining.

The resin (C) has at least either a fluorine atom or a silicon atom, whereby the hydrophobicity (water followability) on the resist surface is enhanced and the development residue (scum) is reduced.

While the resin (C) is a resin having a plurality of polarity conversion groups and having at least either a fluorine atom or a silicon atom, the fluorine atom may be the electron-withdrawing group of $X_{kb1}$ and $X_{kb2}$ in formula (KB-1).

The fluorine atom or silicon atom in the resin (C) may be present in the main chain of the resin or may be substituted on the side chain.

The resin (C) is preferably a resin having, as the fluorine atom-containing partial structure, a fluorine atom-containing alkyl group, a fluorine atom-containing cycloalkyl group or a fluorine atom-containing aryl group.

The fluorine atom-containing alkyl group (preferably having a carbon number of 1 to 10, more preferably from 1 to 4) is a linear or branched alkyl group with at least one hydrogen atom being replaced by a fluorine atom and may further have other substituents.

The fluorine atom-containing cycloalkyl group is a monocyclic or polycyclic cycloalkyl group with at least one hydrogen atom being replaced by a fluorine atom and may further have other substituents.

The fluorine atom-containing aryl group is an aryl group (e.g., phenyl, naphthyl) with at least one hydrogen atom being replaced by a fluorine atom and may further have other substituents.

Preferred examples of the fluorine atom-containing alkyl group, fluorine atom-containing cycloalkyl group and fluorine atom-containing aryl group include groups represented by the following formulae (F2) to (F4), but the present invention is not limited thereto.

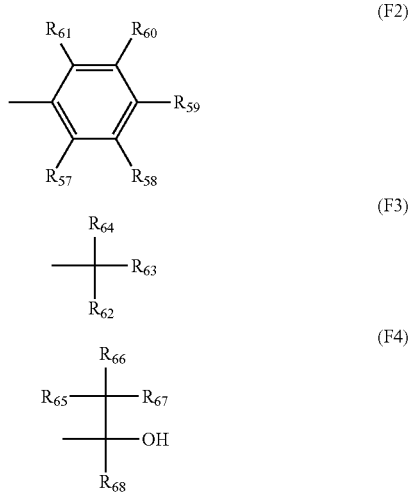

In formulae (F2) to (F4), each of $R_{57}$ to $R_{68}$ independently represents a hydrogen atom, a fluorine atom, a linear or branched alkyl group (preferably a linear or branched alkyl group having a carbon number of 1 to 4) or an aryl group (preferably an aryl group having a carbon number of 6 to 14), provided that at least one of $R_{57}$ to $R_{61}$, at least one of $R_{62}$ to $R_{64}$ and at least one of $R_{65}$ to $R_{68}$ are a fluorine atom or an alkyl group (preferably having a carbon number of 1 to 4) with at least one hydrogen atom being replaced by a fluorine atom. It is preferred that $R_{57}$ to $R_{61}$ and $R_{65}$ to $R_{67}$ all are a fluorine atom. Each of $R_{62}$, $R_{63}$ and $R_{68}$ is preferably an alkyl group (preferably having a carbon number of 1 to 4) with at least one hydrogen atom being replaced by a fluorine atom, more preferably a perfluoroalkyl group having a carbon number of 1 to 4. $R_{62}$ and $R_{63}$ may combine with each other to form a ring.

Specific examples of the group represented by formula (F2) include a p-fluorophenyl group, a pentafluorophenyl group and a 3,5-di(trifluoromethyl)phenyl group.

Specific examples of the group represented by formula (F3) include a trifluoromethyl group, a pentafluoropropyl group, a pentafluoroethyl group, a heptafluorobutyl group, a hexafluoroisopropyl group, a heptafluoroisopropyl group, a hexafluoro(2-methyl)isopropyl group, a nonafluorobutyl group, an octafluoroisobutyl group, a nonafluorohexyl group, a nonafluoro-tert-butyl group, a perfluoroisopentyl group, a perfluorooctyl group, a perfluoro(trimethyl)hexyl group, a 2,2,3,3-tetrafluorocyclobutyl group and a perfluorocyclohexyl group. Among these, a hexafluoroisopropyl group, a heptafluoroisopropyl group, a hexafluoro(2-methyl)isopropyl group, an octafluoroisobutyl group, a nonafluoro-tert-butyl group and a perfluoroisopentyl group are preferred, and a hexafluoroisopropyl group and a heptafluoroisopropyl group are more preferred.

Specific examples of the group represented by formula (F4) include —C(CF$_3$)$_2$OH, —C(C$_2$F$_5$)$_2$OH, —C(CF$_3$)(CH$_3$)OH and —CH(CF$_3$)OH, with —C(CF$_3$)$_2$OH being preferred.

The resin (C) is preferably a resin having an alkylsilyl structure (preferably a trialkylsilyl group) or a cyclic siloxane structure, as the silicon atom-containing partial structure.

Specific examples of the alkylsilyl structure and cyclic siloxane structure include groups represented by the following formulae (CS-1) to (CS-3), but the present invention is not limited thereto.

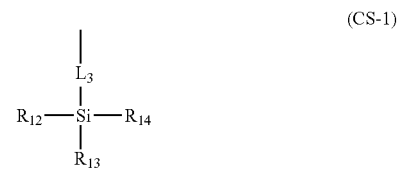

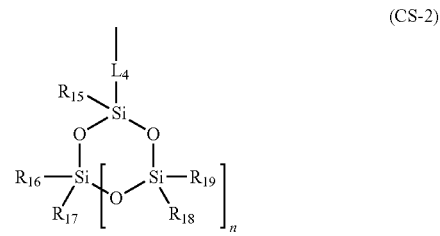

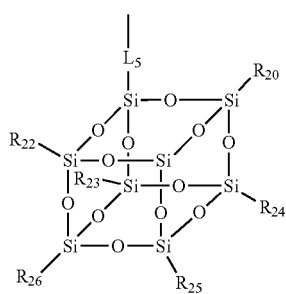

(CS-3)

In formulae (CS-1) to (CS-3), each of $R_{12}$ to $R_{26}$ independently represents a linear or branched alkyl group (preferably having a carbon number of 1 to 20) or a cycloalkyl group (preferably having a carbon number of 3 to 20).

Each of $L_3$ to $L_5$ represents a single bond or a divalent linking group. The divalent linking group is a sole group or a combination of two or more groups selected from the group consisting of an alkylene group, a cycloalkylene group, a phenylene group, an ether group, a thioether group, a carbonyl group, an ester group, an amide group, a urethane group and a ureylene group.

n represents an integer of 1 to 5. n is preferably an integer of 2 to 4.

The group represented by formulae (F2) to (F4) and formula (CS-1) to (CS-3) is preferably contained in an acrylate or methacrylate repeating unit.

Specific examples of the repeating unit (c) are set forth below, but the present invention is not limited thereto. Ra represents a hydrogen atom, a fluorine atom, a methyl group or a trifluoromethyl group.

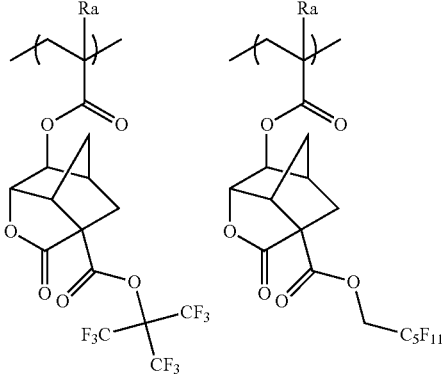

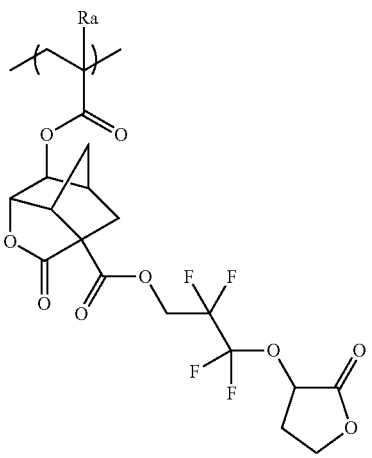

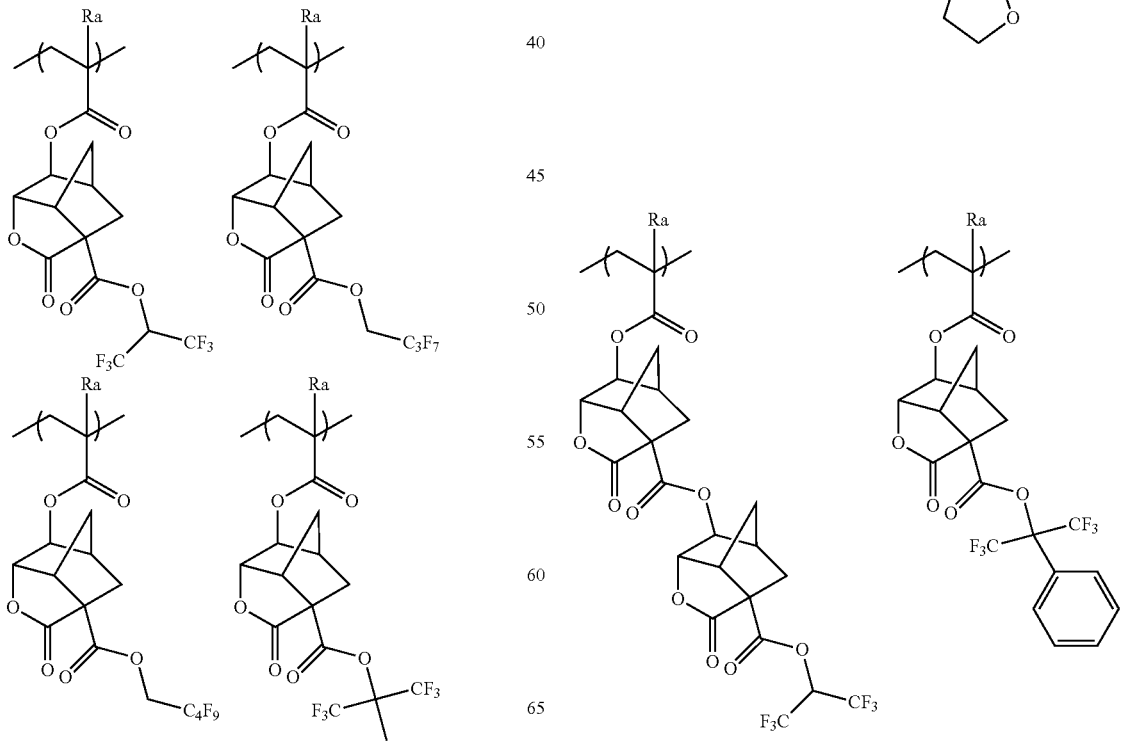

131
-continued
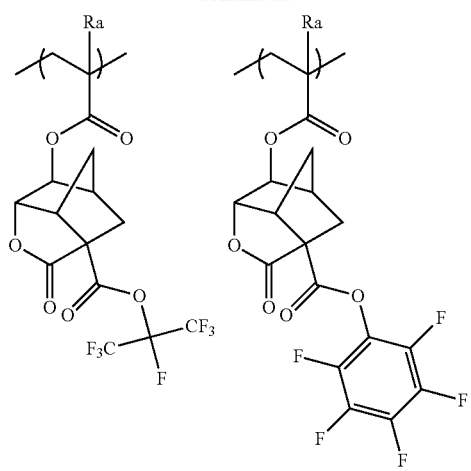
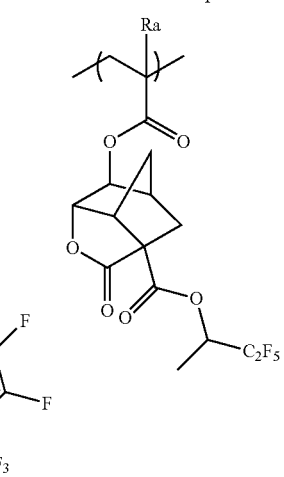
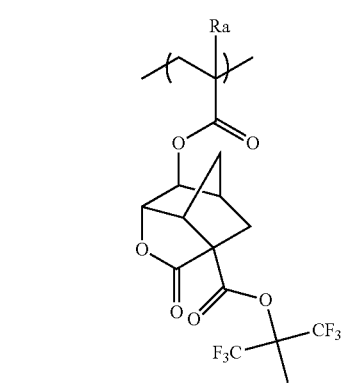
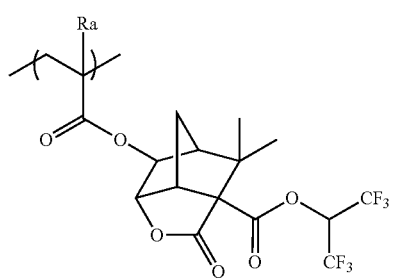
132
-continued
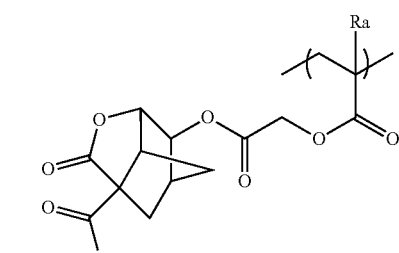
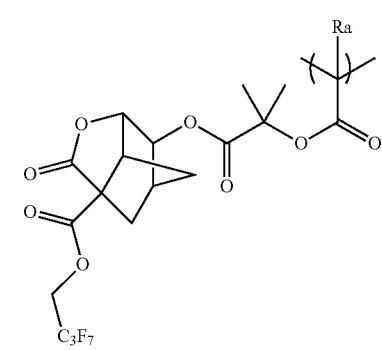
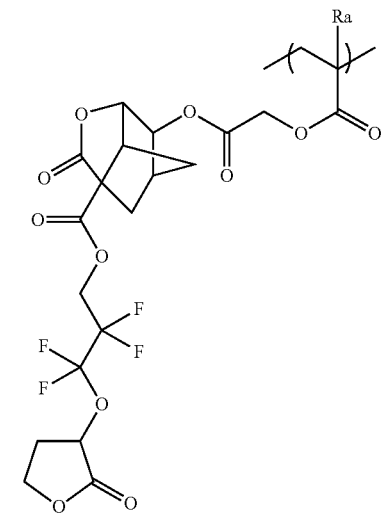

133
-continued
134
-continued
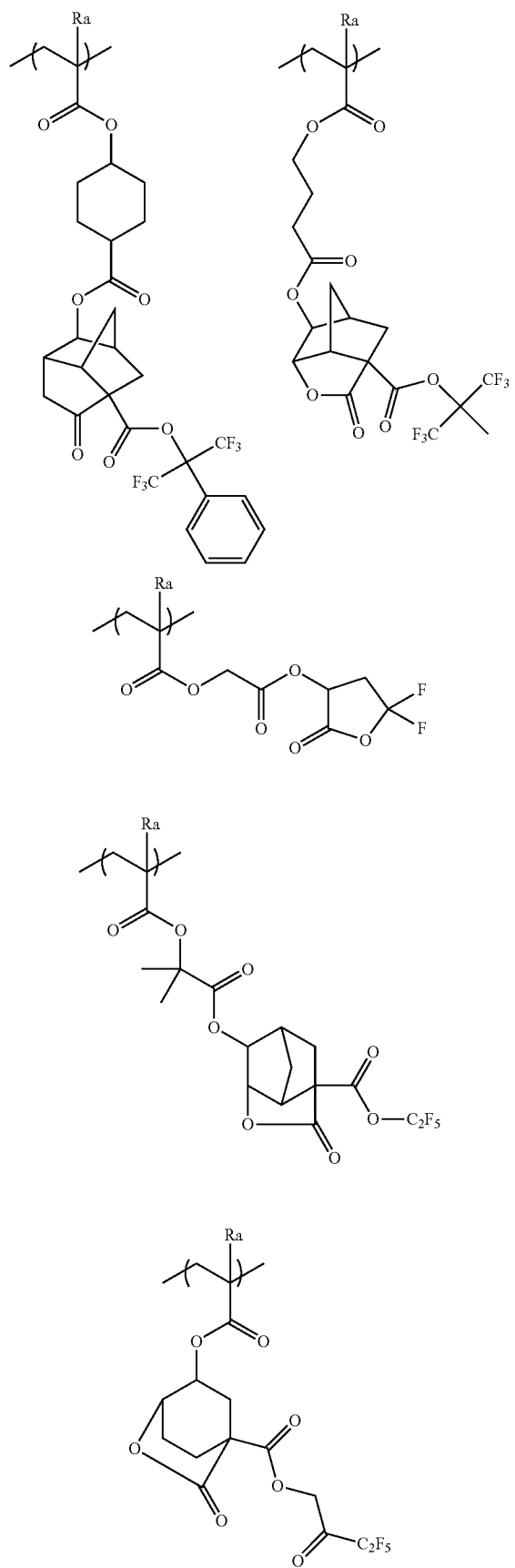
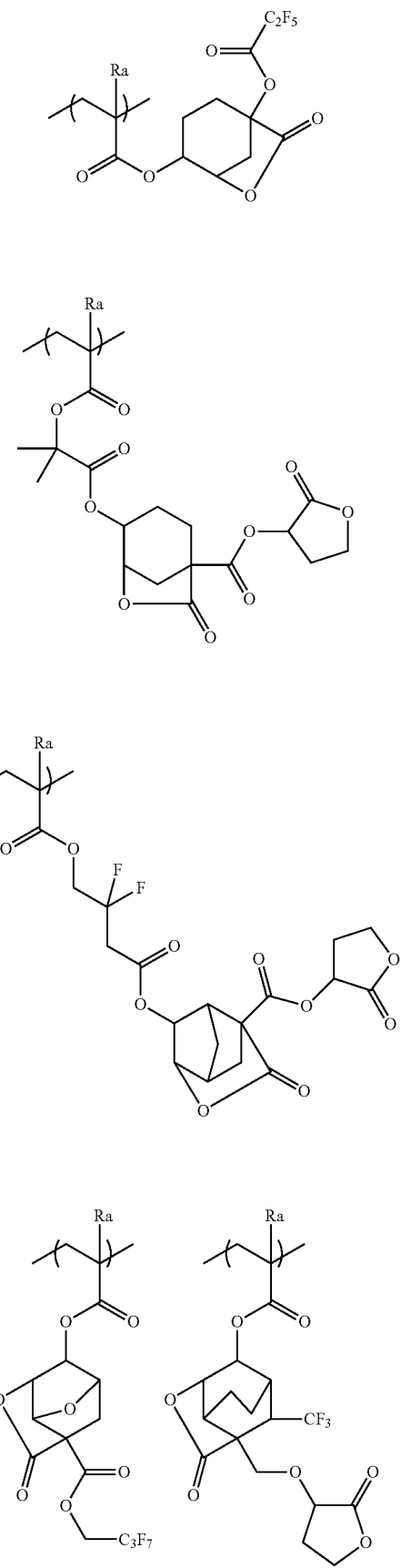

135
-continued
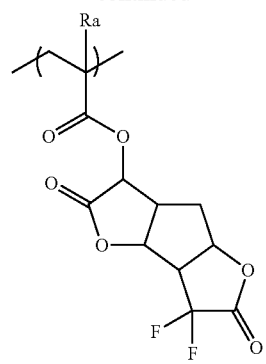
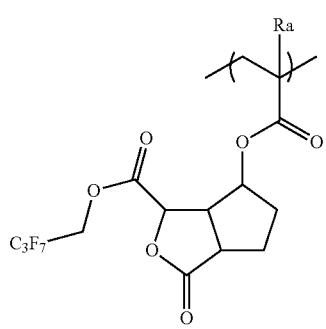
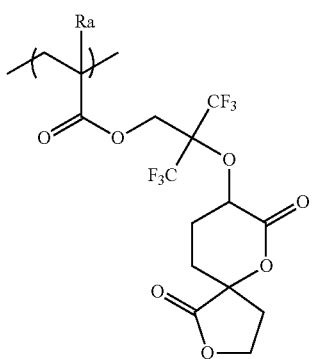
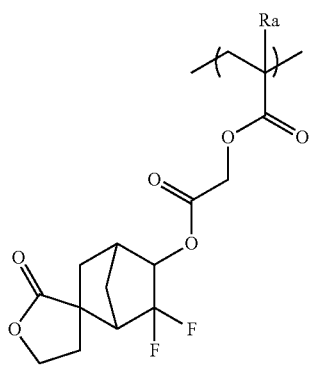
136
-continued
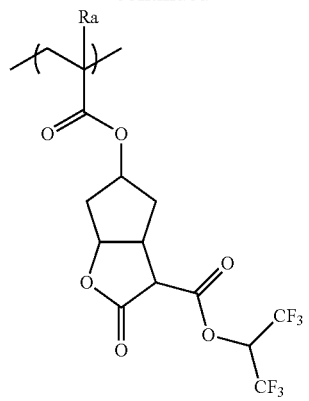
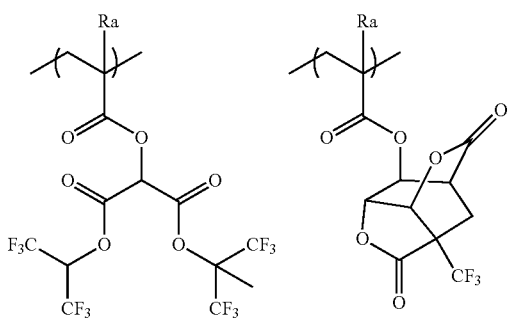
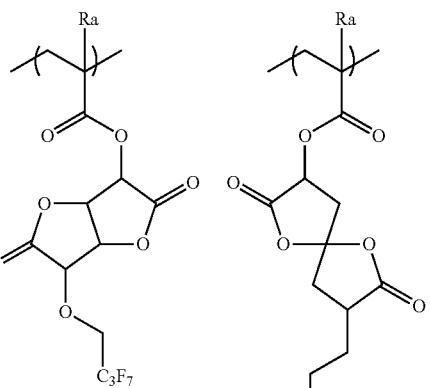
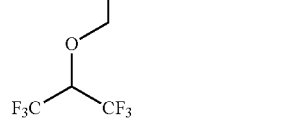
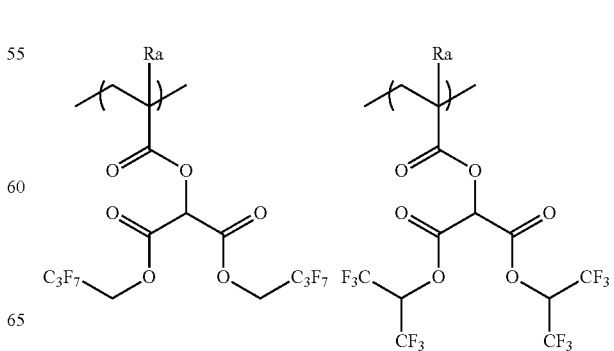

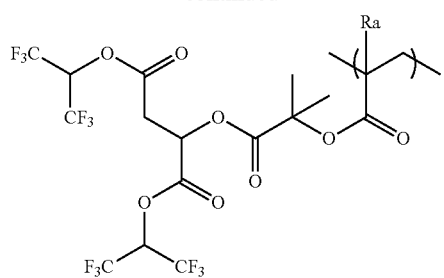
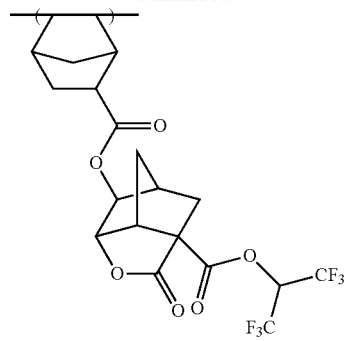
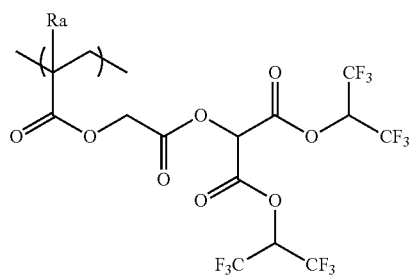
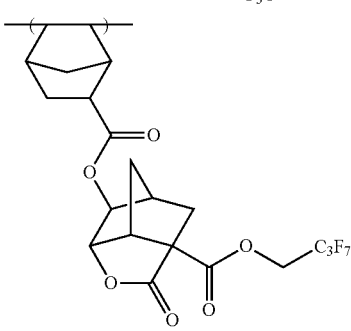
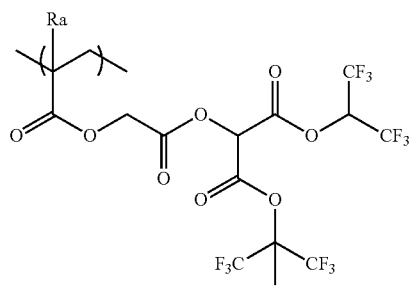
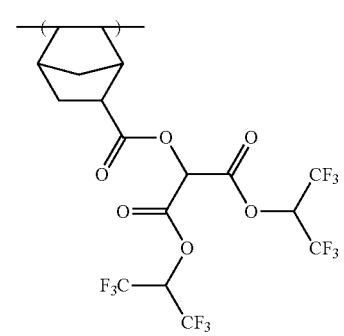
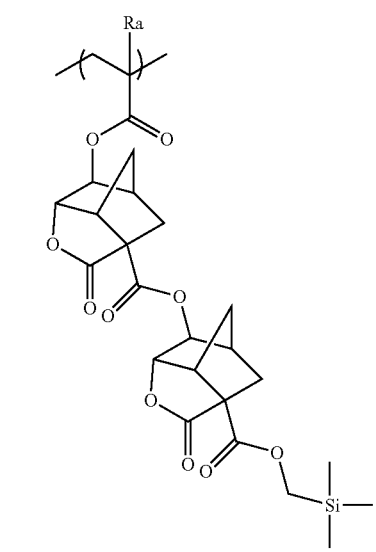
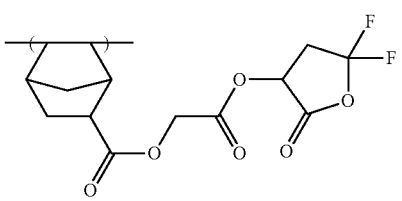
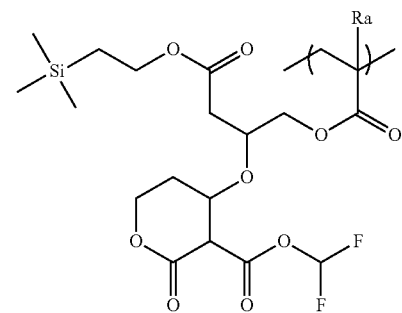
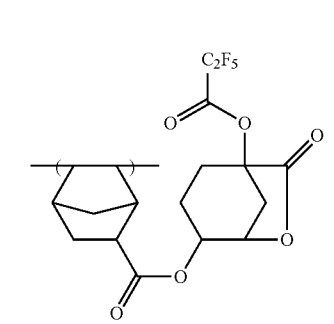

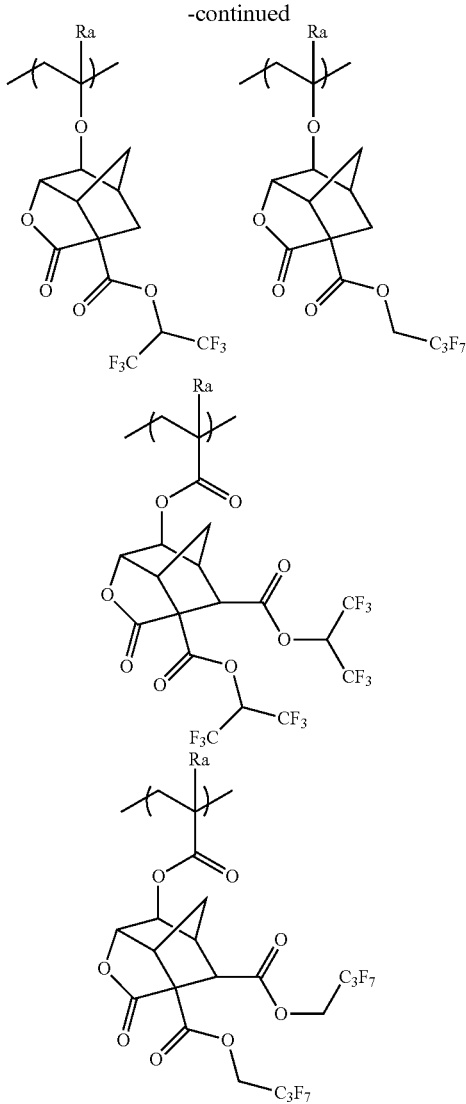

In the resin (C), the content of the repeating unit (c) is preferably from 10 to 100 mol %, more preferably from 20 to 100 mol %, still more preferably from 30 to 100 mol %, and most preferably from 40 to 100 mol %, based on all repeating units in the resin (C).

The content of the repeating unit (c') is preferably from 10 to 100 mol %, more preferably from 20 to 100 mol %, still more preferably from 30 to 100 mol %, and most preferably from 40 to 100 mol %, based on all repeating units in the resin (C).

The content of the repeating unit (c*) is preferably from 10 to 90 mol %, more preferably from 15 to 85 mol %, still more preferably from 20 to 80 mol %, and most preferably from 25 to 75 mol %, based on all repeating units in the resin (C). The content of the repeating unit having at least either a fluorine atom or a silicon atom, which is used together with the repeating unit (c*), is preferably from 10 to 90 mol %, more preferably from 15 to 85 mol %, still more preferably from 20 to 80 mol %, and most preferably from 25 to 75 mol %, based on all repeating units in the resin (C).

The content of the repeating unit (c") is preferably from 10 to 100 mol %, more preferably from 20 to 100 mol %, still more preferably from 30 to 100 mol %, and most preferably from 40 to 100 mol %, based on all repeating units in the resin (C).

The resin (C) may further contain (c1) a repeating unit having at least either a fluorine atom or a silicon atom and being different from the repeating units (c') and (c").

The fluorine atom or silicon atom in the repeating unit (c1) may be present in the main chain of the resin or may be substituted on the side chain.

The fluorine atom-containing partial structure in the repeating unit (c1) includes the same as those described above, and a fluorine atom may be bonded directly to the partial structure or may be bonded through a sole group or a combination of two or more groups selected from the group consisting of an alkylene group, a phenylene group, an ether group, a thioether group, a carbonyl group, an ester group, an amide group, a urethane group and a ureylene group. The fluorine atom-containing partial structure is preferably a group represented by formulae (F2) to (F4).

The followings are suitable for the fluorine atom-containing partial structure as the repeating unit (c1).

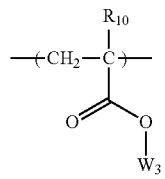
(C-Ia)

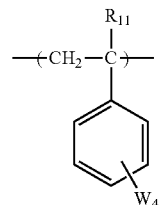
(C-Ib)

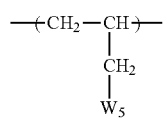
(C-Ic)

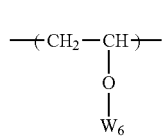
(C-Id)

In the formulae, each of $R_{10}$ and $R_{11}$ independently represents a hydrogen atom, a fluorine atom or an alkyl group (preferably a linear or branched alkyl group having a carbon number of 1 to 4; the alkyl group having a substituent includes particularly a fluorinated alkyl group).

Each of $W_3$ to $W_6$ independently represents an organic group containing at least one or more fluorine atoms. Specifically, the organic group includes the atomic groups of (F2) to (F4).

Other than these repeating units, a resin having the following unit may also be applicable.

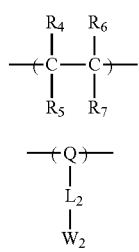

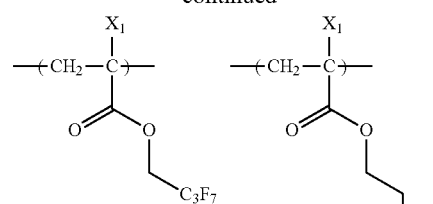

In the formulae, each of $R_4$ to $R_7$ independently represents a hydrogen atom, a fluorine atom or an alkyl group (preferably a linear or branched alkyl group having a carbon number of 1 to 4; the alkyl group having a substituent includes particularly a fluorinated alkyl group), provided that at least one of $R_4$ to $R_7$ represents a fluorine atom. $R_4$ and $R_5$, or $R_6$ and $R_7$ may form a ring.

Q represents an alicyclic structure. The alicyclic structure may be monocyclic or polycyclic and may have a substituent. The monocyclic alicyclic structure is preferably a cycloalkyl group having a carbon number of 3 to 9, and examples thereof include a cyclopentyl group, a cyclohexyl group, a cyclobutyl group and a cyclooctyl group. Examples of the polycyclic alicyclic structure include a group having a bicyclo, tricyclo or tetracyclo structure and having a carbon number of 5 or more. A cycloalkyl group having a carbon number of 6 to 20 is preferred, and examples thereof include an adamantyl group, a norbornyl group, a dicyclopentyl group, a tricyclodecanyl group and a tetracyclododecyl group. Incidentally, a part of carbon atoms in the cycloalkyl group may be replaced by a heteroatom such as oxygen atom. The alicyclic structure of Q is preferably an alicyclic structure having a carbon number of 5 to 9.

$W_2$ represents an organic group containing at least one fluorine atom. Specifically, the organic group includes the atomic groups of (F2) to (F4).

$L_2$ represents a single bond or a divalent linking group. The divalent linking group is a substituted or unsubstituted arylene group, a substituted or unsubstituted alkylene group, a substituted or unsubstituted cycloalkylene group, —O—, —SO$_2$—, —CO—, —N(R)— (wherein R represents a hydrogen atom or an alkyl group), —NHSO$_2$—, or a divalent linking group formed by combining a plurality of these groups.

The silicon atom-containing partial structure in the repeating unit (c1) includes the same as those described above and is preferably a group represented by formulae (CS-1) to (CS-3).

The repeating unit (c1) is preferably a (meth)acrylate-based repeating unit.

Specific examples of the repeating unit (c 1) are set forth below, but the present invention is not limited thereto. In specific examples, $X_1$ represents a hydrogen atom, —CH$_3$, —F or —CF$_3$, and $X_2$ represents —F or —CF$_3$.

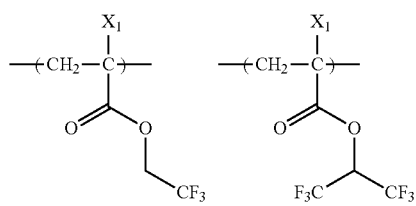

-continued

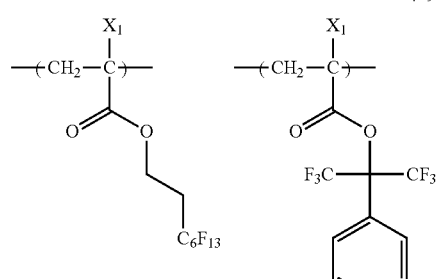

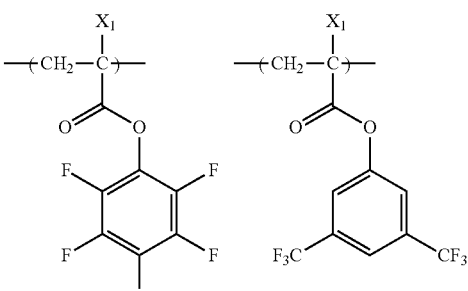

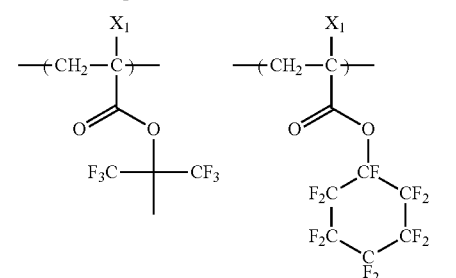

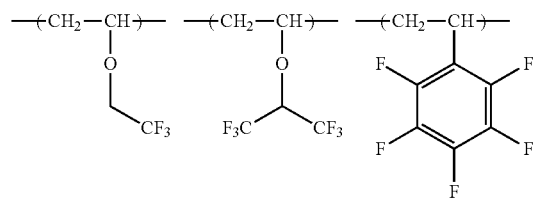

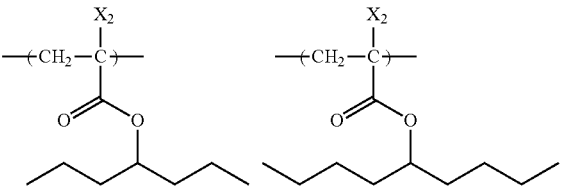

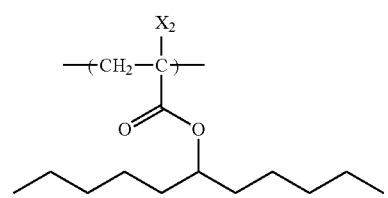

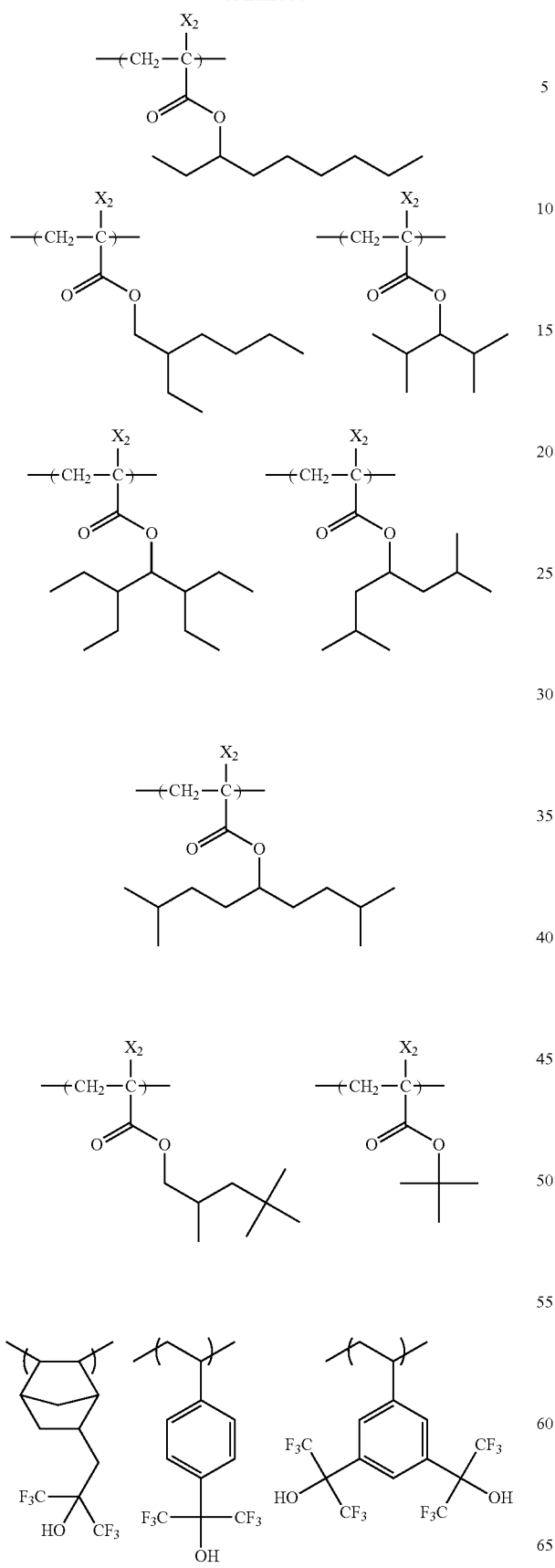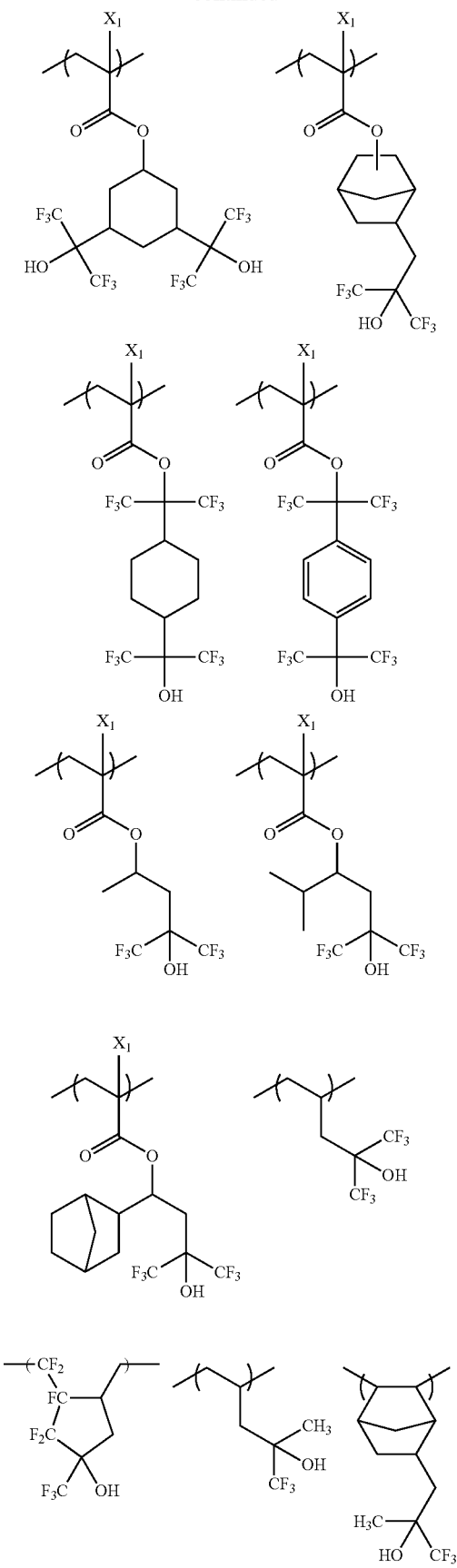

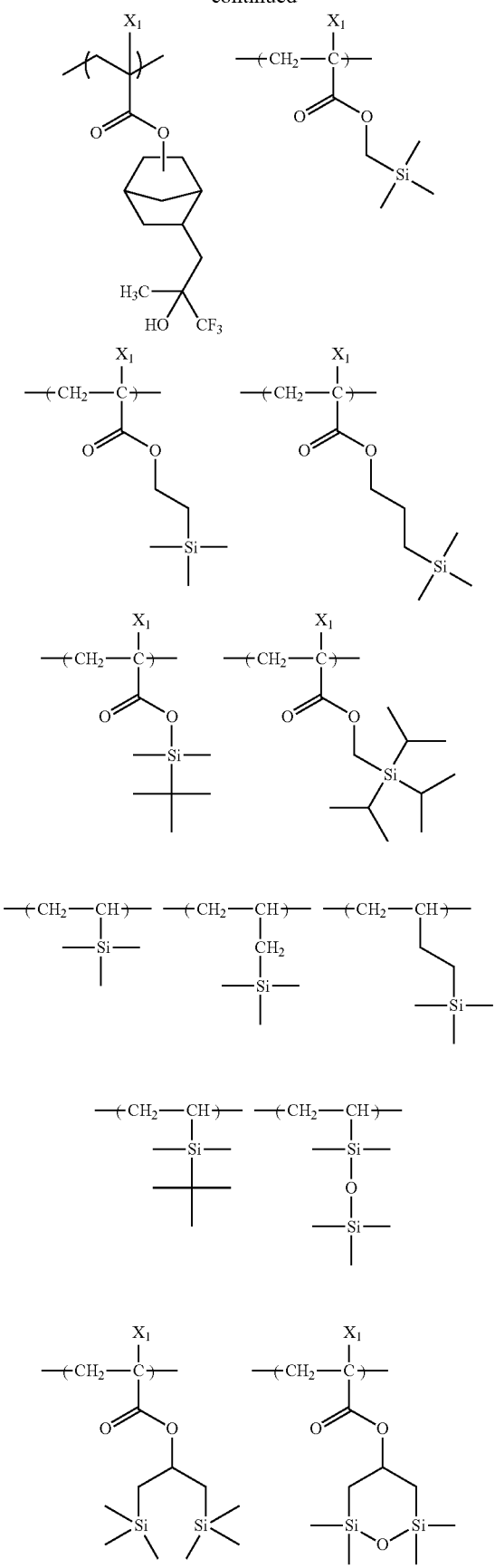
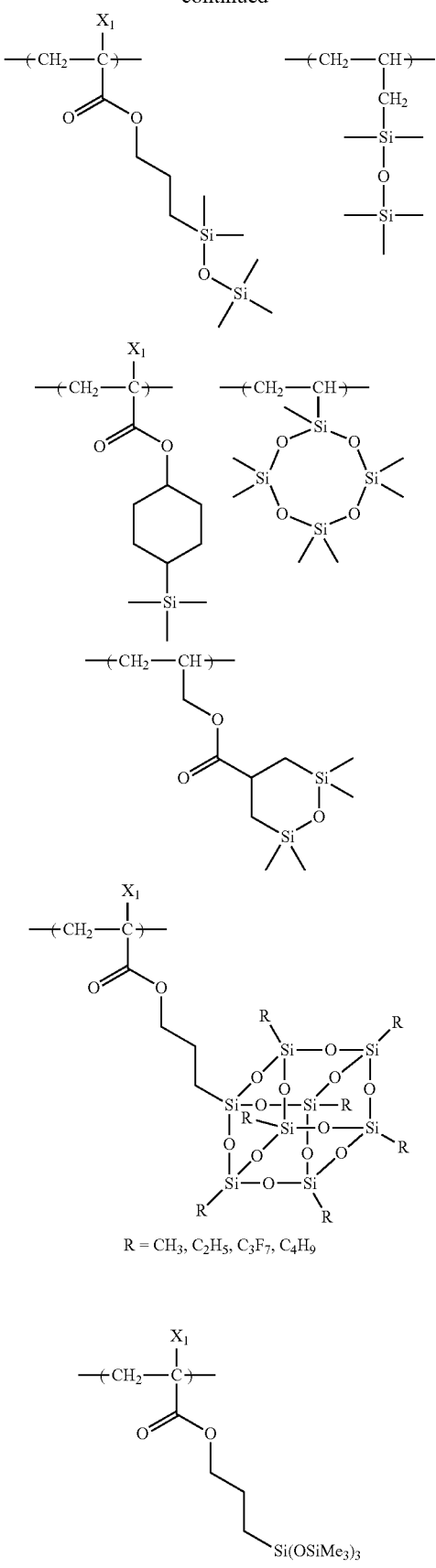

The resin (C) may further contain at least one group selected from the following groups (x), (y) and (z):

(x) an alkali-soluble group, (y) a group capable of decomposing by the action of an alkali developer to increase the solubility in an alkali developer, and (z) a group capable of decomposing by the action of an acid.

Examples of the (x) alkali-soluble group include a phenolic hydroxyl group, a carboxylic acid group, a fluorinated alcohol group, a sulfonic acid group, a sulfonamide group, a sulfonylimide group, an (alkylsulfonyl)(alkylcarbonyl)methylene group, an (alkylsulfonyl)(alkylcarbonyl)imide group, a bis(alkylcarbonyl)methylene group, a bis(alkylcarbonyl)imide group, a bis(alkylsulfonyl)methylene group, a bis(alkylsulfonyl)imide group, a tris(alkylcarbonyl)methylene group and a tris(alkylsulfonyl)methylene group.

Preferred alkali-soluble groups include a fluorinated alcohol group (preferably hexafluoroisopropanol), a sulfonimide group and a bis(carbonyl)methylene group.

The repeating unit having (x) an alkali-soluble group includes a repeating unit where an alkali-soluble group is directly bonded to the resin main chain, such as repeating unit by an acrylic acid or a methacrylic acid, a repeating unit where an alkali-soluble group is bonded to the resin main chain through a linking group, and a repeating unit where an alkali-soluble group is introduced into the polymer chain terminal by using an alkali-soluble group-containing polymerization initiator or chain transfer agent at the polymerization, and these repeating units all are preferred.

The content of the repeating unit having (x) an alkali-soluble group is preferably from 1 to 50 mol %, more preferably from 3 to 35 mol %, still more preferably from 5 to 30 mol %, based on all repeating units in the resin (C).

Specific examples of the repeating unit having (x) and alkali-soluble group are set forth below, but the present invention is not limited thereto. In specific examples, Rx represents H, $CH_3$, $CH_2OH$ or $CF_3$.

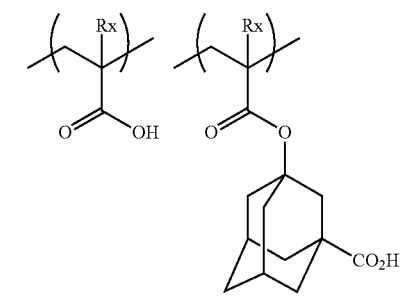

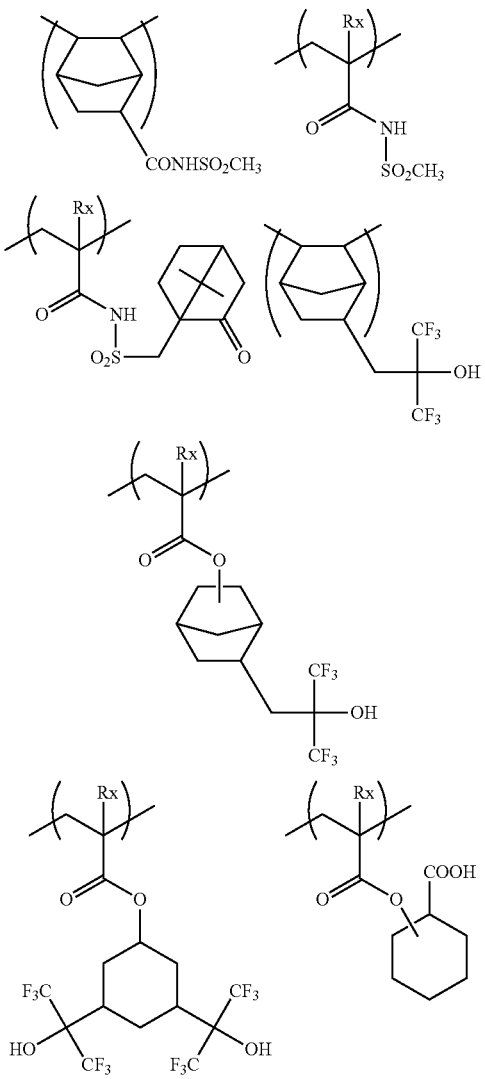

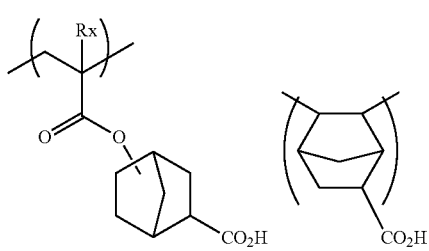

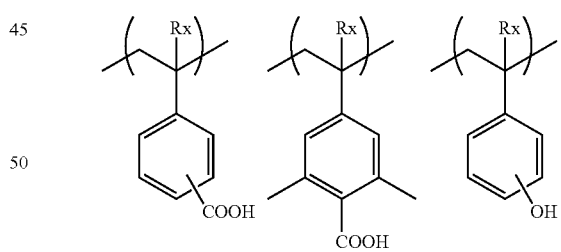

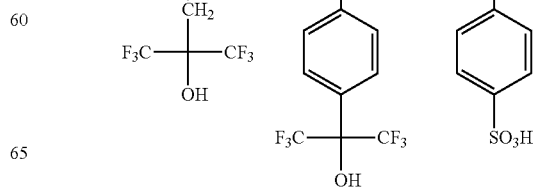

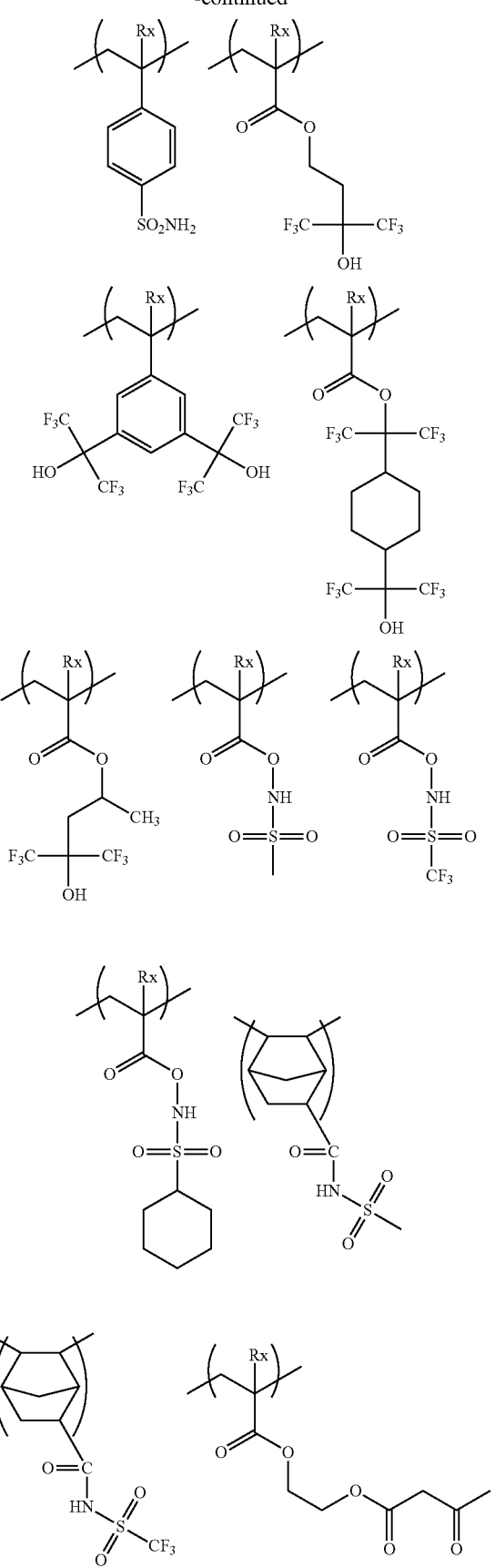

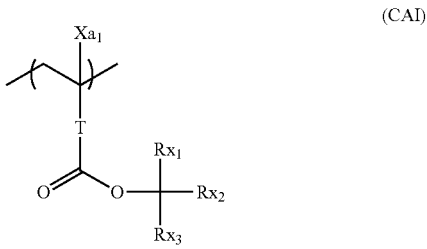

Examples of the (y) group capable of decomposing by the action of an alkali developer to increase the solubility in an alkali developer, contained in the resin (C), include a lactone structure-containing group, an acid anhydride group and an acid imide group, with a lactone structure-containing group being preferred.

The repeating unit having (y) a group capable of decomposing by the action of an alkali developer to increase the solubility in an alkali developer is preferably a repeating unit having only one polarity conversion group in the repeating unit (c) having at least two or more polarity conversion groups, and both a repeating unit where (y) a group capable of decomposing by the action of an alkali developer to increase the solubility in an alkali developer is bonded to the resin main chain, such as repeating unit by an acrylic acid ester or a methacrylic acid ester, and a repeating unit where (y) a group capable of increasing the solubility in an alkali developer is introduced into the polymer chain terminal by using a polymerization initiator or chain transfer agent containing the group (y) at the polymerization, are preferred.

The content of the repeating unit having (y) a group capable of increasing the solubility in an alkali developer is preferably from 1 to 50 mol %, more preferably from 3 to 35 mol %, still more preferably from 5 to 20 mol %, based on all repeating units in the resin (C).

Specific examples of the repeating unit having (y) a group capable of increasing the solubility in an alkali developer are the same as those of the repeating unit having a lactone structure described for the resin of the component (A).

Examples of the repeating unit having (z) a group capable of decomposing by the action of an acid, contained in the resin (C), are the same as those of the repeating unit having an acid-decomposable group described for the resin of the component (A). The acid-decomposable group is preferably a cumyl ester group, an enol ester group, an acetal ester group, a tertiary alkyl ester group or the like, more preferably a tertiary alkyl ester group.

The repeating unit having an acid-decomposable group is preferably a repeating unit represented by the following formula (CAI):

(CAI)

In formula (CAI), $Xa_1$ represents a hydrogen atom, a methyl group or a group represented by —$CH_2$—$R_9$. $R_9$ represents a hydroxyl group or a monovalent organic group, and examples thereof include an alkyl group having a carbon number of 5 or less and an acyl group. The monovalent organic group is preferably an alkyl group having a carbon number of 3 or less, more preferably a methyl group. $Xa_1$ is preferably a hydrogen atom, a methyl group, a trifluoromethyl group or a hydroxymethyl group.

T represents a single bond or a divalent linking group.

Each of $Rx_1$ to $Rx_3$ independently represents an alkyl group (linear or branched) or a cycloalkyl group (monocyclic or polycyclic).

Two members out of $Rx_1$ to $Rx_3$ may combine to form a cycloalkyl group (monocyclic or polycyclic).

Examples of the divalent linking group of T include an alkylene group, a —COO—Rt-group and a —O-Rt- group, wherein Rt represents an alkylene group or a cycloalkylene group.

T is preferably a single bond or a —COO—Rt- group. Rt is preferably an alkylene group having a carbon number of 1 to 5, more preferably a —$CH_2$— group or a —$(CH_2)_3$— group.

The alkyl group of $Rx_1$ to $Rx_3$ is preferably an alkyl group having a carbon number of 1 to 4, such as methyl group, ethyl group, n-propyl group, isopropyl group, n-butyl group, isobutyl group and tert-butyl group.

The cycloalkyl group of $Rx_1$ to $Rx_3$ is preferably a monocyclic cycloalkyl group such as cyclopentyl group and cyclohexyl group, or a polycyclic cycloalkyl group such as norbornyl group, tetracyclodecanyl group, tetracyclododecanyl group and adamantyl group.

The cycloalkyl group formed by combining two members out of $Rx_1$ to $Rx_3$ is preferably a monocyclic cycloalkyl group such as cyclopentyl group and cyclohexyl group, or a polycyclic cycloalkyl group such as norbornyl group, tetracyclodecanyl group, tetracyclododecanyl group and adamantyl group, more preferably a monocyclic cycloalkyl group having a carbon number of 5 to 6.

An embodiment where $Rx_1$ is a methyl group or an ethyl group and $Rx_2$ and $Rx_3$ are combined to form the above-described cycloalkyl group is preferred.

Each of these groups may have a substituent, and examples of the substituent include an alkyl group (having a carbon number of 1 to 4), a halogen atom, a hydroxyl group, an alkoxy group (having a carbon number of 1 to 4), a carboxyl group and an alkoxycarbonyl group (having a carbon number of 2 to 6). The carbon number of the substituent is preferably 8 or less.

In the resin (C), the content of the repeating unit having (z) a group capable of decomposing by the action of an acid is preferably from 1 to 80 mol %, more preferably from 10 to 80 mol %, still more preferably from 20 to 60 mol %, based on all repeating units in the resin (C). By virtue of having (z) a group capable of decomposing by the action of an acid, LWR can be improved.

The resin (C) may further contain other repeating units. Preferred embodiments of other repeating units include the followings:

(cy1) a repeating unit having a fluorine atom and/or a silicon atom and being stable to an acid and sparingly soluble or insoluble in an alkali developer;

(cy2) a repeating unit having no fluorine atom and no silicon atom and being stable to an acid and sparingly soluble or insoluble in an alkali developer;

(cy3) a repeating unit having a fluorine atom and/or a silicon atom and having a polar group except for (x) and (z) above; and (cy4) a repeating unit having no fluorine atom and no silicon atom and having a polar group except for (x) and (z) above.

The expression "sparingly soluble or insoluble in an alkali developer" in the repeating units of (cy1) and (cy2) means that (cy1) and (cy2) do not contain an alkali-soluble group or a group capable of producing an alkali-soluble group by the action of an acid or an alkali developer (for example, an acid-decomposable group or a polarity conversion group).

The repeating units (cy1) and (cy2) preferably have an alicyclic hydrocarbon structure containing no polar group.

Preferred embodiments of the repeating units (cy1) to (cy4) are described below.

The repeating units (cy1) and (cy2) are preferably a repeating unit represented by the following formula (CIII):

$$\text{(CIII)}$$

$$\begin{array}{c} R_{c31} \\ | \\ -(CH_2 - C)- \\ | \\ L_{c3} \\ | \\ R_{c32} \end{array}$$

In formula (CIII), $R_{c31}$ represents a hydrogen atom, an alkyl group which may be substituted by fluorine, a cyano group or a —$CH_2$—O—$R_{ac2}$ group, wherein $R_{ac2}$ represents a hydrogen atom, an alkyl group or an acyl group. $R_{c31}$ is preferably a hydrogen atom, a methyl group, a hydroxymethyl group or a trifluoromethyl group, more preferably a hydrogen atom or a methyl group.

$R_{c32}$ represents an alkyl group, a cycloalkyl group, an alkenyl group, a cycloalkenyl group or an aryl group. Each of these groups may be substituted by a group containing a silicon atom or a fluorine atom, etc.

$L_{c3}$ represents a single bond or a divalent linking group.

In formula (CIII), the alkyl group of $R_{c32}$ is preferably a linear or branched alkyl group having a carbon number of 3 to 20.

The cycloalkyl group is preferably a cycloalkyl group having a carbon number of 3 to 20.

The alkenyl group is preferably an alkenyl group having a carbon number of 3 to 20.

The cycloalkenyl group is preferably a cycloalkenyl group having a carbon number of 3 to 20.

The aryl group is preferably an aryl group having a carbon number of 6 to 20, more preferably a phenyl group or a naphthyl group, and each of these groups may have a substituent.

$R_{c32}$ is preferably an unsubstituted alkyl group or a fluorine atom-substituted alkyl group.

The divalent linking group of $L_{c3}$ is preferably an alkylene group (preferably having a carbon number of 1 to 5), an oxy group, a phenylene group or an ester bond (a group represented by —COO—).

The repeating units (cy1) and (cy2) are preferably a repeating unit represented by the following formula (C4) or (C5):

$$\text{(C4)}$$

$$\begin{array}{c} R_{ac} \\ \diagup\!\!\!\diagdown \\ O \quad O \\ | \\ R_{c5} \end{array}$$

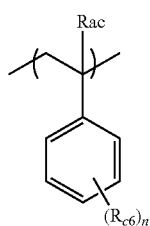
(C5)

In the formulae, $R_{c5}$ represents a hydrocarbon group having at least one cyclic structure and having neither a hydroxyl group nor a cyano group.

$R_{ac}$ represents a hydrogen atom, an alkyl group which may be substituted by fluorine, a cyano group or a —$CH_2$—O—$R_{ac2}$ group, wherein $R_{ac2}$ represents a hydrogen atom, an alkyl group or an acyl group. $R_{ac}$ is preferably a hydrogen atom, a methyl group, a hydroxymethyl group or a trifluoromethyl group, more preferably a hydrogen atom or a methyl group.

The cyclic structure possessed by $R_{c5}$ includes a monocyclic hydrocarbon group and a polycyclic hydrocarbon group. Examples of the monocyclic hydrocarbon group include a cycloalkyl group having a carbon number of 3 to 12, and a cycloalkenyl group having a carbon number of 3 to 12. The monocyclic hydrocarbon group is preferably a monocyclic hydrocarbon group having a carbon number of 3 to 7.

The polycyclic hydrocarbon group includes a ring gathered hydrocarbon group and a crosslinked cyclic hydrocarbon group. Examples of the crosslinked cyclic hydrocarbon ring include a bicyclic hydrocarbon ring, a tricyclic hydrocarbon ring and a tetracyclic hydrocarbon ring. The crosslinked hydrocarbon ring also includes a condensed cyclic hydrocarbon ring (for example, a condensed ring formed by condensing a plurality of 5- to 8-membered cycloalkane rings). Preferred examples of the crosslinked cyclic hydrocarbon ring include a norbornyl group and an adamantyl group.

Such an alicyclic hydrocarbon group may have a substituent, and preferred examples of the substituent include a halogen atom, an alkyl group, a hydroxyl group protected by a protective group, and an amino group protected by a protective group. The halogen atom is preferably bromine atom, chlorine atom or fluorine atom, and the alkyl group is preferably a methyl group, an ethyl group, a butyl group or a tert-butyl group. This alkyl group may further have a substituent, and the substituent which the alkyl group may further have includes a halogen atom, an alkyl group, a hydroxyl group protected by a protective group, and an amino group protected by a protective group.

Examples of the protective group include an alkyl group, a cycloalkyl group, an aralkyl group, a substituted methyl group, a substituted ethyl group, an alkoxycarbonyl group and an aralkyloxycarbonyl group. The alkyl group is preferably an alkyl group having a carbon number of 1 to 4, the substituted methyl group is preferably a methoxymethyl group, a methoxythiomethyl group, a benzyloxymethyl group, a tert-butoxymethyl group or a 2-methoxyethoxymethyl group, the substituted ethyl group is preferably a 1-ethoxyethyl group or a 1-methyl-1-methoxyethyl group, the acyl group is preferably an aliphatic acyl group having a carbon number of 1 to 6, such as formyl group, acetyl group, propionyl group, butyryl group, isobutyryl group, valeryl group and pivaloyl group, and the alkoxycarbonyl group is preferably an alkoxycarbonyl group having a carbon number of 1 to 4.

$R^{c6}$ represents an alkyl group, a cycloalkyl group, an alkenyl group, a cycloalkenyl group, an alkoxycarbonyl group or an alkylcarbonyloxy group. Each of these groups may be substituted by a group containing a silicon atom or a fluorine atom, etc.

The alkyl group of $R_{c6}$ is preferably a linear or branched alkyl group having a carbon number of 1 to 20, and the cycloalkyl group is preferably a cycloalkyl group having a carbon number of 3 to 20.

The alkenyl group is preferably an alkenyl group having a carbon number of 3 to 20.

The cycloalkenyl group is preferably a cycloalkenyl group having a carbon number of 3 to 20.

The alkoxycarbonyl group is preferably an alkoxycarbonyl group having a carbon number of 2 to 20.

The alkoxycarbonyloxy group is preferably an alkoxycarbonyloxy group having a carbon number of 2 to 20.

n represents an integer of 0 to 5. When n is an integer of 2 or more, each $R_{c6}$ may be the same as or different from every other $R_{c6}$.

$R_{c6}$ is preferably an unsubstituted alkyl group or an alkyl group substituted by a fluorine atom, more preferably a trifluoromethyl group or a tert-butyl group.

The repeating units (cy1) and (cy2) are also preferably a repeating unit represented by the following formula (CII-AB):

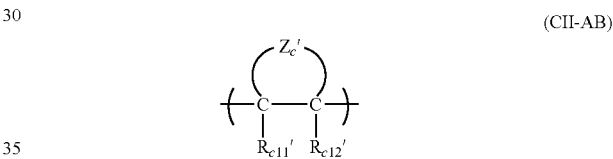
(CII-AB)

In formula (CII-AB), each of $R_{c11}'$ and $R_{c12}'$ independently represents a hydrogen atom, a cyano group, a halogen atom or an alkyl group.

$Z_c'$ represents an atomic group for forming an alicyclic structure containing two bonded carbon atoms (C—C).

Formula (CII-AB) is preferably the following formula (CII-AB1) or (CII-AB2):

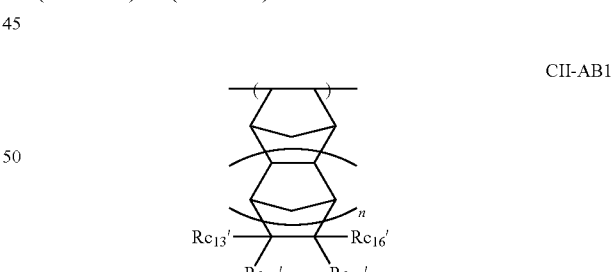
CII-AB1

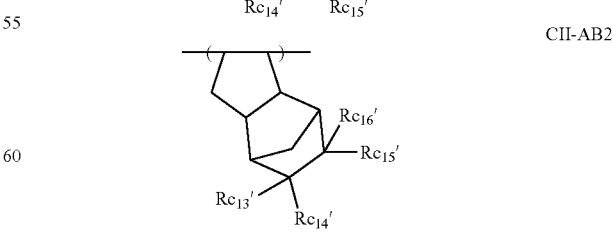
CII-AB2

In formulae (CII-AB1) and (CII-AB2), each of $R_{c13}'$ to $R_{c16}'$ independently represents a hydrogen atom, a halogen atom, an alkyl group or a cycloalkyl group.

At least two members out of $R_{c13}'$ to $R_{c16}'$ may combine to form a ring.
n represents 0 or 1.
Specific examples of (cy1) and (cy2) are set forth below, but the present invention is not limited thereto. In the formulae, Ra represents H, $CH_3$, $CH_2OH$, $CF_3$ or CN.
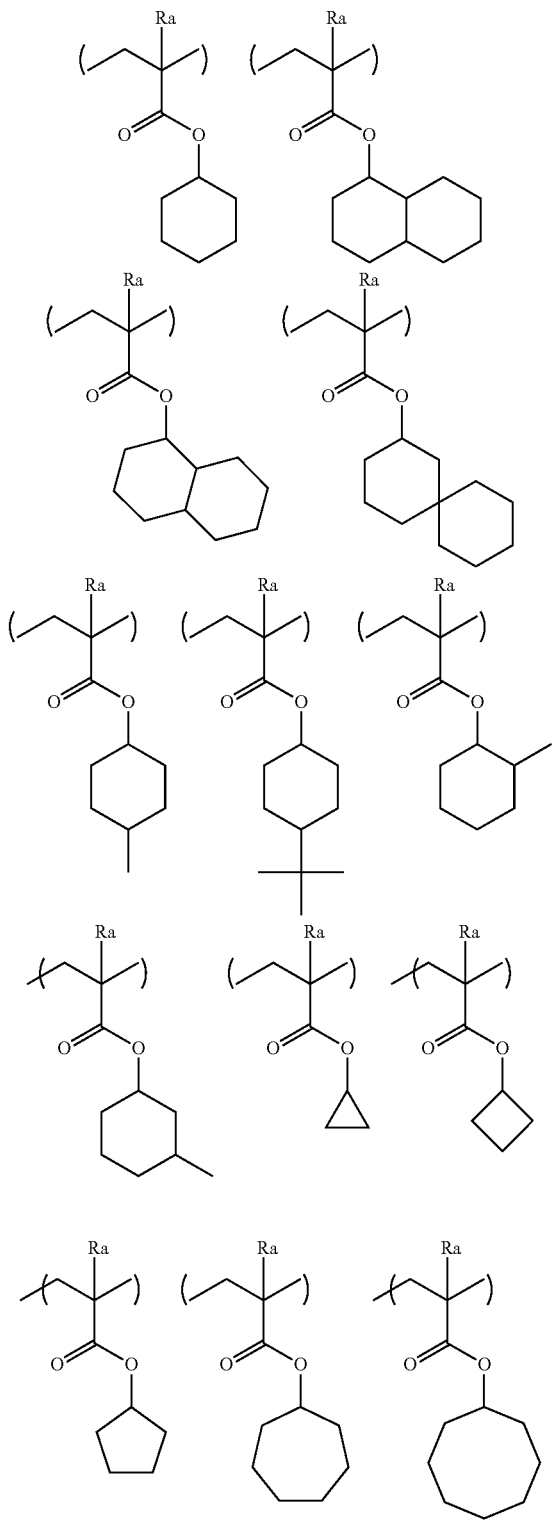
-continued
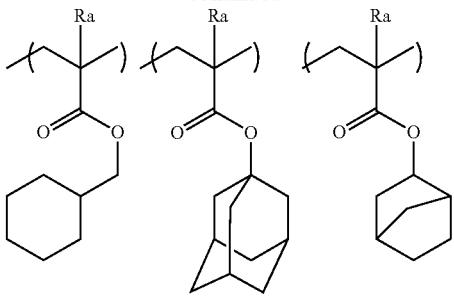
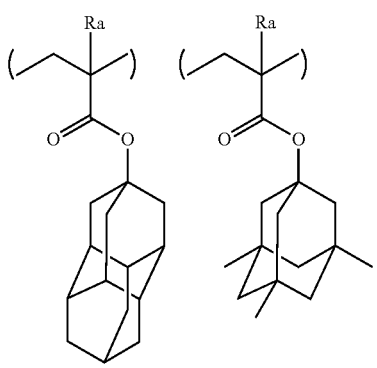
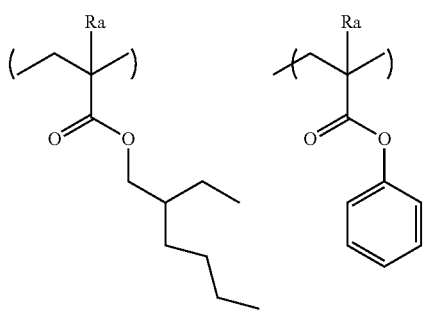
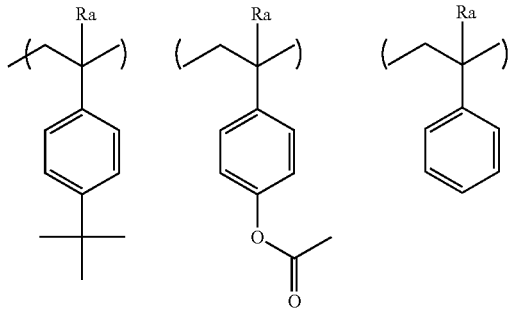
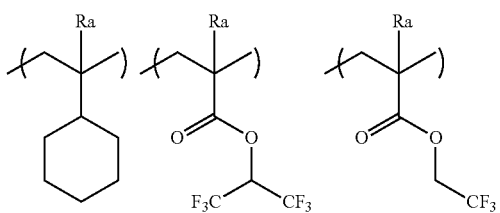

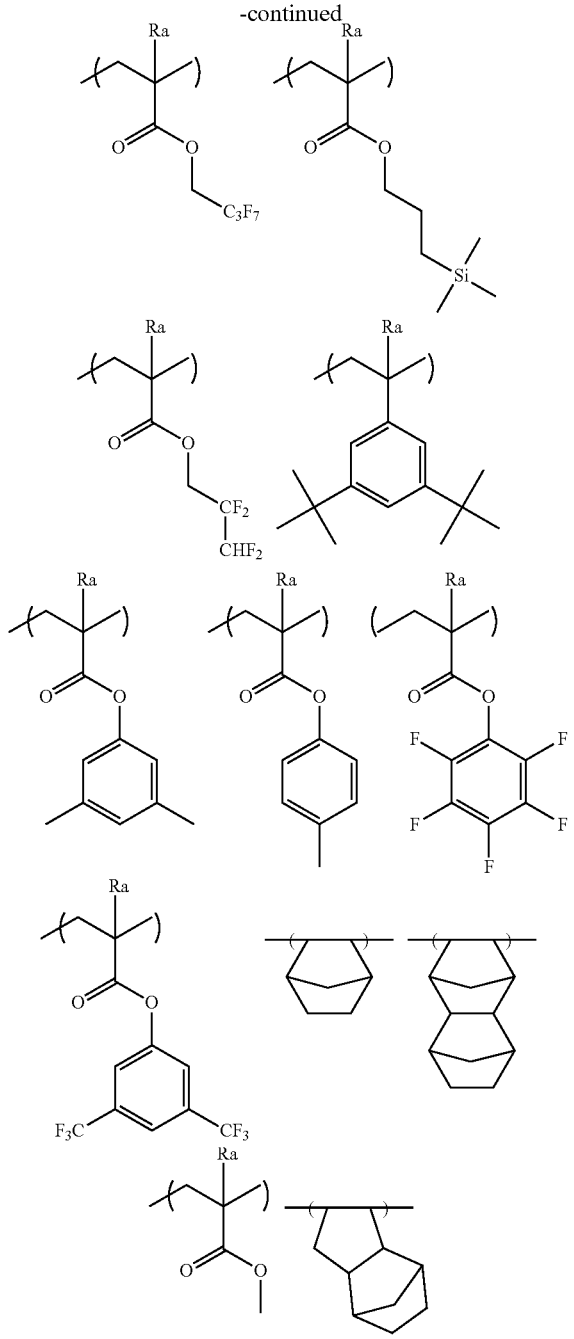

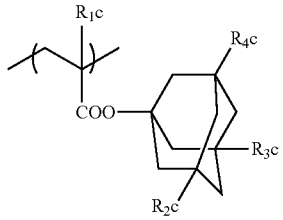

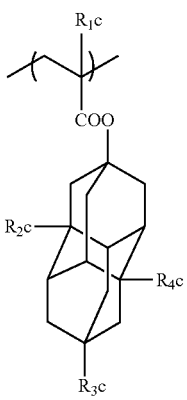

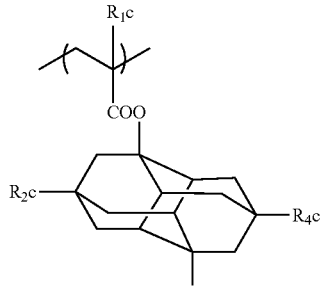

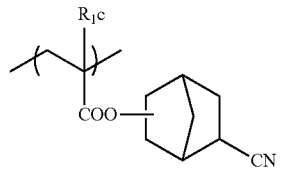

As for (cy3) and (cy4), it is preferred to contain a repeating unit having a hydroxyl group or a cyano group as the polar group. Thanks to this repeating unit, the affinity for developer is enhanced. The repeating unit having a hydroxyl group or a cyano group is preferably a repeating unit having an alicyclic hydrocarbon structure substituted by a hydroxyl group or a cyano group. The alicyclic hydrocarbon structure in the alicyclic hydrocarbon structure substituted by a hydroxyl group or a cyano group is preferably an adamantyl group, a diamantyl group or a norbornyl group. Preferred examples of the alicyclic hydrocarbon structure substituted by a hydroxyl group or a cyano group include a monohydroxyadamantyl group, a dihydroxyadamantyl group, a monohydroxydiamantyl group, a dihydroxydiamantyl group and a norbornyl group substituted by a cyano group.

The repeating unit having such an atomic group includes repeating units represented by the following formulae (CAIIa) to (CAIId):

In formulae (CAIIa) to (CAIId), $R_1c$ represents a hydrogen atom, a methyl group, a trifluoromethyl group or a hydroxymethyl group.

Each of $R_2c$ to $R_4c$ independently represents a hydrogen atom, a hydroxyl group or a cyano group, provided that at least one of $R_2c$ to $R_4c$ represents a hydroxyl group or a cyano group. A structure where one or two members out of $R_2c$ to $R_4c$ are a hydroxyl group with the remaining being a hydrogen atom is preferred. In formula (CAIIa), it is more preferred that two members out of $R_2c$ to $R_1c$ are a hydroxyl group and the remaining is a hydrogen atom.

Specific examples of the repeating unit having a hydroxyl group or a cyano group are set forth below, but the present invention is not limited thereto.

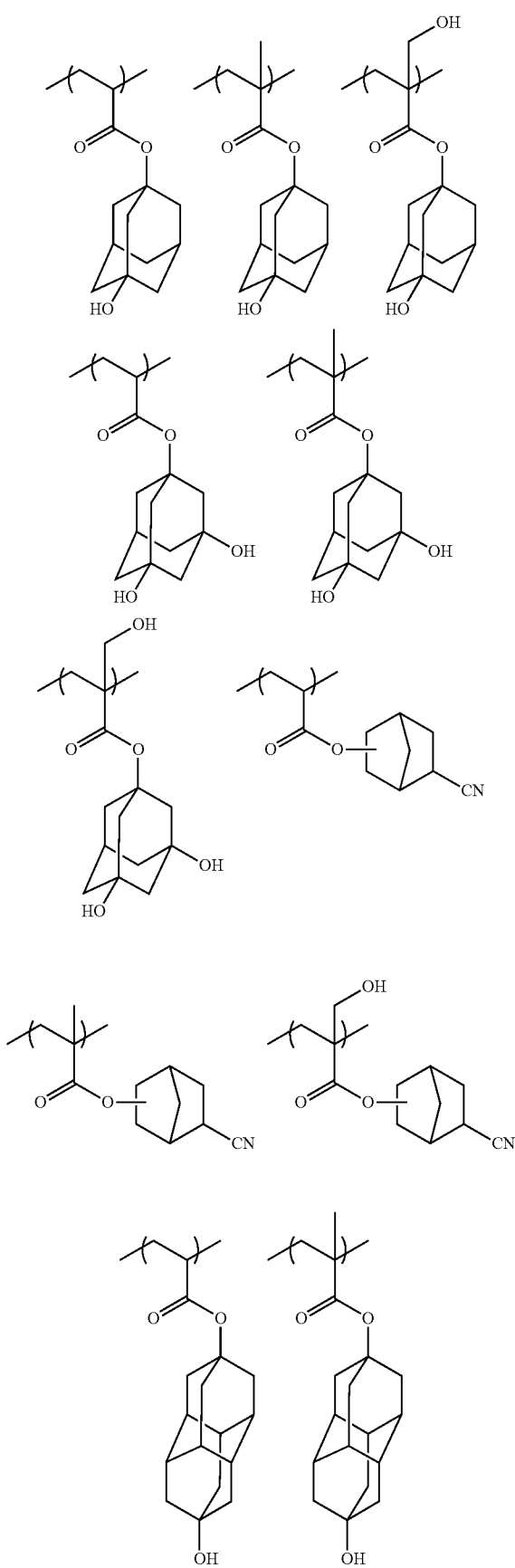

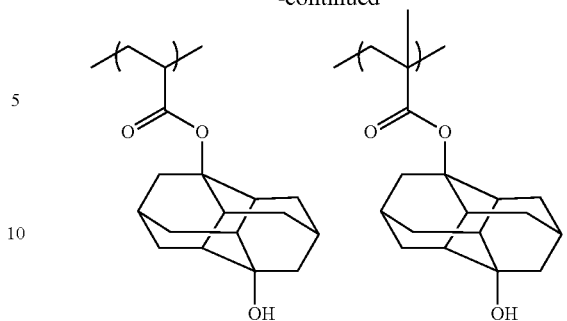

The content of the repeating unit represented by (cy1) to (cy4) is preferably from 5 to 40 mol %, more preferably from 5 to 30 mol %, still more preferably from 10 to 25 mol %, based on all repeating units in the resin (C). The resin (C) may have a plurality of repeating units represented by (cy1) to (cy4).

In the case where the resin (C) contains a fluorine atom, the fluorine atom content is preferably from 5 to 80 mass %, more preferably from 10 to 80 mass %, based on the molecular weight of the resin (C). Also, the fluorine atom-containing repeating unit preferably occupies from 10 to 100 mass %, more preferably from 30 to 100 mass %, based on all repeating units in the resin (C).

In the case where the resin (C) contains a silicon atom, the silicon atom content is preferably from 2 to 50 mass %, more preferably from 2 to 30 mass %, based on the molecular weight of the resin (C). Also, the silicon atom-containing repeating unit preferably occupies from 10 to 90 mass %, more preferably from 20 to 80 mass %, based on all repeating units in the resin (C).

The standard polystyrene-reduced weight average molecular of the resin (C) is preferably from 1,000 to 100,000, more preferably from 1,000 to 50,000, still more preferably from 2,000 to 15,000.

Similarly to the resin of the component (A), in the resin (C), it is of course preferred that the amount of impurities such as metal is small, but also, the content of residual monomers or oligomer components is preferably from 0 to 10 mass %, more preferably from 0 to 5 mass %, still more preferably from 0 to 1 mass %. By satisfying these conditions, a resist composition free of extraneous substances in the liquid or change with aging in the sensitivity and the like can be obtained. Furthermore, in view of resolution, resist profile, side wall of resist pattern, roughness and the like, the molecular weight distribution (Mw/Mn, also called polydispersity) is preferably from 1 to 3, more preferably from 1 to 2, still more preferably from 1 to 1.8, and most preferably from 1 to 1.5.

As for the resin (C), various commercially available products may be used or the resin may be synthesized by an ordinary method (for example, radical polymerization)). Examples of the synthesis method in general include a batch polymerization method of dissolving monomer species and an initiator in a solvent and heating the solution, thereby effecting the polymerization, and a dropping polymerization method of adding dropwise a solution containing monomer species and an initiator to a heated solvent over 1 to 10 hours. A dropping polymerization method is preferred. Examples of the reaction solvent include ethers such as diisopropyl ether, tetrahydrofuran, 1,4-dioxane, ketones such as methyl ethyl ketone and methyl isobutyl ketone, an ester solvent such as ethyl acetate, an amide solvent such as dimethylformamide and dimethylacetamide, and the later-described solvent capable of dissolving the composition of the present invention, such as propylene glycol monomethyl ether acetate (PGMEA, also known as 1-methoxy-2-acetoxypropane), propylene glycol monomethyl ether (PGME, also known as 1-methoxy-2-propanol) and cyclohexanone. The polymerization is more preferably performed using the same solvent as the solvent used in the actinic ray-sensitive or radiation-sensitive resin composition of the present invention. By the use of the same solvent, production of particles during storage can be suppressed.

The polymerization reaction is preferably performed in an inert gas atmosphere such as nitrogen or argon. As for the polymerization initiator, the polymerization is started using a commercially available radical initiator (e.g., azo-based initiator, peroxide). The radical initiator is preferably an azo-based initiator, and an azo-based initiator having an ester group, a cyano group or a carboxyl group is preferred. Preferred examples of the initiator include azobisisobutyronitrile, azobisdimethylvaleronitrile and dimethyl 2,2'-azobis(2-methylpropionate). The reaction concentration is usually from 5 to 50 mass %, preferably from 30 to 50 mass %, and the reaction temperature is usually from 10 to 150° C., preferably from 30 to 120° C., more preferably from 60 to 100° C.

After the completion of reaction, the reaction solution is allowed to cool to room temperature and purified. The purification may be performed by a normal method, for example, a liquid-liquid extraction method of applying water washing or combining an appropriate solvent to remove residual monomers or oligomer components; a purification method in a solution sate, such as ultrafiltration of removing by extraction only those having a molecular weight not more than a specific value; a reprecipitation method of adding dropwise the resin solution in a poor solvent to solidify the resin in the poor solvent and thereby remove residual monomers and the like; and a purification method in a solid state, such as a method of subjecting a resin slurry separated by filtration to washing with a poor solvent. For example, the resin is precipitated as a solid by contacting the reaction solution with a solvent in which the resin is sparingly soluble or insoluble (poor solvent) and which is in a volumetric amount of 10 times or less, preferably from 10 to 5 times, the reaction solution.

The solvent used at the operation of precipitation or reprecipitation from the polymer solution (precipitation or reprecipitation solvent) may be sufficient if it is a poor solvent to the polymer, and the solvent which can be used may be appropriately selected, for example, from a hydrocarbon, a halogenated hydrocarbon, a nitro compound, an ether, a ketone, an ester, a carbonate, an alcohol, a carboxylic acid, water, and a mixed solvent containing such a solvent, according to the kind of the polymer. Among these solvents, a solvent containing at least an alcohol (particularly, methanol or the like) or water is preferred as the precipitation or reprecipitation solvent.

The amount of the precipitation or reprecipitation solvent used may be appropriately selected by taking into consideration the efficiency, yield and the like, but in general, the amount used is from 100 to 10,000 parts by mass, preferably from 200 to 2,000 parts by mass, more preferably from 300 to 1,000 parts by mass, per 100 parts by mass of the polymer solution.

The temperature at the precipitation or reprecipitation may be appropriately selected by taking into consideration the efficiency or operability but is usually on the order of 0 to 50° C., preferably in the vicinity of room temperature (for example, approximately from 20 to 35° C.). The precipitation or reprecipitation operation may be performed using a commonly employed mixing vessel such as stirring tank, by a known method such as batch system and continuous system.

The precipitated or reprecipitated polymer is usually subjected to commonly employed solid-liquid separation such as filtration and centrifugation, then dried and used. The filtration is performed using a solvent-resistant filter element preferably under pressure. The drying is performed under atmospheric pressure or reduced pressure (preferably under reduced pressure) at a temperature of approximately from 30 to 100° C., preferably on the order of 30 to 50° C.

Incidentally, after the resin is once precipitated and separated, the resin may be again dissolved in a solvent and then put into contact with a solvent in which the resin is sparingly soluble or insoluble. That is, there may be used a method comprising, after the completion of radical polymerization reaction, bringing the polymer into contact with a solvent in which the polymer is sparingly soluble or insoluble, to precipitate a resin (step a), separating the resin from the solution (step b), anew dissolving the resin in a solvent to prepare a resin solution A (step c), bringing the resin solution A into contact with a solvent in which the resin is sparingly soluble or insoluble and which is in a volumetric amount of less than 10 times (preferably 5 times or less) the resin solution A, to precipitate a resin solid (step d), and separating the precipitated resin (step e).

Specific examples of the resin (C) are set forth below, but the present invention is not limited thereto. Also, the molar ratio of repeating units (corresponding to repeating units starting from the left in the structural formula), weight average molecular weight (Mw) and polydispersity (Mw/Mn) of each resin are shown in the Table below.

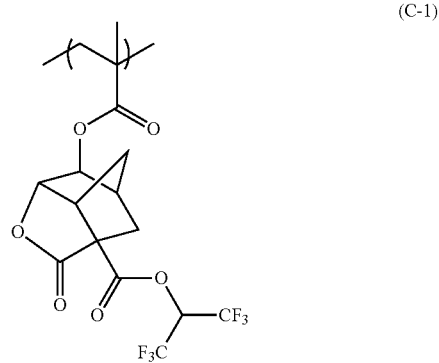

(C-1)

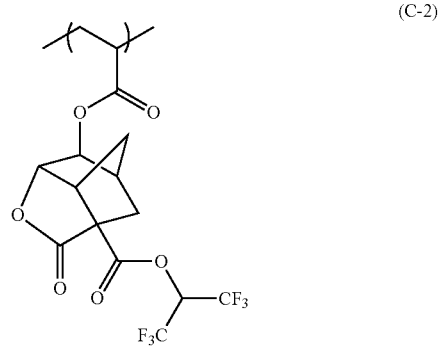

(C-2)

(C-3)
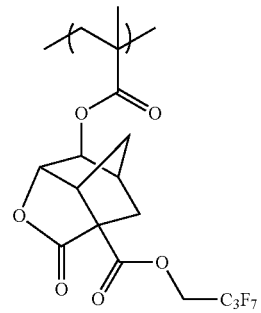
(C-6)
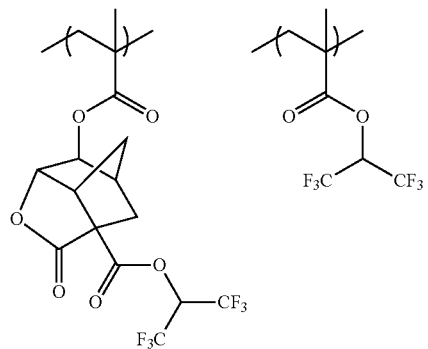
(C-7)
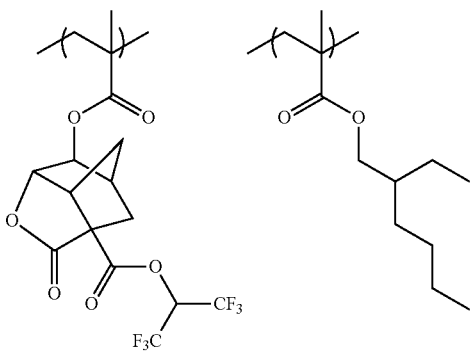
(C-8)
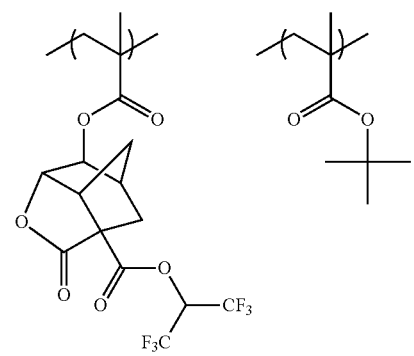
(C-9)
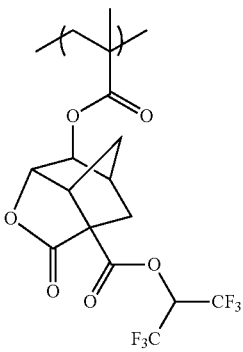 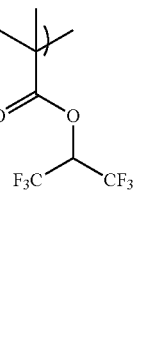
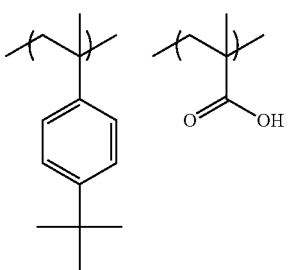
(C-10)
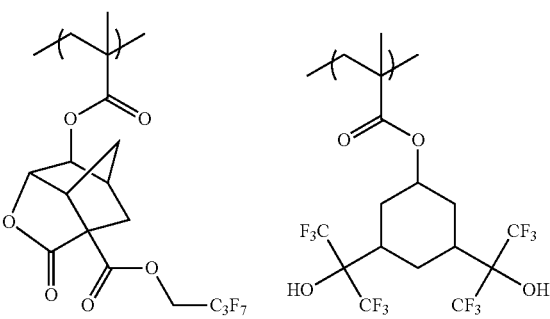
(C-11)
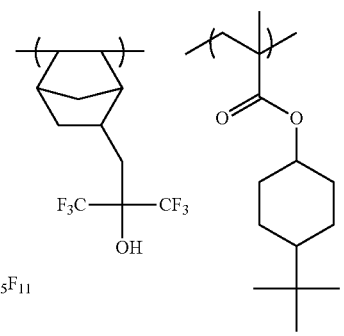

(C-12)
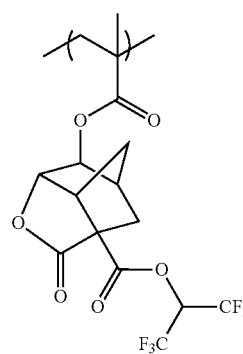
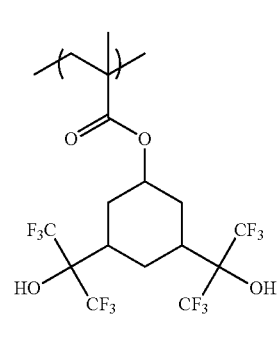
(C-14)
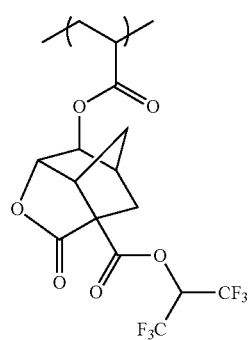
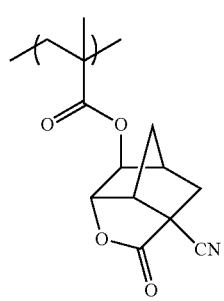
(C-16)
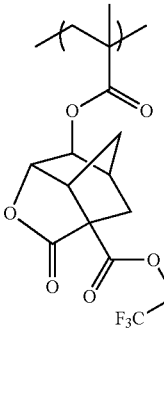
(C-17)
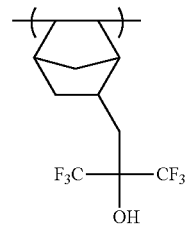
(C-18)
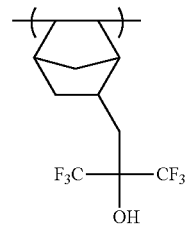
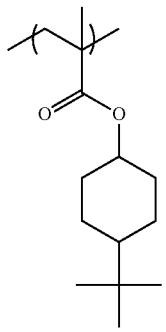
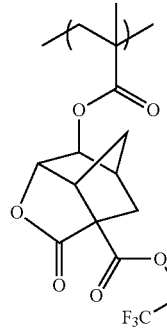
(C-21)
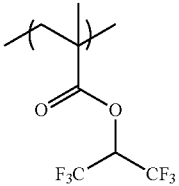
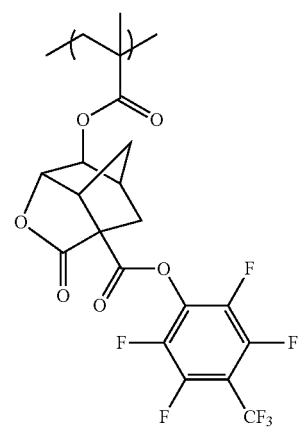
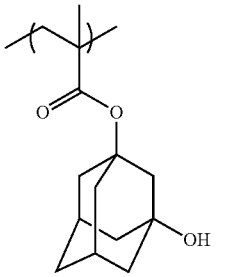
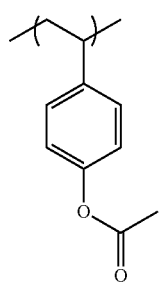

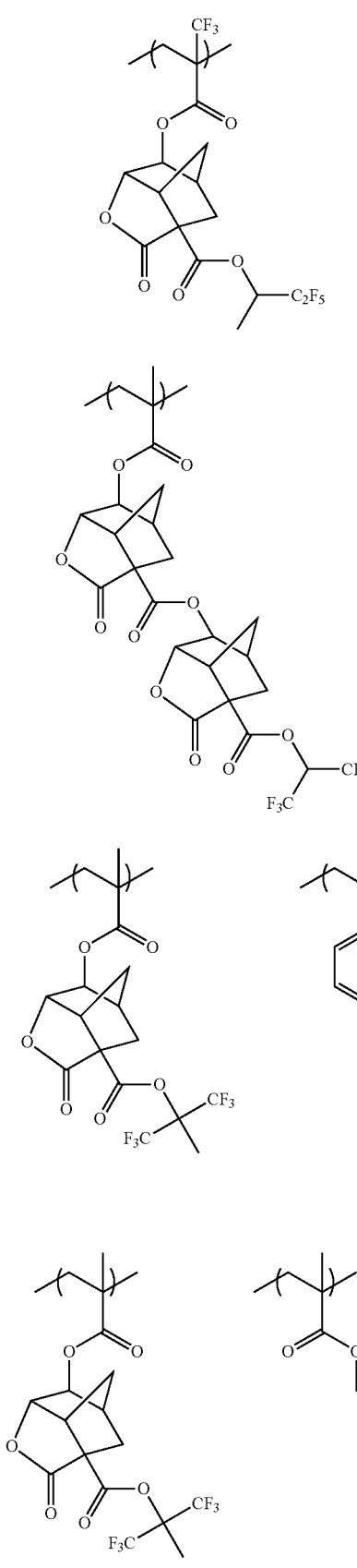
(C-22)
(C-23)
(C-24)
(C-25)
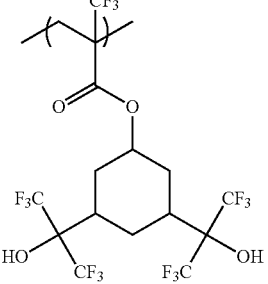
(C-26)
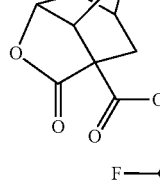
(C-27)
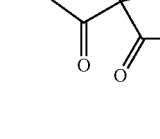
(C-28)
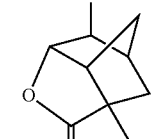

-continued
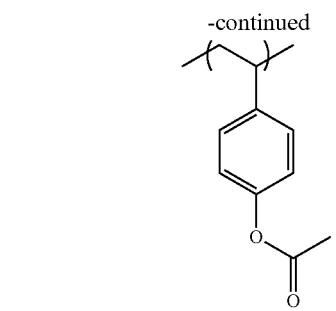
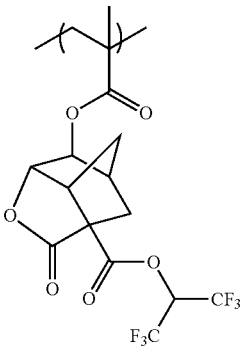
(C-33)
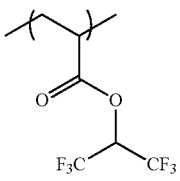
(C-30)
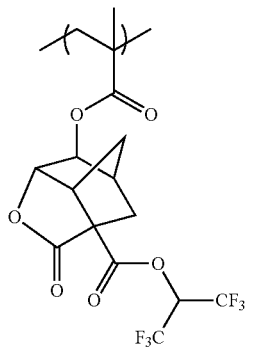 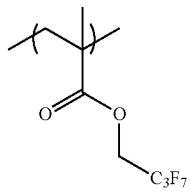
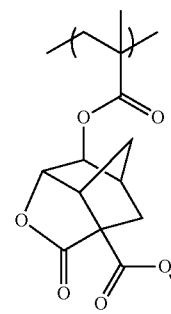
(C-34)
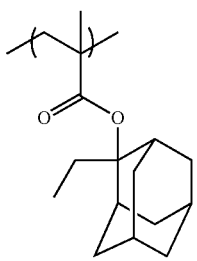
(C-31)
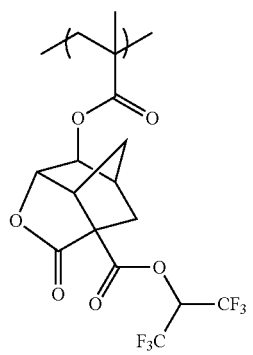 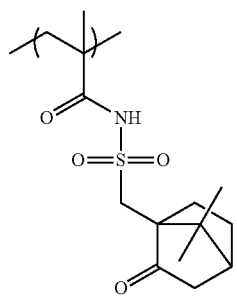
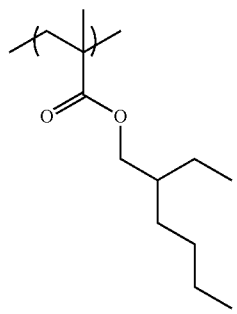
(C-32)
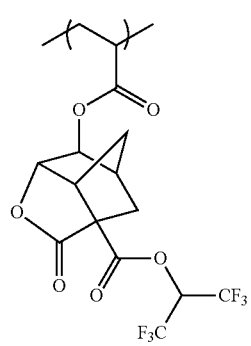 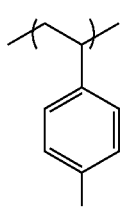
(C-35)
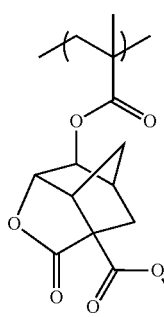 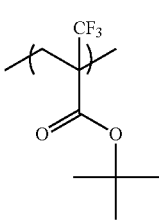 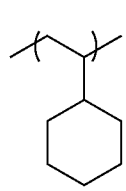

(C-36)
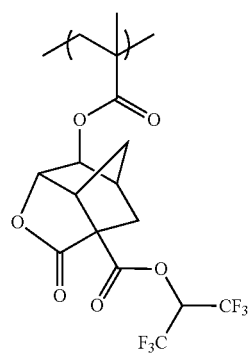 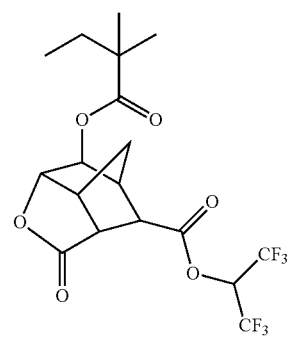
(C-38)
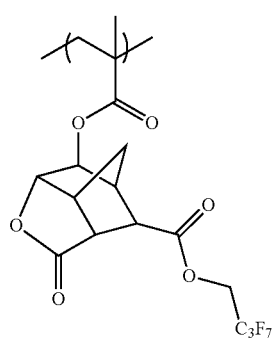 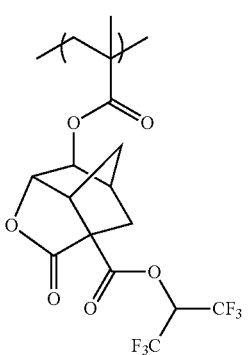
(C-39)
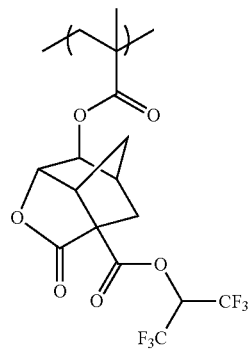 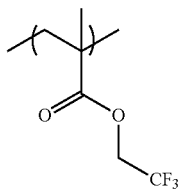
(C-40)
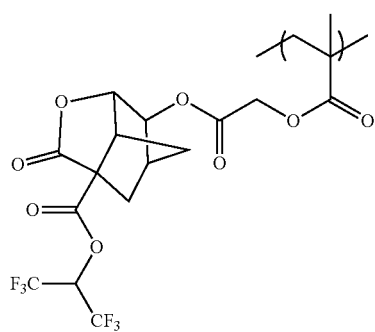
(C-43)
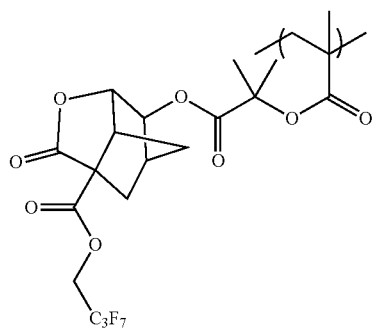 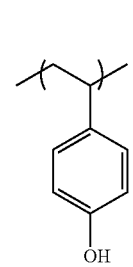
(C-44)
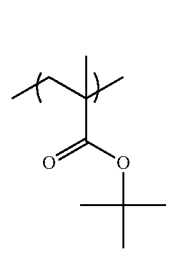 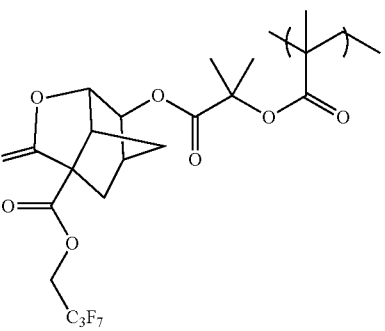
(C-49)
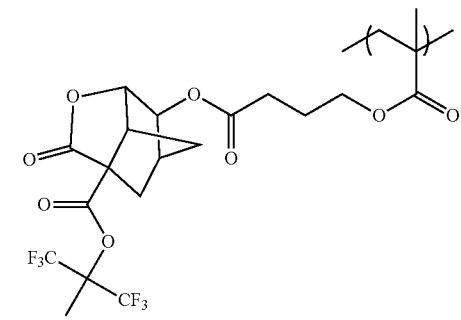
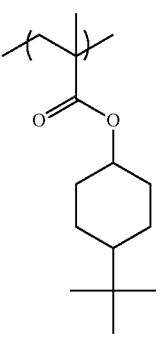 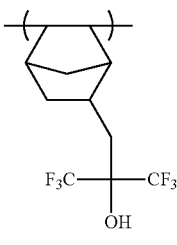

(C-50)
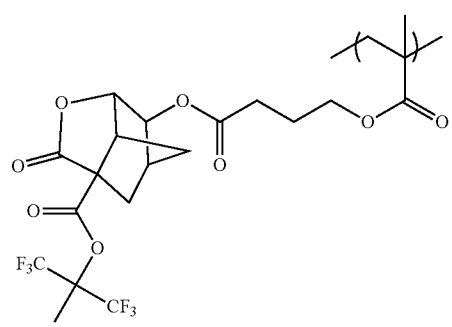
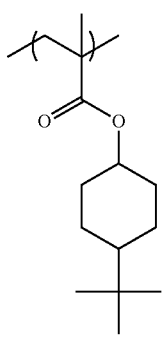
(C-51)
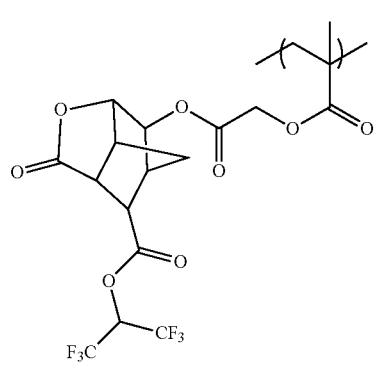
(C-53)
(C-54)
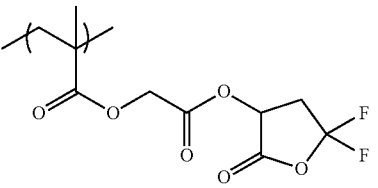 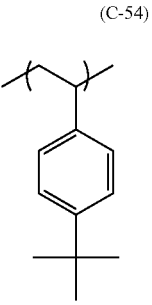
 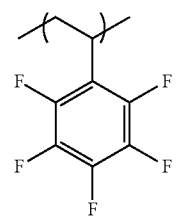
(C-55)
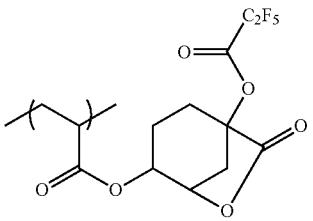 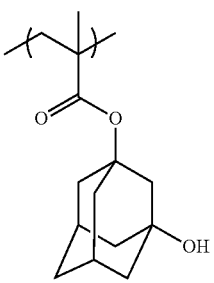
(C-56)
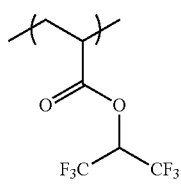
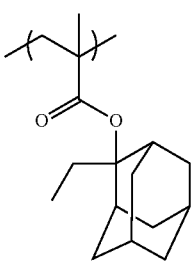

(C-62)
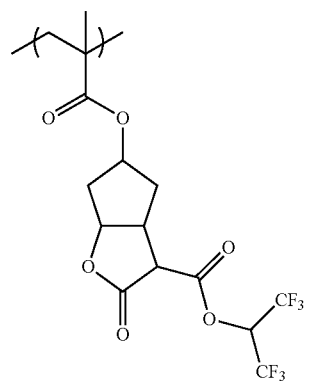
(C-63)
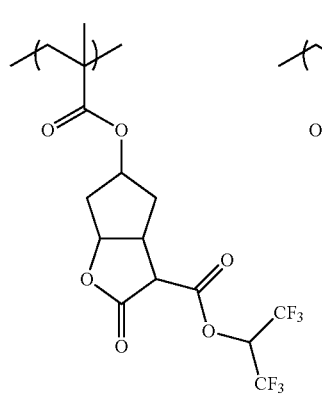
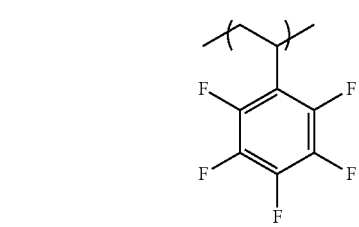
(C-64)
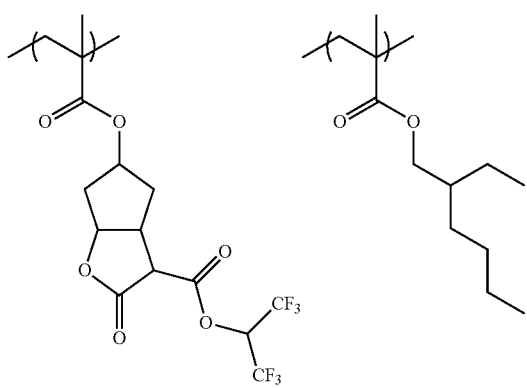
(C-67)
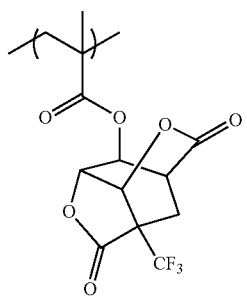
(C-68)
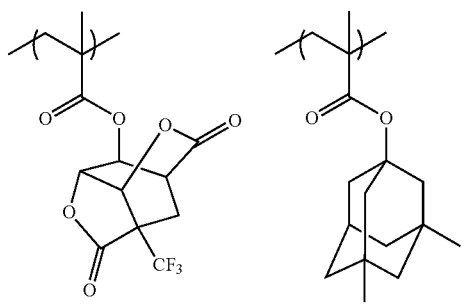
(C-69)
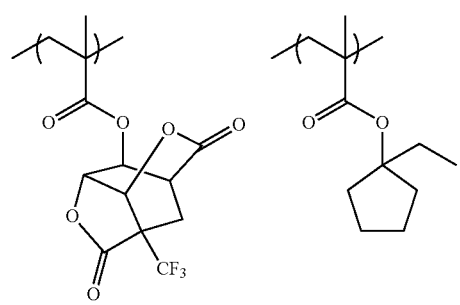
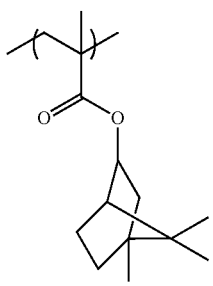

(C-70)
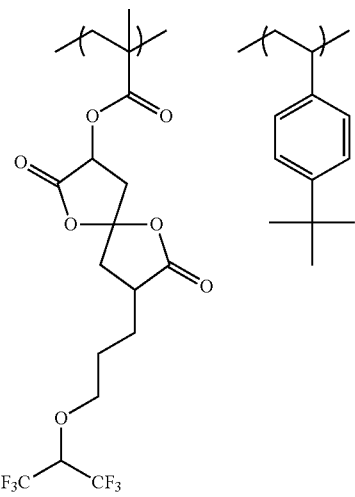 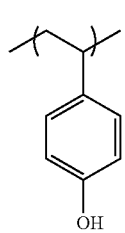 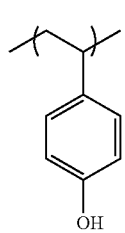
(C-71)
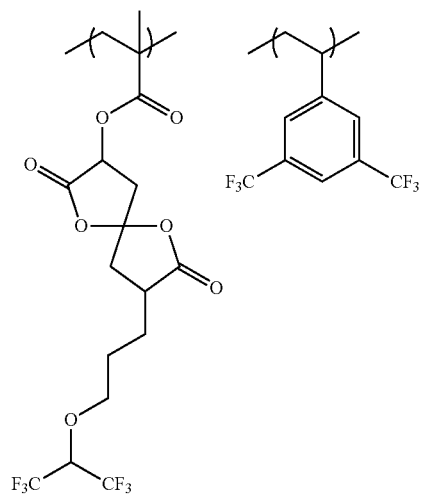 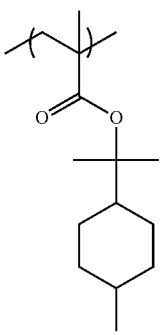
(C-72)
(C-73)
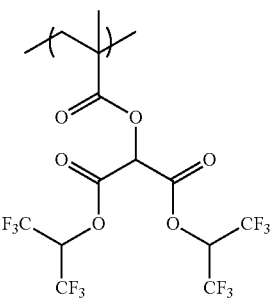 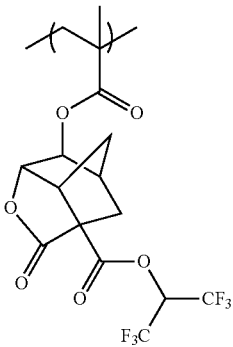
(C-74)
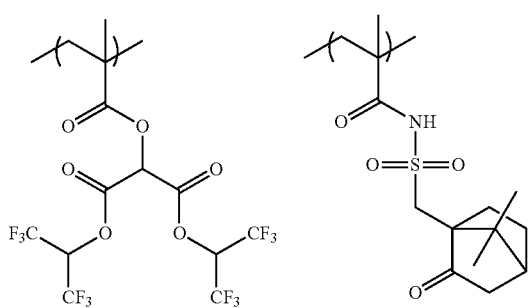
(C-75)
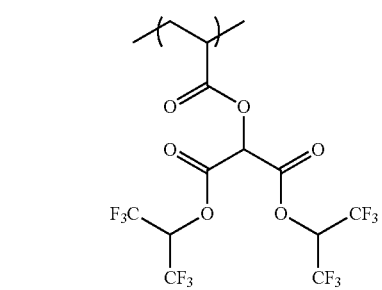
(C-76)
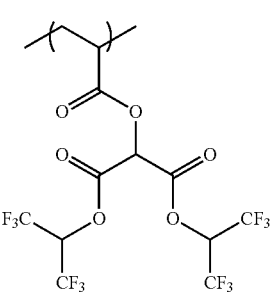 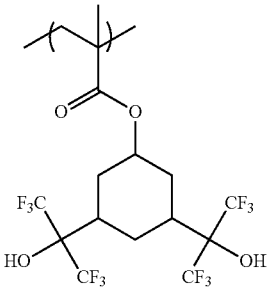

(C-77)
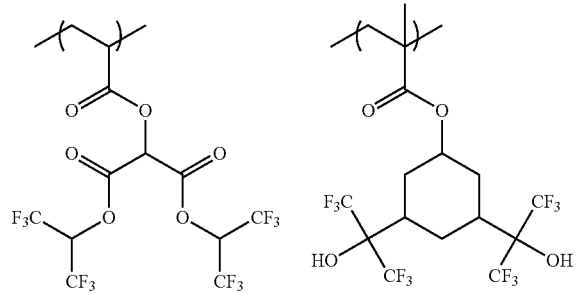
(C-80)
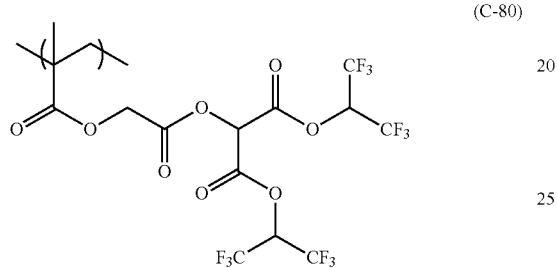
(C-81)
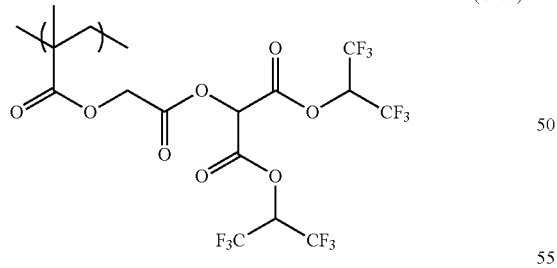
(C-88)
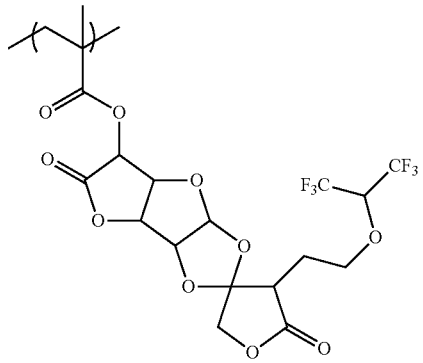
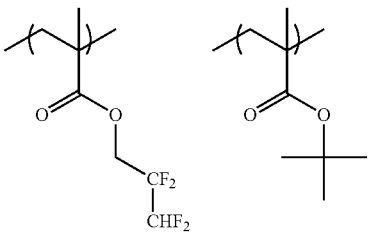
(C-89)
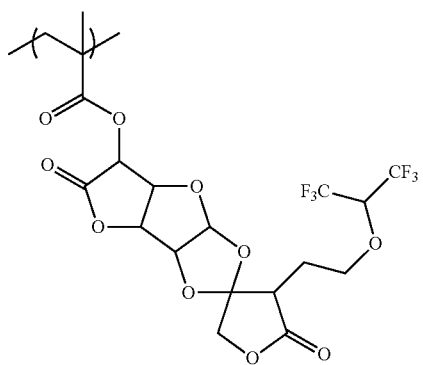
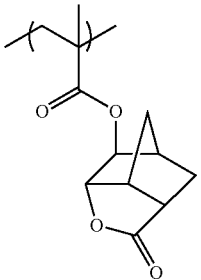
(C-96)
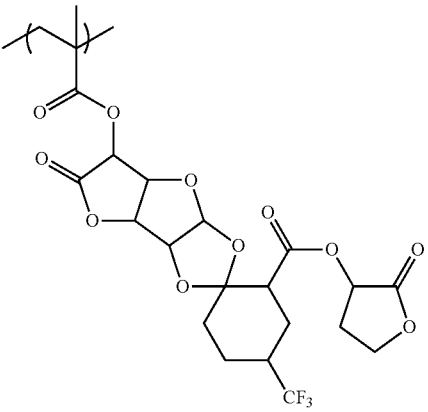

(C-101)
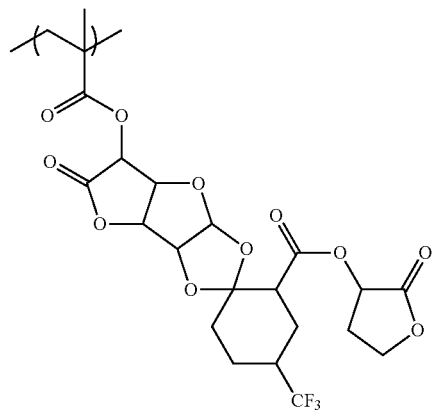
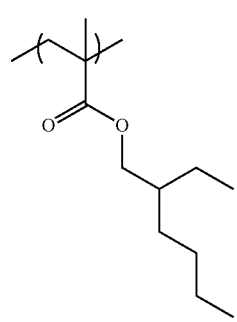
(C-102)
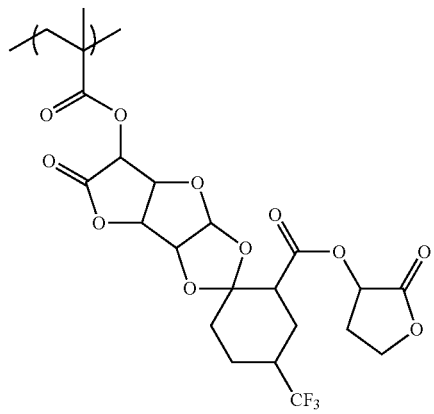
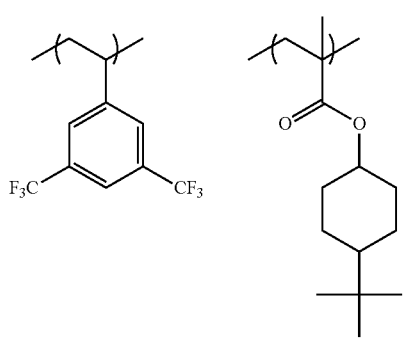
(C-114)
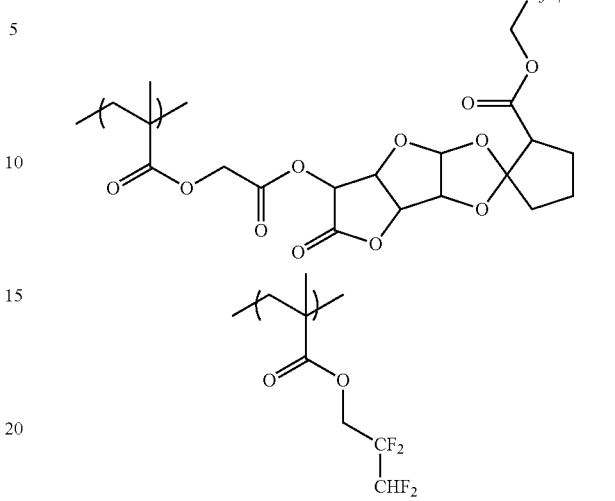
(C-115)
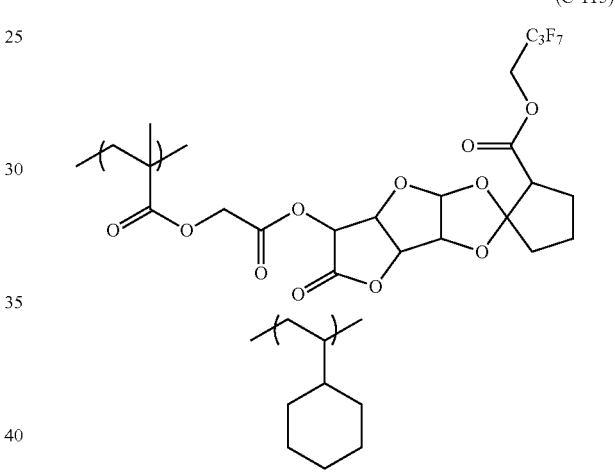
(C-117)
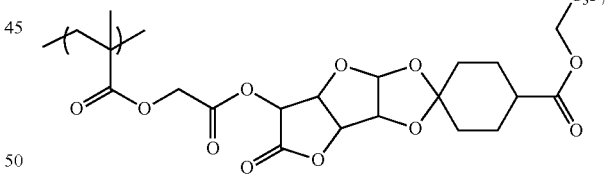
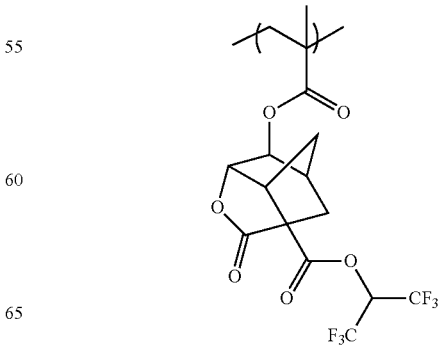

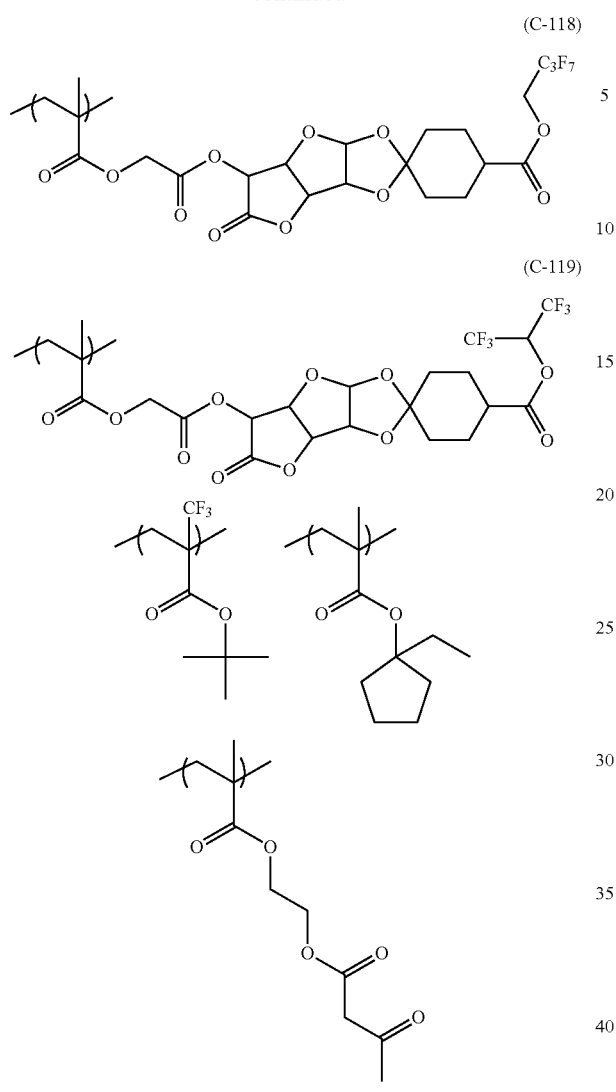
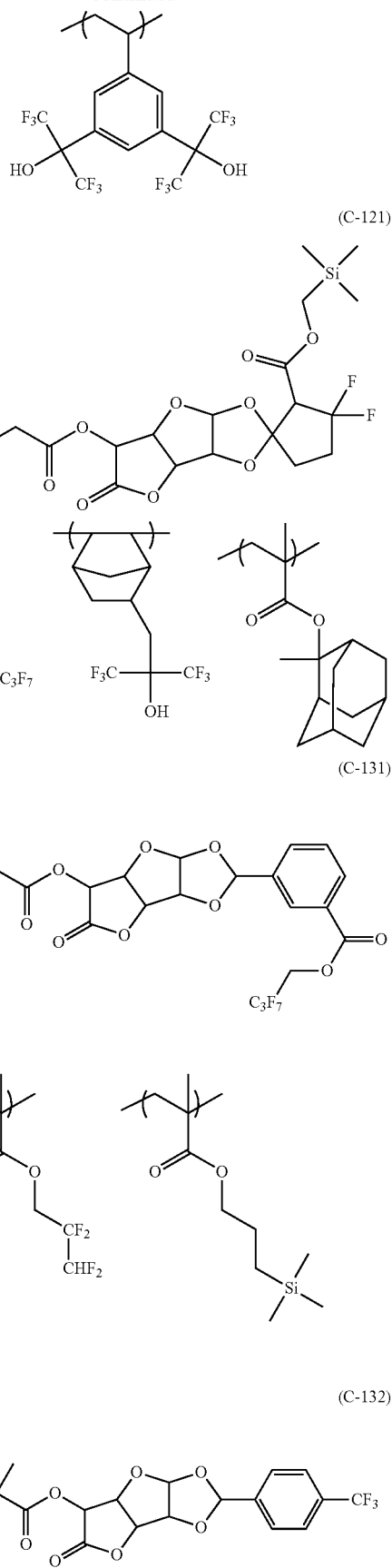

185
-continued
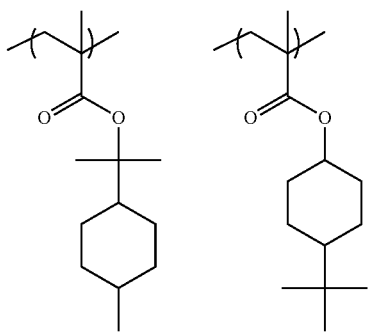
(C-133)
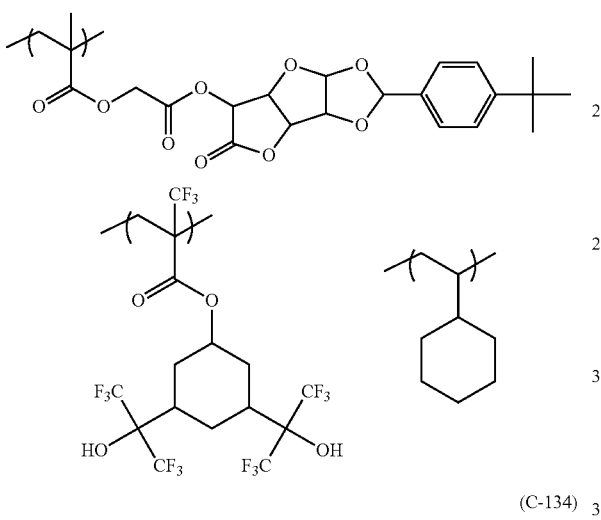
(C-134)
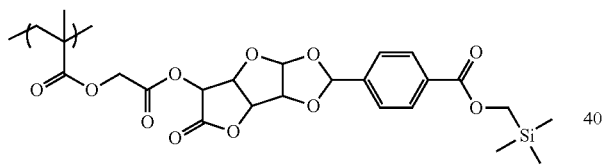
(C-135)
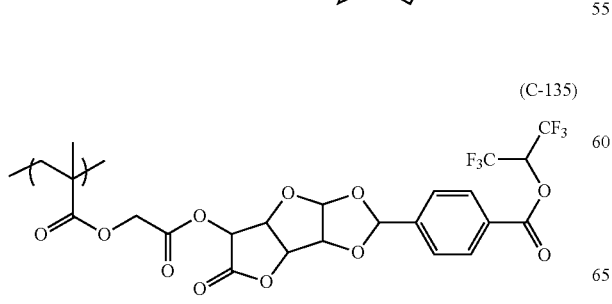
186
-continued
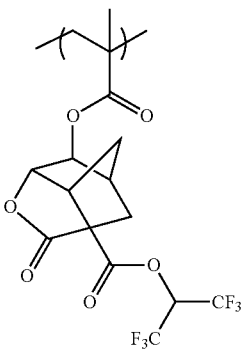
(C-136)
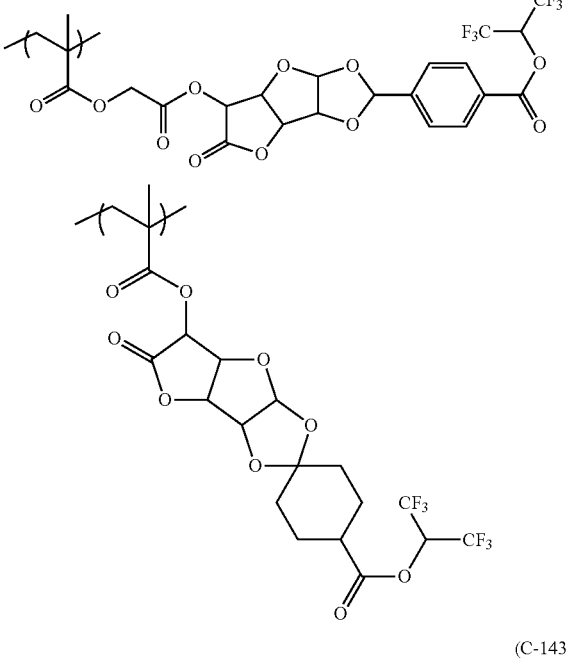
(C-143)
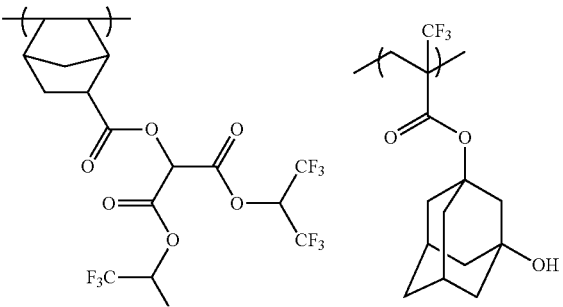
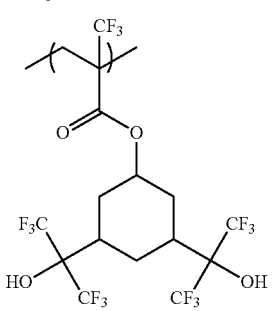

(C-146)
(C-147)
(C-148)
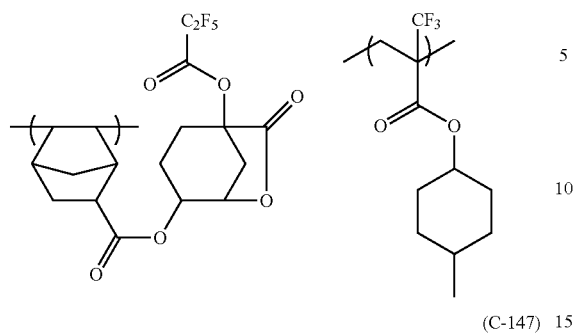
(C-149)
(C-155)
(C-171)
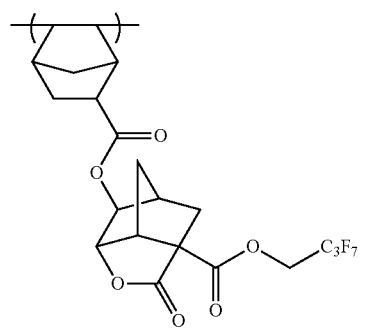
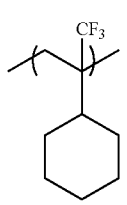
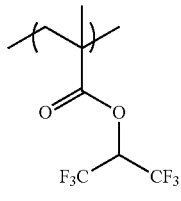
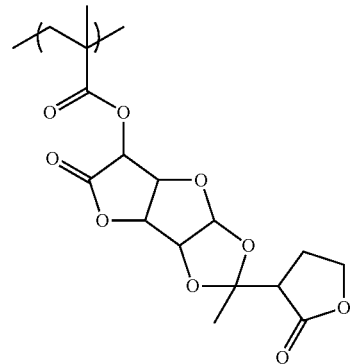
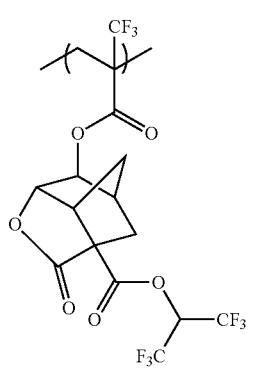
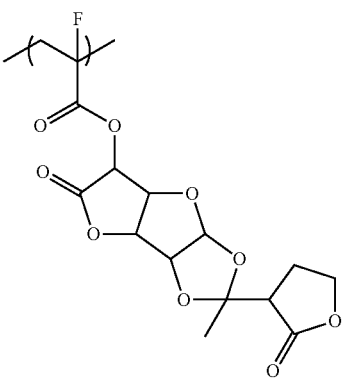

(C-172)
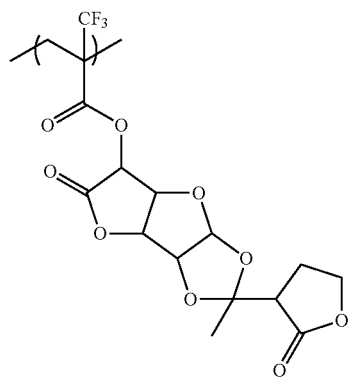
(C-173)
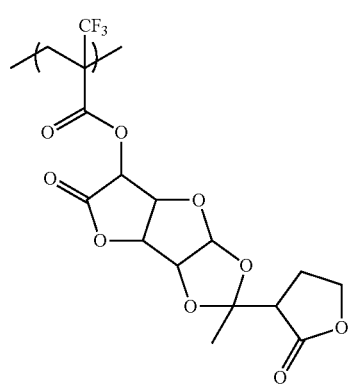
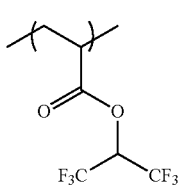
(C-156)
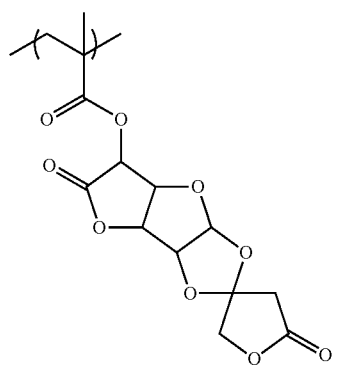
(C-164)
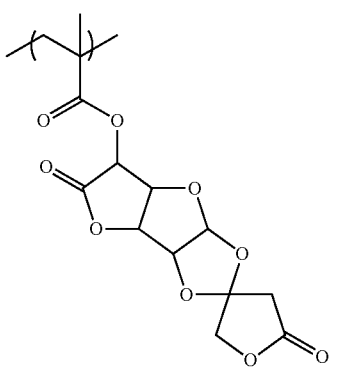
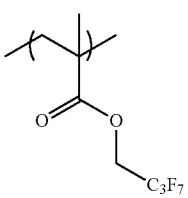
(C-170)
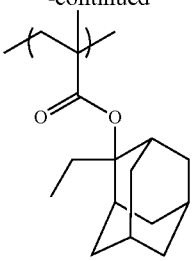
(C-165)
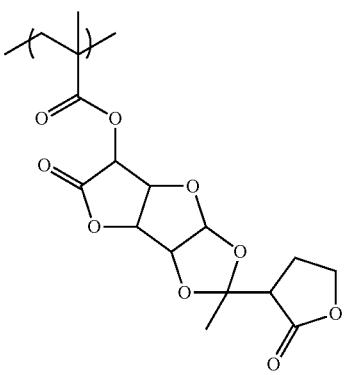
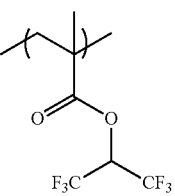
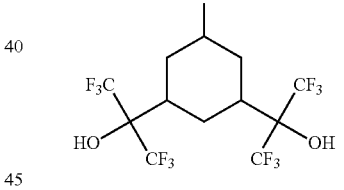
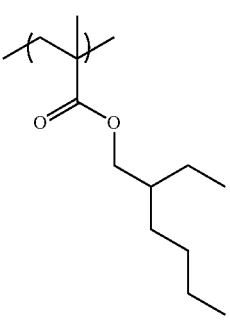
(C-174)
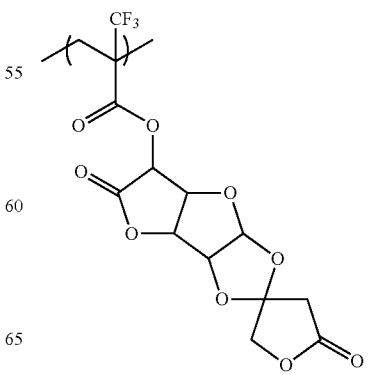
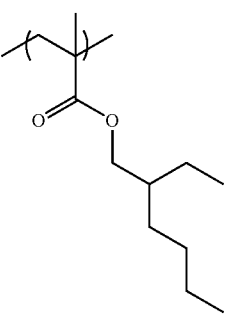
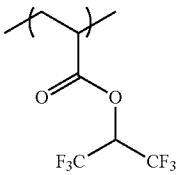

(C-179)
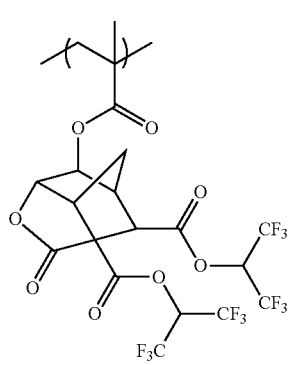
(C-180)
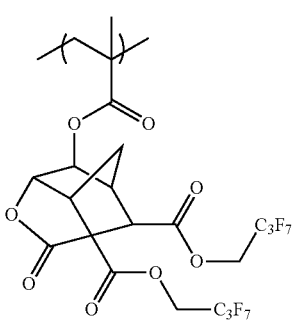
(C-191)
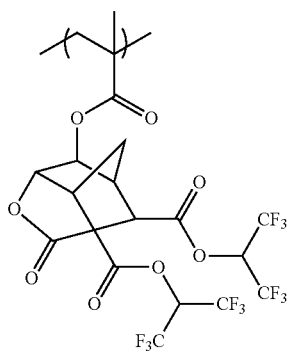 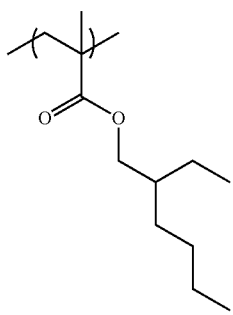
(C-192)
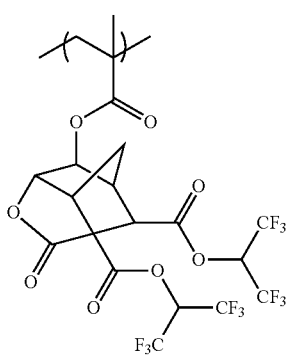 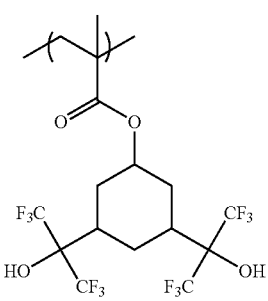
(C-193)
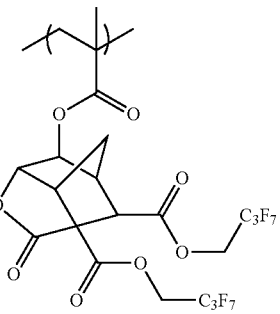 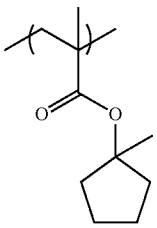
(C-194)
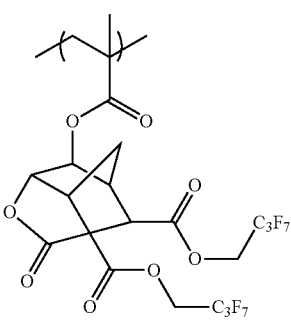 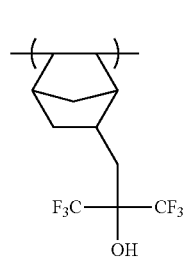
(C-200)
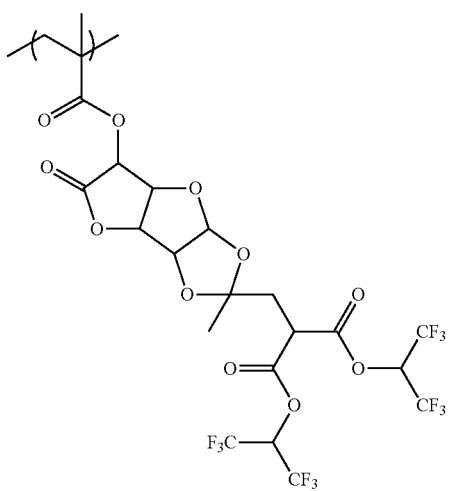
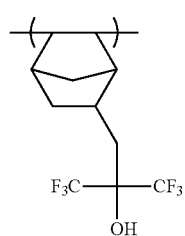

(C-199)
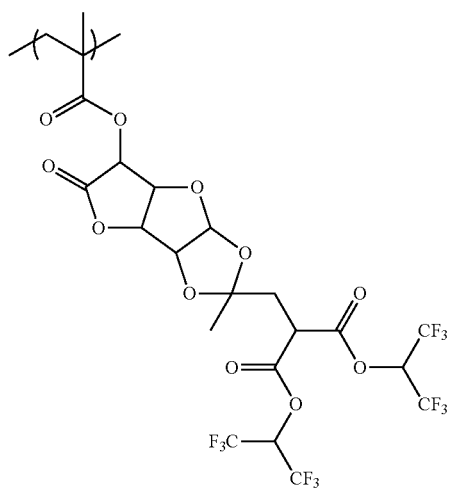
(C-201)
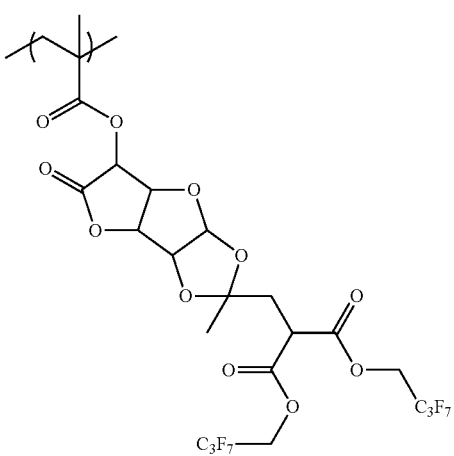
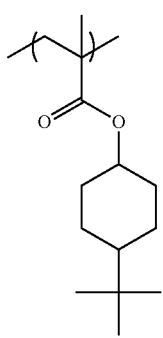
(C-205)
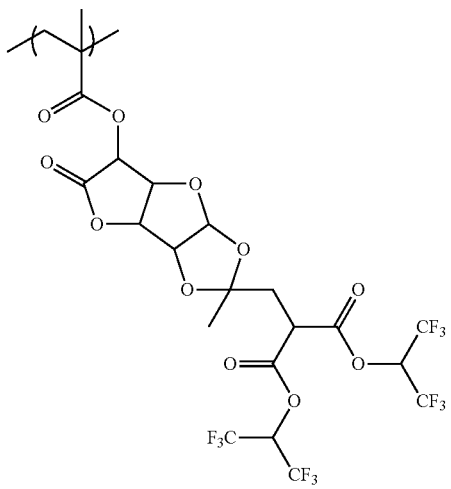
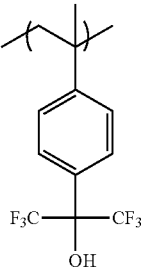
(C-207)
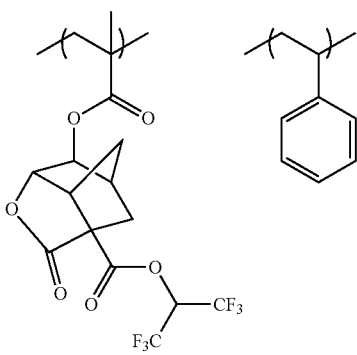
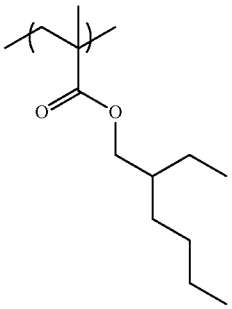

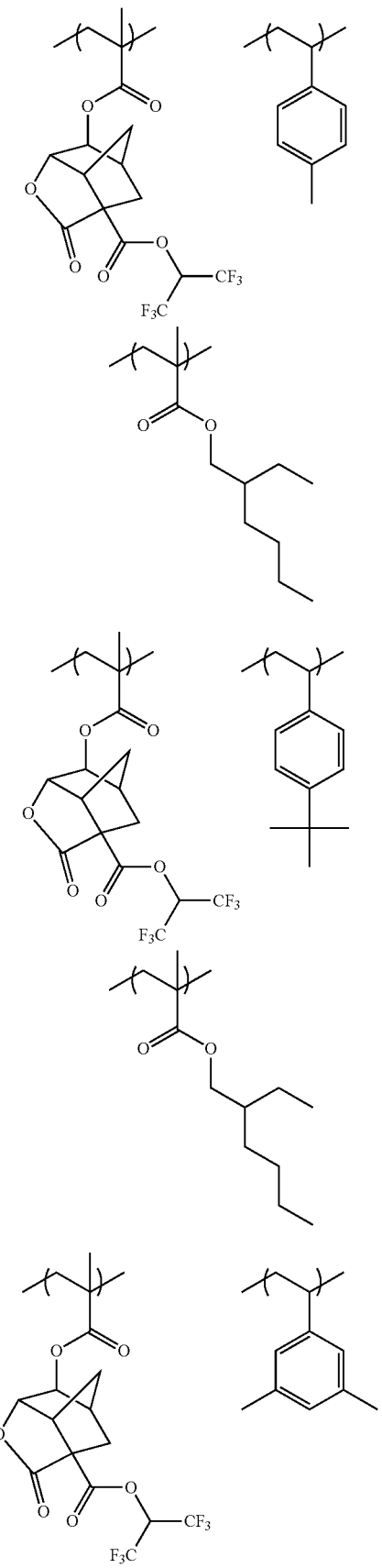
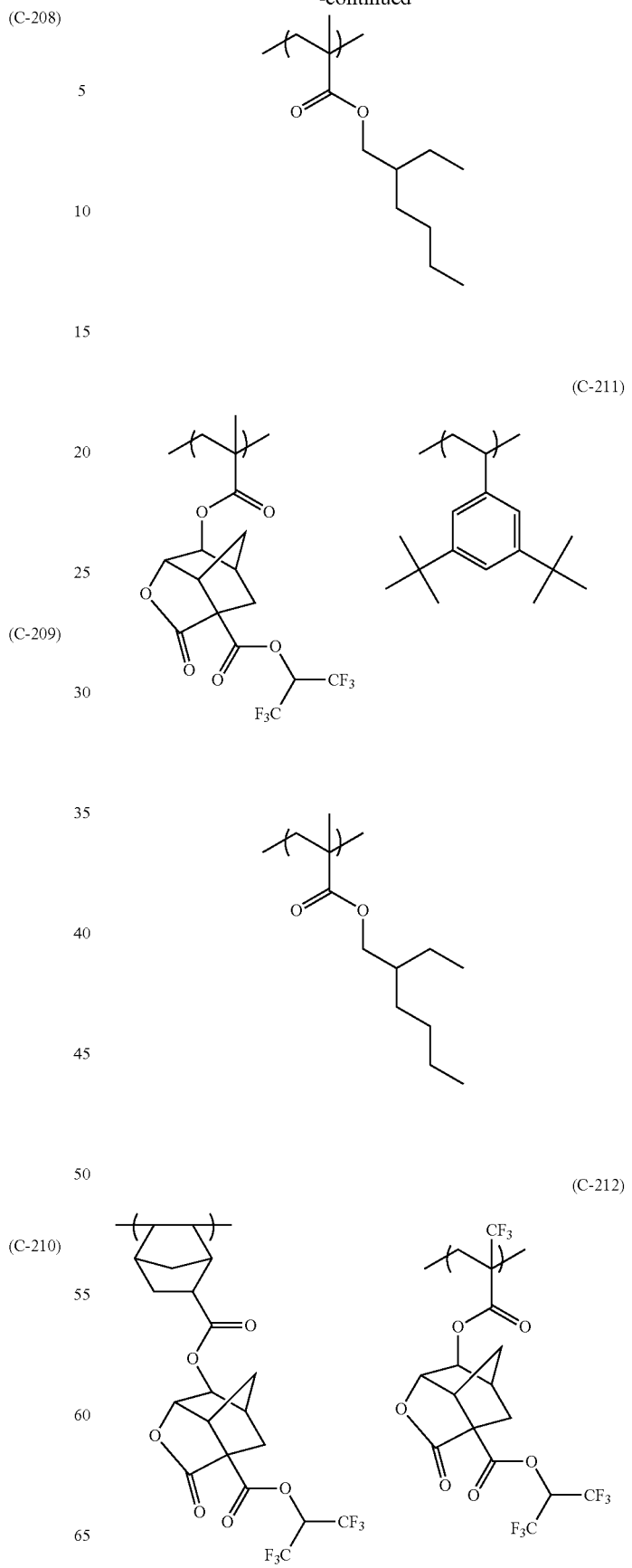

(C-213) 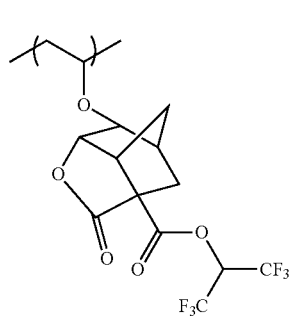 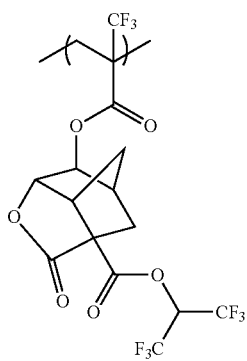
(C-214) 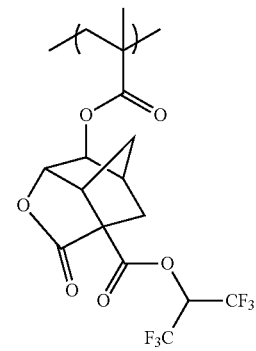 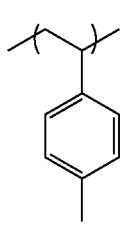
(C-215) 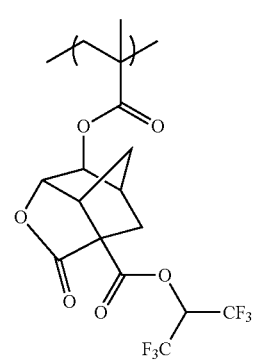 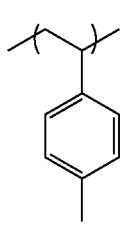
(C-216) 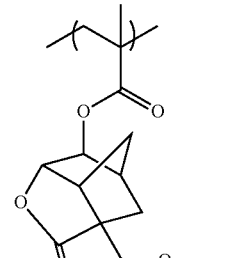 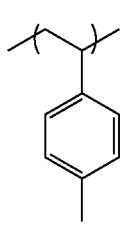
(C-217) 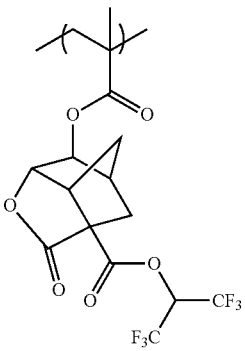 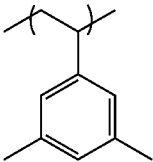
(C-218) 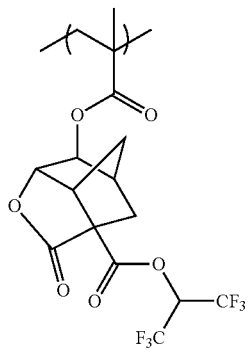 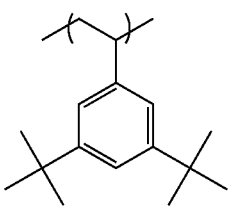
(C-219) 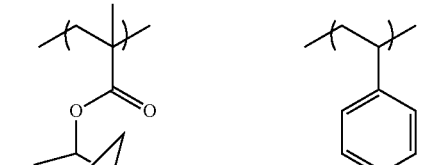 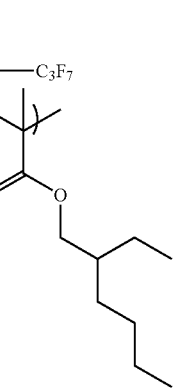
(C-220) 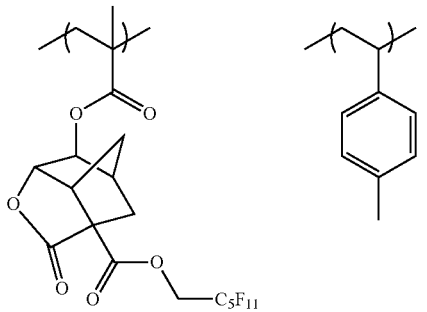

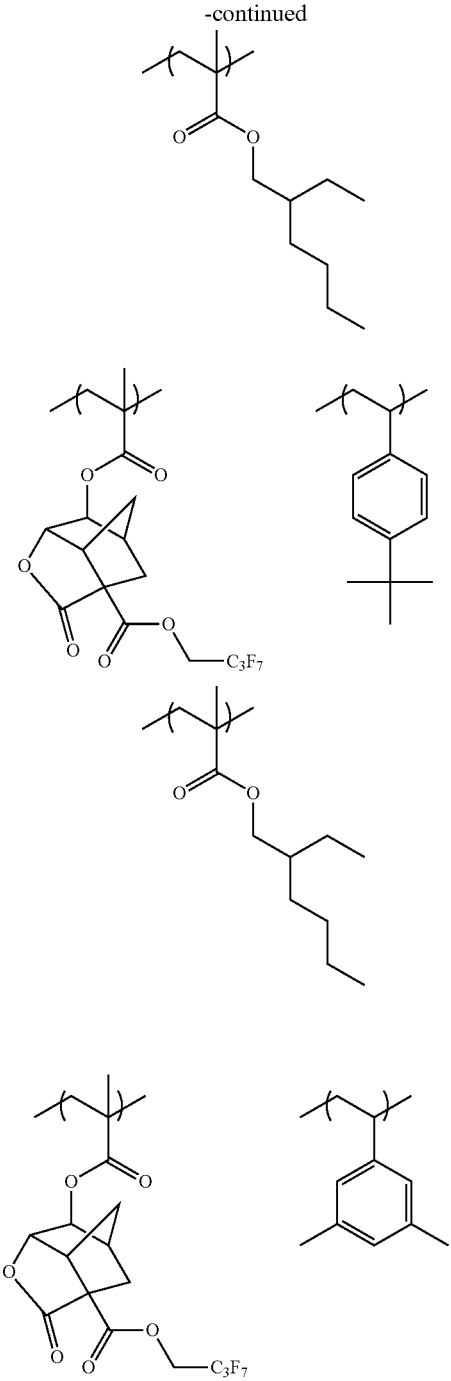
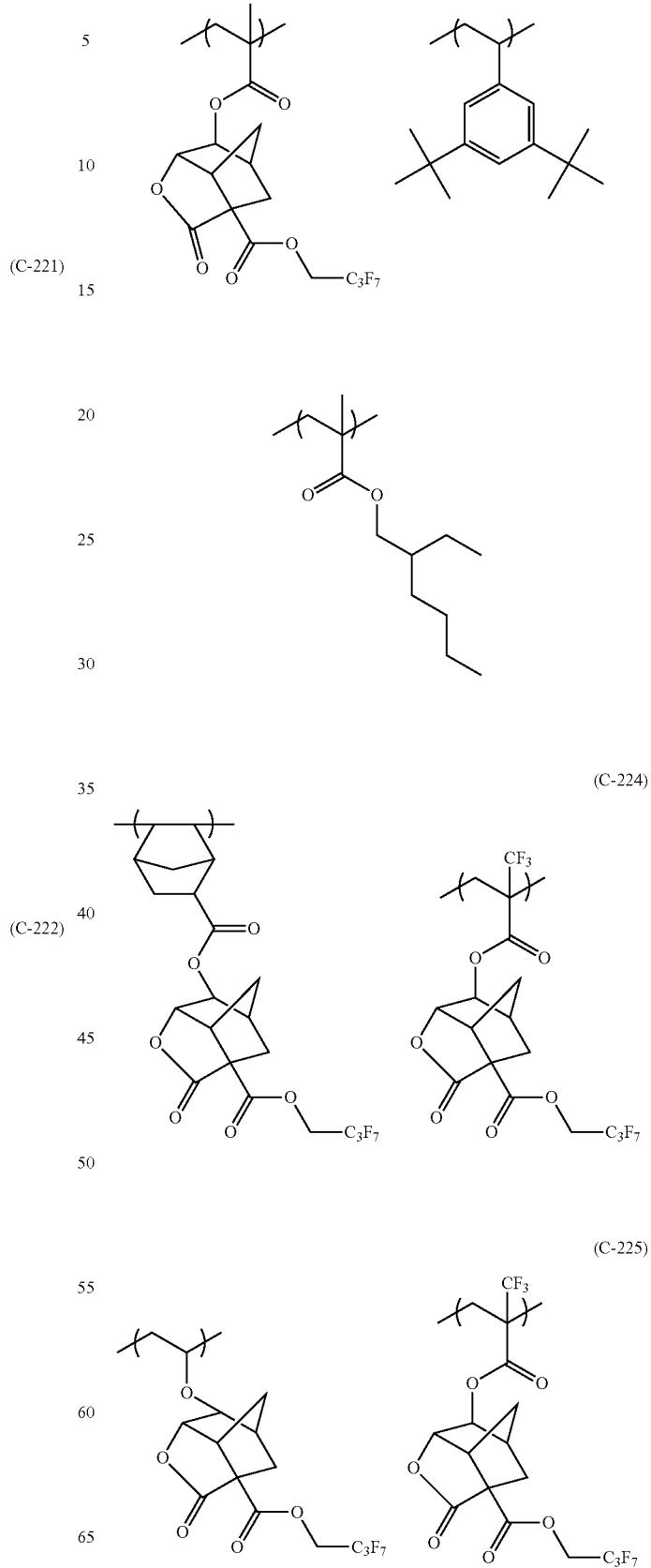

-continued
(C-226)
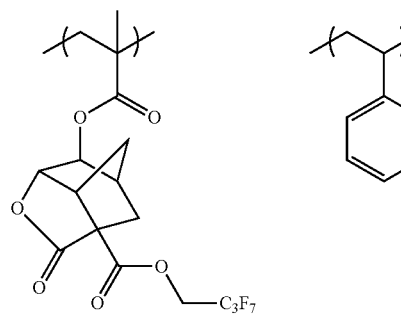 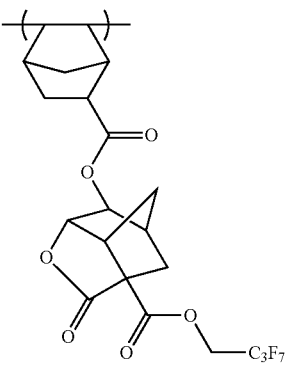
(C-227)
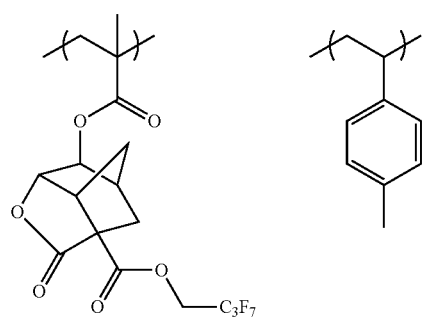 
(C-228)
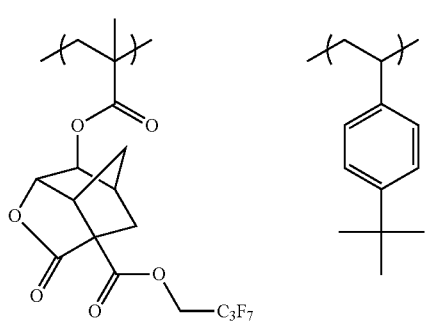 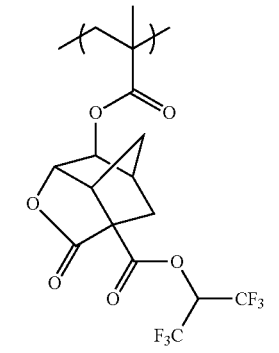
(C-229)
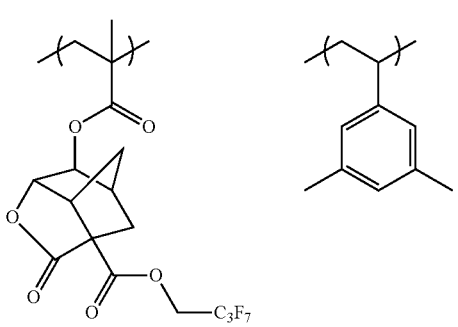 
(C-230)
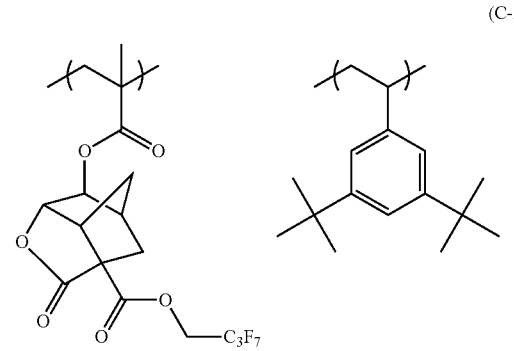
-continued
(C-231)
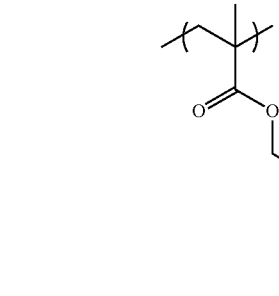
(C-232)
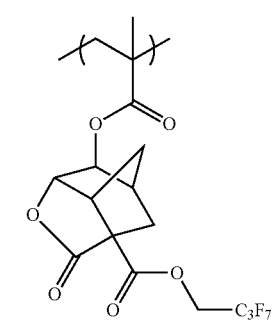
(C-233)

-continued
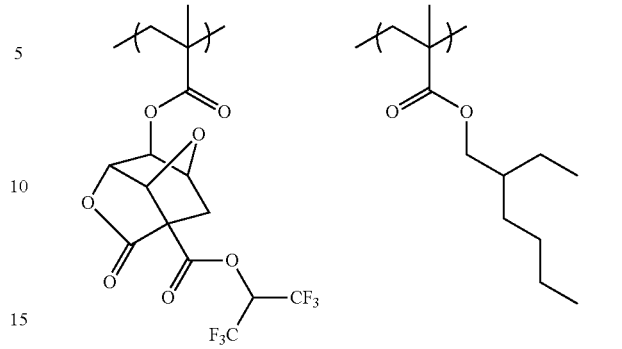
(C-237)
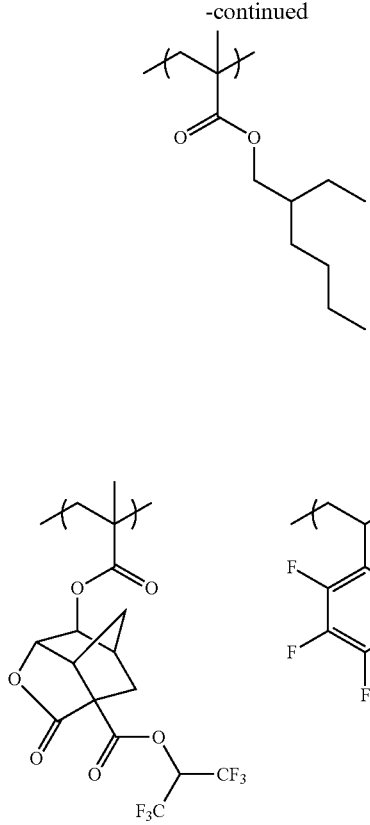
(C-234)
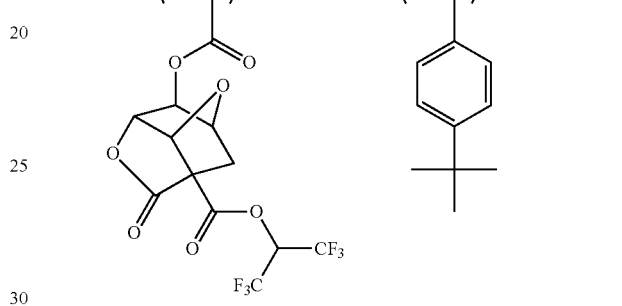
(C-238)
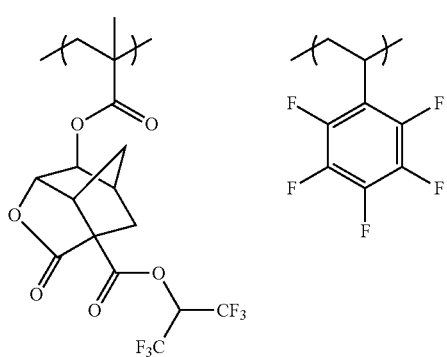
(C-235)
(C-239)
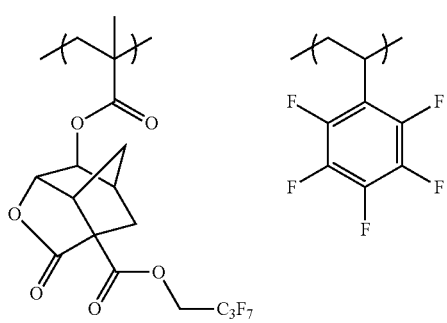
(C-240)
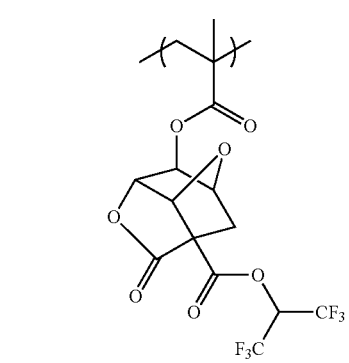
(C-236)
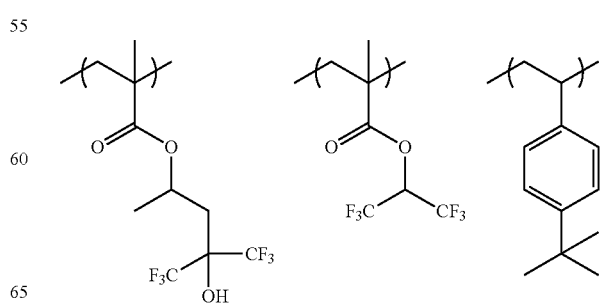

TABLE 1

| Resin | Composition | Mw | Mw/Mn |
|---|---|---|---|
| C-1 | 100 | 6000 | 1.5 |
| C-2 | 100 | 7500 | 1.4 |
| C-3 | 100 | 6000 | 1.4 |
| C-6 | 50/50 | 6500 | 1.4 |
| C-7 | 90/10 | 8000 | 1.4 |
| C-8 | 60/40 | 8000 | 1.3 |
| C-9 | 30/30/30/10 | 9500 | 1.4 |
| C-10 | 70/30 | 7000 | 1.4 |
| C-11 | 50/10/40 | 9000 | 1.6 |
| C-12 | 80/20 | 6000 | 1.4 |
| C-14 | 50/50 | 8000 | 1.4 |
| C-16 | 100 | 6000 | 1.4 |
| C-17 | 100 | 8000 | 1.4 |
| C-18 | 40/20/40 | 6000 | 1.4 |
| C-21 | 40/40/10/10 | 6000 | 1.4 |
| C-22 | 100 | 5500 | 1.4 |
| C-23 | 100 | 9500 | 1.5 |
| C-24 | 70/30 | 8500 | 1.4 |
| C-25 | 50/30/20 | 5000 | 1.4 |
| C-26 | 50/20/30 | 5500 | 1.4 |
| C-27 | 50/50 | 9000 | 1.5 |
| C-28 | 50/40/10 | 9000 | 1.4 |
| C-30 | 70/30 | 6500 | 1.4 |
| C-31 | 70/30 | 9000 | 1.5 |
| C-32 | 90/10 | 9000 | 1.5 |
| C-33 | 70/20/10 | 7000 | 1.4 |
| C-34 | 80/10/10 | 8500 | 1.5 |
| C-35 | 60/30/10 | 7500 | 1.4 |
| C-36 | 50/50 | 5000 | 1.5 |
| C-38 | 50/50 | 4500 | 1.4 |
| C-39 | 80/20 | 5000 | 1.4 |
| C-40 | 100 | 5000 | 1.4 |
| C-43 | 90/10 | 8500 | 1.4 |
| C-44 | 30/30/30/10 | 5500 | 1.4 |
| C-49 | 60/30/10 | 6000 | 1.4 |
| C-50 | 60/40 | 8000 | 1.5 |
| C-51 | 50/50 | 9500 | 1.4 |
| C-53 | 100 | 7000 | 1.5 |
| C-54 | 70/10/10/10 | 5500 | 1.4 |
| C-55 | 80/20 | 6500 | 1.4 |
| C-56 | 30/30/40 | 6000 | 1.4 |
| C-62 | 100 | 6500 | 1.4 |
| C-63 | 80/10/10 | 7000 | 1.5 |
| C-64 | 90/10 | 9000 | 1.5 |
| C-67 | 100 | 6500 | 1.4 |
| C-68 | 80/20 | 6500 | 1.4 |
| C-69 | 70/20/10 | 7000 | 1.4 |
| C-70 | 60/30/10 | 9000 | 1.5 |
| C-71 | 60/20/20 | 8000 | 1.4 |
| C-72 | 100 | 9500 | 1.5 |
| C-73 | 40/60 | 8000 | 1.4 |
| C-74 | 60/10/30 | 7000 | 1.5 |
| C-75 | 100 | 5500 | 1.5 |
| C-76 | 90/10 | 6500 | 1.4 |
| C-77 | 90/10 | 7500 | 1.3 |
| C-80 | 70/10/20 | 8500 | 1.5 |
| C-81 | 80/20 | 5500 | 1.3 |
| C-88 | 40/30/30 | 6000 | 1.3 |
| C-89 | 70/30 | 6500 | 1.3 |
| C-96 | 100 | 6000 | 1.5 |
| C-101 | 80/20 | 7000 | 1.3 |
| C-102 | 50/20/30 | 4500 | 1.3 |
| C-114 | 80/20 | 7000 | 1.5 |
| C-115 | 90/10 | 6000 | 1.2 |
| C-117 | 50/50 | 6000 | 1.5 |
| C-118 | 100 | 9500 | 1.4 |
| C-119 | 50/20/20/10 | 8000 | 1.5 |
| C-120 | 75/10/10/5 | 7000 | 1.3 |
| C-121 | 30/30/10/30 | 5500 | 1.3 |
| C-131 | 60/20/20 | 4000 | 1.4 |
| C-132 | 50/30/20 | 6500 | 1.4 |
| C-133 | 70/10/20 | 7000 | 1.4 |
| C-134 | 80/10/10 | 9000 | 1.4 |
| C-135 | 60/40 | 8000 | 1.5 |
| C-136 | 30/70 | 9000 | 1.4 |
| C-143 | 50/40/10 | 7000 | 1.4 |
| C-146 | 50/50 | 9000 | 1.5 |
| C-147 | 48/50/2 | 6000 | 1.4 |
| C-148 | 50/50 | 9000 | 1.5 |
| C-149 | 50/25/25 | 6000 | 1.4 |
| C-155 | 50/50 | 6000 | 1.5 |
| C-156 | 50/50 | 4000 | 1.5 |
| C-164 | 25/50/25 | 6000 | 1.5 |
| C-165 | 40/40/10/10 | 6500 | 1.4 |
| C-171 | 100 | 4500 | 1.4 |
| C-172 | 100 | 3500 | 1.4 |
| C-173 | 60/40 | 5000 | 1.4 |
| C-174 | 90/10 | 6000 | 1.4 |
| C-179 | 100 | 6000 | 1.4 |
| C-180 | 100 | 7000 | 1.3 |
| C-191 | 90/10 | 5500 | 1.4 |
| C-192 | 75/25 | 9000 | 1.4 |
| C-193 | 70/30 | 10000 | 1.5 |
| C-194 | 70/30 | 5000 | 1.4 |
| C-199 | 100 | 5000 | 1.4 |
| C-200 | 80/20 | 6000 | 1.4 |
| C-201 | 80/20 | 8000 | 1.5 |
| C-205 | 80/20 | 7000 | 1.4 |
| C-207 | 80/15/5 | 10000 | 1.4 |
| C-208 | 85/10/5 | 5000 | 1.5 |
| C-209 | 90/8/2 | 13000 | 1.5 |
| C-210 | 85/10/5 | 6000 | 1.5 |
| C-211 | 90/8/2 | 8000 | 1.4 |
| C-212 | 50/50 | 12000 | 1.5 |
| C-213 | 50/50 | 8000 | 1.3 |
| C-214 | 85/15 | 6500 | 1.5 |
| C-215 | 85/15 | 4000 | 1.5 |
| C-216 | 90/10 | 7500 | 1.6 |
| C-217 | 90/10 | 3500 | 1.5 |
| C-218 | 95/5 | 5500 | 1.4 |
| C-219 | 85/10/5 | 5000 | 1.5 |
| C-220 | 88/10/2 | 13000 | 1.4 |
| C-221 | 90/8/2 | 12000 | 1.5 |
| C-222 | 90/8/2 | 11000 | 1.4 |
| C-223 | 90/8/2 | 9000 | 1.5 |
| C-224 | 50/50 | 6000 | 1.5 |
| C-225 | 50/50 | 8000 | 1.5 |
| C-226 | 80/20 | 4500 | 1.3 |
| C-227 | 85/15 | 8500 | 1.6 |
| C-228 | 90/10 | 10000 | 1.4 |
| C-229 | 90/10 | 3500 | 1.5 |
| C-230 | 95/5 | 4500 | 1.5 |
| C-231 | 50/50 | 4000 | 1.5 |
| C-232 | 80/18/2 | 6000 | 1.5 |
| C-233 | 90/8/2 | 9500 | 1.5 |
| C-234 | 80/20 | 6500 | 1.4 |
| C-235 | 90/10 | 8000 | 1.5 |
| C-236 | 100 | 8000 | 1.5 |
| C-237 | 95/5 | 4500 | 1.5 |
| C-238 | 90/10 | 10000 | 1.5 |
| C-239 | 100 | 6500 | 1.7 |
| C-240 | 40/20/20/20 | 12000 | 1.8 |

As for the resin (C), one kind may be used alone, or two or more kinds may be used in combination.

Also, (CP) a resin having at least either a fluorine atom or a silicon atom and being different from the resin (C) is preferably used in combination.

(CP) Resin Having at Least Either a Fluorine Atom or a Silicon Atom

The actinic ray-sensitive or radiation-sensitive resin composition of the present invention may further contain (CP) a resin having at least either a fluorine atom or a silicon atom, separately from the resin (C). By virtue of containing the resin (C) and resin (CP), the resin (C) and the resin (CP) are unevenly distributed to the film surface layer and when the immersion medium is water, the film formed can be enhanced in the receding contact angle for water on the resist film surface as well as in the followability of the immersion liquid. The receding contact angle of the film is preferably from 60 to 90°, more preferably 70° or more. The resin (CP) may be used by appropriately adjusting its content to give a film having a receding contact angle in the range above, but the content is preferably from 0.01 to 10 mass %, more preferably from 0.1 to 5 mass %, still more preferably from 0.1 to 4 mass %, yet still more preferably from 0.1 to 3 mass %, based on the entire solid content of the actinic ray-sensitive or radiation-sensitive resin composition. The resin (CP) is, as described above, unevenly distributed to the interface but unlike a surfactant, need not have necessarily a hydrophilic group in the molecule and may not contribute to uniform mixing of polar/nonpolar substances.

In the immersion exposure step, the immersion liquid needs to move on a wafer following the movement of an exposure head that is scanning the wafer at a high speed and forming an exposure pattern. Therefore, the contact angle of the immersion liquid with the film in a dynamic state is important, and the resist is required to have a performance of allowing a liquid droplet to follow the high-speed scanning of an exposure head with no remaining.

Thank to use of the resin (C) and the resin (CP) in combination, the hydrophobicity (water followability) on the film surface is enhanced and the development residue (scum) is reduced.

The fluorine atom or silicon atom in the (CP) resin having at least either a fluorine atom or a silicon atom may be present in the main chain of the resin or may be substituted on the side chain.

The resin (CP) is preferably a resin having, as the fluorine atom-containing partial structure, a fluorine atom-containing alkyl group, a fluorine atom-containing cycloalkyl group or a fluorine atom-containing aryl group.

The fluorine atom-containing alkyl group (preferably having a carbon number of 1 to 10, more preferably from 1 to 4) is a linear or branched alkyl group with at least one hydrogen atom being replaced by a fluorine atom and may further have other substituents.

The fluorine atom-containing cycloalkyl group is a monocyclic or polycyclic cycloalkyl group with at least one hydrogen atom being replaced by a fluorine atom and may further have other substituents.

The fluorine atom-containing aryl group is an aryl group (e.g., phenyl, naphthyl) with at least one hydrogen atom being replaced by a fluorine atom and may further have other substituents.

Preferred examples of the fluorine atom-containing alkyl group, fluorine atom-containing cycloalkyl group and fluorine atom-containing aryl group include groups represented by formulae (F2) to (F4) described above with respect to the resin (C), but the present invention is not limited thereto.

In the present invention, the group represented by formulae (F2) to (F4) is preferably contained in a (meth)acrylate-based repeating unit.

Specific examples of the repeating unit having a fluorine atom are set forth below, but the present invention is not limited thereto.

In specific examples, $X_1$ represents a hydrogen atom, $-CH_3$, $-F$ or $-CF_3$.

$X_2$ represents $-F$ or $-CF_3$.

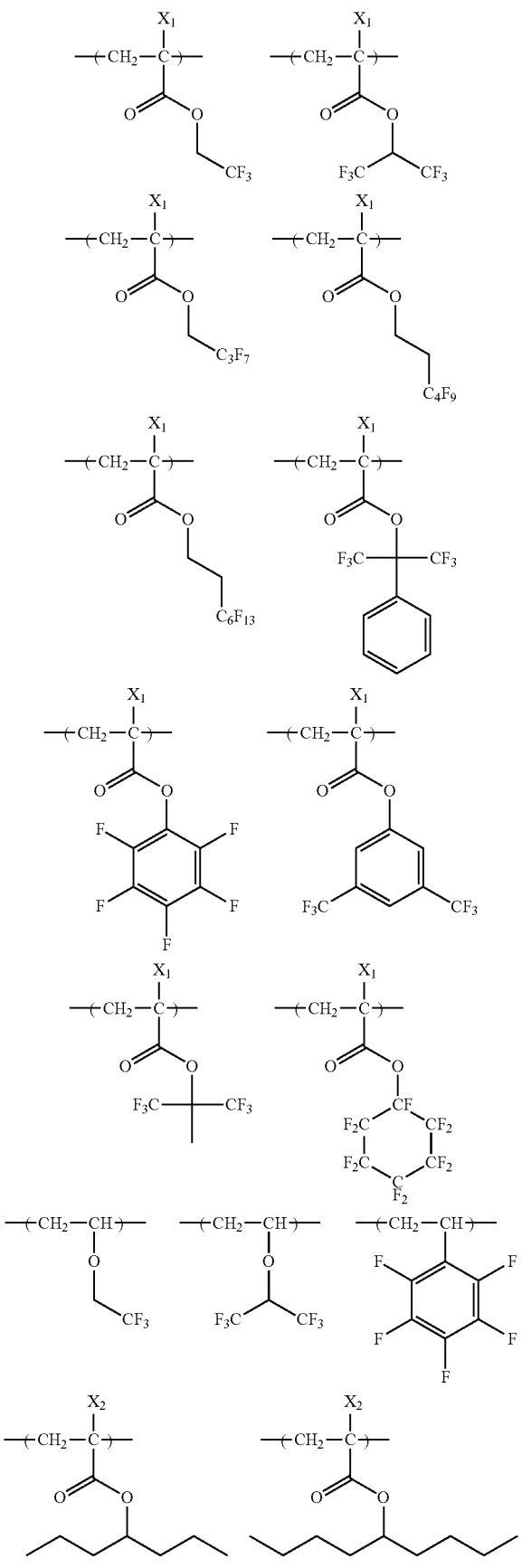

209
-continued
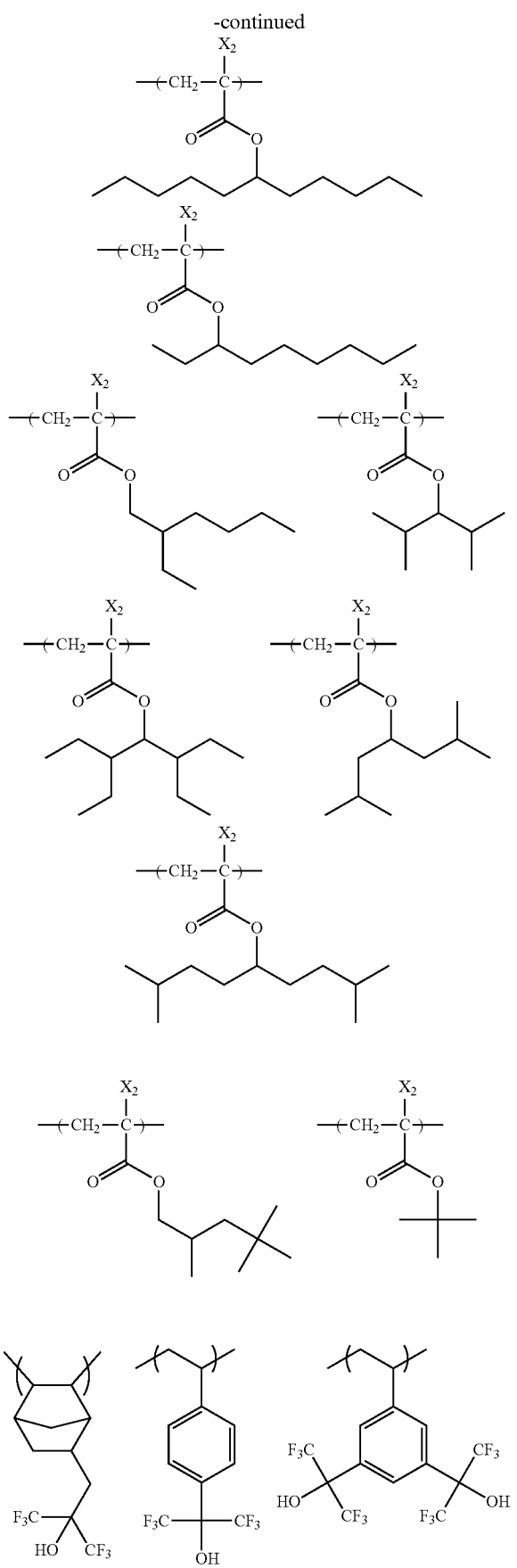
210
-continued
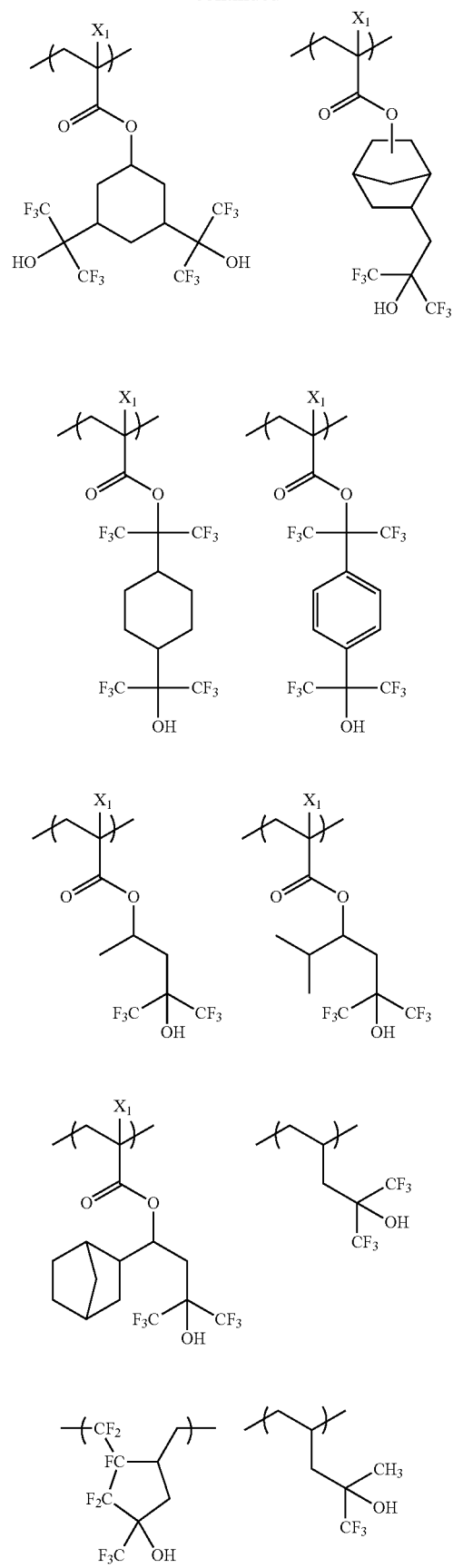

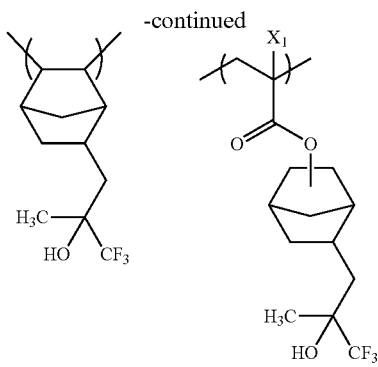

The resin (CP) is preferably a resin having an alkylsilyl structure (preferably a trialkylsilyl group) or a cyclic siloxane structure as the silicon atom-containing partial structure.

Specific examples of the alkylsilyl structure and cyclic siloxane structure include groups represented by formulae (CS-1) to (CS-3) described above with respect to the resin (C).

Furthermore, the resin (CP) may contain at least one group selected from the group consisting of the following (x) to (z):

(x) an alkali-soluble group, (y) a group capable of decomposing by the action of an alkali developer to increase the solubility in an alkali developer, and (z) a group capable of decomposing by the action of an acid.

Specific examples of these groups are the same as those described above with respect to the resin (C).

The content of the repeating unit having (y) a group capable of increasing the solubility in an alkali developer is preferably from 1 to 50 mol %, more preferably from 3 to 35 mol %, still more preferably from 5 to 20 mol %, based on all repeating units in the resin (CP).

Specific examples of the repeating unit having (y) a group capable of increasing the solubility in an alkali developer are the same as those of the repeating unit having a lactone structure described for the resin of the component (A).

Examples of the repeating unit having (z) a group capable of decomposing by the action of an acid, contained in the resin (CP), are the same as those of the repeating unit having an acid-decomposable group described for the resin of the component (A). In the resin (CP), the content of the repeating unit having (z) a group capable of decomposing by the action of an acid is preferably from 1 to 80 mol %, more preferably from 10 to 80 mol %, still more preferably from 20 to 60 mol %, based on all repeating units in the resin (CP).

The resin (CP) may further have a repeating unit represented by formula (III) described above with respect to the resin (C).

In the case where the resin (CP) contains a fluorine atom, the fluorine atom content is preferably from 5 to 80 mass %, more preferably from 10 to 80 mass %, based on the molecular weight of the resin (CP). Also, the fluorine atom-containing repeating unit preferably occupies from 10 to 100 mass %, more preferably from 30 to 100 mass %, based on all repeating units in the resin (CP).

In the case where the resin (CP) contains a silicon atom, the silicon atom content is preferably from 2 to 50 mass %, more preferably from 2 to 30 mass %, based on the molecular weight of the resin (CP). Also, the silicon atom-containing repeating unit preferably occupies from 10 to 100 mass %, more preferably from 20 to 100 mass %, based on all repeating units in the resin (CP).

The standard polystyrene-equivalent weight average molecular of the resin (CP) is preferably from 1,000 to 100,000, more preferably from 1,000 to 50,000, still more preferably from 2,000 to 15,000.

Similarly to the resin of the component (A), in the resin (CP), it is of course preferred that the amount of impurities such as metal is small, but also the content of residual monomers or oligomer components is preferably from 0 to 10 mass %, more preferably from 0 to 5 mass %, still more preferably from 0 to 1 mass %. By satisfying these conditions, an actinic ray-sensitive or radiation-sensitive resin composition free of extraneous substances in the liquid or change with aging in the sensitivity and the like can be obtained. Furthermore, in view of resolution, resist profile, side wall of resist pattern, roughness and the like, the molecular weight distribution (Mw/Mn, also called polydispersity) is preferably from 1 to 3, more preferably from 1 to 2, still more preferably from 1 to 1.8, and most preferably from 1 to 1.5.

As for the resin (CP), various commercially available products may be used or the resin may be synthesized by an ordinary method (for example, radical polymerization)). Specifically, the resin may be synthesized in the same manner as the resin (C).

Specific examples of the resin (CP) having at least either a fluorine atom or a silicon atom are set forth below.

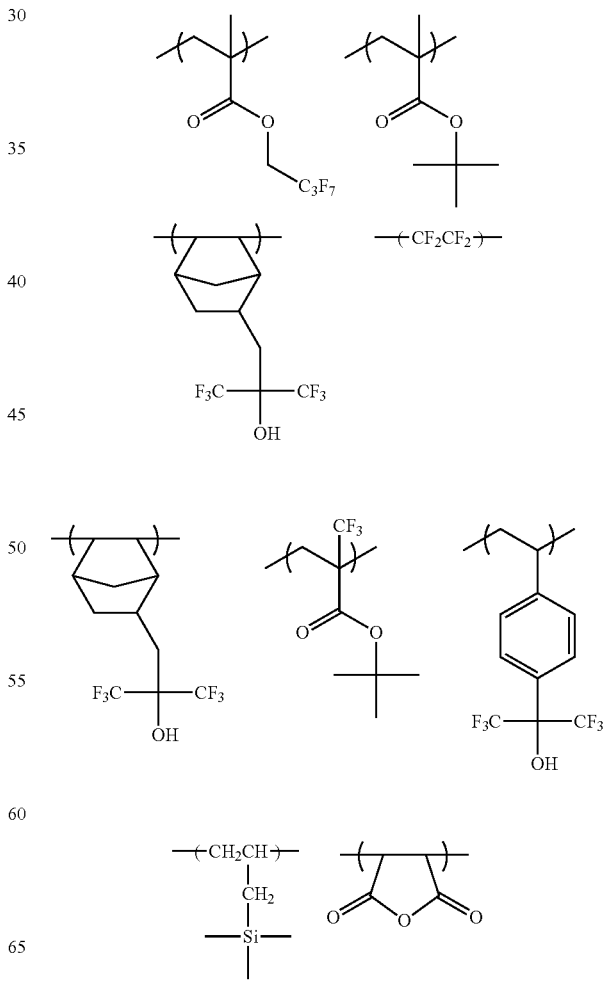

213
-continued
214
-continued
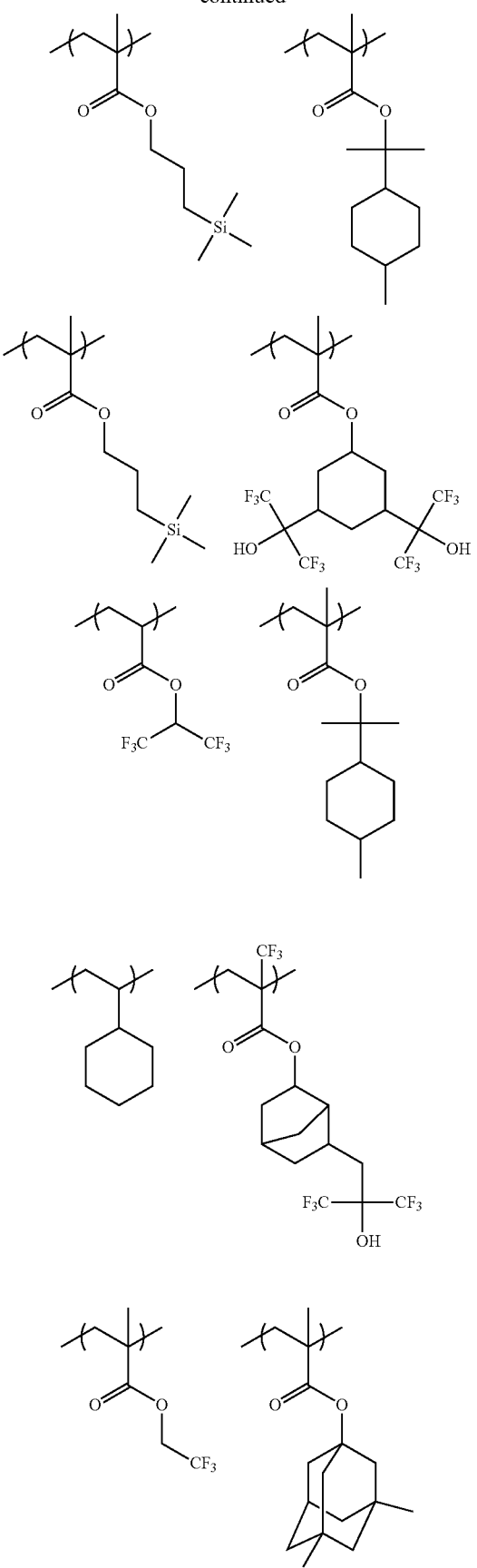
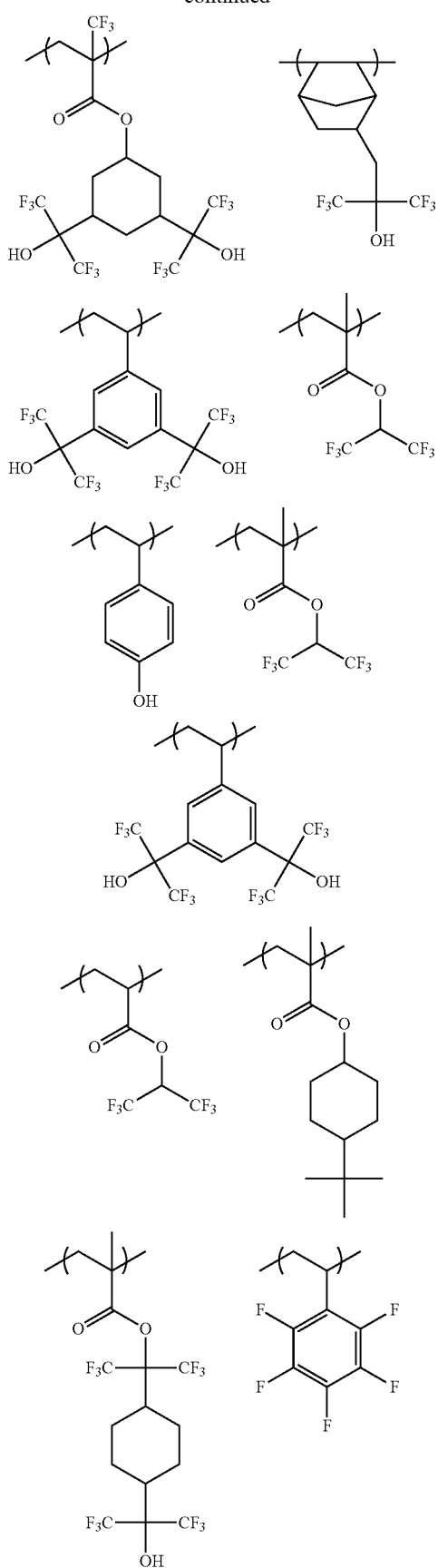

215
-continued
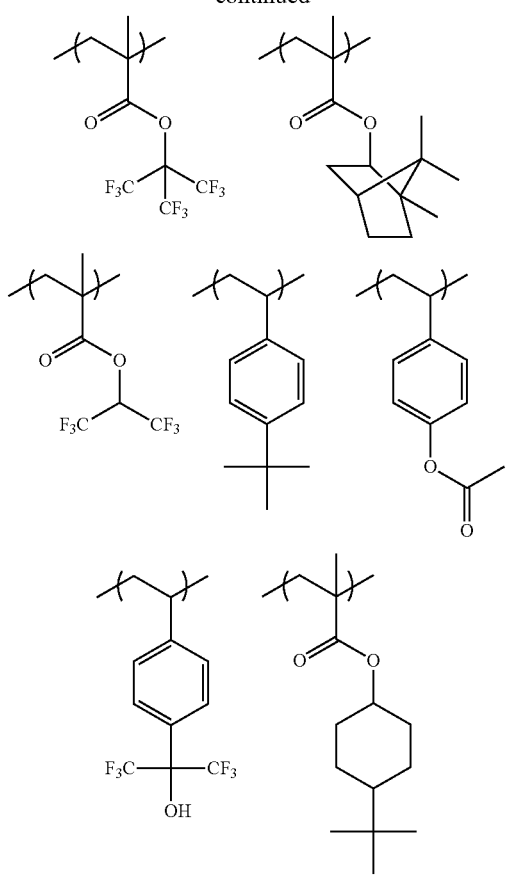
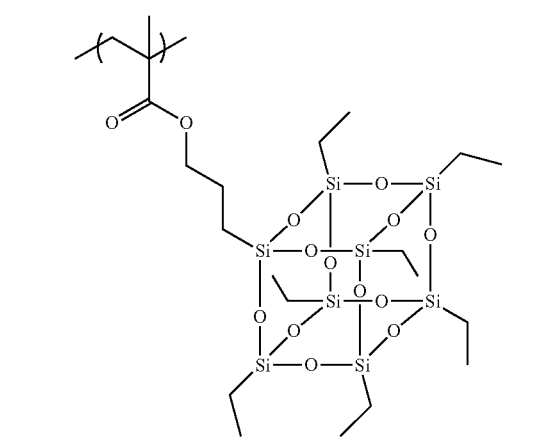
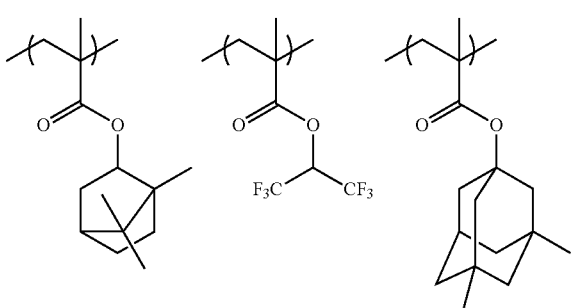
216
-continued
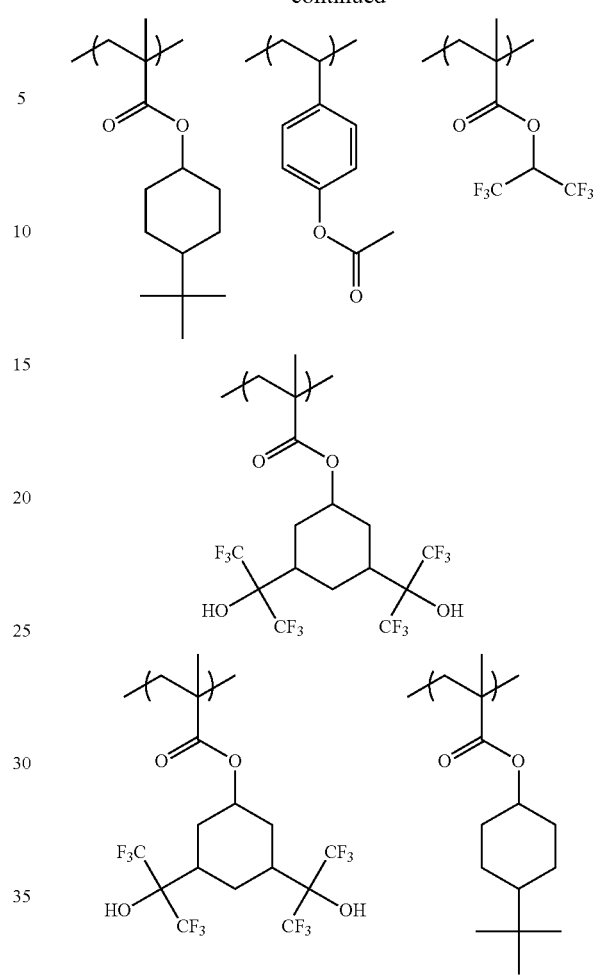
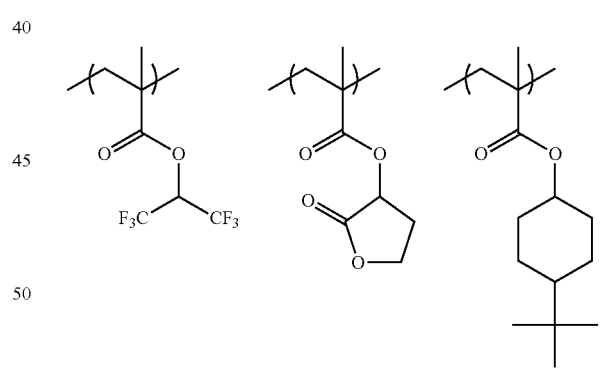
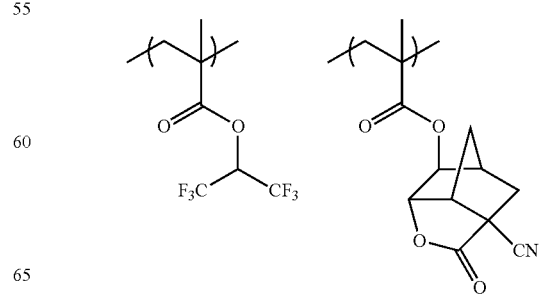

217
-continued
218
-continued
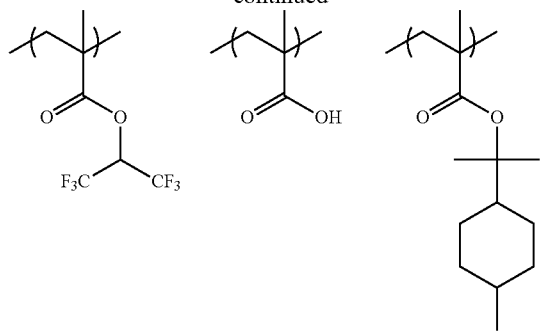
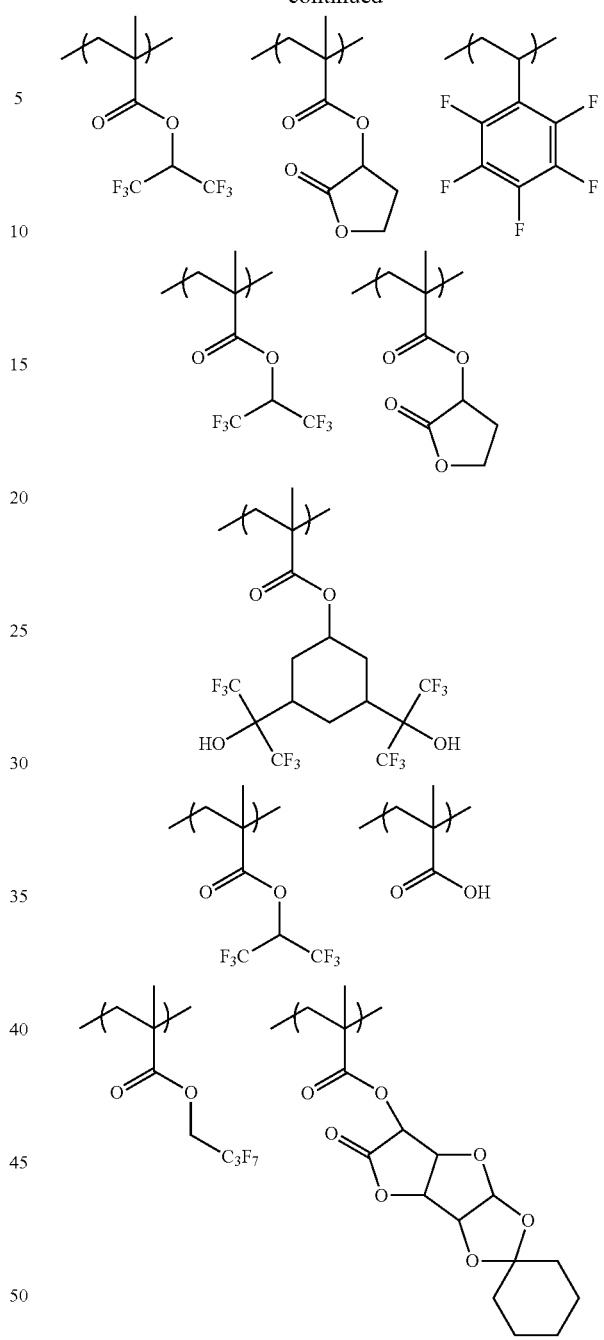
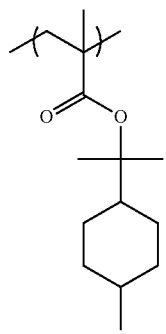
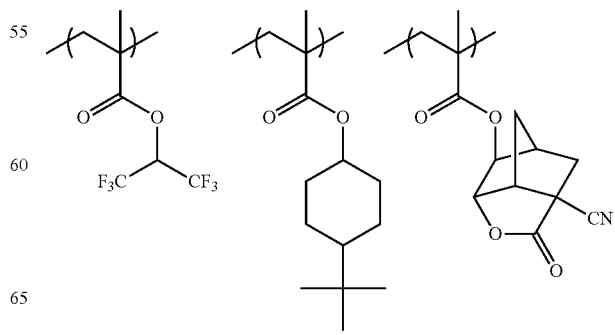

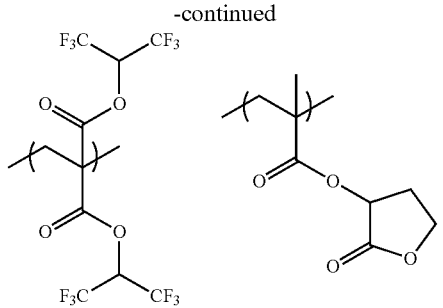
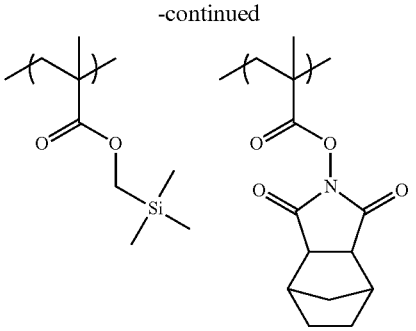
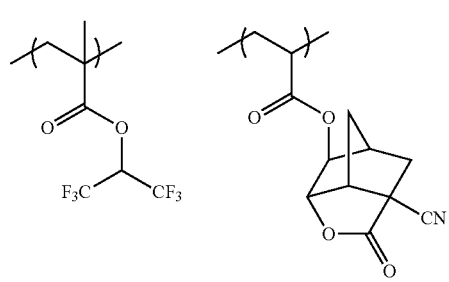
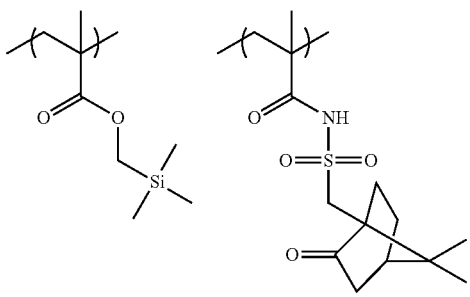
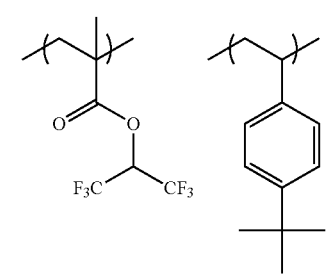
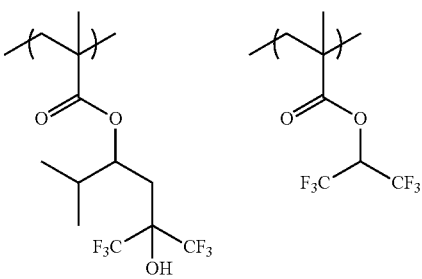
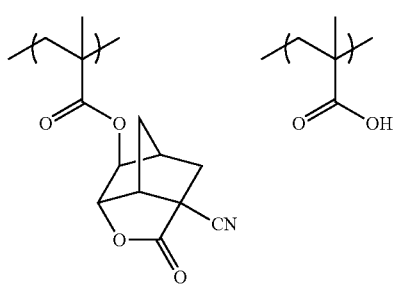
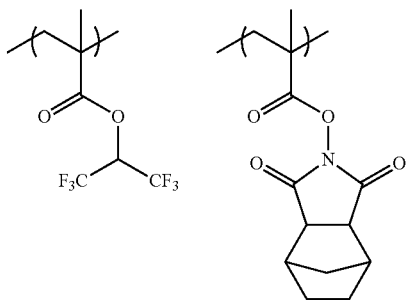
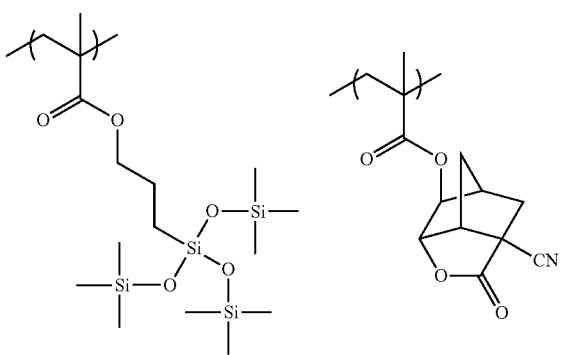
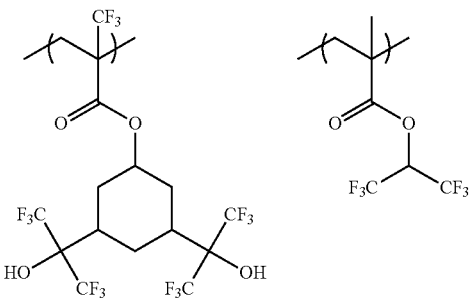
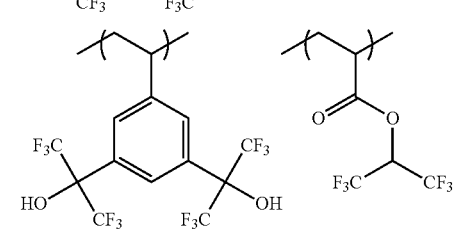

221
-continued
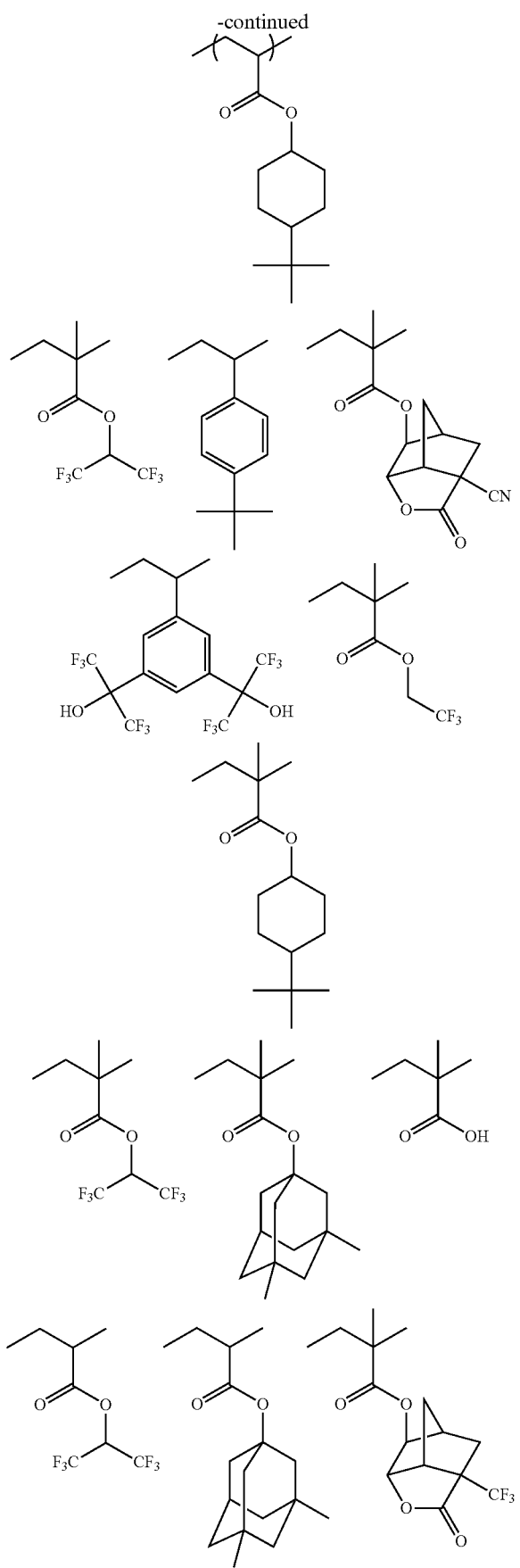
222
-continued
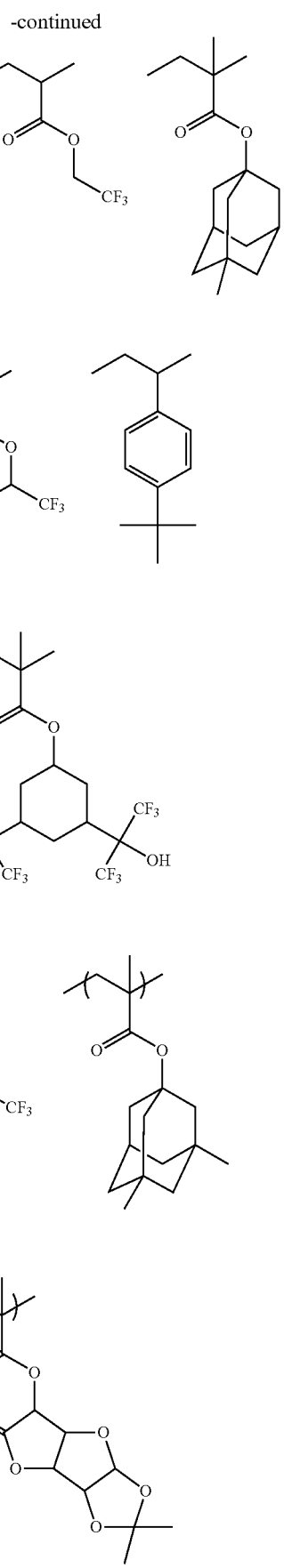

223
-continued
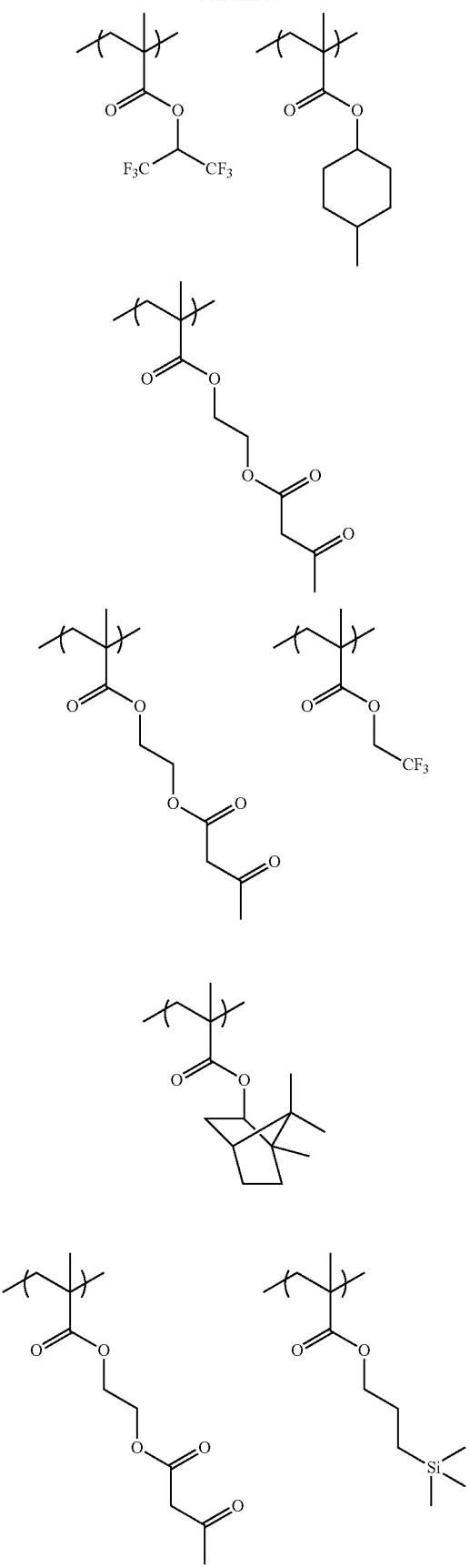
224
-continued
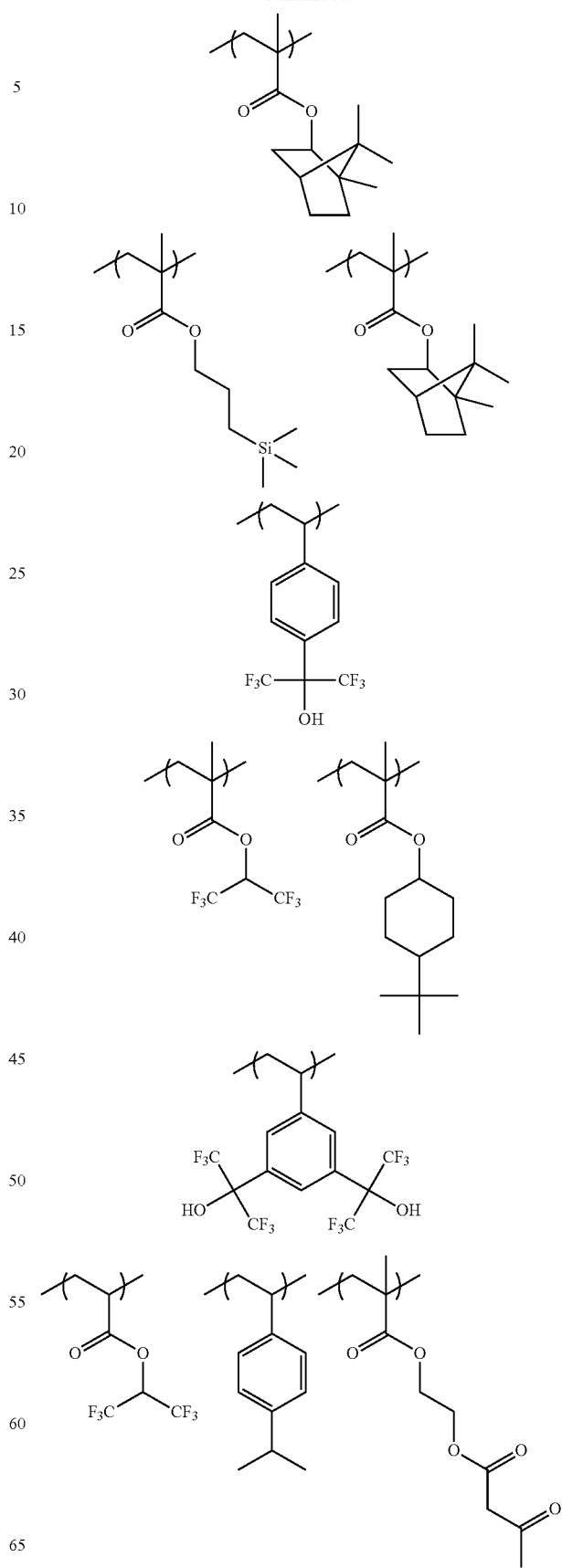

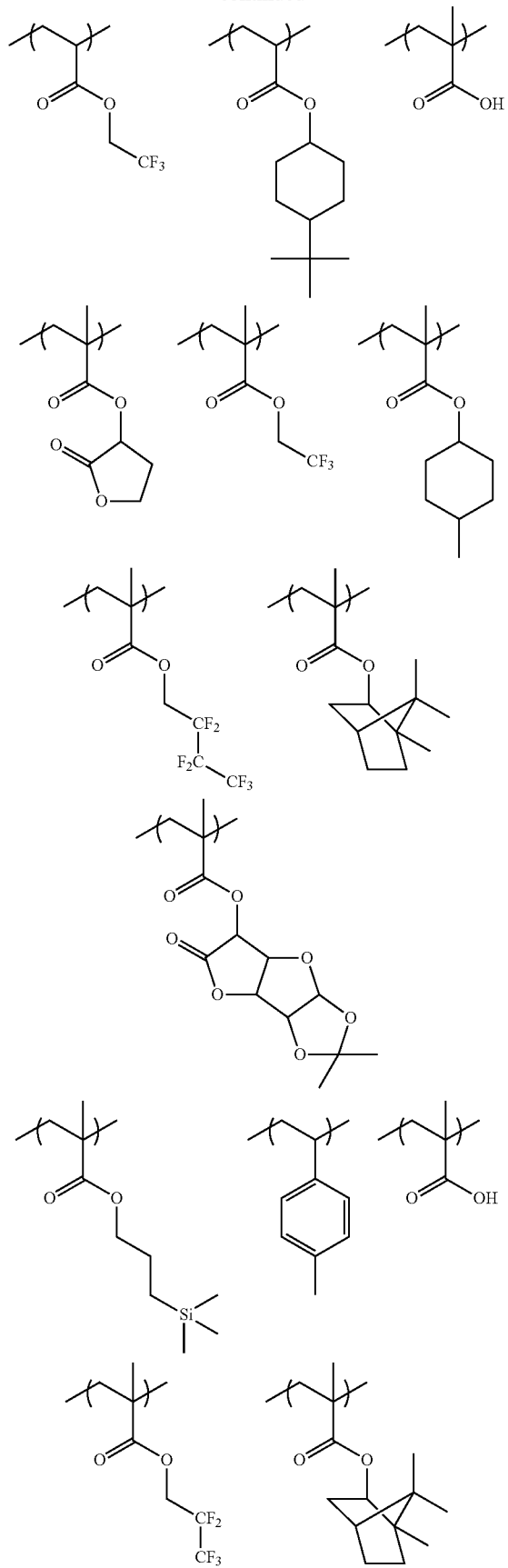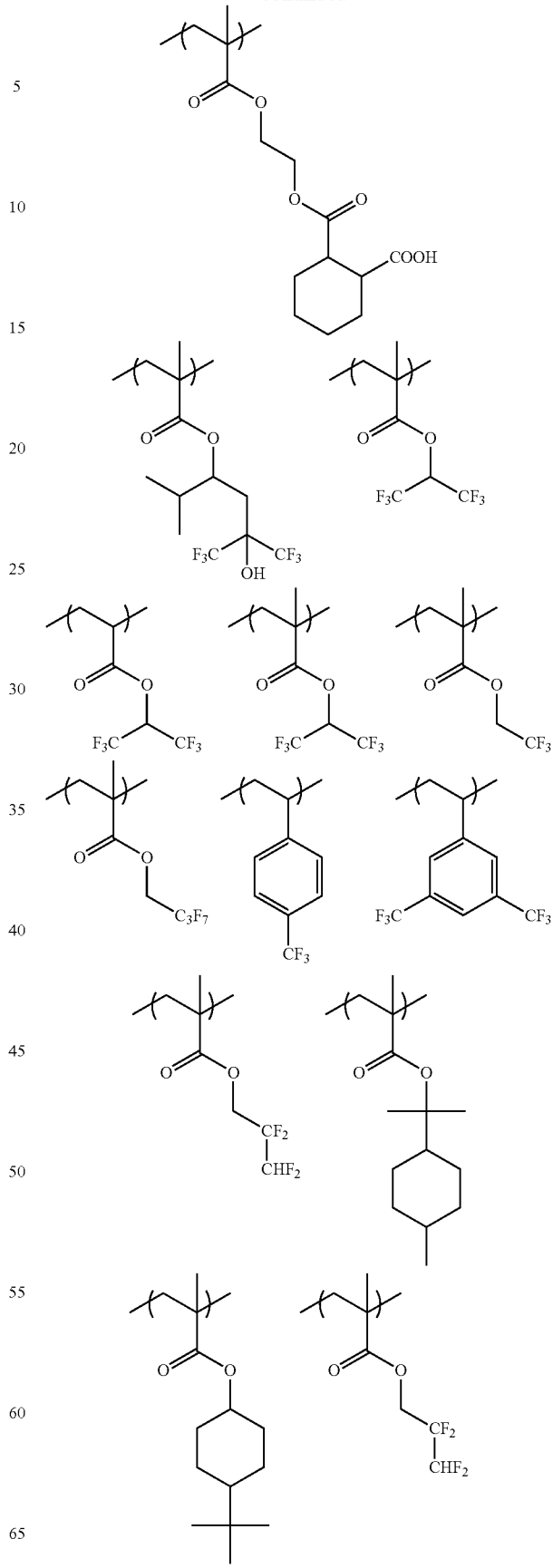

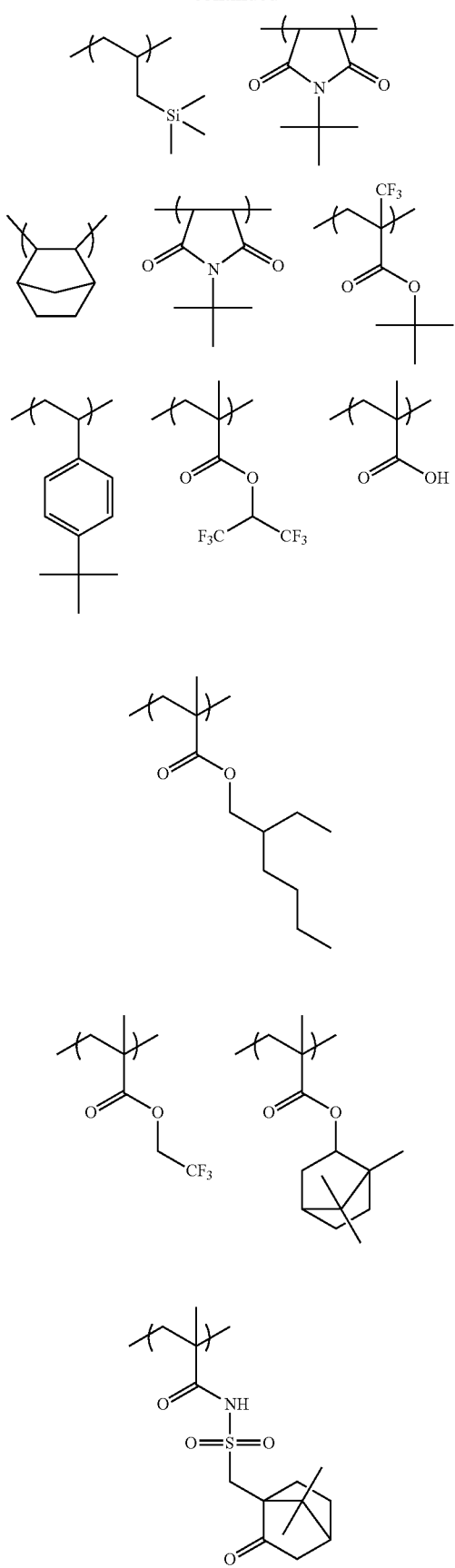
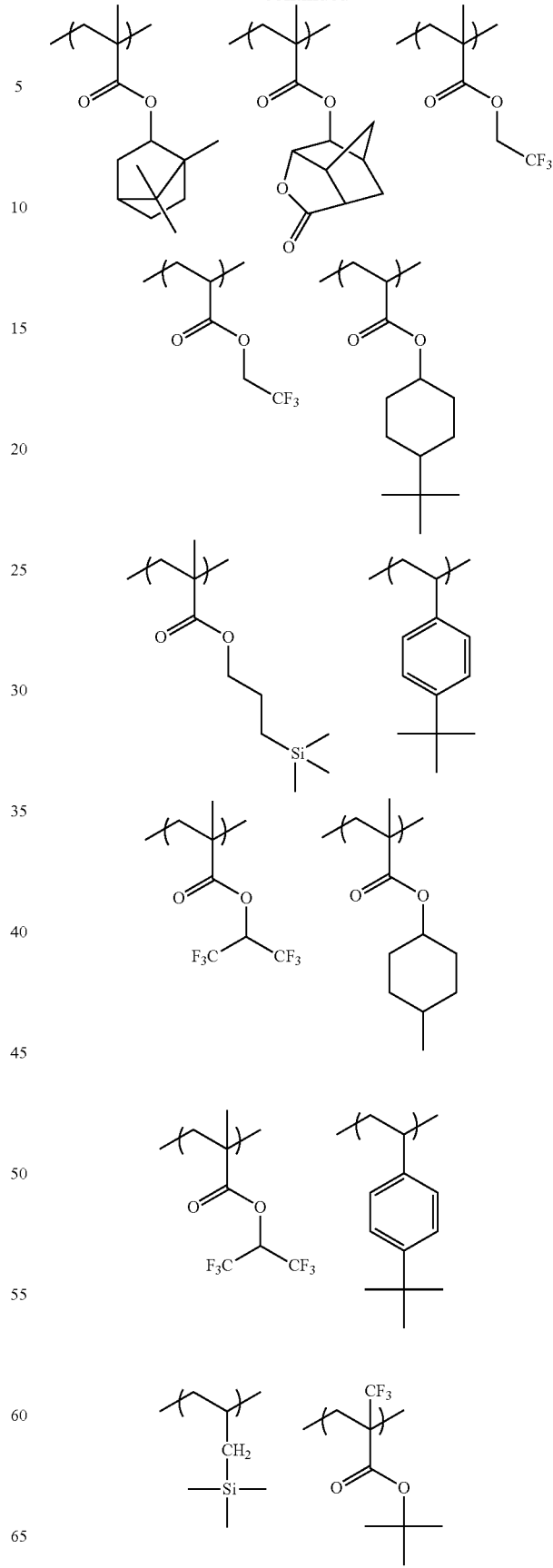

-continued
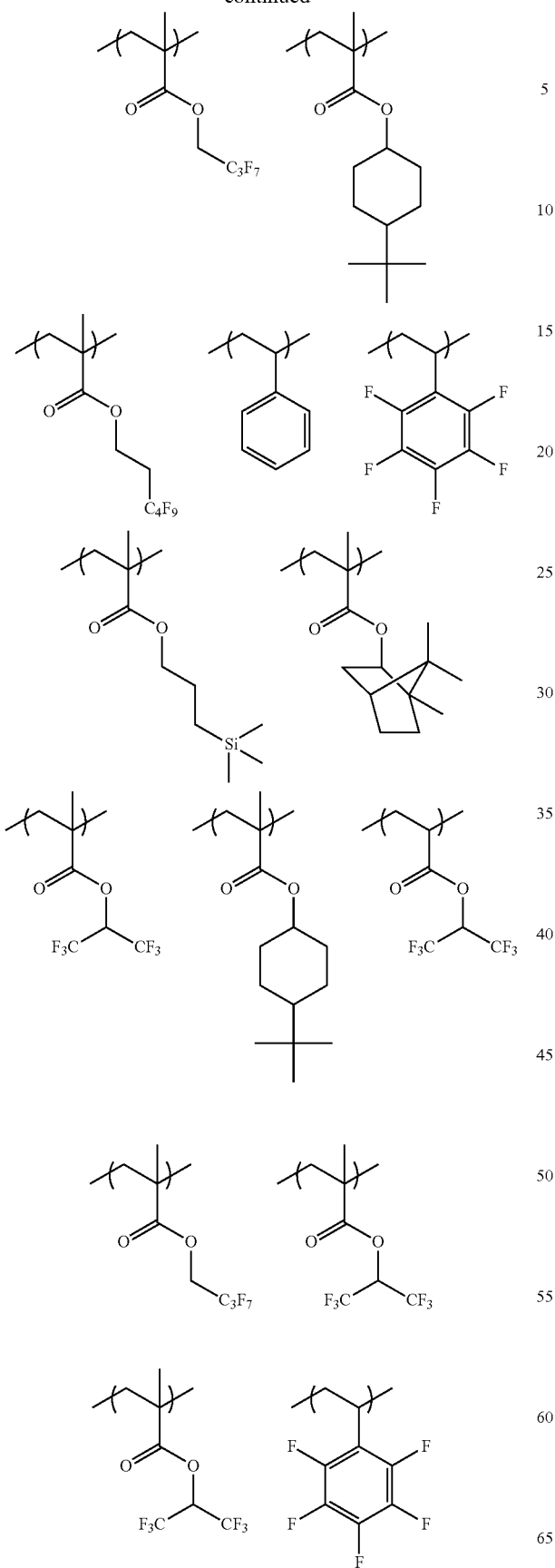
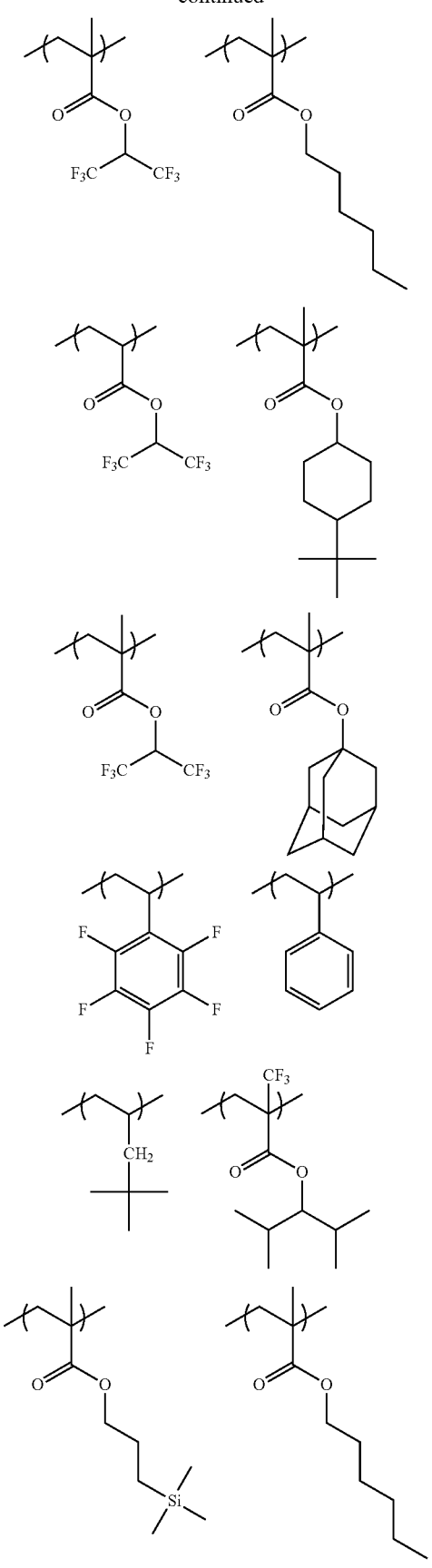

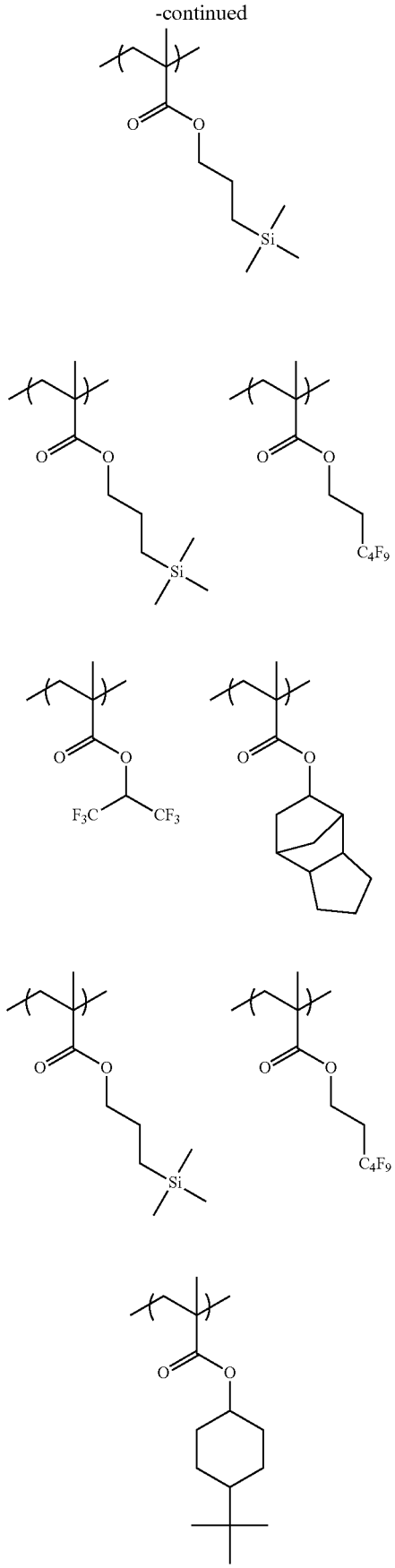
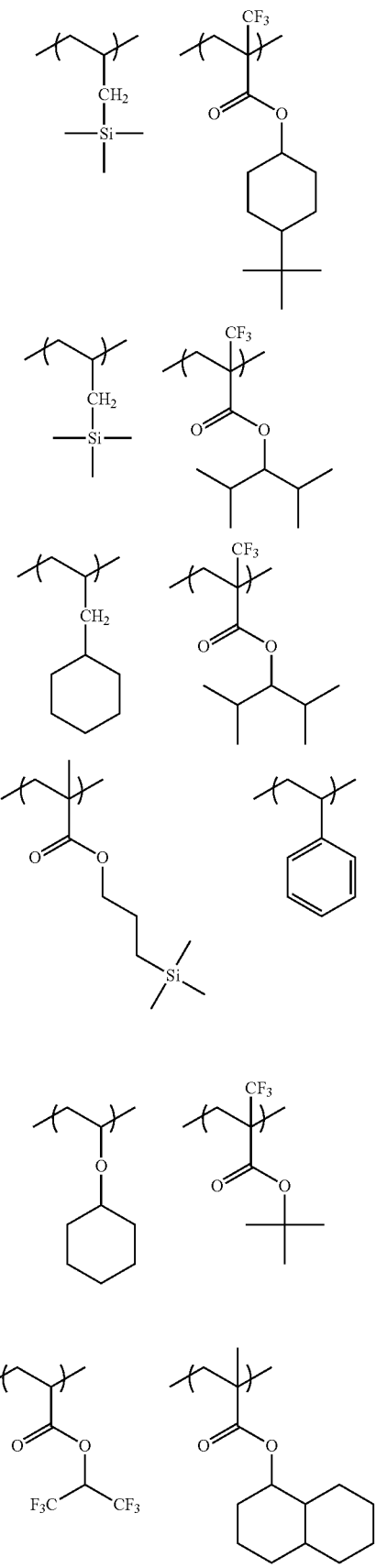

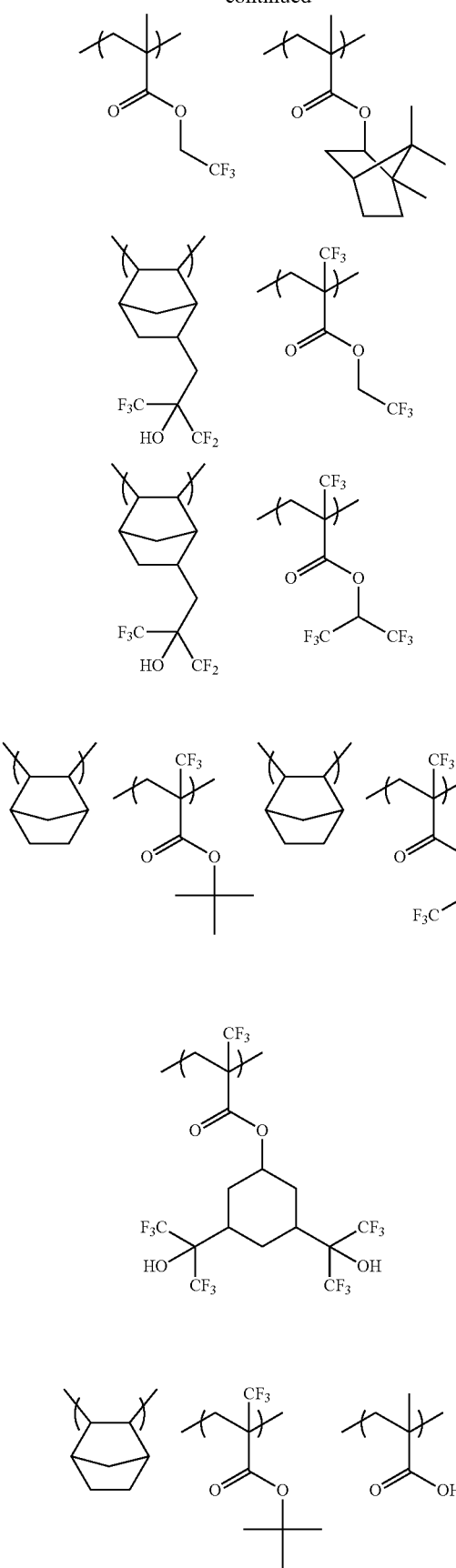
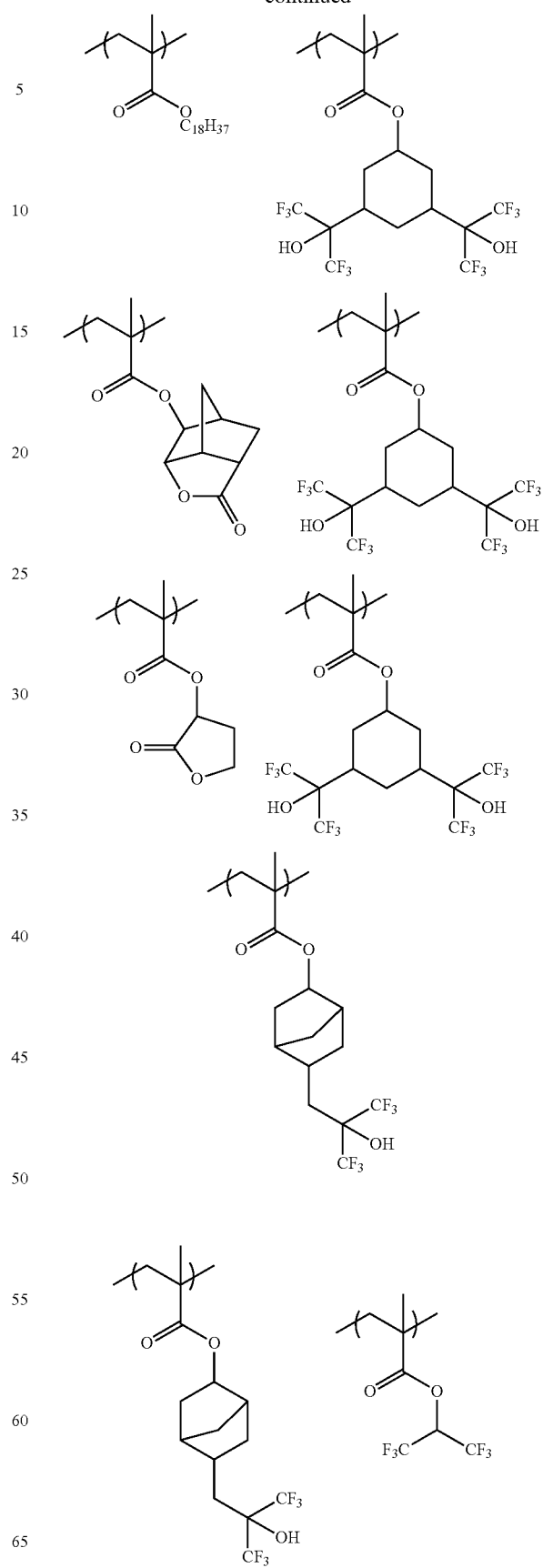

235
-continued
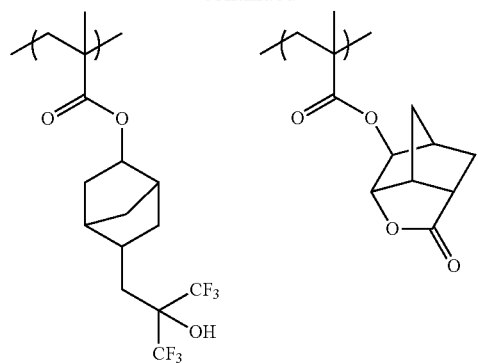
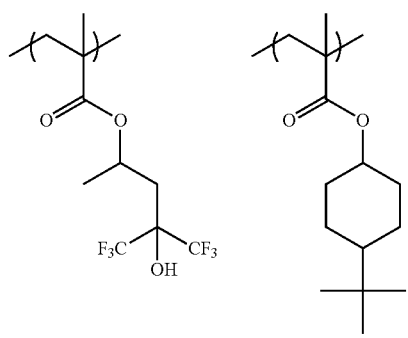
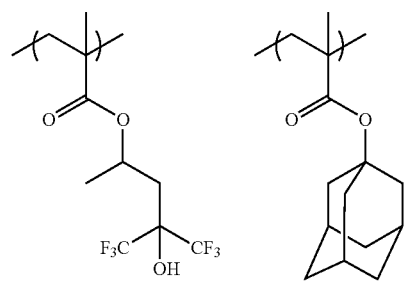
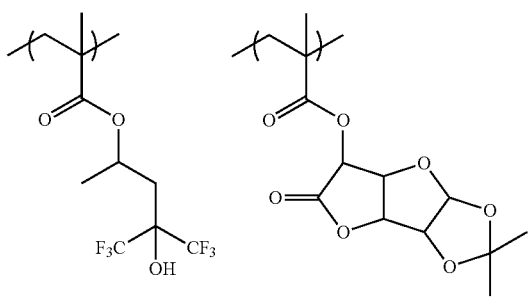
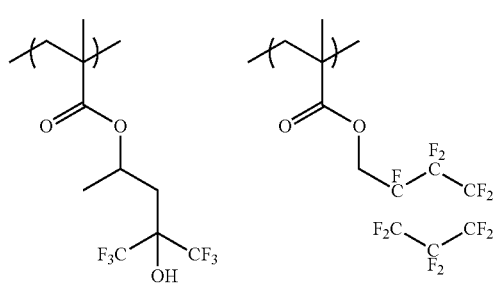
236
-continued
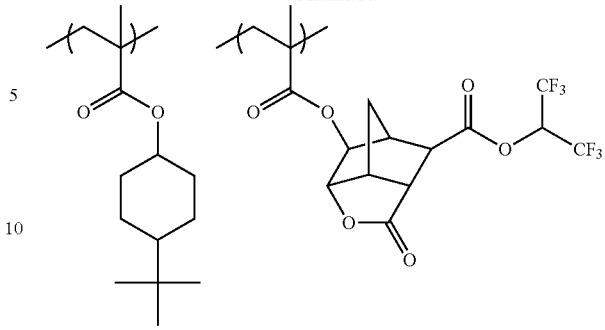
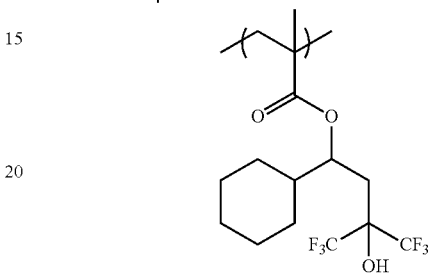
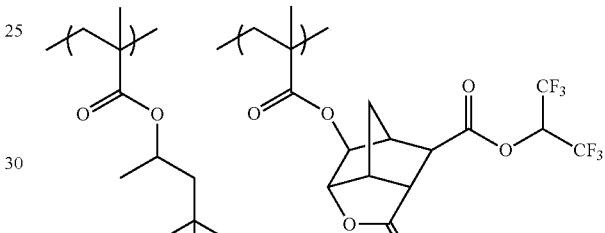
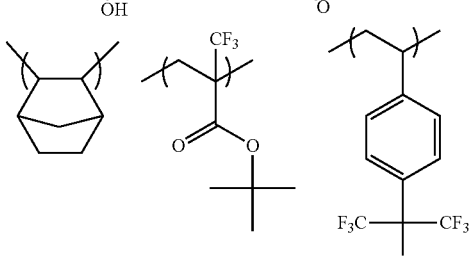
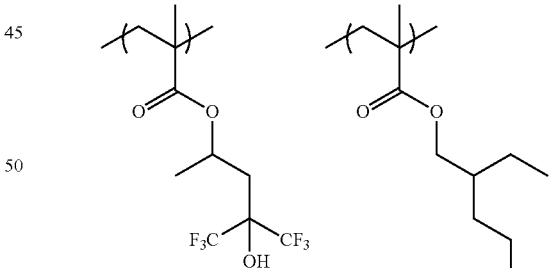
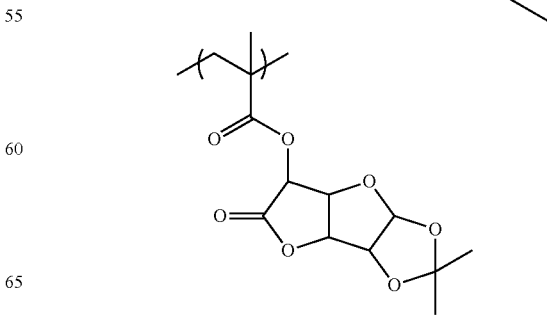

-continued

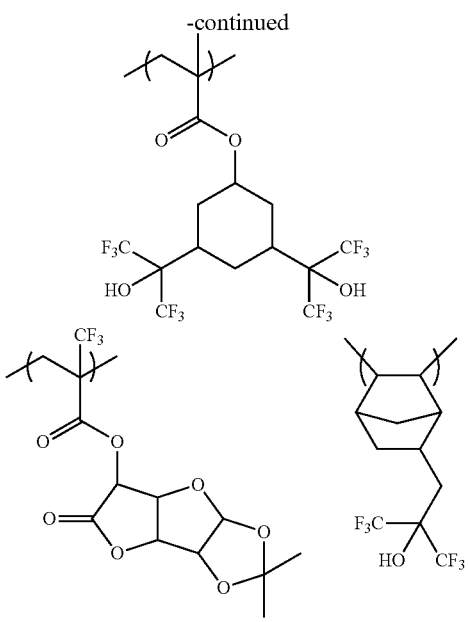

[4] Solvent

Examples of the solvent that can be used at the time of preparing the actinic ray-sensitive or radiation-sensitive resin composition by dissolving the above-described components include an organic solvent such as alkylene glycol monoalkyl ether carboxylate, alkylene glycol monoalkyl ether, alkyl lactate, alkyl alkoxypropionate, cyclic lactone (preferably having a carbon number of 4 to 10), monoketone compound (preferably having a carbon number of 4 to 10) which may contain a ring, alkylene carbonate, alkyl alkoxyacetate and alkyl pyruvate.

Preferred examples of the alkylene glycol monoalkyl ether carboxylate include propylene glycol monomethyl ether acetate (PGMEA, also known as 1-methoxy-2-acetoxypropane), propylene glycol monoethyl ether acetate, propylene glycol monopropyl ether acetate, propylene glycol monobutyl ether acetate, propylene glycol monomethyl ether propionate, propylene glycol monoethyl ether propionate, ethylene glycol monomethyl ether acetate and ethylene glycol monoethyl ether acetate.

Preferred examples of the alkylene glycol monoalkyl ether include propylene glycol monomethyl ether (PGME, also known as 1-methoxy-2-propanol), propylene glycol monoethyl ether, propylene glycol monopropyl ether, propylene glycol monobutyl ether, ethylene glycol monomethyl ether and ethylene glycol monoethyl ether.

Preferred examples of the alkyl lactate include methyl lactate, ethyl lactate, propyl lactate and butyl lactate.

Preferred examples of the alkyl alkoxypropionate include ethyl 3-ethoxypropionate, methyl 3-methoxypropionate, methyl 3-ethoxypropionate and ethyl 3-methoxypropionate.

Preferred examples of the cyclic lactone include β-propiolactone, β-butyrolactone, γ-butyrolactone, α-methyl-γ-butyrolactone, β-methyl-γ-butyrolactone, γ-valerolactone, γ-caprolactone, γ-octanoic lactone and α-hydroxy-γ-butyrolactone.

Preferred examples of the monoketone compound which may contain a ring include 2-butanone, 3-methylbutanone, pinacolone, 2-pentanone, 3-pentanone, 3-methyl-2-pentanone, 4-methyl-2-pentanone, 2-methyl-3-pentanone, 4,4-dimethyl-2-pentanone, 2,4-dimethyl-3-pentanone, 2,2,4,4-tetramethyl-3-pentanone, 2-hexanone, 3-hexanone, 5-methyl-3-hexanone, 2-heptanone, 3-heptanone, 4-heptanone, 2-methyl-3-heptanone, 5-methyl-3-heptanone, 2,6-dimethyl-4-heptanone, 2-octanone, 3-octanone, 2-nonanone, 3-nonanone, 5-nonanone, 2-decanone, 3-decanone, 4-decanone, 5-hexen-2-one, 3-penten-2-one, cyclopentanone, 2-methylcyclopentanone, 3-methylcyclopentanone, 2,2-dimethylcyclopentanone, 2,4,4-trimethylcyclopentanone, cyclohexanone, 3-methylcyclohexanone, 4-methylcyclohexanone, 4-ethylcyclohexanone, 2,2-dimethylcyclohexanone, 2,6-dimethylcyclohexanone, 2,2,6-trimethylcyclohexanone, cycloheptanone, 2-methylcycloheptanone and 3-methylcycloheptanone.

Preferred examples of the alkylene carbonate include propylene carbonate, vinylene carbonate, ethylene carbonate and butylene carbonate.

Preferred examples of the alkyl alkoxyacetate include 2-methoxyethyl acetate, 2-ethoxyethyl acetate, 2-(2-ethoxyethoxy)ethyl acetate, 3-methoxy-3-methylbutyl acetate and 1-methoxy-2-propyl acetate.

Preferred examples of the alkyl pyruvate include methyl pyruvate, ethyl pyruvate and propyl pyruvate.

The solvent that can be preferably used is a solvent having a boiling point of 130° C. or more at ordinary temperature under atmospheric pressure, and specific examples thereof include cyclopentanone, γ-butyrolactone, cyclohexanone, ethyl lactate, ethylene glycol monoethyl ether acetate, propylene glycol monomethyl ether acetate, ethyl 3-ethoxypropionate, ethyl pyruvate, 2-ethoxyethyl acetate, 2-(2-ethoxyethoxy)ethyl acetate and propylene carbonate.

In the present invention, one of these solvents may be used alone, or two or more kinds thereof may be used in combination.

In the present invention, a mixed solvent prepared by mixing a solvent containing a hydroxyl group in the structure and a solvent not containing a hydroxyl group may be used as the organic solvent.

Examples of the solvent containing a hydroxyl group include ethylene glycol, ethylene glycol monomethyl ether, ethylene glycol monoethyl ether, propylene glycol, propylene glycol monomethyl ether, propylene glycol monoethyl ether and ethyl lactate. Among these, propylene glycol monomethyl ether and ethyl lactate are preferred.

Examples of the solvent not containing a hydroxyl group include propylene glycol monomethyl ether acetate, ethyl ethoxypropionate, 2-heptanone, γ-butyrolactone, cyclohexanone, butyl acetate, N-methylpyrrolidone, N,N-dimethylacetamide and dimethylsulfoxide. Among these, propylene glycol monomethyl ether acetate, ethyl ethoxypropionate, 2-heptanone, γ-butyrolactone, cyclohexanone and butyl acetate are preferred, and propylene glycol monomethyl ether acetate, ethyl ethoxypropionate and 2-heptanone are most preferred.

The mixing ratio (by mass) of the solvent containing a hydroxyl group to the solvent not containing a hydroxyl group is usually from 1/99 to 99/1, preferably from 10/90 to 90/10, more preferably from 20/80 to 60/40. A mixed solvent in which the solvent not containing a hydroxyl group is contained in a ratio of 50 mass % or more is particularly preferred in view of coating uniformity.

The solvent is preferably a mixed solvent of two or more kinds of solvents containing propylene glycol monomethyl ether acetate (PGMEA).

[5] Basic Compound

The actinic ray-sensitive or radiation-sensitive resin composition of the present invention preferably contains a basic compound for reducing the change of performance with aging from exposure until heating.

The basic compound is preferably a compound having a structure represented by the following formulae (A) to (E):

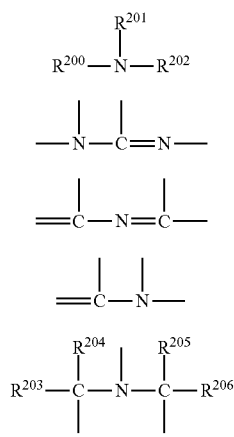

In formulae (A) and (E), each of $R^{200}$, $R^{201}$ and $R^{202}$, which may be the same or different, represents a hydrogen atom, an alkyl group (preferably having a carbon number of 1 to 20), a cycloalkyl group (preferably having a carbon number of 3 to 20) or an aryl group (having a carbon number of 6 to 20), and $R^{201}$ and $R^{202}$ may combine together to form a ring.

Each of $R^{203}$, $R^{204}$, $R^{205}$ and $R^{206}$, which may be the same or different, represents an alkyl group having a carbon number of 1 to 20.

As for the alkyl group, the alkyl group having a substituent is preferably an aminoalkyl group having a carbon number of 1 to 20, a hydroxyalkyl group having a carbon number of 1 to 20, or a cyanoalkyl group having a carbon number of 1 to 20.

The alkyl group in formulae (A) and (E) is more preferably unsubstituted.

Preferred examples of the compound include guanidine, aminopyrrolidine, pyrazole, pyrazoline, piperazine, aminomorpholine, aminoalkylmorpholine and piperidine. More preferred examples of the compound include a compound having an imidazole structure, a diazabicyclo structure, an onium hydroxide structure, an onium carboxylate structure, a trialkylamine structure, an aniline structure or a pyridine structure; an alkylamine derivative having a hydroxyl group and/or an ether bond; and an aniline derivative having a hydroxyl group and/or an ether bond.

Examples of the compound having an imidazole structure include imidazole, 2,4,5-triphenylimidazole, benzimidazole and 2-phenylbenzimidazole. Examples of the compound having a diazabicyclo structure include 1,4-diazabicyclo[2,2,2]octane, 1,5-diazabicyclo[4,3,0]non-5-ene and 1,8-diazabicyclo[5,4,0]undec-7-ene. Examples of the compound having an onium hydroxide structure include tetrabutylammonium hydroxide, triarylsulfonium hydroxide, phenacylsulfonium hydroxide and sulfonium hydroxide having a 2-oxoalkyl group, specifically, triphenylsulfonium hydroxide, tris(tert-butylphenyl)sulfonium hydroxide, bis(tert-butylphenyl)iodonium hydroxide, phenacylthiophenium hydroxide and 2-oxopropylthiophenium hydroxide. Examples of the compound having an onium carboxylate structure include a compound where the anion moiety of the compound having an onium hydroxide structure becomes a carboxylate, such as acetate, adamantane-1-carboxylate and perfluoroalkyl carboxylate. Examples of the compound having a trialkylamine structure include tri(n-butyl)amine and tri(n-octyl)amine.

Examples of the aniline compound include 2,6-diisopropylaniline, N,N-dimethylaniline, N,N-dibutylaniline and N,N-dihexylaniline. Examples of the alkylamine derivative having a hydroxyl group and/or an ether bond include ethanolamine, diethanolamine, triethanolamine, N-phenyldiethanolamine and tris(methoxyethoxyethyl)amine. Examples of the aniline derivative having a hydroxyl group and/or an ether bond include N,N-bis(hydroxyethyl)aniline.

Other preferred basic compounds include a phenoxy group-containing amine compound, a phenoxy group-containing ammonium salt compound, a sulfonic acid ester group-containing amine compound and a sulfonic acid ester group-containing ammonium salt compound.

As for the amine compound, a primary, secondary or tertiary amine compound can be used, and an amine compound where at least one alkyl group is bonded to the nitrogen atom is preferred. The amine compound is more preferably a tertiary amine compound. In the amine compound, as long as at least one alkyl group (preferably having a carbon number of 1 to 20) is bonded to the nitrogen atom, a cycloalkyl group (preferably having a carbon number of 3 to 20) or an aryl group (preferably having a carbon number of 6 to 12) may be bonded to the nitrogen atom, in addition to the alkyl group. The amine compound preferably has an oxygen atom in the alkyl chain to form an oxyalkylene group. The number of oxyalkylene groups within the molecule is 1 or more, preferably from 3 to 9, more preferably from 4 to 6. Among oxyalkylene groups, an oxyethylene group (—$CH_2CH_2O$—) and an oxypropylene group (—$CH(CH_3)CH_2O$— or —$CH_2CH_2CH_2O$—) are preferred, and an oxyethylene group is more preferred.

As for the ammonium salt compound, a primary, secondary, tertiary or quaternary ammonium salt compound can be used, and an ammonium salt compound where at least one alkyl group is bonded to the nitrogen atom is preferred. In the ammonium salt compound, as long as at least one alkyl group (preferably having a carbon number of 1 to 20) is bonded to the nitrogen atom, a cycloalkyl group (preferably having a carbon number of 3 to 20) or an aryl group (preferably having a carbon number of 6 to 12) may be bonded to the nitrogen atom, in addition to the alkyl group. The ammonium salt compound preferably has an oxygen atom in the alkyl chain to form an oxyalkylene group. The number of oxyalkylene groups within the molecule is 1 or more, preferably from 3 to 9, more preferably from 4 to 6. Among oxyalkylene groups, an oxyethylene group (—$CH_2CH_2O$—) and an oxypropylene group (—$CH(CH_3)CH_2O$— or —$CH_2CH_2CH_2O$—) are preferred, and an oxyethylene group is more preferred.

Examples of the anion of the ammonium salt compound include a halogen atom, a sulfonate, a borate and a phosphate, with a halogen atom and a sulfonate being preferred. The halogen atom is preferably chloride, bromide or iodide, and the sulfonate is preferably an organic sulfonate having a carbon number of 1 to 20. The organic sulfonate includes an alkylsulfonate having a carbon number of 1 to 20 and an arylsulfonate. The alkyl group of the alkylsulfonate may have a substituent, and examples of the substituent include fluorine, chlorine, bromine, an alkoxy group, an acyl group and an aryl group. Specific examples of the alkylsulfonate include methanesulfonate, ethanesulfonate, butanesulfonate, hexanesulfonate, octanesulfonate, benzylsulfonate, trifluoromethanesulfonate, pentafluoroethanesulfonate and nonafluorobutanesulfonate. The aryl group of the arylsulfonate includes a benzene ring, a naphthalene ring and an anthracene ring. The benzene ring, naphthalene ring and anthracene ring may have a substituent, and the substituent is preferably a linear or branched alkyl group having a carbon number of 1 to 6, or a cycloalkyl group having a carbon number of 3 to 6. Specific examples of the linear or branched alkyl group and cycloalkyl group include methyl, ethyl, n-propyl, isopropyl, n-butyl, i-butyl, tert-butyl, n-hexyl and cyclohexyl. Other examples of the substituent include an alkoxy group having a carbon number of 1 to 6, a halogen atom, cyano, nitro, an acyl group and an acyloxy group.

The phenoxy group-containing amine compound and the phenoxy group-containing ammonium salt compound are a compound where the alkyl group of an amine compound or ammonium salt compound has a phenoxy group at the terminal opposite the nitrogen atom. The phenoxy group may have a substituent. Examples of the substituent of the phenoxy group include an alkyl group, an alkoxy group, a halogen atom, a cyano group, a nitro group, a carboxyl group, a carboxylic acid ester group, a sulfonic acid ester group, an aryl group, an aralkyl group, an acyloxy group and an aryloxy group. The substitution site of the substituent may be any of 2- to 6-positions, and the number of substituents may be any in the range from 1 to 5.

The compound preferably has at least one oxyalkylene group between the phenoxy group and the nitrogen atom. The number of oxyalkylene groups within the molecule is 1 or more, preferably from 3 to 9, more preferably from 4 to 6. Among oxyalkylene groups, an oxyethylene group (—CH$_2$CH$_2$O—) and an oxypropylene group (—CH(CH$_3$)CH$_2$O— or —CH$_2$CH$_2$CH$_2$O—) are preferred, and an oxyethylene group is more preferred.

The sulfonic acid ester group in the sulfonic acid ester group-containing amine compound and sulfonic acid ester group-containing ammonium salt compound may be any of an alkylsulfonic acid ester, a cycloalkylsulfonic acid ester and an arylsulfonic acid ester. In the case of an alkylsulfonic acid ester, the alkyl group preferably has a carbon number of 1 to 20; in the case of a cycloalkylsulfonic acid ester, the cycloalkyl group preferably has a carbon number of 3 to 20; and in the case of an arylsulfonic acid ester, the aryl group preferably has a carbon number of 6 to 12. The alkylsulfonic acid ester, cycloalkylsulfonic acid ester and arylsulfonic acid ester may have a substituent, and the substituent is preferably a halogen atom, a cyano group, a nitro group, a carboxyl group, a carboxylic acid ester group or a sulfonic acid ester group.

The compound preferably has at least one oxyalkylene group between the sulfonic acid ester group and the nitrogen atom. The number of oxyalkylene groups within the molecule is 1 or more, preferably from 3 to 9, more preferably from 4 to 6. Among oxyalkylene groups, an oxyethylene group (—CH$_2$CH$_2$O—) and an oxypropylene group (—CH(CH$_3$)CH$_2$O— or —CH$_2$CH$_2$CH$_2$O—) are preferred, and an oxyethylene group is more preferred.

The following compounds are also preferred as the basic compound.

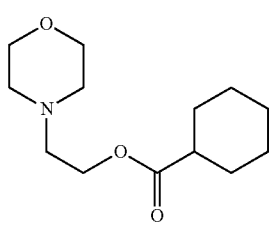
(MO-1)

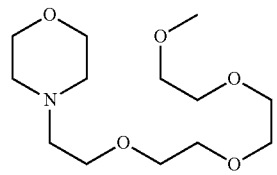
(MO-2)

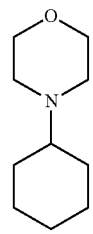
(MO-3)

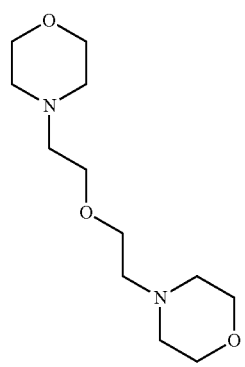
(MO-4)

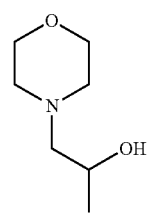
(MO-5)

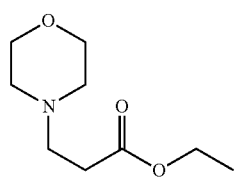
(MO-6)

One of these basic compounds may be used alone, or two or more thereof may be used in combination.

The amount used of the basic compound is usually from 0.001 to 10 mass %, preferably from 0.01 to 5 mass %, based on the entire solid content of the actinic ray-sensitive or radiation-sensitive resin composition.

The ratio of acid generator and basic compound blended in the composition is preferably acid generator/basic compound (by mol)=from 2.5 to 300. That is, the molar ratio is preferably 2.5 or more in view of sensitivity and resolution and preferably 300 or less from the standpoint of suppressing the reduction in resolution due to thickening of the resist pattern with aging after exposure to heat treatment. The acid generator/basic compound (by mol) is more preferably from 5.0 to 200, still more preferably from 7.0 to 150.

Such a basic compound is preferably used, in terms of a ratio to the below-described (D) low molecular compound having a group capable of leaving by the action of an acid, in a molar ratio ((D) low molecular compound having a group capable of leaving by the action of an acid/basic compound) of 100/0 to 10/90, more specifically in a molar ratio ((D) low molecular compound having a group capable of leaving by the action of an acid/basic compound) of 100/0 to 30/70, still more preferably in a molar ratio ((D) low molecular compound having a group capable of leaving by the action of an acid/basic compound) of 100/0 to 50/50.

Incidentally, the basic compound here does not include (D) a low molecular compound having a group capable of leaving by the action of an acid when this is also a basic compound.

[6] Low Molecular Compound Having a Group Capable of Leaving by the Action of an Acid (D)

The composition of the present invention may contain (D) a low molecular compound having a group capable of leaving by the action of an acid (sometimes referred to as the component (D)). The group capable of leaving by the action of an acid is not particularly limited but is preferably an acetal group, a carbonate group, a carbamate group, a tertiary ester group, a tertiary hydroxyl group or a hemiaminal ether group, more preferably a carbamate group or a hemiaminal ether group.

The molecular weight of the low molecular compound having a group capable of leaving by the action of an acid is preferably from 100 to 1,000, more preferably from 100 to 700, still more preferably from 100 to 500.

In the case where the low molecular compound having a group capable of leaving by the action of an acid has a tertiary ester structure, the compound is preferably a carboxylic acid ester or unsaturated carboxylic acid ester represented by the following formula (1a):

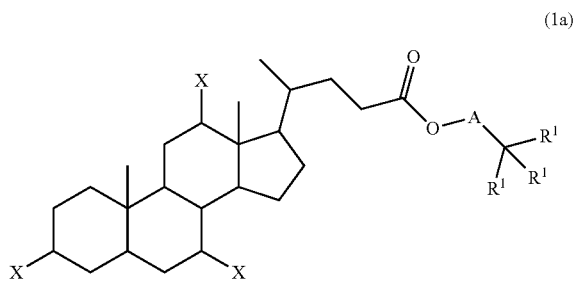

(1a)

In formula (1a), each $R^1$ independently represents a monovalent alicyclic hydrocarbon group (preferably having a carbon number of 4 to 20) or a derivative thereof or an alkyl group (preferably having a carbon number of 1 to 4) and at the same time, at least one $R^1$ is the alicyclic hydrocarbon group or a derivative thereof or while any two $R^1$'s are combined with each other to form a divalent alicyclic hydrocarbon group (preferably having a carbon number of 4 to 20) or a derivative thereof together with the carbon atom to which they are bonded, the remaining $R^1$ represents an alkyl group (preferably having a carbon number of 1 to 4) or a monovalent alicyclic hydrocarbon group (preferably having a carbon number of 4 to 20) or a derivative thereof.

Each X independently represents a hydrogen atom or a hydroxy group, and at least one X is a hydroxy group.

A represents a single bond or a divalent linking group and is preferably a single bond or a group represented by -D-COO— (wherein D represents an alkylene group (preferably having a carbon number of 1 to 4)).

In formula (1a), examples of the divalent linking group as A include a methylene group, a methylenecarbonyl group, a methylenecarbonyloxy group, an ethylene group an ethylenecarbonyl group, an ethylenecarbonyloxy group, a propylene group, a propylenecarbonyl group, a propylenecarbonyloxy group, with a methylene carbonyloxy group being preferred.

In formula (1a), examples of the monovalent alicyclic hydrocarbon group (preferably having a carbon number of 4 to 20) of $R^1$ and the divalent alicyclic hydrocarbon group (preferably having a carbon number of 4 to 20) formed by combining any two $R^1$'s with each other include a group composed of an alicyclic ring derived from norbornane, tricyclodecane, tetracyclododecane or cycloalkanes such as cyclobutane, cyclopentane, cyclohexane, cycloheptane and cyclooctane; and a group where the group composed of an alicyclic ring is substituted by one or more kinds of or one or more groups of an alkyl group having a carbon number of 1 to 4, such as methyl group, ethyl group, n-propyl group, i-propyl group, n-butyl group, 2-methylpropyl group, 1-methylpropyl group and tert-butyl group, and a cycloalkyl group. Among these alicyclic hydrocarbon groups, preferred are a group composed of an alicyclic ring derived from norbornane, tricyclodecane, tetracyclododecane, adamantane, cyclopentane or cyclohexane, and a group where the group composed of an alicyclic ring is substituted by the alkyl group above.

Examples of the derivative of the alicyclic hydrocarbon group include a group having one or more kinds of or one or more groups of the substituents such as a hydroxyl group; a carboxyl group; an oxo group (i.e., =O); a hydroxyalkyl group having a carbon number of 1 to 4, e.g., hydroxymethyl group, 1-hydroxyethyl group, 2-hydroxyethyl group, 1-hydroxypropyl group, 2-hydroxypropyl group, 3-hydroxypropyl group, 1-hydroxybutyl group, 2-hydroxybutyl group, 3-hydroxybutyl group and 4-hydroxybutyl group; an alkoxyl group having a carbon number of 1 to 4, e.g., methoxy group, ethoxy group, n-propoxy group, i-propoxy group, n-butoxy group, 2-methylpropoxy group, 1-methylpropoxy group and tert-butoxy group; a cyano group; and a cyanoalkyl group having a carbon number of 2 to 5, e.g., cyanomethyl group, 2-cyanoethyl group, 3-cyanopropyl group and 4-cyanobutyl group. Among these substituents, a hydroxyl group, a carboxyl group, a hydroxymethyl group, a cyano group and a cyanomethyl group are preferred.

Examples of the alkyl group of $R^1$ include an alkyl group having a carbon number of 1 to 4, such as methyl group, ethyl group, n-propyl group, i-propyl group, n-butyl group, 2-methylpropyl group, 1-methylpropyl group and tert-butyl group. Among these alkyl groups, a methyl group, an ethyl group, an n-propyl group and an i-propyl group are preferred.

Specific preferred examples include the following compounds.

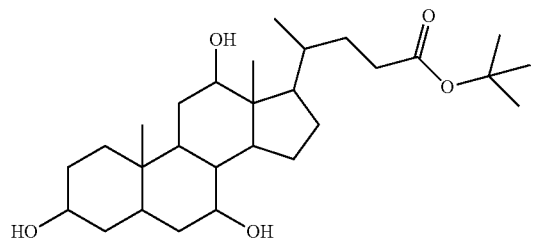

-continued

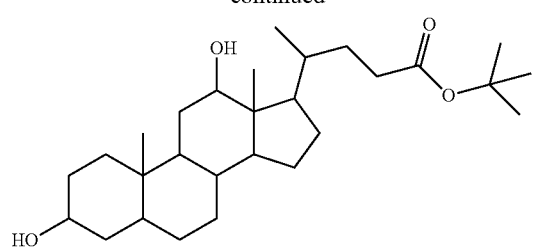
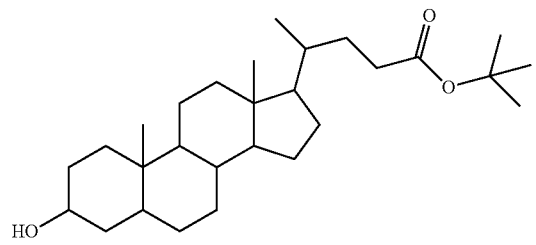
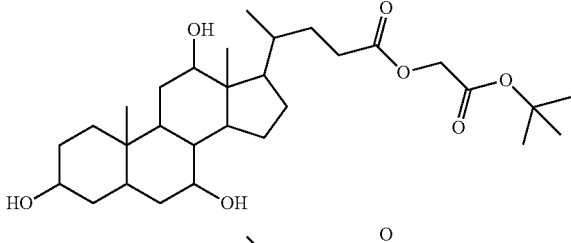
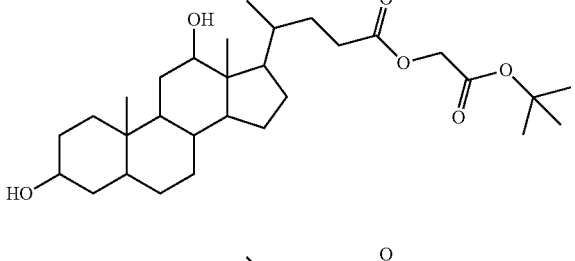
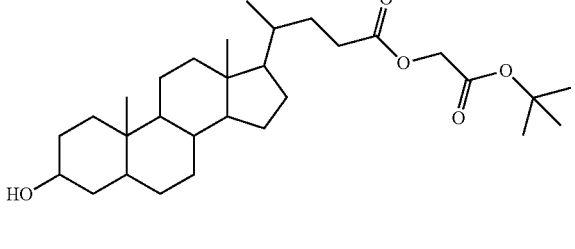
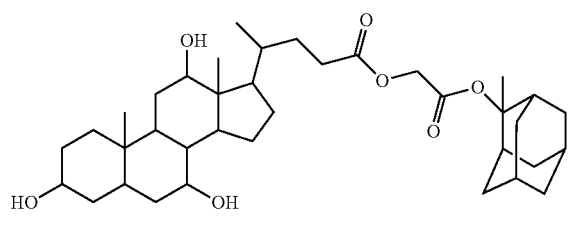
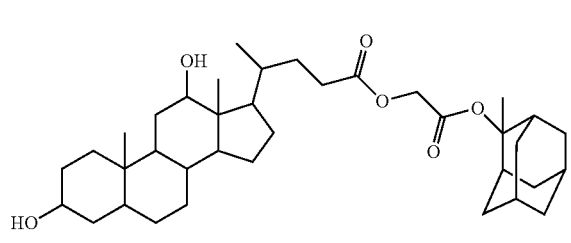

-continued

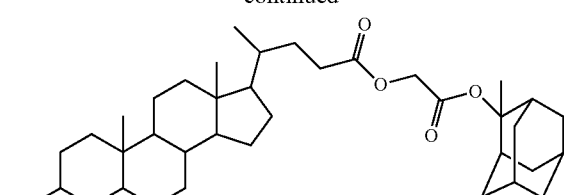
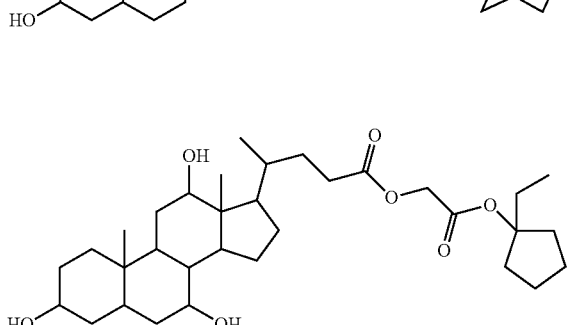
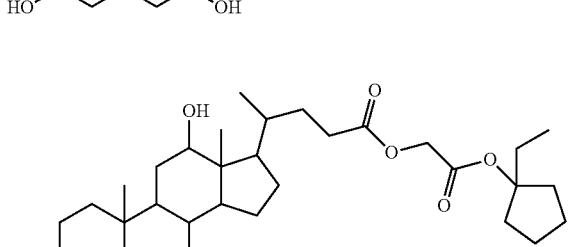
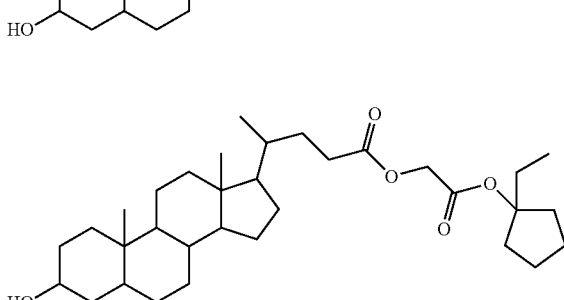
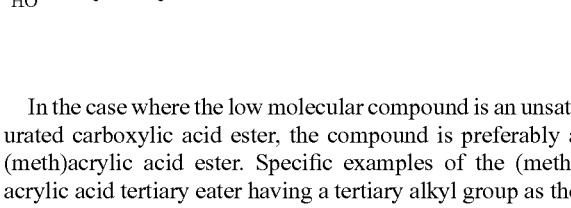

In the case where the low molecular compound is an unsaturated carboxylic acid ester, the compound is preferably a (meth)acrylic acid ester. Specific examples of the (meth)acrylic acid tertiary eater having a tertiary alkyl group as the group capable of leaving by the action of an acid are set forth below, but the present invention is not limited thereto. (In the formulae, Rx represents H, CH$_3$, CF$_3$ or CH$_2$OH, and each of Rxa and Rxb represents an alkyl group having a carbon number of 1 to 4.)

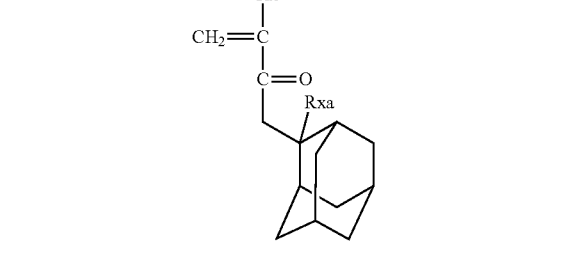

1

2
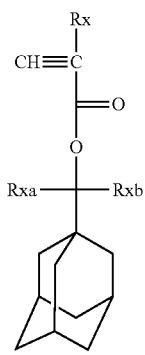
3
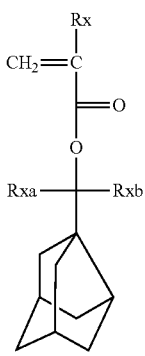
4
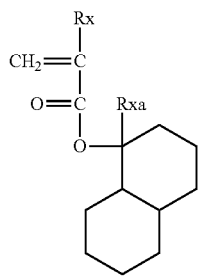
5
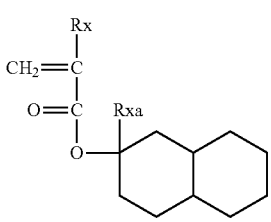
6
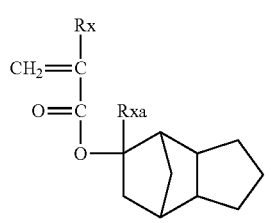
7
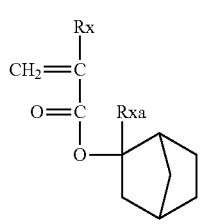
8
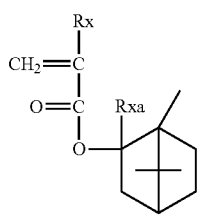
9
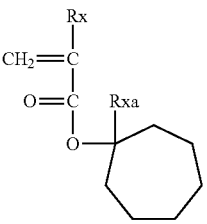
10
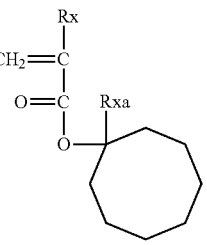
11
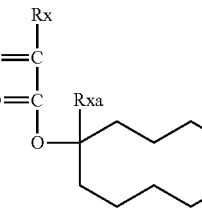
12
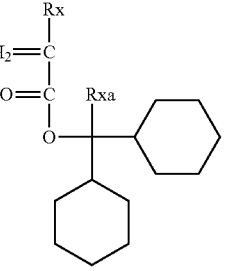
13
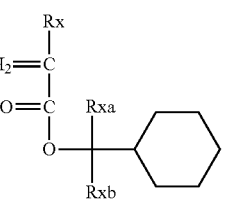
14
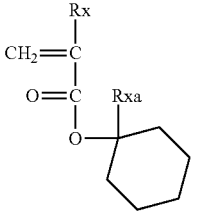

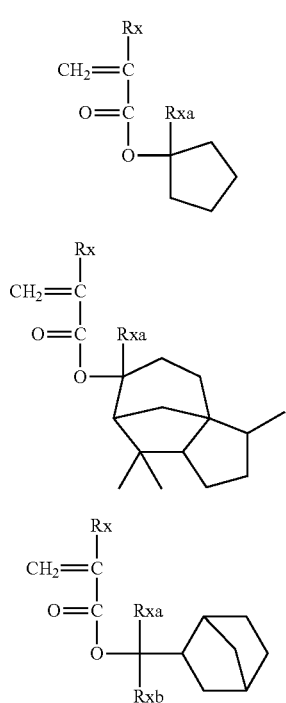

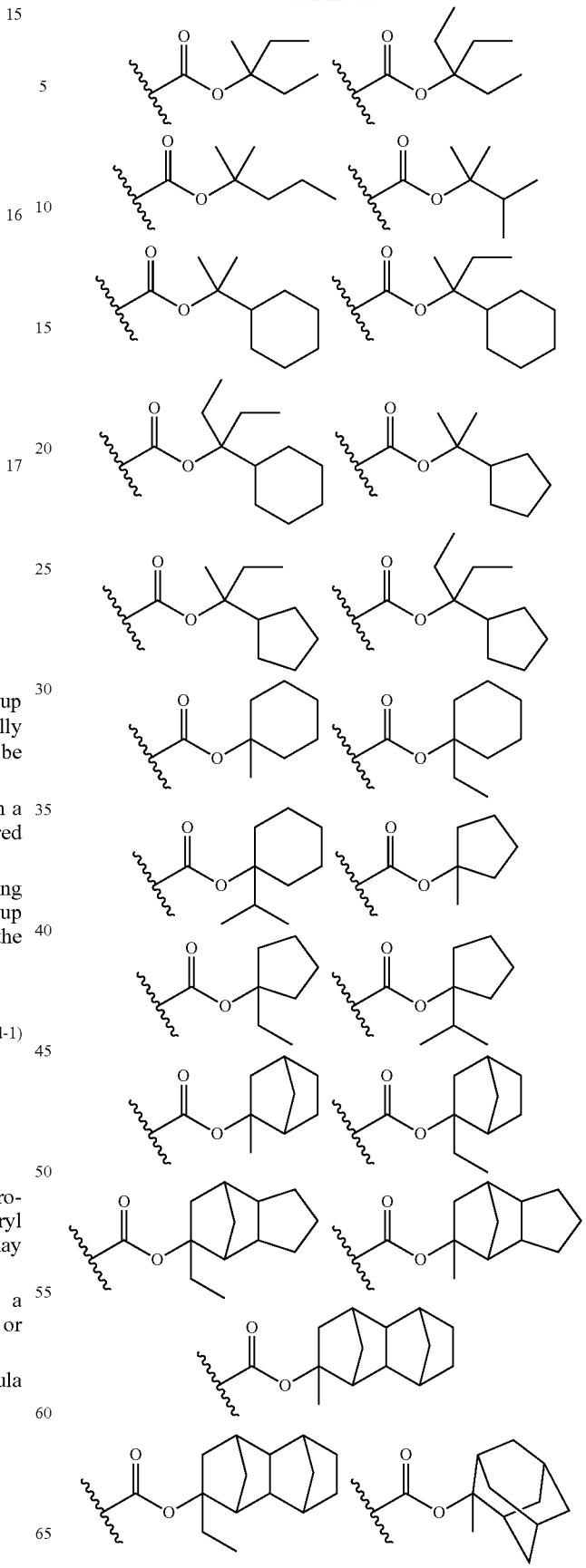

As for the (D) low molecular compound having a group capable of leaving by the action of an acid, a commercially available product may be used or the compound may be synthesized by a known method.

Also, an amine derivative having on the nitrogen atom a group capable of leaving by the action of an acid is preferred as the component D.

The component D may have a protective group-containing carbamate group on the nitrogen atom. The protective group constituting the carbamate group can be represented by the following formula (d-1):

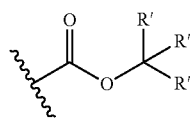
(d-1)

In formula (d-1), each R' independently represents a hydrogen atom, a linear, branched or cyclic alkyl group, an aryl group, an aralkyl group or an alkoxyalkyl group. Each R' may combine with every other R' to form a ring.

R' is preferably a linear or branched alkyl group, a cycloalkyl group or an aryl group, more preferably a linear or branched alkyl group or a cycloalkyl group.

Specific structures of the group represented by formula (d-1) are set forth below.

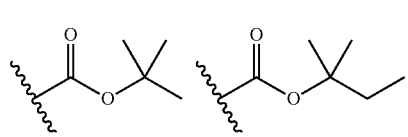

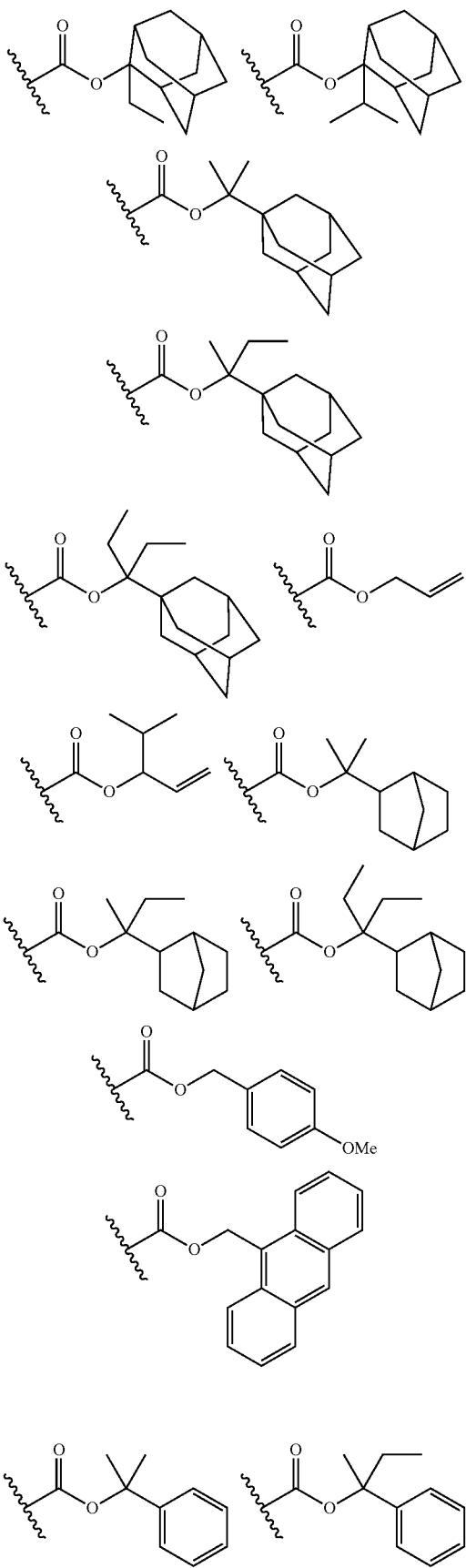

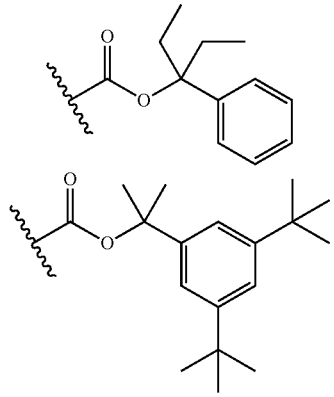

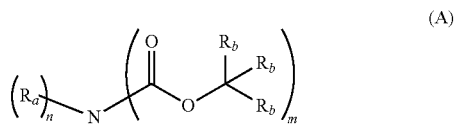

The component D may also be composed by arbitrarily combining the above-described basic compound and the structure represented by formula (d-1).

The component D is more preferably a compound having a structure represented by the following formula (A).

Incidentally, the component D may be a compound corresponding to the above-described basic compound as long as it is a low molecular compound having a group capable of leaving by the action of an acid.

$$\left( R_a \right)_n - N \underbrace{\left( \begin{matrix} O \\ \parallel \\ C - O - C \end{matrix} \begin{matrix} R_b \\ R_b \\ R_b \end{matrix} \right)}_{m} \quad (A)$$

In formula (A), each $R_a$ independently represents a hydrogen atom, an alkyl group, a cycloalkyl group, an aryl group or an aralkyl group. Also, when n=2, two $R_a$'s may be the same or different, and two $R_a$'s may combine with each other to form a heterocyclic hydrocarbon group (preferably having a carbon number of 20 or less) or a derivative thereof.

Each $R_b$ independently represents a hydrogen atom, an alkyl group, a cycloalkyl group, an aryl group or an aralkyl group.

At least two $R_b$'s may combine to form an alicyclic hydrocarbon group, an aromatic hydrocarbon group, a heterocyclic hydrocarbon group or a derivative thereof n represents an integer of 0 to 2, m represents an integer of 1 to 3, and n+m=3.

In formula (A), each of the alkyl group, cycloalkyl group, aryl group and aralkyl group of $R_a$ and $R_b$ may be substitute by a functional group such as hydroxyl group, cyano group, amino group, pyrrolidino group, piperidino group, morpholino group and oxo group, an alkoxy group or a halogen atom.

Examples of the alkyl group, cycloalkyl group, aryl group and aralkyl group (each of these alkyl group, cycloalkyl group, aryl group and aralkyl group may be substituted by the above-described functional group, an alkoxy group or a halogen atom) of $R_a$ and $R_b$ include:

a group derived from a linear or branched alkane such as methane, ethane, propane, butane, pentane, hexane, heptane, octane, nonane, decane, undecane and dodecane, or a group where the group derived from an alkane is substituted by one or more kinds of or one or more groups of cycloalkyl groups such as cyclobutyl group, cyclopentyl group and cyclohexyl group;

a group derived from a cycloalkane such as cyclobutane, cyclopentane, cyclohexane, cycloheptane, cyclooctane, norbornane, adamantane and noradamantane, or a group where the group derived from a cycloalkane is substituted by one or more kinds of or one or more groups of linear or branched alkyl groups such as methyl group, ethyl group, n-propyl group, i-propyl group, n-butyl group, 2-methylpropyl group, 1-methylpropyl group and tert-butyl group;

a group derived from an aromatic compound such as benzene, naphthalene and anthracene, or a group where the group derived from an aromatic compound is substituted by one or more kinds of or one or more groups of linear or branched alkyl groups such as methyl group, ethyl group, n-propyl group, i-propyl group, n-butyl group, 2-methylpropyl group, 1-methylpropyl group and tert-butyl group;

a group derived from a heterocyclic compound such as pyrrolidine, piperidine, morpholine, tetrahydrofuran, tetrahydropyran, indole, indoline, quinoline, perhydroquinoline, indazole and benzimidazole, or a group where the group derived from a heterocyclic compound is substituted by one or more kinds of or one or more groups of linear or branched alkyl groups or aromatic compound-derived groups; a group where the group derived from a linear or branched alkane or the group derived from a cycloalkane is substituted by one or more kinds of or one or more groups of aromatic compound-derived groups such as phenyl group, naphthyl group and anthracenyl group; and a group where the substituent above is substituted by a functional group such as hydroxyl group, cyano group, amino group, pyrrolidino group, piperidino group, morpholino group and oxo group.

Examples of the divalent heterocyclic hydrocarbon group (preferably having a carbon number of 1 to 20) formed by combining $R_a$'s with each other or a derivative thereof include a group derived from a heterocyclic compound such as pyrrolidine, piperidine, morpholine, 1,4,5,6-tetrahydropyrimidine, 1,2,3,4-tetrahydroquinoline, 1,2,3,6-tetrahydropyridine, homopiperazine, 4-azabenzimidazole, benzotriazole, 5-azabenzotriazole, 1H-1,2,3-triazole, 1,4,7-triazacyclononane, tetrazole, 7-azaindole, indazole, benzimidazole, imidazo[1,2-a]pyridine, (1S,4S)-(+)-2,5-diazabicyclo[2.2.1]heptane, 1,5,7-triazabicyclo[4.4.0]dec-5-ene, indole, indoline, 1,2,3,4-tetrahydroquinoxaline, perhydroquinoline and 1,5,9-triazacyclododecane, and a group where the group derived from a heterocyclic compound is substituted by one or more kinds of or one or more groups of linear or branched alkane-derived groups, cycloalkane-derived groups, aromatic compound-derived groups, heterocyclic compound-derived group, and functional groups such as hydroxyl group, cyano group, amino group, pyrrolidino group, piperidino group, morpholino group and oxo group.

Specific examples particularly preferred in the present invention include N-tert-butoxycarbonyldi-n-octylamine, N-tert-butoxycarbonyldi-n-nonylamine, N-tert-butoxycarbonyldi-n-decylamine, N-tert-butoxycarbonyldicyclohexylamine, N-tert-butoxycarbonyl-1-adamantylamine, N-tert-butoxycarbonyl-2-adamantylamine, N-tert-butoxycarbonyl-N-methyl-1-adamantylamine, (S)-(−)-1-(tert-butoxycarbonyl)-2-pyrrolidinemethanol, (R)-(+)-1-(tert-butoxycarbonyl)-2-pyrrolidinemethanol, N-tert-butoxycarbonyl-4-hydroxypiperidine, N-tert-butoxycarbonylpyrrolidine, N-tert-butoxycarbonylmorpholine, N-tert-butoxycarbonylpiperazine, N,N-di-tert-butoxycarbonyl-1-adamantylamine, N,N-di-tert-butoxycarbonyl-N-methyl-1-adamantylamine, N-tert-butoxycarbonyl-4,4'-diaminodiphenylmethane, N,N'-di-tert-butoxycarbonylhexamethylenediamine, N,N,N',N'-tetra-tert-butoxycarbonylhexamethylenediamine, N,N'-di-tert-butoxycarbonyl-1,7-diaminoheptane, N,N'-di-tert-butoxycarbonyl-1,8-diaminooctane, N,N'-di-tert-butoxycarbonyl-1,9-diaminononane, N,N'-di-tert-butoxycarbonyl-1,10-diaminodecane, N,N'-di-tert-butoxycarbonyl-1,12-diaminododecane, N,N'-di-tert-butoxycarbonyl-4,4'-diaminodiphenylmethane, N-tert-butoxycarbonylbenzimidazole, N-tert-butoxycarbonyl-2-methylbenzimidazole and N-tert-butoxycarbonyl-2-phenylbenzimidazole.

Specific examples of the component D particularly preferred in the present invention are set forth below, but the present invention is not limited thereto.

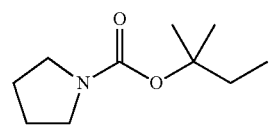

(D-1)

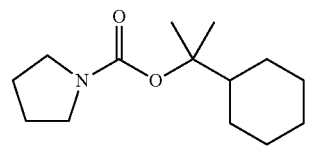

(D-2)

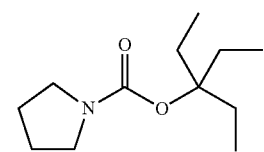

(D-3)

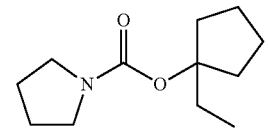

(D-4)

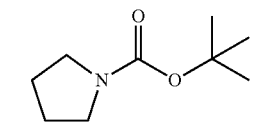

(D-5)

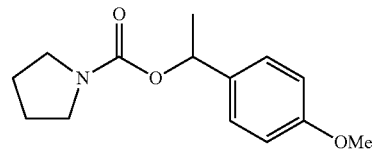

(D-6)

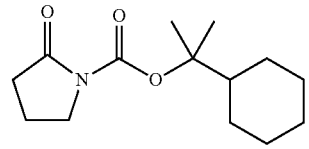

(D-7)

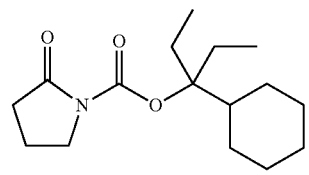

(D-8)

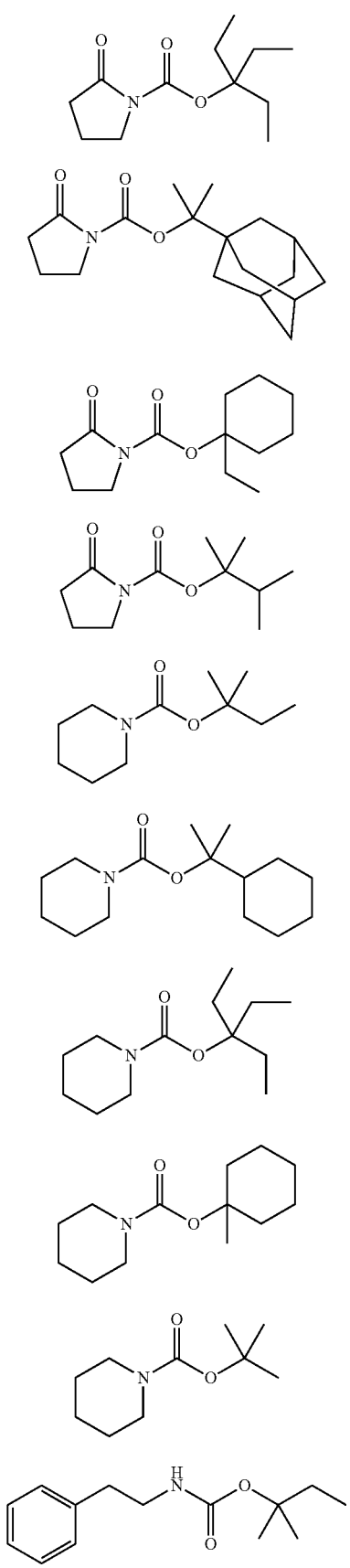
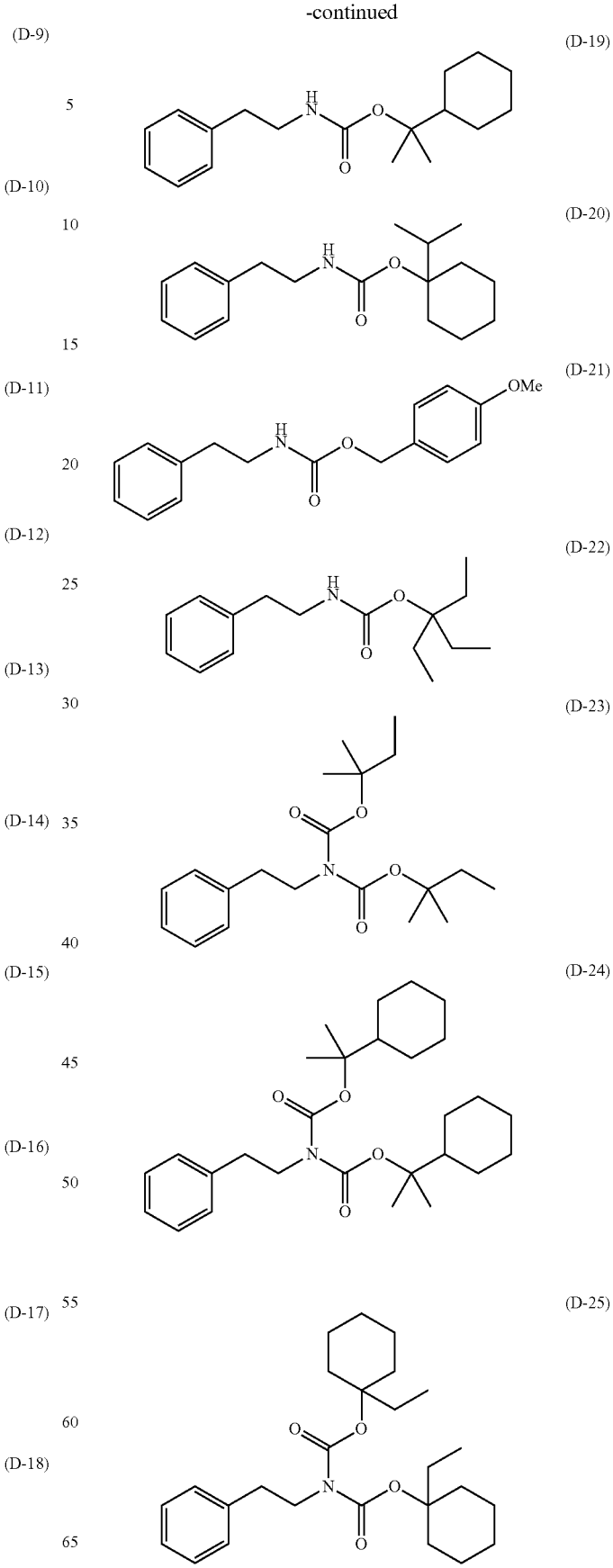

(D-26)
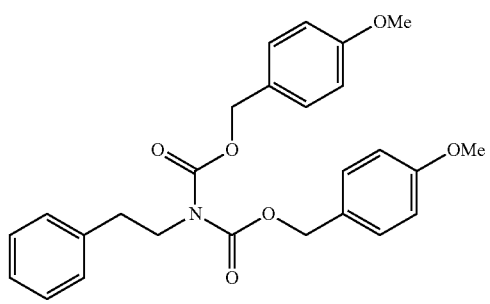
(D-27)
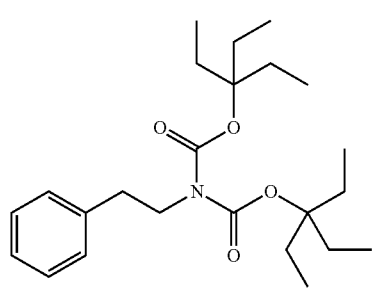
(D-28)
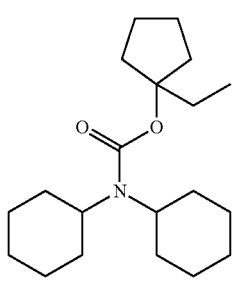
(D-29)
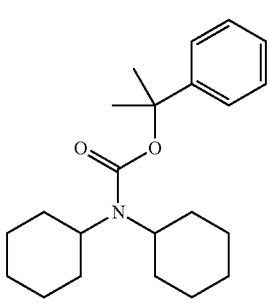
(D-30)
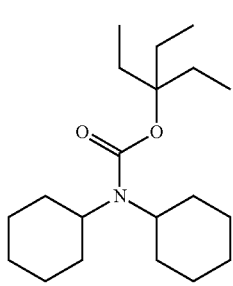
(D-31)
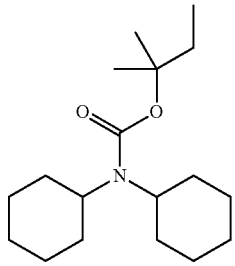
(D-32)
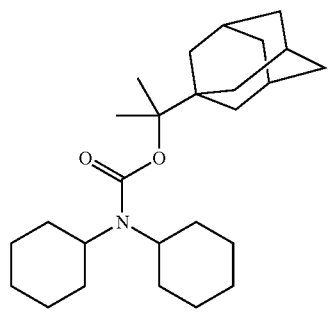
(D-33)
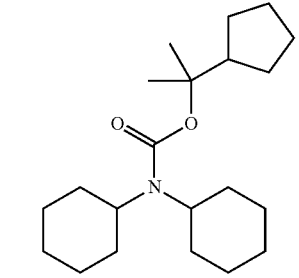
(D-34)
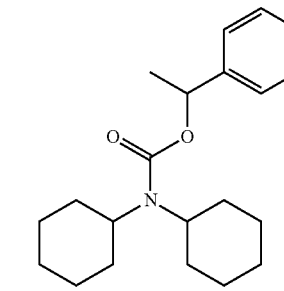
(D-35)
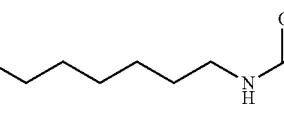
(D-36)
(D-37)
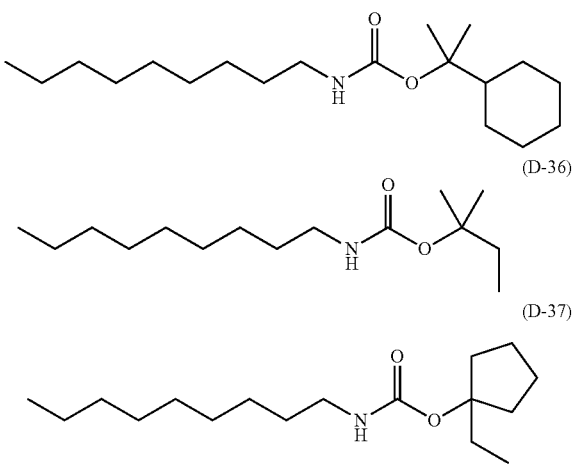

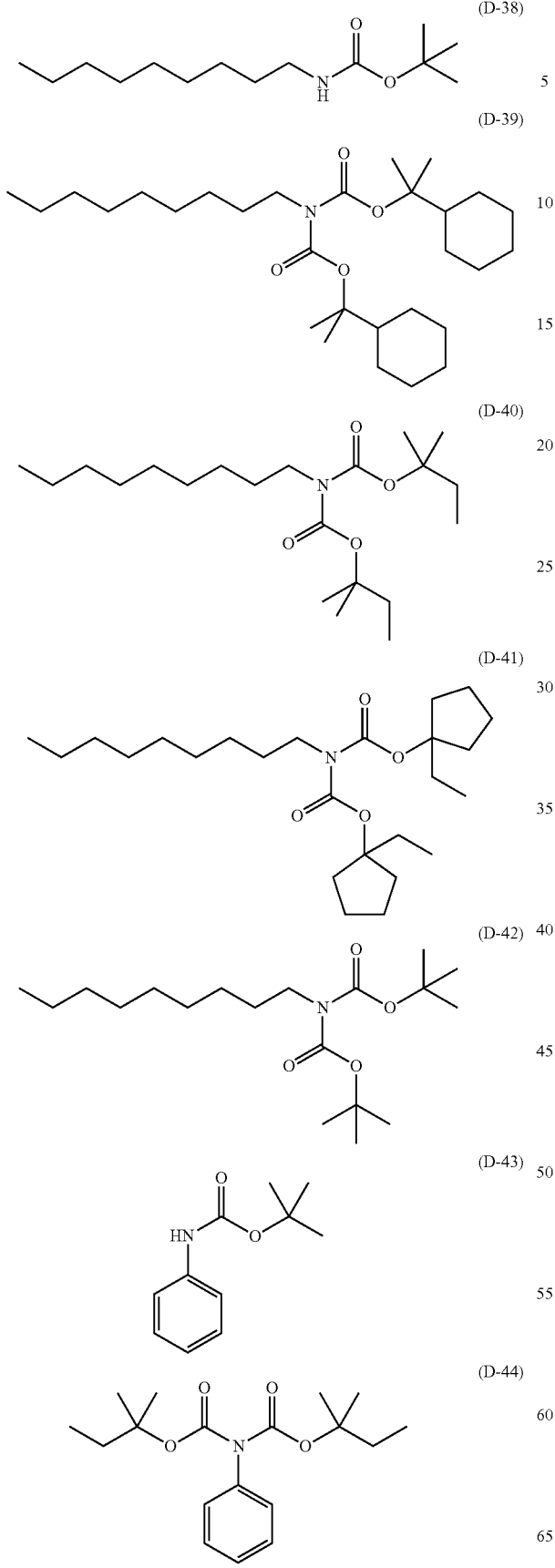
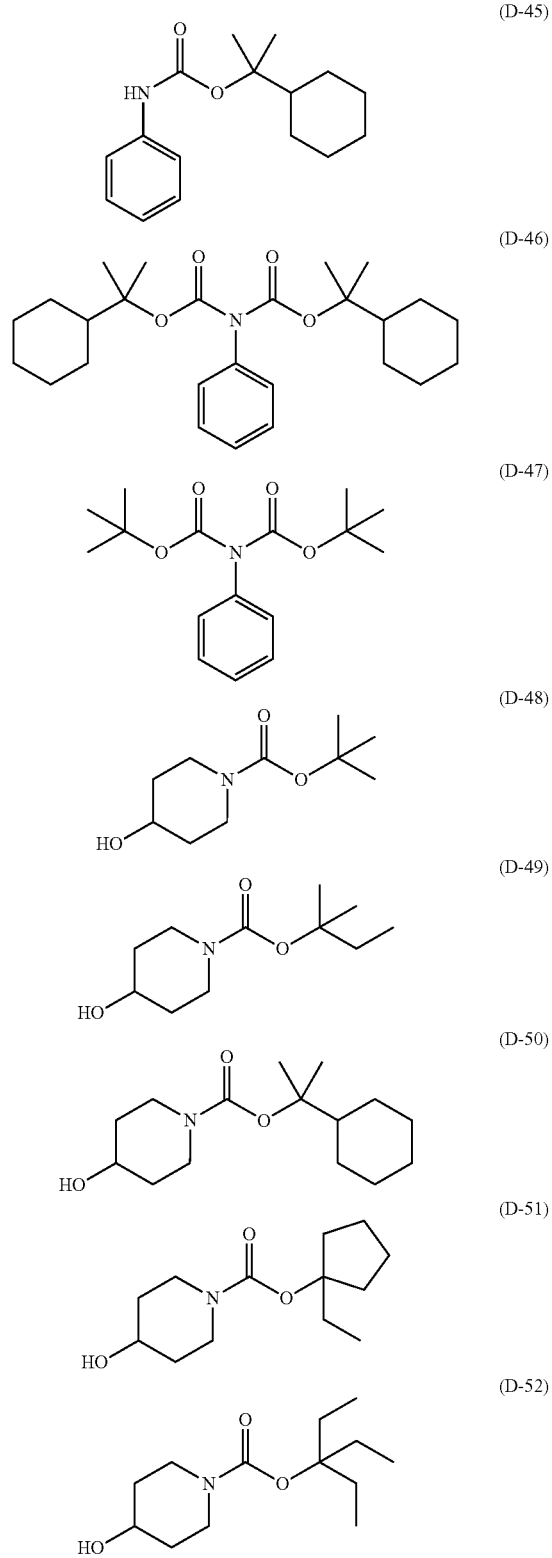
The compound represented by formula (A) can be easily synthesized from a commercially available amine by a method described, for example, Protective Groups in Organic Synthesis, 4th edition. A most general method is a method of causing a dicarbonic acid ester or a haloformic acid ester to act on a commercially available amine to obtain the compound. In the formulae, X represents a halogen atom, and $R_a$ and $R_b$ have the same meanings as $R_a$ and $R_b$ in formula (A) above.

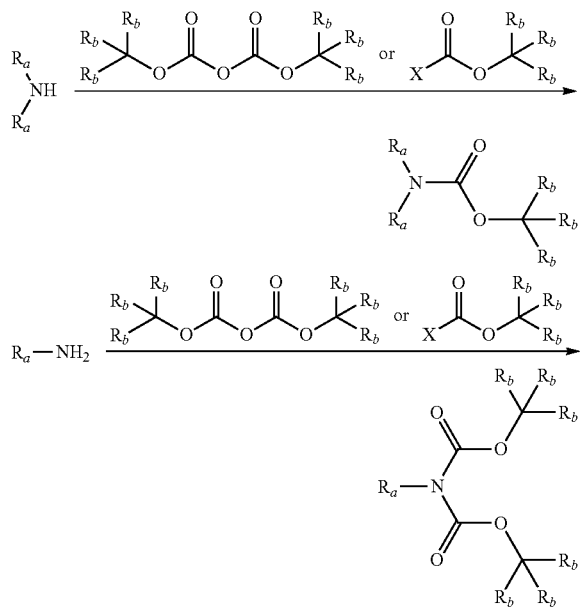

In the present invention, one kind of (D) a low molecular compound having a group capable of leaving by the action of an acid may be used alone, or two or more kinds of the compounds may be mixed and used.

In the present invention, the amount used of the (D) low molecular compound having a group capable of leaving by the action of an acid is usually from 0.001 to 20 mass %, preferably from 0.001 to 10 mass %, more preferably from 0.01 to 5 mass %, based on the entire solid compound of the composition combined with the blow-mentioned basic compound.

When the acid generator and the low molecular compound having a group capable of leaving by the action of an acid are used in the composition, the ratio therebetween is preferably acid generator/[(D) low molecular compound having a group capable of leaving by the action of an acid+basic compound described above] (by mol)=from 2.5 to 300. That is, the molar ratio is preferably 2.5 or more in view of sensitivity and resolution and preferably 300 or less from the standpoint of suppressing the reduction in resolution due to thickening of the resist pattern with aging after exposure to heat treatment. The acid generator/[(D) low molecular compound having a group capable of leaving by the action of an acid+basic compound described above] (by mol) is more preferably from 5.0 to 200, still more preferably from 7.0 to 150.

[7] Surfactant

The actinic ray-sensitive or radiation-sensitive resin composition of the present invention may further contain a surfactant and in the case of containing a surfactant, the composition preferably contains any one of fluorine-containing and/or silicon-containing surfactants (a fluorine-containing surfactant, a silicon-containing surfactant and a surfactant containing both a fluorine atom and a silicon atom), or two or more kinds thereof.

By virtue of incorporating the above-described surfactant into the actinic ray-sensitive or radiation-sensitive resin composition of the present invention, a resist pattern with good performance in terms of sensitivity, resolution and adherence as well as less development defects can be provided when using an exposure light source of 250 nm or less, particularly 220 nm or less.

On the other hand, when the amount added of the surfactant is made small, for example, set to 10 ppm or less, uneven distribution of the component (C) to the surface is more successfully allowed, so that the resist film surface can be made more hydrophobic and the followability of water at the immersion exposure can be enhanced.

Examples of the fluorine-containing and/or silicon-containing surfactant include surfactants described in JP-A-62-36663, JP-A-61-226746, JP-A-61-226745, JP-A-62-170950, JP-A-63-34540, JP-A-7-230165, JP-A-8-62834, JP-A-9-54432, JP-A-9-5988, JP-A-2002-277862 and U.S. Pat. Nos. 5,405,720, 5,360,692, 5,529,881, 5,296,330, 5,436,098, 5,576,143, 5,294,511 and 5,824,451. The following commercially available surfactants each may also be used as it is.

Examples of the commercially available surfactant which can be used include a fluorine-containing surfactant and a silicon-containing surfactant, such as EFtop EF301 and EF303 (produced by Shin-Akita Kasei K.K.); Florad FC430, 431 and 4430 (produced by Sumitomo 3M Inc.); Megaface F171, F173, F176, F189, F113, F110, F177, F120 and R08 (produced by Dainippon Ink & Chemicals, Inc.); Surflon S-382, SC101, 102, 103, 104, 105 and 106 (produced by Asahi Glass Co., Ltd.); Troysol S-366 (produced by Troy Chemical); GF-300 and GF-150 (produced by Toagosei Chemical Industry Co., Ltd.); Surflon S-393 (produced by Seimi Chemical Co., Ltd.); EFtop EF121, EF122A, EF122B, RF122C, EF125M, EF135M, EF351, EF352, EF801, EF802 and EF601 (produced by JEMCO Inc.); PF636, PF656, PF6320 and PF6520 (produced by OMNOVA); and FTX-204G, 208G, 218G, 230G, 204D, 208D, 212D, 218D and 222D (produced by NEOS Co., Ltd.). In addition, polysiloxane polymer KP-341 (produced by Shin-Etsu Chemical Co., Ltd.) may also be used as the silicon-containing surfactant.

As for the surfactant, other than these known surfactants, a surfactant using a polymer having a fluoro-aliphatic group derived from a fluoro-aliphatic compound that is produced by a telomerization process (also called a telomer process) or an oligomerization process (also called an oligomer process), may be used. The fluoro-aliphatic compound can be synthesized by the method described in JP-A-2002-90991.

The polymer having a fluoro-aliphatic group is preferably a copolymer of a fluoro-aliphatic group-containing monomer with a (poly(oxyalkylene)) acrylate and/or a (poly(oxyalkylene)) methacrylate, and the polymer may have an irregular distribution or may be a block copolymer. Examples of the poly(oxyalkylene) group include a poly(oxyethylene) group, a poly(oxypropylene) group and a poly(oxybutylene) group. This group may also be a unit having alkylenes differing in the chain length within the same chain, such as block-linked poly(oxyethylene, oxypropylene and oxyethylene) and block-linked poly(oxyethylene and oxypropylene). Furthermore, the copolymer of a fluoro-aliphatic group-containing monomer and a (poly(oxyalkylene)) acrylate (or methacrylate) is not limited only to a binary copolymer but may also be a ternary or greater copolymer obtained by simultaneously copolymerizing two or more different fluoro-aliphatic group-containing monomers or two or more different (poly(oxyalkylene)) acrylates (or methacrylates).

Examples thereof include, as the commercially available surfactant, Megaface F178, F-470, F-473, F-475, F-476 and F-472 (produced by Dainippon Ink & Chemicals, Inc.) and further include a copolymer of a $C_6F_{13}$ group-containing acrylate (or methacrylate) with a (poly(oxyalkylene)) acrylate (or methacrylate), and a copolymer of a $C_3F_7$ group-containing acrylate (or methacrylate) with a (poly(oxyethylene)) acrylate (or methacrylate) and a (poly(oxypropylene)) acrylate (or methacrylate).

In the present invention, a surfactant other than the fluorine-containing and/or silicon-containing surfactant may also be used. Specific examples thereof include a nonionic surfactant such as polyoxyethylene alkyl ethers (e.g., polyoxyethylene lauryl ether, polyoxyethylene stearyl ether, polyoxyethylene cetyl ether, polyoxyethylene oleyl ether), polyoxyethylene alkylaryl ethers (e.g., polyoxyethylene octylphenol ether, polyoxyethylene nonylphenol ether), polyoxyethylene•polyoxypropylene block copolymers, sorbitan fatty acid esters (e.g., sorbitan monolaurate, sorbitan monopalmitate, sorbitan monostearate, sorbitan monooleate, sorbitan trioleate, sorbitan tristearate), and polyoxyethylene sorbitan fatty acid esters (e.g., polyoxyethylene sorbitan monolaurate, polyoxyethylene sorbitan monopalmitate, polyoxyethylene sorbitan monostearate, polyoxyethylene sorbitan trioleate, polyoxyethylene sorbitan tristearate).

One of such surfactants may be used alone, or some of them may be used in combination.

The amount used of the surfactant is preferably from 0 to 2 mass %, more preferably from 0.0001 to 2 mass %, still more preferably from 0.0005 to 1 mass %, based on the entire solid content of the actinic ray-sensitive or radiation-sensitive resin composition (the entire amount excluding the solvent).

[8] Onium Carboxylate

The actinic ray-sensitive or radiation-sensitive resin composition of the present invention may contain an onium carboxylate. Examples of the onium carboxylate include sulfonium carboxylate, iodonium carboxylate and ammonium carboxylate. In particular, the onium carboxylate is preferably an iodonium salt or a sulfonium salt. Furthermore, the carboxylate residue of the onium carboxylate for use in the present invention preferably contains no aromatic group and no carbon-carbon double bond. The anion moiety is preferably a linear or branched, monocyclic or polycyclic alkylcarboxylate anion having a carbon number of 1 to 30, more preferably the carboxylate anion above with the alkyl group being partially or entirely fluorine-substituted. The alkyl chain may contain an oxygen atom. Thanks to such a construction, the transparency to light at 220 nm or less is ensured, the sensitivity and resolution are enhanced, and the iso/dense bias and exposure margin are improved.

Examples of the fluorine-substituted carboxylate anion include fluoroacetate, difluoro acetate, trifluoroacetate, pentafluoropropionate, heptafluorobutyrate, nonafluoropentanoate, perfluorododecanoate, perfluorotridecanoate, perfluorocyclohexanecarboxylate and 2,2-bistrifluoromethylpropionate anions.

These onium carboxylates can be synthesized by reacting a sulfonium, iodonium or ammonium hydroxide and a carboxylic acid with silver oxide in an appropriate solvent.

The content of the onium carboxylate in the composition is generally from 0.1 to 20 mass %, preferably from 0.5 to 10 mass %, more preferably from 1 to 7 mass %, based on the entire solid content of the composition.

[9] Dissolution Inhibiting Compound Having a Molecular Weight of 3,000 or Less and being Capable of Decomposing by the Action of an Acid to Increase the Solubility in an Alkali Developer The actinic ray-sensitive or radiation-sensitive resin composition of the present invention may contain a dissolution inhibiting compound having a molecular weight of 3,000 or less and being capable of decomposing by the action of an acid to increase the solubility in an alkali developer (hereinafter, sometimes referred to as a "dissolution inhibiting compound"). The dissolution inhibiting compound is preferably an alicyclic or aliphatic compound containing an acid-decomposable group, such as acid-decomposable group-containing cholic acid derivative described in Proceeding of SPIE, 2724, 355 (1996), so as not to reduce the transparency to light at 220 nm or less. Examples of the acid-decomposable group and alicyclic structure are the same as those described above with respect to the resin of the component (A).

In the case where the actinic ray-sensitive or radiation-sensitive resin composition of the present invention is exposed by a KrF excimer laser or irradiated with an electron beam, the composition preferably contains a structure where the phenolic hydroxyl group of a phenol compound is substituted by an acid-decomposable group. The phenol compound is preferably a compound containing from 1 to 9 phenol skeletons, more preferably from 2 to 6 phenol skeletons.

The molecular weight of the dissolution inhibiting compound for use in the present invention is 3,000 or less, preferably from 300 to 3,000, more preferably from 500 to 2,500.

The amount added of the dissolution inhibiting compound is preferably from 2 to 50 mass %, more preferably from 3 to 30 mass %, still more preferably from 5 to 10 mass %, based on the entire solid content of the actinic ray-sensitive or radiation-sensitive resin composition.

Specific examples of the dissolution inhibiting compound are set forth below, but the present invention is not limited thereto.

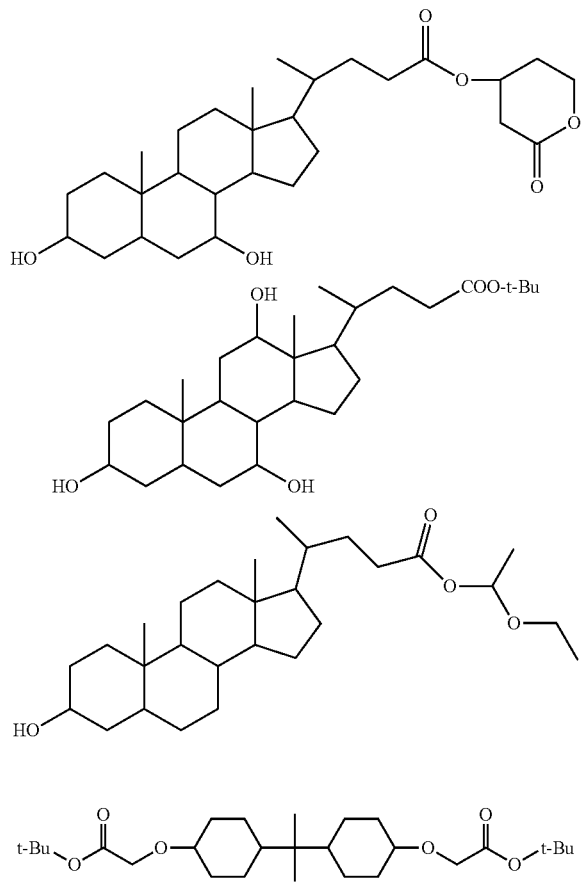

-continued

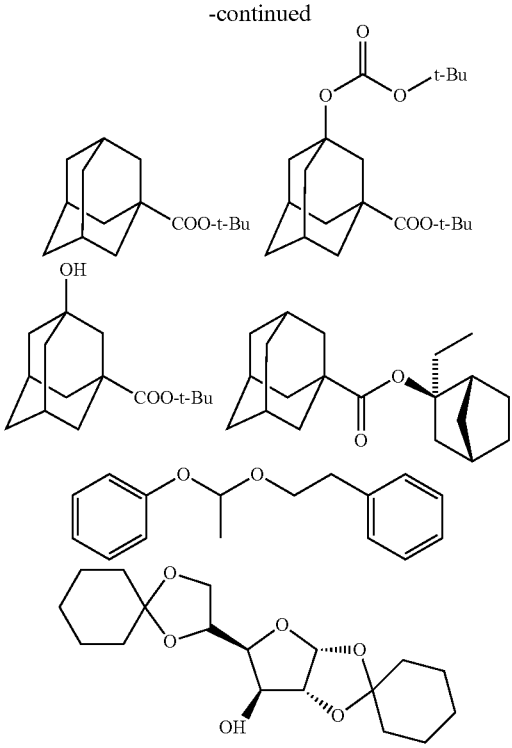

[10] Other Additives

The actinic ray-sensitive or radiation-sensitive resin composition of the present invention may further contain, for example, a dye, a plasticizer, a photosensitizer, a light absorber and a compound for accelerating dissolution in a developer (for example, a phenol compound having a molecular weight of 1,000 or less, or a carboxyl group-containing alicyclic or aliphatic compound), if desired.

The phenol compound having a molecular weight of 1,000 or less can be easily synthesized by one skilled in the art with reference to the methods described, for example, in JP-A-4-122938, JP-A-2-28531, U.S. Pat. No. 4,916,210 and European Patent 219294.

Specific examples of the carboxyl group-containing alicyclic or aliphatic compound include, but are not limited to, a carboxylic acid derivative having a steroid structure, such as cholic acid, deoxycholic acid and lithocholic acid, an adamantanecarboxylic acid derivative, an adamantanedicarboxylic acid, a cyclohexanecarboxylic acid and a cyclohexanedicarboxylic acid.

[11] Pattern Forming Method

The present invention also relates to a resist film formed using the actinic ray-sensitive or radiation-sensitive resin composition of the present invention.

Furthermore, the pattern forming method of the present invention comprises steps of immersion-exposing and developing the resist film.

The actinic ray-sensitive or radiation-sensitive resin composition of the present invention is preferably used in a film thickness of 30 to 250 nm, more preferably from 30 to 200 nm, from the standpoint of enhancing the resolution. Such a film thickness can be obtained by setting the solid content concentration in the actinic ray-sensitive or radiation-sensitive resin composition to an appropriate range, thereby imparting an appropriate viscosity and enhancing the coatability and film-forming property.

The entire solid content concentration in the actinic ray-sensitive or radiation-sensitive resin composition is generally from 1.0 to 10 mass %, preferably from 1.0 to 8.0 mass %, more preferably from 1.0 to 6.0 mass %.

The actinic ray-sensitive or radiation-sensitive resin composition of the present invention is used by dissolving the components above in a predetermined organic solvent, preferably in the above-described mixed solvent, filtering the solution, and applying it on a predetermined support as follows. The filter used for filtration is preferably a polytetrafluoroethylene-, polyethylene- or nylon-made filter having a pore size of 0.1 μm or less, more preferably 0.05 μm or less, still more preferably 0.03 μm or less.

For example, the actinic ray-sensitive or radiation-sensitive resin composition is applied on such a substrate (e.g., silicon/silicon dioxide-coated substrate) as used in the production of a precision integrated circuit device, by an appropriate coating method such as spinner or coater and dried to form a resist film.

The resist film is irradiated with an actinic ray or radiation through a predetermined mask, then preferably baked (heated), and subjected to development and rinsing, whereby a good pattern can be obtained.

Examples of the actinic ray or radiation include infrared light, visible light, ultraviolet light, far ultraviolet light, extreme-ultraviolet ray, X-ray and electron beam, but the radiation is preferably far ultraviolet light at a wavelength of 250 nm or less, more preferably 220 nm or less, still more preferably from 1 to 200 nm. Specific examples thereof include KrF excimer laser light (248 nm), ArF excimer laser light (193 nm), $F_2$ excimer laser light (157 nm), X-ray and electron beam, with ArF excimer laser light, $F_2$ excimer laser light and EUV (13 nm) being preferred.

Incidentally, in the present invention, an electromagnetic wave such as ultraviolet light and X-ray is included in the radiation.

Before forming the resist film, an antireflection film may be previously provided by coating on the substrate.

The antireflection film used may be either an inorganic film type such as titanium, titanium dioxide, titanium nitride, chromium oxide, carbon and amorphous silicon, or an organic film type composed of a light absorber and a polymer material. As for the organic antireflection film, there may be also used a commercially available organic antireflection film such as DUV30 Series and DUV-40 Series produced by Brewer Science, Inc. and AR-2, AR-3 and AR-5 produced by Shipley Co., Ltd.

In the development step, an alkali developer is used as follows. The alkali developer which can be used for the positive resist composition is an alkaline aqueous solution of, for example, inorganic alkalis such as sodium hydroxide, potassium hydroxide, sodium carbonate, sodium silicate, sodium metasilicate and aqueous ammonia, primary amines such as ethylamine and n-propylamine, secondary amines such as diethylamine and di-n-butylamine, tertiary amines such as triethylamine and methyldiethylamine, alcohol amines such as dimethylethanolamine and triethanolamine, quaternary ammonium salts such as tetramethylammonium hydroxide and tetraethylammonium hydroxide, or cyclic amines such as pyrrole and piperidine.

Furthermore, this alkali developer may be used after adding thereto alcohols and a surfactant each in an appropriate amount.

The alkali concentration of the alkali developer is usually from 0.1 to 20 mass %.

The pH of the alkali developer is usually from 10.0 to 15.0.

Also, the above-described alkaline aqueous solution may be used after adding thereto alcohols and a surfactant each in an appropriate amount.

As for the rinsing solution, pure water is used, and the pure water may be used after adding thereto a surfactant in an appropriate amount.

After the development or rinsing, a treatment of removing the developer or rinsing solution adhering on the pattern by a supercritical fluid may be performed.

The exposure may also be performed by filling a liquid (immersion medium) having a refractive index higher than that of air between the resist film and a lens at the irradiation with an actinic ray or radiation (immersion exposure). By this exposure, the resolution can be enhanced. The immersion medium used may be any liquid as long as it has a refractive index higher than that of air, but pure water is preferred.

The immersion liquid used in the immersion exposure is described below.

The immersion liquid is preferably a liquid being transparent to light at the exposure wavelength and having as small a temperature coefficient of refractive index as possible so as to minimize the distortion of an optical image projected on the resist film. Particularly, when the exposure light source is an ArF excimer laser (wavelength: 193 nm), water is preferably used in view of easy availability and easy handleability in addition to the above-described aspects.

Furthermore, a medium having a refractive index of 1.5 or more can also be used from the standpoint that the refractive index can be more enhanced. This medium may be either an aqueous solution or an organic solvent.

In the case of using water as the immersion liquid, for the purpose of decreasing the surface tension of water and increasing the surface activity, an additive (liquid) which does not dissolve the resist film on a wafer and at the same time, gives only a negligible effect on the optical coat at the undersurface of the lens element, may be added in a small ratio. The additive is preferably an aliphatic alcohol having a refractive index nearly equal to that of water, and specific examples thereof include methyl alcohol, ethyl alcohol and isopropyl alcohol. By virtue of adding an alcohol having a refractive index nearly equal to that of water, even when the alcohol component in water is evaporated and its content concentration is changed, the change in the refractive index of the entire liquid can be advantageously made very small. On the other hand, if a substance opaque to light at 193 nm or an impurity greatly differing in the refractive index from water is intermixed, this incurs distortion of the optical image projected on the resist film. Therefore, the water used is preferably distilled water. Pure water obtained by further filtering the distilled water through an ion exchange filter or the like may also be used.

The electrical resistance of water is preferably 18.3 MΩcm or more, and TOC (total organic carbon) is preferably 20 ppb or less. Also, the water is preferably subjected to a deaeration treatment.

The lithography performance can be enhanced by increasing the refractive index of the immersion liquid. From such a standpoint, an additive for increasing the refractive index may be added to water, or deuterium water ($D_2O$) may be used in place of water.

In order to prevent the resist film from directly contacting with the immersion liquid, a film (hereinafter, sometimes referred to as a "topcoat") sparingly soluble in an immersion liquid may be provided between the immersion liquid and the resist film formed of the actinic ray-sensitive or radiation-sensitive resin composition of the present invention. The functions required of the topcoat are suitability for coating as an overlayer of the resist, transparency to actinic ray or radiation (particularly at 193 nm), and sparing solubility in the immersion liquid. The topcoat is preferably unmixable with the resist and capable of being uniformly applied as an overlayer of the resist.

In view of transparency to light at 193 nm, the topcoat is preferably a polymer not abundantly containing an aromatic, and specific examples thereof include a hydrocarbon polymer, an acrylic acid ester polymer, a polymethacrylic acid, a polyacrylic acid, a polyvinyl ether, a silicon-containing polymer and a fluorine-containing polymer. The above-described hydrophobic resin (C) is also suitable as the topcoat. If impurities are dissolved out into the immersion liquid from the topcoat, the optical lens is contaminated. In this viewpoint, the amount of residual monomer components of the polymer contained in the topcoat is preferably smaller.

On peeling off the topcoat, a developer may be used or a releasing agent may be separately used. The releasing agent is preferably a solvent less permeating the resist film. From the standpoint that the peeling step can be performed simultaneously with the development step of the resist film, the topcoat is preferably peelable with an alkali developer and for enabling the peeling with an alkali developer, the topcoat is preferably acidic, but in view of non-intermixing with the resist film, the topcoat may be neutral or alkaline.

With no difference in the refractive index between the topcoat and the immersion liquid, the resolution is enhanced. In the case of using water as the immersion liquid at the exposure with an ArF excimer laser (wavelength: 193 nm), the topcoat for ArF immersion exposure preferably has a refractive index close to the refractive index of the immersion liquid. From the standpoint of making the refractive index close to that of the immersion liquid, the topcoat preferably contains a fluorine atom. Also, in view of transparency and refractive index, the topcoat is preferably a thin film.

The topcoat is preferably unmixable with the resist film and further unmixable with the immersion liquid. From this standpoint, when the immersion liquid is water, the topcoat solvent is preferably a medium that is sparingly soluble in the solvent used for the positive resist composition and insoluble in water. Furthermore, when the immersion liquid is an organic solvent, the topcoat may be either water-soluble or water-insoluble.

EXAMPLES

The present invention is described in greater detail below by referring to Examples, but the contents of the present invention should not be construed as being limited thereto.

Monomer Synthesis Example 1 (Synthesis of Compound (4))

The following Compound (1) was synthesized by the method described in International Publication No. WO07/037,213, pamphlet.

To 35.00 g of Compound (1), 150.00 g of water was added, and 27.30 g of NaOH was further added. The obtained mixture was stirred for 9 hours under heating and refluxing conditions, made acidic by adding hydrochloric acid and then extracted with ethyl acetate. The organic layer was combined and concentrated to obtain 36.90 g of Compound (2) (yield: 93%).

$^1$H-NMR (400 MHz in $(CD_3)_2CO$): δ (ppm)=1.56-1.59 (1H), 1.68-1.72 (1H), 2.13-2.15 (1H), 2.13-2.47 (2H), 3.49-3.51 (1H), 3.68 (1H), 4.45-4.46 (1H).

To 20.00 g of Compound (2), 200 ml of CHCl$_3$ was added, and 50.90 g of 1,1,1,3,3,3-hexafluoroisopropyl alcohol and 30.00 g of 4-dimethylaminopyridine were further added. The obtained mixture was stirred and to the resulting solution, 22.00 g of 1-ethyl-3-(3-dimethylaminopropyl)carbodiimide hydrochloride was added. After stirring for 3 hours, the reaction solution was added to 500 ml of 1N HCl and the reaction was stopped. The organic layer was further washed with 1N HCl, then washed with water and concentrated to obtain 30.00 g of Compound (3) (yield: 85%).

$^1$H-NMR (400 MHz in (CD$_3$)$_2$CO): δ (ppm)=1.62 (1H), 1.91-1.95 (1H), 2.21-2.24 (1H), 2.45-2.53 (2H), 3.61-3.63 (1H), 3.76 (1H), 4.32-4.58 (1H), 6.46-6.53 (1H).

To 15.00 g of Compound (3), 300.00 g of toluene was added, and 3.70 g of methacrylic acid and 4.20 g of p-toluenesulfonic acid monohydrate were further added. The obtained mixture was refluxed for 15 hours while removing produced water by azeotropy. The reaction solution was concentrated, and the concentrate was purified by column chromatography to obtain 11.70 g of Compound (4) (yield: 65%).

$^1$H-NMR (400 MHz in (CD$_3$)$_2$CO): δ (ppm)=1.76-1.79 (1H), 1.93 (3H), 2.16-2.22 (2H), 2.57-2.61 (1H), 2.76-2.81 (1H), 3.73-3.74 (1H), 4.73 (1H), 4.84-4.86 (1H), 5.69-5.70 (1H), 6.12 (1H), 6.50-6.56 (1H).

further added. The obtained mixture was cooled to 0° C., and 20.85 g of methacrylic acid chloride was added dropwise thereto. The resulting solution was returned to room temperature, stirred for 2 hours and after adding an aqueous sodium hydrogencarbonate solution, extracted with ethyl acetate. The organic layer was collected, and MgSO$_4$ was added thereto. This mixture was filtered and concentrated to obtain 28.51 g of Compound (6) (yield: 95%).

$^1$H-NMR (400 MHz in (CD$_3$)$_2$CO): δ (ppm)=1.94-2.04 (3H), 3.71-3.72 (3H), 4.73 (2H), 5.72 (1H), 6.15 (1H).

To 28.5 g of Compound (6), 180 ml of acetone was added. The resulting mixture was cooled to 0° C. and added dropwise to 180 ml of aqueous 1N NaOH. After stirring for 30 minutes, the solution was made acidic by adding hydrochloric acid and then extracted with ethyl acetate. The organic layer was collected, and MgSO$_4$ was added thereto. This mixture was filtered and concentrated to obtain 21.2 g of Compound (7) (yield: 82%).

$^1$H-NMR (400 MHz in (CD$_3$)$_2$CO): δ (ppm)=1.94-1.97 (3H), 4.71-4.72 (2H), 5.70-5.71 (1H), 6.15 (1H).

To 15.00 g of Compound (7), 300 g of toluene was added, and 7.00 g of Compound (3) and 3.80 g of p-toluenesulfonic acid monohydrate were further added. The obtained mixture was refluxed for 6 hours while removing produced water by azeotropy. The reaction solution was concentrated, and the concentrate was purified by column chromatography to obtain 13.52 g of Compound (8) (yield: 71%).

$^1$H-NMR (400 MHz in (CD$_3$)$_2$CO): δ (ppm)=1.77-1.78 (1H), 1.95-1.96 (3H), 2.11-2.20 (2H), 2.56-2.61 (1H), 2.73-2.74 (1H), 3.73-3.75 (1H), 4.77-4.82 (4H), 5.74 (1H), 6.16 (1H), 6.52-6.53 (1H).

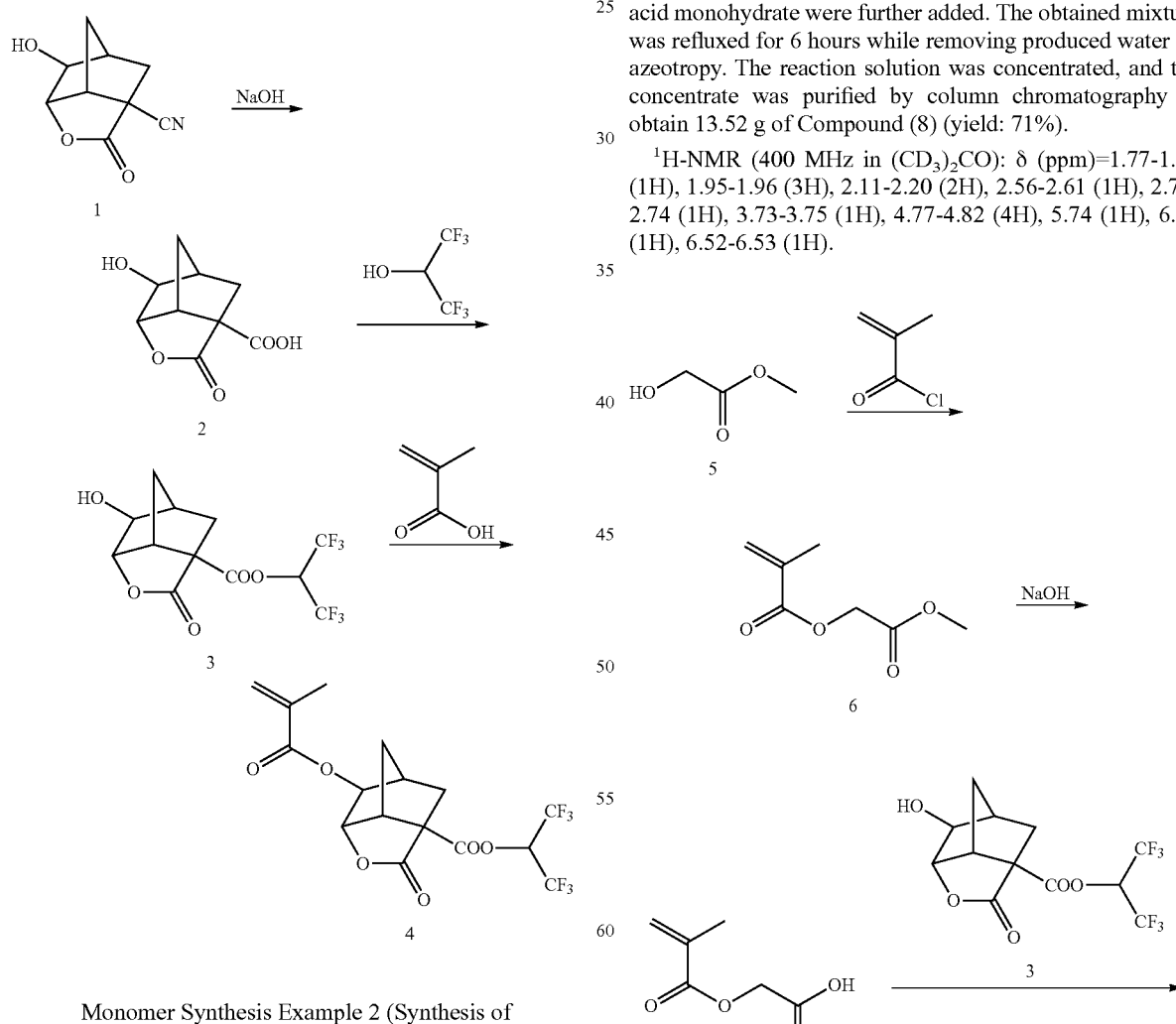

Monomer Synthesis Example 2 (Synthesis of Compound (8))

To 17.09 g of methyl glycolate (5) (produced by TCI), 30.00 g of THF was added, and 21.15 g of triethylamine was

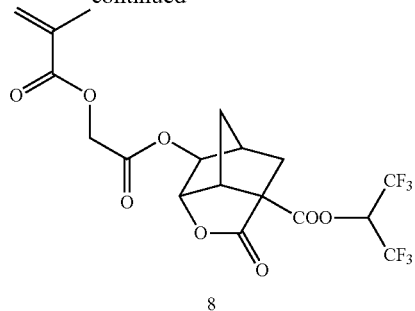

8

Monomer Synthesis Example 3 (Synthesis of Compound (9))

Compound (9) was synthesized in the same manner as in Monomer Synthesis Example 1 except for using 2,2,3,3,4,4,4-heptafluoro-1-butanol in place of 1,1,1,3,3,3-hexafluoroisopropyl alcohol (yield of three steps: 30%).

$^1$H-NMR (400 MHz in $(CD_3)_2CO$): δ (ppm)=1.73-1.76 (1H), 1.93 (3H), 2.13-2.17 (1H), 2.57-2.61 (1H), 2.71-2.72 (1H), 2.77-2.81 (1H), 3.65-3.67 (1H), 4.69 (1H), 4.79-4.80 (1H), 4.91-5.00 (2H), 5.68-5.69 (1H), 6.11-6.12 (1H).

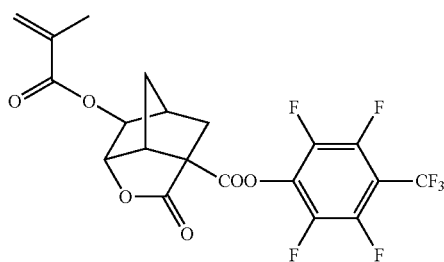

9

Monomer Synthesis Example 4 (Synthesis of Compound (10))

Compound (10) was synthesized in the same manner as in Monomer Synthesis Example 1 except for using 1H,1H-tridecafluoro-1-heptanol in place of 1,1,1,3,3,3-hexafluoroisopropyl alcohol (yield of three steps: 42%).

$^1$H-NMR (400 MHz in $(CD_3)_2CO$): δ (ppm)=1.73-1.88 (1H), 1.93 (3H), 2.08-2.17 (1H), 2.56-2.61 (1H), 2.71-2.72 (1H), 2.77-2.81 (1H), 3.66-3.68 (1H), 4.69 (1H), 4.79-4.81 (1H), 4.93-5.01 (2H), 5.68-5.69 (1H), 6.11-6.12 (1H).

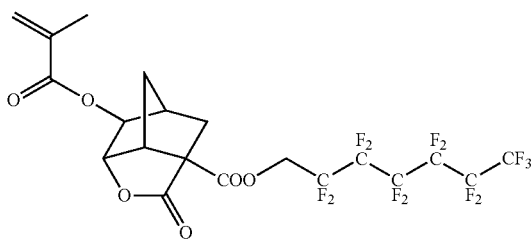

10

Monomer Synthesis Example 5 (Synthesis of Compound (11))

Compound (11) was synthesized in the same manner as in Monomer Synthesis Example 1 except for using 2,3,5,6-tetrafluoro-4-(trifluoromethyl)phenol in place of 1,1,1,3,3,3-hexafluoroisopropyl alcohol (yield of three steps: 23%).

$^1$H-NMR (400 MHz in $(CD_3)_2CO$): δ (ppm)=1.88-1.91 (1H), 1.94 (3H), 2.10-2.28 (2H), 2.66-2.71 (1H), 2.80 (1H), 3.92-3.93 (1H), 4.77 (1H), 4.90-4.92 (1H), 5.70-5.71 (1H), 6.13-6.14 (1H).

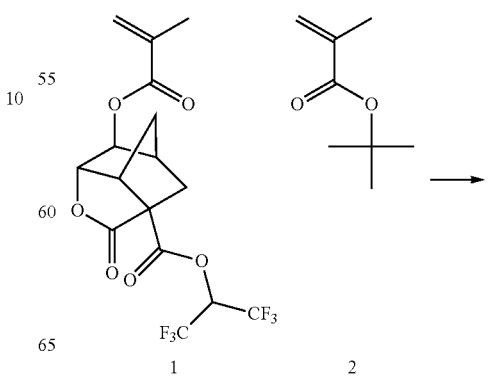

11

Synthesis Example 1 (Synthesis of Resin (C-8))

In a nitrogen atmosphere, 6.4 g of propylene glycol monomethyl ether acetate (PGMEA) was charged into a three-neck flask and heated to 80° C. Thereto, a solution prepared by dissolving 17.5 g of Compound (1), 4.0 g of Compound (2) and polymerization initiator V-601 (produced by Wako Pure Chemical Industries, Ltd.) in a ratio of 5.0 mol % based on the monomers, in 58.0 g of PGMEA was added dropwise over 4 hours. After the completion of dropwise addition, the reaction was further allowed to proceed at 80° C. for 4 hours. The resulting reaction solution was left standing to cool and then added dropwise to a mixed solution of 1,300 g of methanol/150 g of distilled water over 20 minutes, and the powder precipitated was collected by filtration and dried, as a result, 15.2 g of Polymer (C-8) was obtained.

The weight average molecular weight of Polymer (C-8) obtained was 8,000 in terms of standard polystyrene and the polydispersity (Mw/Mn) was 1.3.

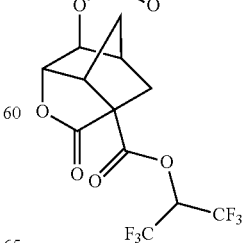 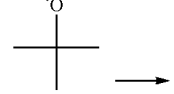

1  2

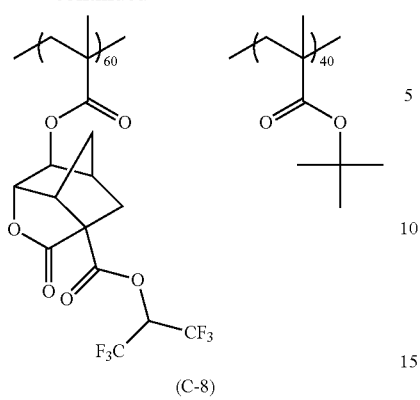

(C-8)

Other resins (C) shown in the Table above were synthesized in the same manner.

Synthesis Example 2 (Synthesis of Resin (1))

In a nitrogen atmosphere, 8.6 g of cyclohexanone was charged into a three-neck flask and heated to 80° C. Thereto, a solution prepared by dissolving 9.8 g of 2-adamantyl-isopropyl methacrylate, 4.4 g of dihydroxyadamantyl methacrylate, 8.9 g of norbornane lactone methacrylate and polymerization initiator V-601 (produced by Wako Pure Chemical Industries, Ltd.) in a ratio of 8 mol % based on the monomers, in 79 g of cyclohexanone was added dropwise over 6 hours. After the completion of dropwise addition, the reaction was further allowed to proceed at 80° C. for 2 hours. The resulting reaction solution was left standing to cool and then added dropwise to a mixed solution of 800 ml of hexane/200 ml of ethyl acetate over 20 minutes, and the powder precipitated was collected by filtration and dried, as a result, 19 g of Resin (1) was obtained. The weight average molecular weight of the obtained resin was 8,800 in terms of standard polystyrene and the polydispersity (Mw/Mn) was 1.9.

Other resins (A) shown below were synthesized in the same manner.

Structures of the acid-decomposable resin (A) used in Examples are shown below. Also, the molar ratio of repeating units (from the left in the structural formula), weight average molecular weight (Mw) and polydispersity (Mw/Mn) in each resin are shown in the Table below.

(1)

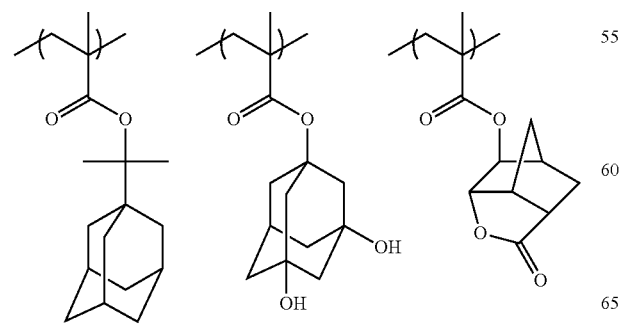

(2)

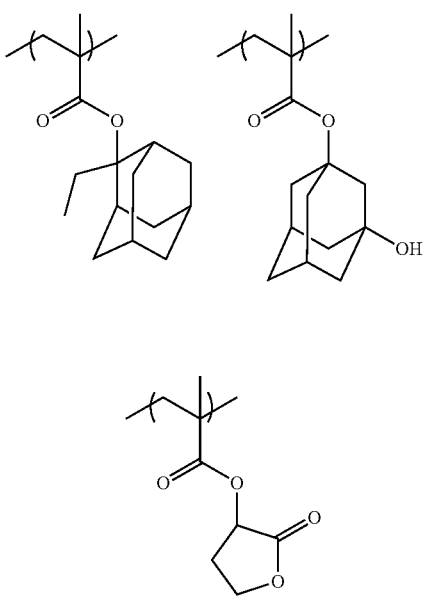

(3)

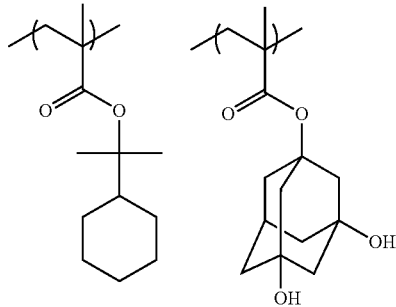

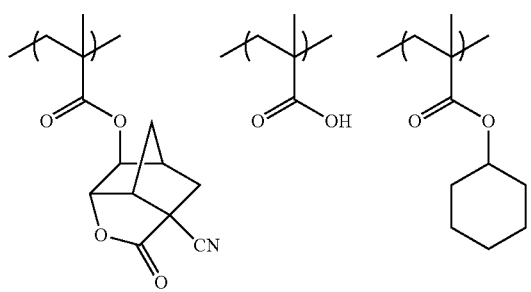

(4)

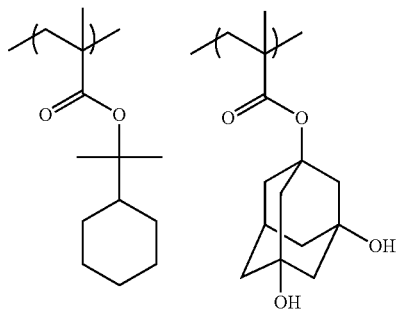

-continued
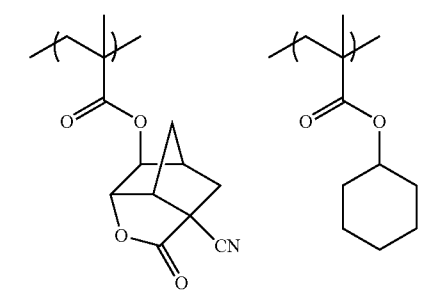
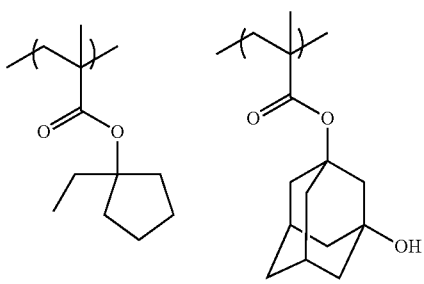
(5)
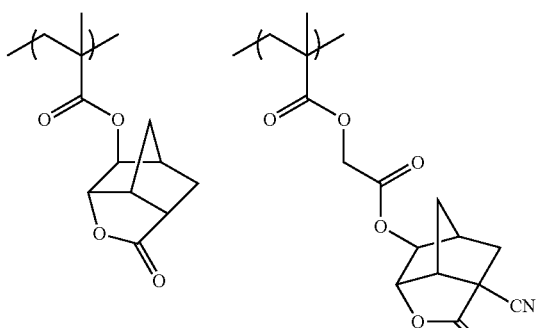
(6)
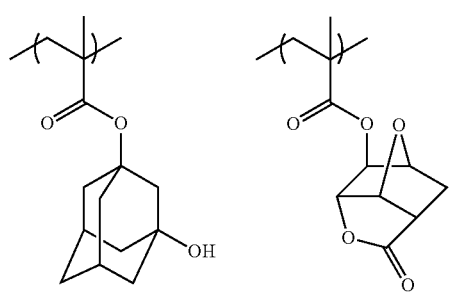
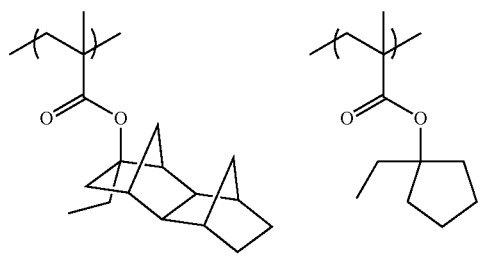
-continued
(7)
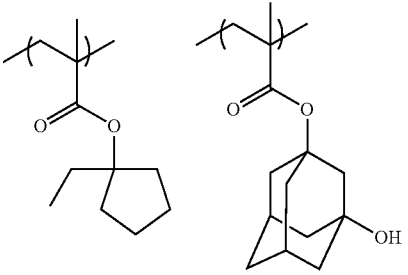
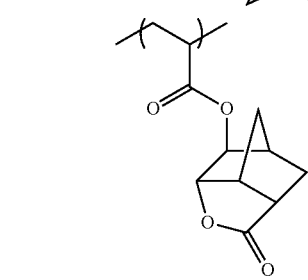
(8)
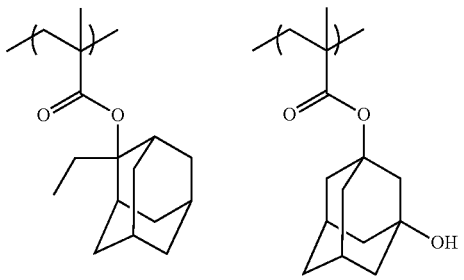
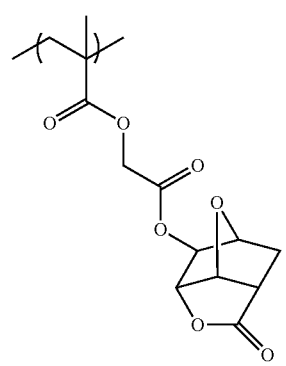
(9)
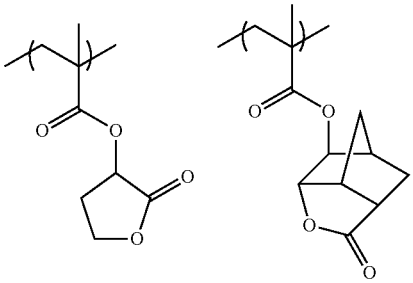

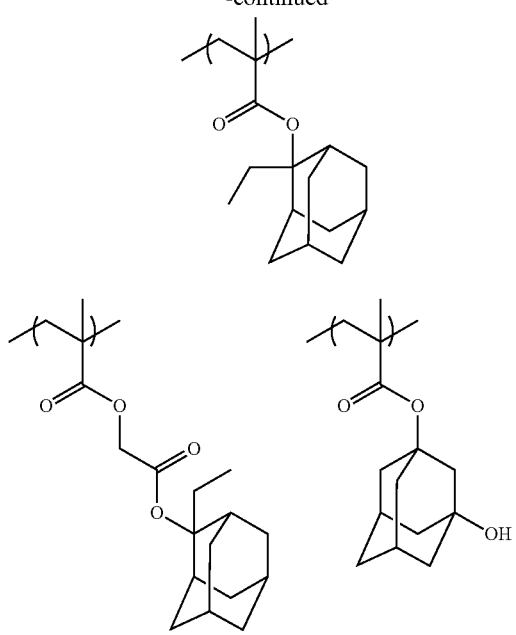
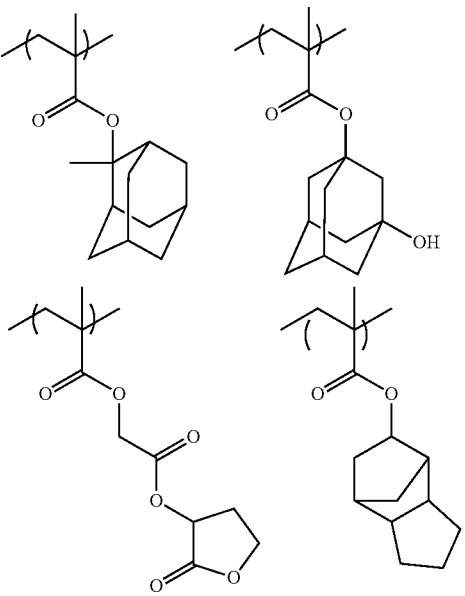
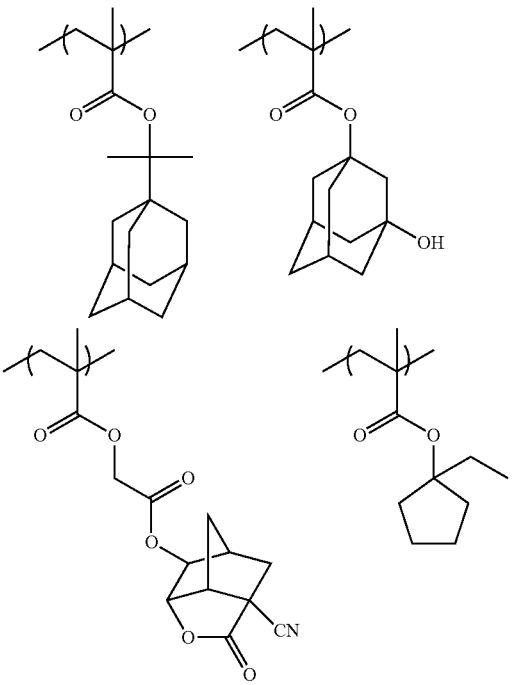
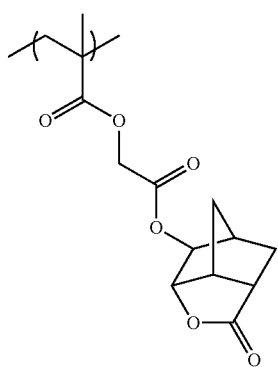

279
-continued
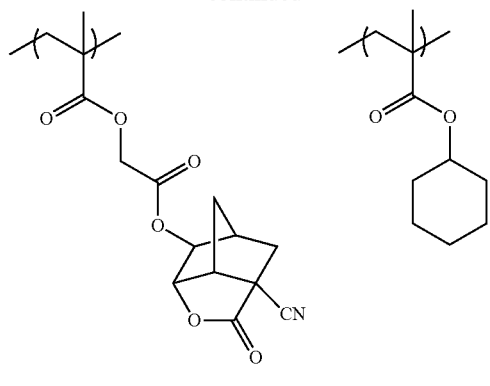
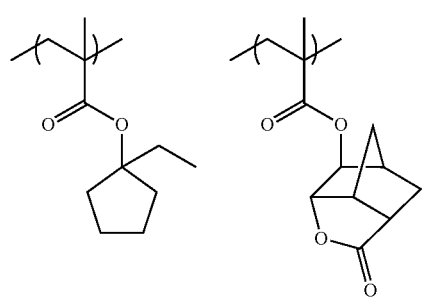
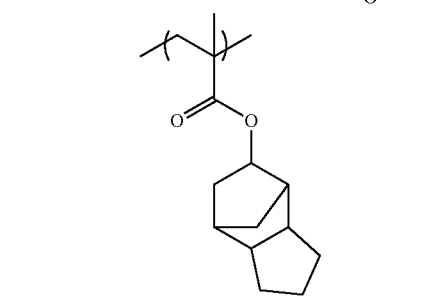
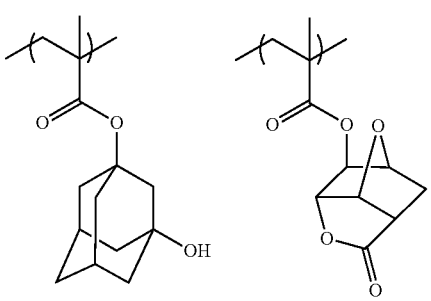
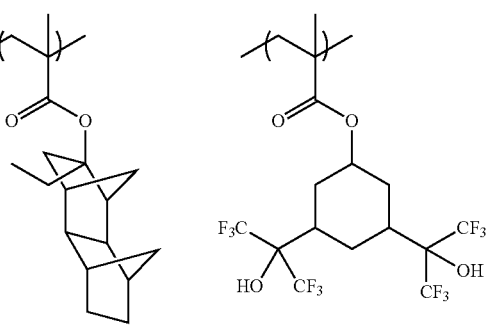
280
-continued
(17)
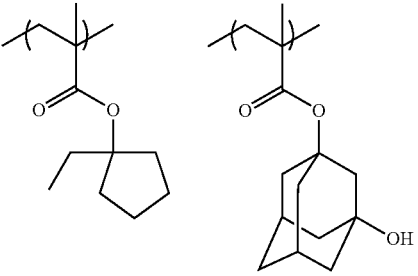
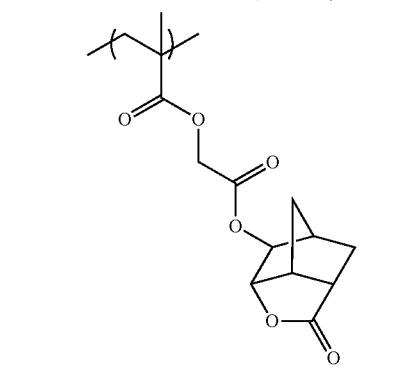
(18)
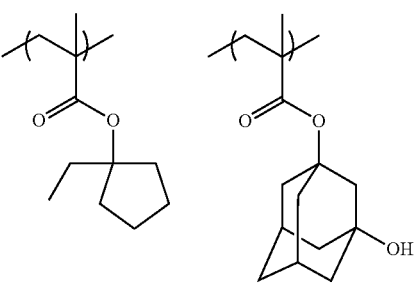
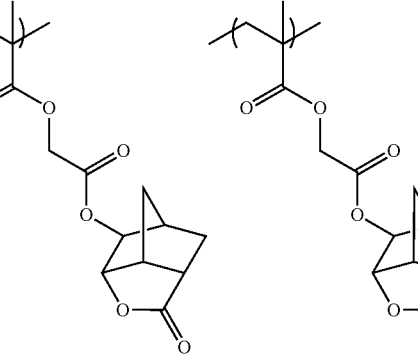
(19)
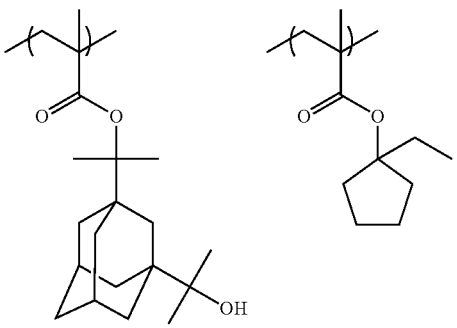

-continued

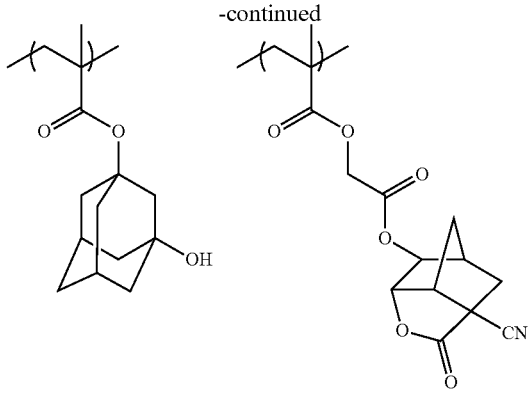

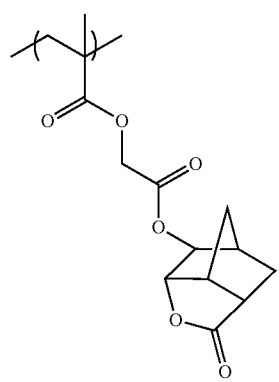

(20)

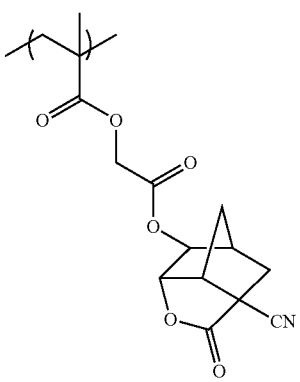

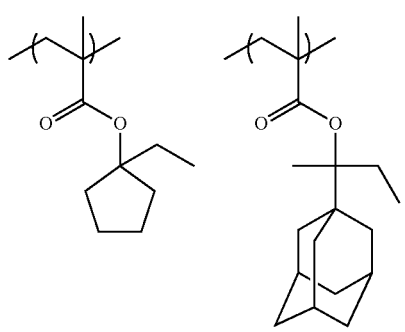

-continued

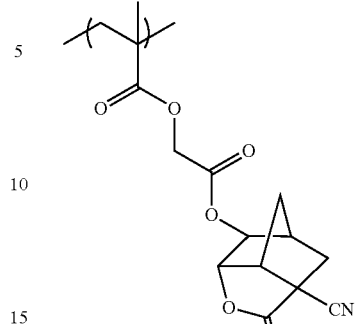

(21)

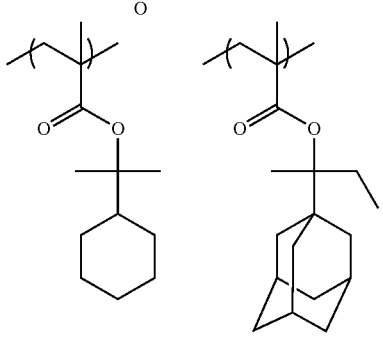

TABLE 2

| Resin (A) | Composition | Mw | Mw/Mn |
|---|---|---|---|
| (1) | 50/10/40 | 8800 | 1.9 |
| (2) | 40/20/40 | 7000 | 1.6 |
| (3) | 40/10/35/5/10 | 10000 | 1.7 |
| (4) | 40/10/40/10 | 11000 | 1.8 |
| (5) | 40/15/20/25 | 8500 | 1.6 |
| (6) | 10/40/25/25 | 12000 | 1.8 |
| (7) | 50/20/30 | 6500 | 1.6 |
| (8) | 40/10/50 | 8000 | 1.7 |
| (9) | 25/25/50 | 9000 | 1.8 |
| (10) | 50/10/40 | 11000 | 1.8 |
| (11) | 50/10/40 | 8000 | 1.7 |
| (12) | 40/10/40/10 | 7000 | 1.7 |
| (13) | 20/15/35/30 | 10000 | 1.7 |
| (14) | 45/10/35/10 | 8500 | 1.7 |
| (15) | 50/40/10 | 10000 | 1.6 |
| (16) | 10/40/40/10 | 9000 | 1.8 |
| (17) | 55/10/35 | 12000 | 1.8 |
| (18) | 40/15/20/25 | 9000 | 1.7 |
| (19) | 15/30/10/28/17 | 10000 | 1.7 |
| (20) | 40/10/32.5/17.5 | 9200 | 1.8 |
| (21) | 40/10/30/20 | 8500 | 1.7 |

<Preparation of Resist>

The components shown in the Tables below were dissolved in a solvent to prepare a solution having a solid content concentration of 5 mass %, and the obtained solution was filtered through a polyethylene filter having a pore size of 0.1 µm to prepare a positive resist composition. The positive resist compositions prepared were evaluated by the following methods, and the results are shown in the Tables. In the Tables, the resin in "Resin (2 g)" means the resin (A).

<Image Performance Test>

[Exposure Conditions: ArF Immersion Exposure]

An organic antireflection film, ARC29A (produced by Nissan Chemical Industries, Ltd.), was applied on a 12 inch-diameter silicon wafer and baked at 205° C. for 60 seconds to form a 98 nm-thick antireflection film, and the positive resist composition prepared above was applied thereon and baked at 120° C. for 60 seconds to form a 120 nm-thick resist film. The obtained wafer was exposed through a 6% halftone mask having a 1:1 line-and-space pattern with a line width of 75 nm by using an ArF excimer laser immersion scanner (XT1250i, manufactured by ASML, NA: 0.85). As for the immersion liquid, ultrapure water was used. Thereafter, the wafer was heated at 120° C. for 60 seconds, developed with an aqueous tetramethylammonium hydroxide solution (2.38 mass %) for 30 seconds, rinsed with pure water and spin-dried to obtain a resist pattern.

[Line Edge Roughness (LER)]

With respect to the range of 5 μm edge in the longitudinal direction of the 1:1 line-and-space pattern with a line width of 75 nm, the distance from the reference line where the edge should be present was measured at 50 points by a Critical Dimension SEM (S-8840, manufactured by Hitachi Ltd.) and after determining the standard deviation, 3σ was computed. The sample was rated A when the value (nm) was less than 5.0, rated B when from 5.0 to less than 7.0, and rated C when 7.0 or more. A smaller value indicates higher performance.

[Scum]

Development residue (scum) in the resist pattern with a line width of 75 nm was observed using a scanning electron microscope (S-4800, manufactured by Hitachi Ltd.), and the sample was rated A when scum was not generated at all, rated D when scum was severely generated, and rated B or C when the level of scum was therebetween.

[Evaluation of Development Defect]

Using a defect inspection apparatus, KLA 2360 (trade name), manufactured by KLA Tencor Ltd., measurement was performed in a random mode by setting the pixel size of the defect inspection apparatus to 0.16 μm and the threshold value to 20 so as to detect development defects extracted from the difference produced when superposing pixel units with a reference image. The number of development defects per unit area (1 cm$^2$) was computed. The sample was rated A when the value was less than 0.5, rated B when from 0.5 to less than 0.7, rated C when from 0.7 to less than 1.0, and rated D when 1.0 or more. A smaller value indicates higher performance.

[Bubble Defect]

An organic antireflection film, ARC29A (produced by Nissan Chemical Industries, Ltd.), was applied on a 12 inch-diameter silicon wafer and baked at 205° C. for 60 seconds to form a 78 nm-thick antireflection film, and the positive resist composition prepared above was applied thereon and heated and dried on a hot plate at 120° C. for 60 seconds to form a 100 nm-thick resist film.

The obtained wafer was exposed through a 6% halftone mask having a 1:1 line-and-space pattern with a line width of 75 nm by using an ArF excimer laser immersion scanner (XT1250i, manufactured by ASML, NA: 0.85).

As for the immersion liquid, ultrapure water was used.

Thereafter, the wafer was heated on a hot plate at 110° C. for 60 seconds, further developed at 23° C. with an aqueous tetramethylammonium hydroxide solution having a concentration of 2.38 mass % for 60 seconds, rinsed with pure water for 40 seconds and then dried to obtain a resist pattern.

The thus-obtained sample wafer was measured for the number of development defects by an apparatus, KLA 2360 (manufactured by KLA Tencor Ltd.).

The development defect part detected was observed using Critical Dimension SEM S9380 manufactured by Hitachi Ltd., and the number of bubble defects was determined.

The sample was rated A when the number of bubble defects was 0/cm$^2$, rated B when from more than 0 to 0.01/cm$^2$ or less, rated C when from more than 0.01 to 0.1/cm$^2$, and rated D when more than 0.1/cm$^2$.

[Pattern Profile]

A 85-nm isolated pattern formed in the same manner as in the evaluation of bubble defect was observed, and the sample was rated A when the pattern profile was rectangular, rated B when nearly rectangular, rated C when slightly tapered, and rated D when film loss was generated.

<Test of Other Performances>

[Elution Amount of Generated Acid]

The prepared positive resist composition was applied on a 8 inch-diameter silicon wafer and baked at 120° C. for 60 seconds to form a 160 nm-thick resist film. Subsequently, the entire surface of the 8-inch wafer was exposed at 30 mJ/cm$^2$ by using an ArF excimer laser exposure machine (PAS5500/1100, manufactured by ASML). The wafer was dipped in a quartz vessel having added thereto 100 mL of pure water deionized using an ultrapure water production apparatus (Milli-Q, manufactured by Nihon Millipore K.K.), and the material eluted into water was collected. This elution amount of acid into an aqueous solution was quantitatively determined by LC-MS.

LC Apparatus: 2695 manufactured by Waters

MS Apparatus: esquire 3000 manufactured by Brucker Daltonics

The detected intensity of ion species having a mass of 299 (corresponding to nonaflate anion) was measured by the LC-MS apparatus, and the elution amount of nonafluorobutanesulfonic acid was computed. The elution amount was computed in the same manner also on other anions. The sample was rated C when the elution amount was $1.0 \times 10^{-10}$ mol/cm$^2$/sec or more, rated B when from $1.0 \times 10^{-12}$ mol/cm$^2$/sec to less than $1.0 \times 10^{-10}$ mol/cm$^2$/sec, and rated A when less than $1.0 \times 10^{-12}$ mol/cm$^2$/sec.

[Receding Contact Angle]

The positive resist composition prepared was applied on a 8 inch-diameter silicon wafer and baked at 120° C. for 60 seconds to form a 160 nm-thick resist film. The receding contact angle of a water droplet was measured using a dynamic contact angle meter (manufactured by Kyowa Interface Science Co., Ltd.) at room temperature 23±3° C. and a humidity of 45±5% by an expansion-contraction method. A droplet having an initial droplet size of 35 μL was suctioned at a rate of 6 μL/sec for 5 seconds, and the value when the dynamic contact angle during suction was stabilized was taken as the receding contact angle. As the numerical value of this receding contact angle is larger, water can follow the scanning at a higher speed.

[Particle (Aging Stability)]

With respect to the positive resist composition prepared above, the number of particles in the solution immediately after preparation (particle initial value) and the number of particles in the solution after standing at 4° C. for 1 week (number of particles after aging) were countered by a particle counter manufactured by RION Co., Ltd., and the increase in the number of particles calculated by (number of particles after aging)−(particle initial value) was determined. Here, particles having a particle diameter of 0.25 μm or more contained in 1 mL of the solution were counted.

The sample was rated A when the increase in the number of particles is 0.2 particles/ml or less, rated B when from more than 0.2 particles/ml to 1/ml, rated C when from more than 1 particle/ml to 5 particles/ml, and rated D when more than 5 particles/ml.

TABLE 3

| | Resist Composition | | | | | | Evaluation Results |
|---|---|---|---|---|---|---|---|
| | Resin (2 g) | Photo-Acid Generator (mg) | Solvent (ratio by mass) | Basic Compound (mg) | Resin (C)/(CP) (mg) | Surfactant (mg) | LER |
| Example 1 | 1 | z38 (100) | SL-2/SL-4 60/40 | N-5/N-1 (7/7) | C-7 (80) | W-4 (2) | A |
| Example 2 | 5 | z55 (90) | SL-4/SL-2 40/60 | N-5 (7) | C-8 (80) | W-1 (3) | A |
| Example 3 | 7 | Y-7 (100) | SL-4/SL-2 40/60 | N-3 (6) | C-72 (80) | W-1 (3) | A |
| Example 4 | 8 | z55 (100) | SL-2/SL-4/SL-6 40/59/1 | N-6 (10) | C-1 (40) | W-3 (3) | A |
| Example 5 | 11 | z2 (100) | SL-2/SL-4 70/30 | N-3 (6) | C-6 (80) | W-6 (3) | A |
| Example 6 | 14 | Y-3 (100) | SL-3/SL-4 30/70 | N-6 (10) | C-9 (80) | W-5 (4) | A |
| Example 7 | 15 | z80 (100) | SL-2/SL-4/SL-5 40/58/2 | N-1 (7) | C-50 (40) | W-1 (4) | A |
| Example 8 | 16 | z66 (100) | SL-1/SL-2/ 60/40 | N-4 (13) | C-56 (80) | W-6 (4) | A |
| Example 9 | 18 | z67 (100) | SL-2/SL-4/SL-6 40/59/1 | N-2 (9) | C-12 (50) | W-3 (3) | A |
| Example 10 | 1 | Z66/Y-65 (60/40) | SL-2/SL-4 60/40 | N-5/N-1 (7/7) | C-14 (80) | W-4 (2) | A |
| Example 11 | 5 | z66 (100) | SL-2/SL-4 60/40 | N-5/N-1 (7/7) | C-72 (80) | W-4 (2) | A |
| Example 12 | 5 | z66 (100) | SL-2/SL-4 60/40 | N-5/N-1 (7/7) | C-7 (160) | W-4 (2) | A |
| Example 13 | 5 | z66 (100) | SL-2/SL-4 60/40 | N-5/N-1 (7/7) | C-7 (80) | W-4 (2) | A |
| Example 14 | 5 | z66 (100) | SL-2/SL-4 60/40 | N-5/N-1 (7/7) | C-7(240) | W-4 (2) | A |
| Example 15 | 5 | z46 (90) | SL-4/SL-2 40/60 | N-7 (7) | C-191 (80) | W-6 (3) | A |
| Example 16 | 8 | Y-1 (100) | SL-2/SL-4 70/30 | N-3 (10) | C-6 (80) | W-6 (2) | A |
| Example 17 | 8 | PAG24 (100) | SL-2/SL-4 60/40 | N-3 (10) | C-9(80) | W-6 (2) | A |
| Example 18 | 4 | z55 (100) | SL-2/SL-4 60/40 | N-8 (10) | C-212 (80) | W-6 (2) | A |
| Example 19 | 4 | z80/z66 (50/50) | SL-2/SL-4 60/40 | N-3/N-8 (7/7) | C-209/CP-75 (80/8) | W-6 (2) | A |
| Example 20 | 5 | PAG16 (100) | SL-2/SL-4 60/40 | N-3/N-8 (7/7) | C-237 (80) | W-6 (2) | A |
| Example 21 | 5 | z80/z66 (50/50) | SL-2/SL-4 60/40 | N-3/N-8 (7/7) | C-232 (80) | W-6 (2) | A |
| Example 22 | 1 | z38 (100) | SL-2/SL-4 60/40 | N-5/N-1 (7/7) | C-7/CP-75 (75/5) | W-4 (2) | A |
| Example 23 | 5 | z55 (90) | SL-4/SL-2 40/60 | N-5 (7) | C-8 (80) | W-1/W-4 (1/1) | A |
| Example 24 | 1/5 (1/1) | z38 (100) | SL-2/SL-4 60/40 | N-5/N-1 (7/7) | C-7 (80) | W-4 (2) | A |
| Example 25 | 5 | Y-1 (100) | SL-2/SL-4 60/40 | N-1 (10) | C-200 (80) | W-5 (2) | A |
| Example 26 | 4 | z1 (100) | SL-1/SL-2 60/40 | N-3 (6) | C-155 (80) | W-2 (3) | A |
| Example 27 | 5 | z66 (100) | SL-2/SL-4 60/40 | N-5/N-1 (7/7) | C-155 (80) | W-4 (2) | A |
| Example 28 | 5 | z66 (100) | SL-2/SL-4 60/40 | N-5/N-1 (7/7) | C-172 (80) | W-4 (2) | A |
| Example 29 | 5 | z66 (100) | SL-2/SL-4 60/40 | N-5/N-1 (7/7) | C-155/CP-23 (40/40) | W-4 (2) | A |
| Example 30 | 4 | z2 (100) | SL-2/SL-4 60/40 | N-1 (10) | C-119 (80) | W-4 (2) | A |
| Example 31 | 5 | z72 (90) | SL-4/SL-2 40/60 | N-5 (7) | C-121 (80) | W-1 (3) | A |
| Example 32 | 7 | z2 (100) | SL-4/SL-2 60/40 | N-3/N-8 (7/7) | C-119/CP-3 (20/60) | W-4 (2) | A |
| Example 33 | 19 | Y-3 (100) | SL-3/SL-4 30/70 | N-6 (10) | C-9 (80) | W-5 (4) | A |
| Example 34 | 20 | Y-3 (100) | SL-3/SL-4 30/70 | N-6 (10) | C-9 (80) | W-5 (4) | A |
| Example 35 | 13 | Y-3 (100) | SL-3/SL-4 30/70 | N-6 (10) | C-9 (80) | W-5 (4) | A |
| Example 36 | 14 | Y-3 (100) | SL-3/SL-4 30/70 | N-6 (10) | C-9 (80) | — | A |
| Example 37 | 1 | z38 (100) | SL-2/SL-4 60/40 | N-5/N-1 (7/7) | C-7/CP-75 (75/5) | — | A |
| Example 38 | 5 | z55 (90) | SL-4/SL-2 40/60 | N-5 (7) | C-8 (80) | — | A |
| Example 39 | 5 | Y-1 (100) | SL-2/SL-4 60/40 | N-1 (10) | C-200 (80) | — | A |
| Example 40 | 21 | z92 (250) | SL-2/SL-5 95/5 | N-9 (10) | C-9 (80) | — | A |
| Comparative Example 1 | 5 | z66 (100) | SL-2/SL-4 60/40 | N-5/N-1 (7/7) | — | W-4 (2) | C |
| Comparative Example 2 | 5 | z80 (100) | SL-2/SL-4 60/40 | N-5/N-1 (7/7) | H-1 (80) | W-4 (2) | B |
| Comparative Example 3 | 5 | z66 (100) | SL-2/SL-4 60/40 | N-5/N-1 (7/7) | H-2 (80) | W-4 (2) | C |
| Comparative Example 4 | 4 | z66 (100) | SL-2/SL-4 60/40 | N-5/N-1 (7/7) | H-3 (80) | W-4 (2) | C |
| Comparative Example 5 | 4 | z80 (110) | SL-1/SL-2 60/40 | N-3 (6) | H-2 (80) | W-2 (3) | C |
| Comparative Example 6 | 4 | z80 (110) | SL-1/SL-2 60/40 | N-3 (6) | H-4 (80) | W-2 (3) | A |
| Comparative Example 7 | H-4 | z66 (110) | SL-2/SL-4 60/40 | N-5/N-1 (7/7) | — | W-4 (3) | C |
| Comparative Example 8 | 5 | z66 (110) | SL-2/SL-4 60/40 | N-5/N-1 (7/7) | H-5 (80) | W-4 (3) | C |
| Comparative Example 9 | 4 | z55 (100) | SL-2/SL-4 60/40 | N-8 (10) | polymer 2 (80) | W-6 (2) | A |
| Comparative Example 10 | 5 | PAG16 (100) | SL-2/SL-4 60/40 | N-3/N-8 (7/7) | polymer 4 (80) | W-6 (2) | A |

| | Evaluation Results | | | | | | |
|---|---|---|---|---|---|---|---|
| | Scum | Development Defect | Elution Amount of Acid | Receding Contact Angle (deg) | Particle | Pattern Profile | Bubble Defect |
| Example 1 | A | B | A | 80 | B | A | A |
| Example 2 | A | A | A | 75 | B | A | A |
| Example 3 | A | B | A | 70 | B | A | A |
| Example 4 | A | B | A | 70 | B | A | A |
| Example 5 | A | A | A | 75 | B | A | A |

TABLE 3-continued

|  |  |  |  |  |  |  |  |
|---|---|---|---|---|---|---|---|
| Example 6 | A | A | A | 75 | B | A | A |
| Example 7 | A | B | A | 70 | B | A | A |
| Example 8 | A | A | A | 70 | B | A | A |
| Example 9 | A | A | A | 75 | B | A | A |
| Example 10 | A | B | A | 80 | B | A | A |
| Example 11 | A | B | A | 80 | B | A | A |
| Example 12 | B | A | A | 75 | B | A | A |
| Example 13 | A | A | A | 70 | B | A | A |
| Example 14 | C | B | A | 80 | B | A | A |
| Example 15 | A | B | A | 80 | B | A | A |
| Example 16 | A | A | A | 75 | B | A | A |
| Example 17 | A | B | A | 75 | B | A | A |
| Example 18 | A | B | A | 75 | B | A | A |
| Example 19 | A | A | A | 80 | B | A | A |
| Example 20 | A | B | A | 70 | B | A | A |
| Example 21 | A | A | A | 75 | B | A | A |
| Example 22 | A | B | A | 80 | B | A | A |
| Example 23 | A | A | A | 75 | B | A | A |
| Example 24 | A | B | A | 80 | B | A | A |
| Example 25 | A | B | A | 75 | A | A | A |
| Example 26 | A | B | B | 75 | A | B | C |
| Example 27 | A | A | A | 70 | A | B | C |
| Example 28 | A | A | A | 80 | A | B | B |
| Example 29 | A | A | A | 80 | A | B | C |
| Example 30 | A | B | A | 70 | A | B | A |
| Example 31 | A | A | A | 75 | A | B | A |
| Example 32 | A | B | A | 80 | A | B | A |
| Example 33 | A | A | A | 75 | B | A | A |
| Example 34 | A | A | A | 75 | B | A | A |
| Example 35 | A | A | A | 75 | B | A | A |
| Example 36 | A | A | A | 76 | B | A | A |
| Example 37 | A | B | A | 81 | B | A | A |
| Example 38 | A | A | A | 76 | B | A | A |
| Example 39 | A | B | A | 76 | A | A | A |
| Example 40 | A | A | A | 77 | B | A | A |
| Comparative Example 1 | D | C | C | 55 | D | D | D |
| Comparative Example 2 | D | C | C | 80 | D | D | D |
| Comparative Example 3 | D | C | B | 75 | C | C | C |
| Comparative Example 4 | D | D | C | 80 | D | D | D |
| Comparative Example 5 | D | C | B | 75 | D | D | D |
| Comparative Example 6 | B | C | A | 75 | C | C | C |
| Comparative Example 7 | D | C | B | 75 | D | D | D |
| Comparative Example 8 | D | C | B | 75 | C | C | C |
| Comparative Example 9 | B | B | A | 70 | C | C | C |
| Comparative Example 10 | B | B | A | 70 | C | C | C |

The denotations in the Tables are as follows.

The acid generators and resins (C) are corresponding to those illustrated above as examples.

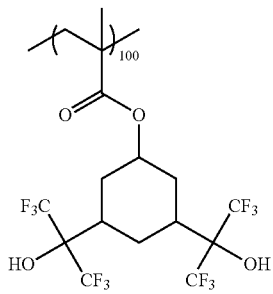

Mw = 9500
Mw/Mn = 1.5

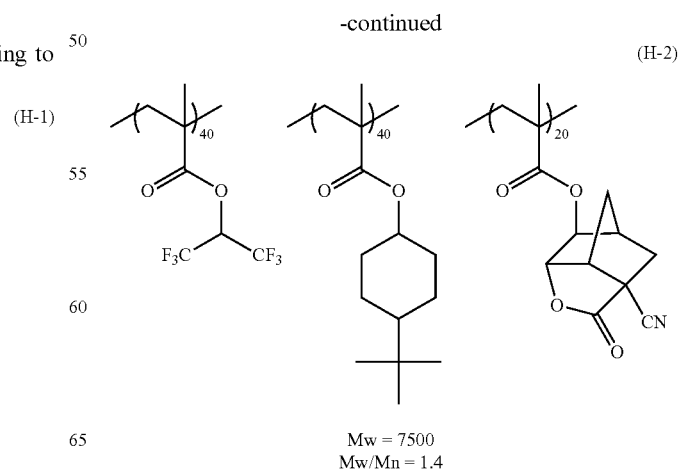

Mw = 7500
Mw/Mn = 1.4

(H-3)
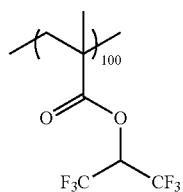
Mw = 6000
Mw/Mn = 1.3
(H-4)
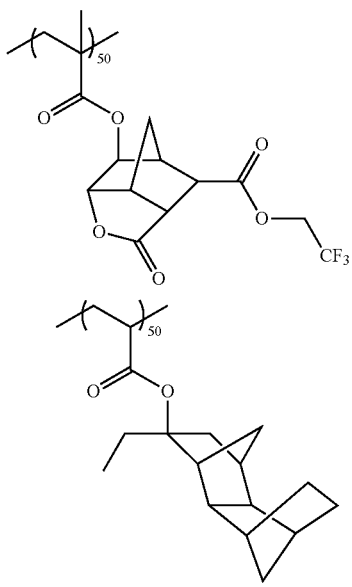
Mw = 7300
Mw/Mn = 1.4
(H-5)
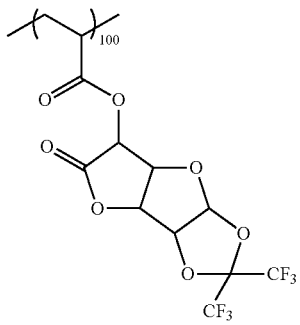
Mw = 6500
Mw/Mn = 1.4
(CP-75)
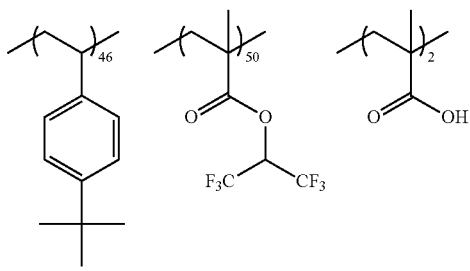
-continued
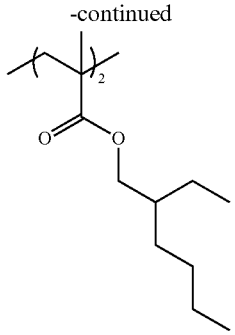
Mw = 4500
Mw/Mn = 1.4
(Polymer2)
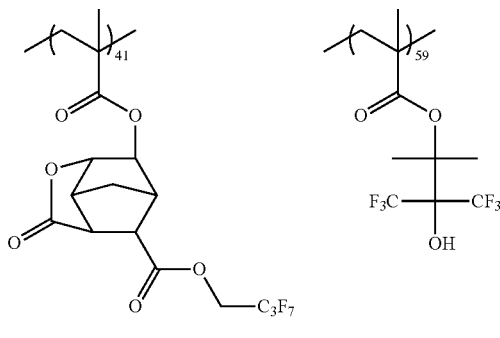
Mw = 7600
Mw/Mn = 1.6
(Polymer4)
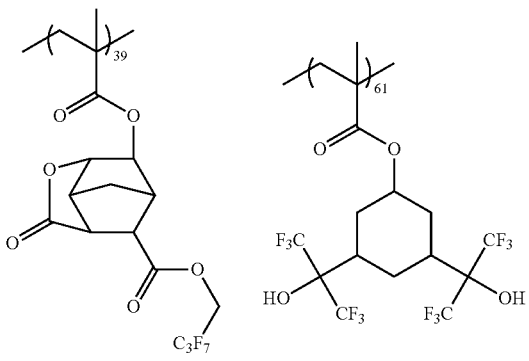
Mw = 7500
Mw/Mn = 1.6
(CP-23)
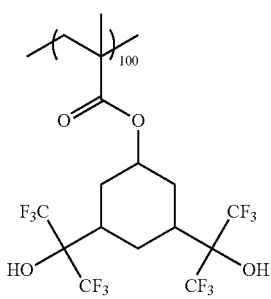
Mw = 9500
Mw/Mn = 1.5

-continued (CP-3)

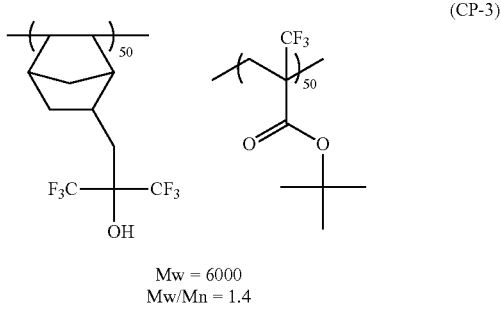

Mw = 6000
Mw/Mn = 1.4

(PAG16)

(PAG24)

(z92)

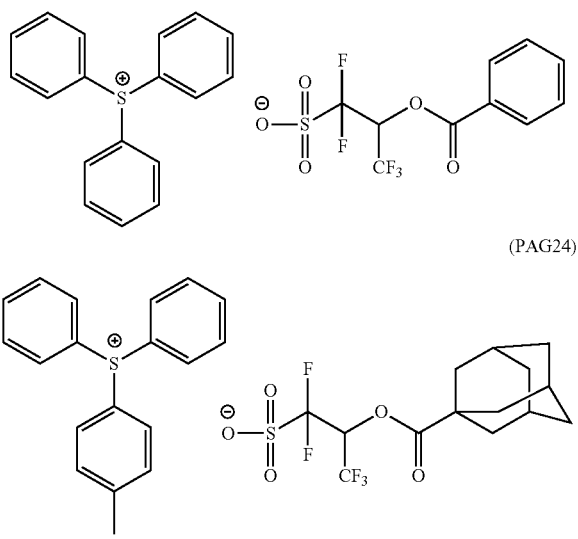

[Basic Compound]
N-1: N,N-Dibutylaniline
N-2: N,N-Dihexylaniline
N-3: 2,6-Diisopropylaniline
N-4: Tri-n-octylamine
N-5: N,N-Dihydroxyethylaniline
N-6: 2,4,5-Triphenylimidazole
N-7: 2-[2-{2-(2,2-Dimethoxy-phenoxyethoxy)ethyl}-bis-(2-methoxyethyl)]-amine
N-8: 2,4,6-Tri-tert-butylaniline
N-9: N-tert-Amyloxycarbonyl-4-hydroxypiperidine

[Surfactant]
W-1: Megaface F176 (produced by Dainippon Ink & Chemicals, Inc., fluorine-containing)
W-2: Megaface R08 (produced by Dainippon Ink & Chemicals, Inc., fluorine- and silicon-containing)
W-3: Polysiloxane Polymer KP-341 (produced by Shin-Etsu Chemical Co., Ltd., silicon-containing)
W-4: Troysol S-366 (produced by Troy Chemical)
W-5: PF656 (produced by OMNOVA, fluorine-containing)
W-6: PF6320 (produced by OMNOVA, fluorine-containing)

[Solvent]
SL-1: Cyclohexanone
SL-2: Propylene glycol monomethyl ether acetate (PGMEA)
SL-3: Ethyl lactate
SL-4: Propylene glycol monomethyl ether (PGME)
SL-5: γ-Butyrolactone
SL-6: Propylene carbonate As seen from Table 3, the resist pattern formed using the positive resist composition of the present invention exhibits excellent performance in terms of all of line edge roughness, scum, development defect, elution amount of acid, followability for immersion liquid at the immersion exposure, particle, pattern profile and bubble defect.

Industrial Applicability

According to the present invention, an actinic ray-sensitive or radiation-sensitive resin composition enabling formation of a pattern improved in the line edge roughness and scum generation and reduced in the development defect and ensuring little elution of an acid into the immersion liquid, good followability for the immersion liquid, and various good performances in terms of particle suppression, pattern profile and bubble defect prevention, and a pattern forming method using the same can be provided.

This application is based on Japanese patent application Nos. JP 2008-317751 filed on Dec. 12, 2008, JP 2008-317752 filed on Dec. 12, 2008, JP 2008-317754 filed on Dec. 12, 2008, JP 2009-054291 filed on Mar. 6, 2009, JP 2009-091616 filed on Apr. 3, 2009, JP 2009-122470 filed on May 20, 2009, JP 2009-131275 filed on May 29, 2009, JP 2009-167004 filed on Jul. 15, 2009 and JP 2009-251478 filed on Oct. 30, 2009, and U.S. Provisional Application No. 61/122,166 filed on Dec. 12, 2008, the entire content of which is hereby incorporated by reference, the same as if set forth at length.

The invention claimed is:

1. An actinic ray-sensitive or radiation-sensitive resin composition, comprising:
(A) a resin capable of increasing a solubility of the resin (A) in an alkali developer by an action of an acid; and
(C) a resin having at least either a fluorine atom or a silicon atom and containing (c) a repeating unit having at least two or more polarity conversion groups represented by —COO— in the structure represented by formula (KA-1) or (KB-1):

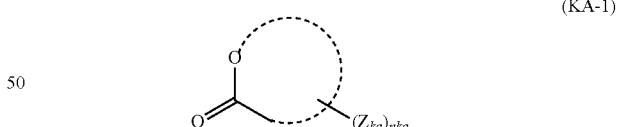

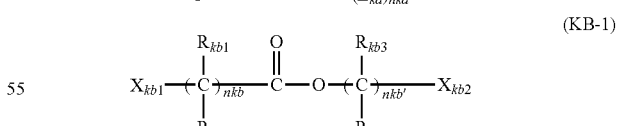

wherein $Z_{ka}$ represents an alkyl group, a cycloalkyl group, an ether group, a hydroxyl group, an amide group, an aryl group, a lactone ring group or an electron-withdrawing group, and when a plurality of $Z_{ka}$'s are present, the plurality of $Z_{ka}$'s are the same or different;
each $Z_{ka}$ may combine with every other $Z_{ka}$ to form a ring;
nka represents an integer of 0 to 10;
each of $X_{kb1}$ and $X_{kb2}$ independently represents an electron-withdrawing group;

each of nkb and nkb' independently represents 0 or 1; and
each of $R_{kb1}$ to $R_{kb4}$ independently represents a hydrogen atom, an alkyl group, a cycloalkyl group, an aryl group or an electron-withdrawing group, at least two members of $R_{kb1}$, $R_{kb2}$ and $X_{kb1}$ may combine with each other to form a ring, and at least two members of $R_{kb3}$, $R_{kb4}$ and $X_{kb2}$ may combine with each other to form a ring,
wherein:
the resin (A) contains no fluorine atom and no silicon atom;
the resin (A) includes a repeating unit represented by the following Formula (AI):

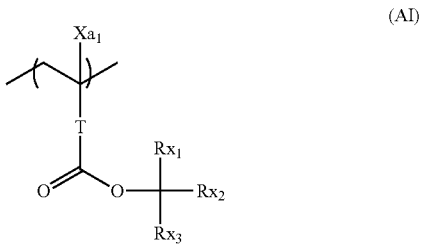

(AI)

wherein in formula (AI), $Xa_1$ represents a hydrogen atom, a methyl group which may have a substituent, or a group represented by —$CH_2$—$R_9$; $R_9$ represents a hydroxyl group or a monovalent organic group;
T represents a single bond or a divalent linking group;
each of $Rx_1$ to $Rx_3$ independently represents a linear or branched alkyl group or a monocyclic or polycyclic cycloalkyl group; and
two members out of $Rx_1$ to $Rx_3$ may combine to form a monocyclic or polycyclic cycloalkyl group; and
the repeating unit (c) has a structure represented by the following formula (KY-2):

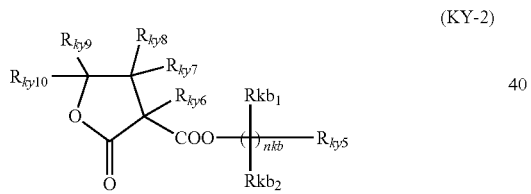

(KY-2)

wherein each of $R_{ky6}$ to $R_{ky10}$ independently represents a hydrogen atom, a halogen atom, an alkyl group, a cycloalkyl group, a carbonyl group, a carbonyloxy group, an oxycarbonyl group, an ether group, a hydroxyl group, a cyano group, an amide group or an aryl group;
two or more members of $R_{ky6}$ to $R_{ky10}$ may combine with each other to form a monocyclic or polycyclic structure;
$R_{ky5}$ represents an electron-withdrawing group; and
$R_{kb1}$, $R_{kb2}$ and nkb have the same meanings as in formula (KB-1).

2. The actinic ray-sensitive or radiation-sensitive resin composition according to claim 1,
wherein the repeating unit (c) is (c') a repeating unit having the at least two or more polarity conversion groups and at least either a fluorine atom or a silicon atom on one side chain.

3. The actinic ray-sensitive or radiation-sensitive resin composition according to claim 1,
wherein the repeating unit (c) is (c*) a repeating unit having the at least two or more polarity conversion groups and having neither a fluorine atom nor a silicon atom, and the resin (C) further contains a repeating unit having at least either a fluorine atom or a silicon atom.

4. The actinic ray-sensitive or radiation-sensitive resin composition according to claim 1,
wherein the repeating unit (c) is (c") a repeating unit having the at least two or more polarity conversion groups on one side chain and at the same time, having at least either a fluorine atom or a silicon atom on a side chain different from said side chain in the same repeating unit.

5. The actinic ray-sensitive or radiation-sensitive resin composition according to claim 1,
wherein the resin (C) has at least one group represented by any one of formulae (F2) to (F4) and formulae (CS-1) to (CS-3):

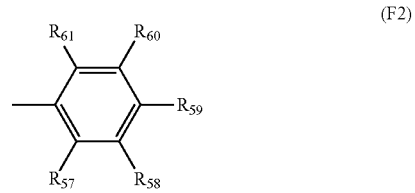

(F2)

(F3)

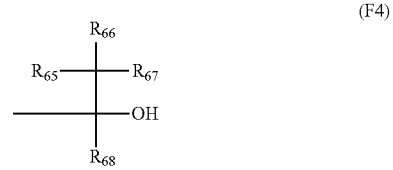

(F4)

wherein each of $R_{57}$ to $R_{68}$ independently represents a hydrogen atom, a fluorine atom, a linear or branched alkyl group or an aryl group, provided that at least one of $R_{57}$ to $R_{61}$, at least one of $R_{62}$ to $R_{64}$ and at least one of $R_{65}$ to $R_{68}$ each independently represent a fluorine atom or an alkyl group with at least one hydrogen atom being replaced by a fluorine atom, and $R_{62}$ and $R_{63}$ may combine with each other to form a ring:

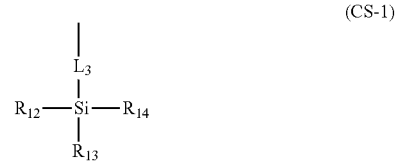

(CS-1)

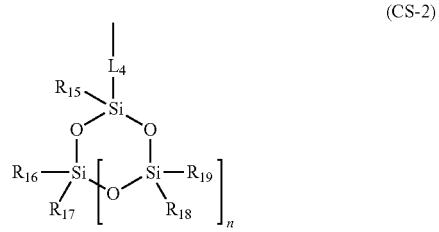

(CS-2)

(CS-3)

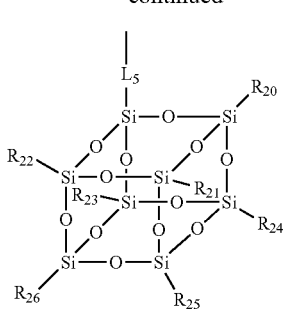

wherein each of $R_{12}$ to $R_{26}$ independently represents a linear or branched alkyl group or a cycloalkyl group;
each of $L_3$ to $L_5$ represents a single bond or a divalent linking group; and
n represents an integer of 1 to 5.

6. The actinic ray-sensitive or radiation-sensitive resin composition according to claim 5,
wherein the resin (C) contains at least one acrylate or methacrylate repeating unit having the group represented by any one of formulae (F2) to (F4) and formulae (CS-1) to (CS-3).

7. The actinic ray-sensitive or radiation-sensitive resin composition according to claim 1,
wherein the content of the resin (C) is from 0.01 to 10 mass % based on the entire solids content in the actinic ray-sensitive or radiation-sensitive resin composition.

8. The actinic ray-sensitive or radiation-sensitive resin composition according to claim 7,
wherein the content of the resin (C) is 0.1 to 5 mass %, based on the entire solids content of the actinic ray-sensitive or radiation-sensitive resin composition.

9. The actinic ray-sensitive or radiation-sensitive resin composition according to claim 1, which further comprises:
(B) a compound capable of generating an acid upon irradiation with an actinic ray or radiation.

10. The actinic ray-sensitive or radiation-sensitive resin composition according to claim 9,
wherein the compound (B) is a compound capable of generating an acid represented by the following formula (1):

(1)

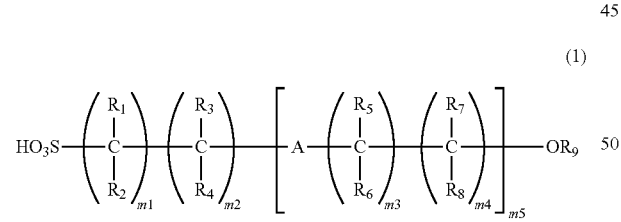

wherein in formula (1), each of $R_1$ to $R_8$ independently represents a hydrogen atom, an alkyl group, a cycloalkyl group, a halogen atom or a hydroxyl group;
$R_9$ represents a hydrogen atom, an alkyl group, a cycloalkyl group, an alkenyl group, —CORx or —SO$_2$Rs;
A represents a heteroatom-containing divalent linking group or a single bond;
Rx represents an alkyl group, a cycloalkyl group, an aryl group or a heteroaryl group;
Rs represents an alkyl group, a cycloalkyl group or an aryl group;
each of m1 to m4 independently represents an integer of 0 to 12, provided that m3+m4≥1;

m5 represents an integer of 1 to 3; and
when any of m1 to m5 is an integer of 2 or more, a plurality of members for each of $R_1$ to $R_8$ and A may be the same or different.

11. The actinic ray-sensitive or radiation-sensitive resin composition according to claim 9,
wherein the compound (B) is a compound represented by the following formula (I):

(I)

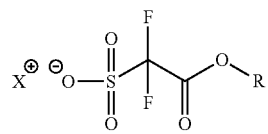

wherein in formula (I), X$^+$ represents an organic counter ion, and R represents a hydrogen atom or an organic group.

12. The actinic ray-sensitive or radiation-sensitive resin composition according to claim 1,
wherein the resin (A) contains a lactone structure-containing repeating unit.

13. A resist film, which is formed from the actinic ray-sensitive or radiation-sensitive resin composition according to claim 1.

14. A pattern forming method, comprising:
immersion-exposing and developing the resist film according to claim 13.

15. The actinic ray-sensitive or radiation-sensitive resin composition according to claim 1,
wherein the resin (A) is a resin where all repeating units are (meth)acrylate-based repeating units.

16. The actinic ray-sensitive or radiation-sensitive resin composition according to claim 1,
wherein the resin (A) contains no aromatic group.

17. The actinic ray-sensitive or radiation-sensitive resin composition according to claim 1,
wherein the resin (A) contains at least two kinds of repeating units represented by the following formula (1):

(1)

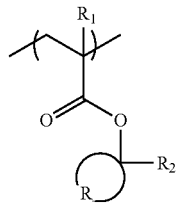

wherein in formula (1), $R_1$ represents a hydrogen atom, a methyl group which may have a substituent, or a group represented by —CH$_2$—R$_9$; $R_9$ represents a hydroxyl group or a monovalent organic group;
$R_2$ represents an alkyl group or a cycloalkyl group; and
R represents an atomic group necessary for forming an alicyclic structure together with the carbon atom.

18. The actinic ray-sensitive or radiation-sensitive resin composition according to claim 1,
wherein the actinic ray-sensitive or radiation-sensitive resin composition further contains a compound represented by the following Formula (A):

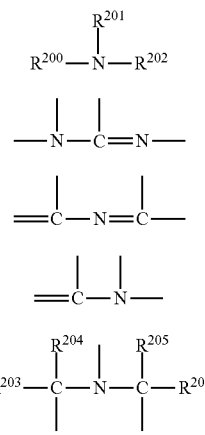

(A)

(B)

(C)

(D)

(E)

wherein in Formula (A), each of $R^{200}$, $R^{201}$ and $R^{202}$, which may be the same or different, represents a hydrogen atom, an alkyl group, a cycloalkyl group or an aryl group, and $R^{201}$ and $R^{202}$ may combine together to form a ring.

19. The actinic ray-sensitive or radiation-sensitive resin composition according to claim 1,
wherein the actinic ray-sensitive or radiation-sensitive resin composition further contains one, as a solvent, selected from the group consisting of cyclohexanone, ethyl lactate, γ-butyrolactone, and propylene carbonate.

20. An actinic ray-sensitive or radiation-sensitive resin composition, comprising:
(A) a resin capable of increasing a solubility of the resin (A) in an alkali developer by an action of an acid; and
(C) a resin having at least either a fluorine atom or a silicon atom and containing (c) a repeating unit having at least two or more polarity conversion groups represented by —COO— in the structure represented by formula (KA-1) or (KB-1):

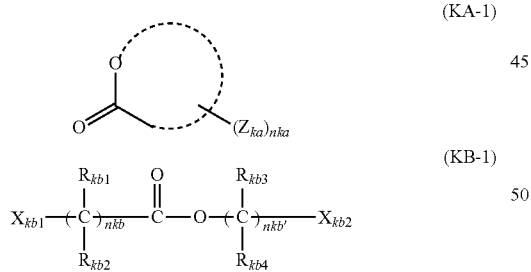

wherein $Z_{ka}$ represents an alkyl group, a cycloalkyl group, an ether group, a hydroxyl group, an amide group, an aryl group, a lactone ring group or an electron-withdrawing group, and when a plurality of $Z_{ka}$'s are present, the plurality of $Z_{ka}$'s are the same or different;
each $Z_{ka}$ may combine with every other $Z_{ka}$ to form a ring;
nka represents an integer of 0 to 10;
each of $X_{kb1}$ and $X_{kb2}$ independently represents an electron-withdrawing group;
each of nkb and nkb' independently represents 0 or 1; and
each of $R_{kb1}$ to $R_{kb4}$ independently represents a hydrogen atom, an alkyl group, a cycloalkyl group, an aryl group or an electron-withdrawing group, at least two members of $R_{kb1}$, $R_{kb2}$ and $X_{kb1}$ may combine with each other to form a ring, and at least two members of $R_{kb3}$, $R_{kb4}$ and $X_{kb2}$ may combine with each other to form a ring,
wherein:
the resin (A) contains no fluorine atom and no silicon atom;
the resin (A) includes a repeating unit represented by the following Formula (AI):

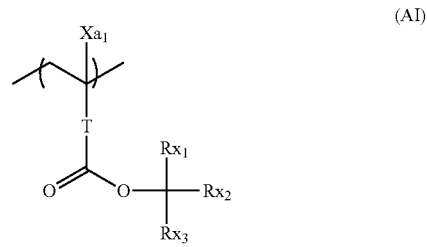

wherein in formula (AI), $Xa_1$ represents a hydrogen atom, a methyl group which may have a substituent, or a group represented by —$CH_2$—$R_9$; $R_9$ represents a hydroxyl group or a monovalent organic group;
T represents a single bond or a divalent linking group;
each of $Rx_1$ to $Rx_3$ independently represents a linear or branched alkyl group or a monocyclic or polycyclic cycloalkyl group; and
two members out of $Rx_1$ to $Rx_3$ may combine to form a monocyclic or polycyclic cycloalkyl group;
and further wherein:
the repeating unit (c) is (c*) a repeating unit having the at least two or more polarity conversion groups and having neither a fluorine atom nor a silicon atom, and
the resin (C) further contains a repeating unit having at least either a fluorine atom or a silicon atom.

21. An actinic ray-sensitive or radiation-sensitive resin composition, comprising:
(A) a resin capable of increasing a solubility of the resin (A) in an alkali developer by an action of an acid; and
(C) a resin having at least either a fluorine atom or a silicon atom and containing (c) a repeating unit having at least two or more polarity conversion groups represented by —COO— in the structure represented by formula (KA-1) or (KB-1):

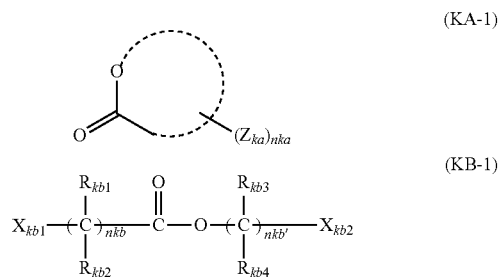

wherein $Z_{ka}$ represents an alkyl group, a cycloalkyl group, an ether group, a hydroxyl group, an amide group, an aryl group, a lactone ring group or an electron-withdrawing group, and when a plurality of $Z_{ka}$'s are present, the plurality of $Z_{ka}$'s are the same or different;
each $Z_{ka}$ may combine with every other $Z_{ka}$ to form a ring;
nka represents an integer of 0 to 10;

each of $X_{kb1}$ and $X_{kb2}$ independently represents an electron-withdrawing group;

each of nkb and nkb' independently represents 0 or 1; and each of $R_{kb1}$ to $R_{kb4}$ independently represents a hydrogen atom, an alkyl group, a cycloalkyl group, an aryl group or an electron-withdrawing group, at least two members of $R_{kb1}$, $R_{kb2}$ and $X_{kb1}$ may combine with each other to form a ring, and at least two members of $R_{kb3}$, $R_{kb4}$ and $X_{kb2}$ may combine with each other to form a ring, wherein:

the resin (A) contains no fluorine atom and no silicon atom;

the resin (A) includes a repeating unit represented by the following Formula (AI):

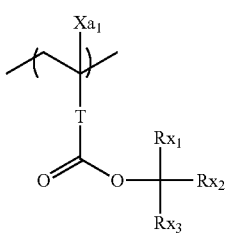

(AI)

wherein in formula (AI), $Xa_1$ represents a hydrogen atom, a methyl group which may have a substituent, or a group represented by —$CH_2$—$R_9$; $R_9$ represents a hydroxyl group or a monovalent organic group;

T represents a single bond or a divalent linking group;

each of $Rx_1$ to $Rx_3$ independently represents a linear or branched alkyl group or a monocyclic or polycyclic cycloalkyl group; and two members out of $Rx_1$ to $Rx_3$ may combine to form a monocyclic or polycyclic cycloalkyl group; and the repeating unit (c) has a structure represented by the following formula (KY-1):

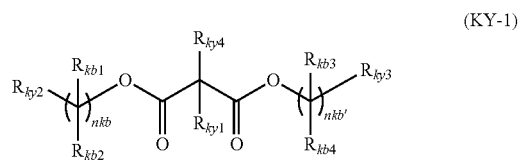

(KY-1)

wherein each of $R_{ky1}$ and $R_{ky4}$ independently represents a hydrogen atom, a halogen atom, an alkyl group, a cycloalkyl group, a carbonyl group, a carbonyloxy group, an oxycarbonyl group, an ether group, a hydroxyl group, a cyano group, an amide group or an aryl group, $R_{ky1}$ and $R_{ky4}$ may be bonded to the same atom to form a double bond;

each of $R_{ky2}$ and $R_{ky3}$ independently represents an electron-withdrawing group, or $R_1$ and $R_{ky2}$ are combined to form a lactone ring and at the same time, $R_{ky3}$ is an electron-withdrawing group;

at least two members of $R_{ky1}$, $R_{ky2}$ and $R_{ky4}$ may combine with each other to form a monocyclic or polycyclic structure; and $R_{kb1}$ to $R_{kb4}$, nkb and nkb' have the same meanings as in formula (KB-1).

* * * * *